United States Patent
Anderson et al.

(10) Patent No.: US 10,457,939 B2
(45) Date of Patent: *Oct. 29, 2019

(54) NEUROPROTECTIVE MOLECULES AND METHODS OF TREATING NEUROLOGICAL DISORDERS AND INDUCING STRESS GRANULES

(71) Applicant: The Brigham and Women's Hospital, Inc., Boston, MA (US)

(72) Inventors: Paul Anderson, Belmont, MA (US); Pavel Ivanov, Brighton, MA (US); Mohammed Emara, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 36 days.

This patent is subject to a terminal disclaimer.

(21) Appl. No.: 15/590,344

(22) Filed: May 9, 2017

(65) Prior Publication Data

US 2017/0292126 A1    Oct. 12, 2017

Related U.S. Application Data

(63) Continuation of application No. 13/808,863, filed as application No. PCT/US2011/043400 on Jul. 8, 2011, now Pat. No. 9,676,810.

(60) Provisional application No. 61/362,526, filed on Jul. 8, 2010.

(51) Int. Cl.
    *C12N 15/113* (2010.01)
    *C12N 15/11* (2006.01)
    *C07H 21/02* (2006.01)

(52) U.S. Cl.
    CPC ........... *C12N 15/113* (2013.01); *C07H 21/02* (2013.01); *C12N 15/11* (2013.01); *C12N 2310/18* (2013.01); *C12N 2310/531* (2013.01)

(58) Field of Classification Search
    None
    See application file for complete search history.

(56) References Cited

U.S. PATENT DOCUMENTS

| | | | |
|---|---|---|---|
| 3,687,808 | A | 8/1972 | Merigan |
| 5,432,272 | A | 7/1995 | Benner |
| 6,043,060 | A | 3/2000 | Imanishi |
| 6,268,490 | B1 | 7/2001 | Imanishi |
| 8,173,616 | B2 | 5/2012 | Amderson et al. |
| 2002/0115080 | A1 | 8/2002 | Shouv |
| 2002/0128381 | A1 | 9/2002 | Jakobsen |
| 2003/0092905 | A1 | 5/2003 | Kochkine |
| 2005/0085555 | A1 | 4/2005 | Murphy et al. |
| 2006/0134748 | A1 | 6/2006 | RajBhandary et al. |
| 2007/0203079 | A1 | 8/2007 | Caldwell |
| 2008/0096191 | A1 | 4/2008 | Kauppinen |
| 2009/0023594 | A1 | 1/2009 | Mouritzen |
| 2009/0286753 | A1 | 11/2009 | Kauppinen |
| 2010/0035968 | A1 | 2/2010 | Rasmussen |
| 2010/0261175 | A1 | 10/2010 | Rasmussen |
| 2010/0267018 | A1 | 10/2010 | Wengel |
| 2010/0279895 | A1 | 11/2010 | Wengel |
| 2010/0286044 | A1 | 11/2010 | Litman |
| 2011/0046209 | A1 | 2/2011 | Anderson |
| 2011/0076675 | A1 | 3/2011 | Jacobsen |
| 2012/0263648 | A1 | 10/2012 | Shapiro et al. |

FOREIGN PATENT DOCUMENTS

WO    WO2009134443    11/2009

OTHER PUBLICATIONS

Nekrasov et al. The mRNA-binding protein YB-1 (p50) Prevents Association of the Eukaryotic Initiation Factor EIF4G with mRNA and Inhibits Protein Synthesis at the Initiation Stage. The Journal of Biological Chemistry. 2003. 278(16), 13936-13943.*

Bochkov et al., Translational efficiency of EMCV IRES in bicistronic vectors is dependent upon IRES sequence and gene location, BioTechniques, vol. 41, pp. 283-284, 286, 288, and 290, 2006.

Buchan et al., Eukaryotic Stress Granules: The Ins and Out of Translation Mol., Cell vol. 36 No. 6, pp. 932, 2009.

Darby and Joho, "Differential Binding of Zinc Fingers from Xenopus TFIIIA and p43 to 5S RNA and the 5S RNA Gene," Mollecular and Cellular Biology, Jul. 1992, 12(7): 3155-3164.

De Gregorio et al., Translational activation of uncapped mRNAs by the central part of human eIF4G is 5' end-dependent, RNA, vol. 4, pp. 828-836, 1998.

Emara et al., Angiogenin-induced tRNA-derived Stress-induced RNAs Promote Stress-induced Stress Granule Assembly, J. Biol. Chem., vol. 285, pp. 10959-10968, 2010.

(Continued)

*Primary Examiner* — Christopher M Babic
*Assistant Examiner* — Kimberly A. Aron
(74) *Attorney, Agent, or Firm* — Fish & Richardson P.C.

(57) ABSTRACT

Provided herein are neuroprotective molecules containing a sequence of 25-35 contiguous nucleotides between nucleotide 1 and nucleotide 50 of a mature human tRNA and at least four contiguous guanosine-containing nucleotides, where the sequence of 25-35 contiguous nucleotides contains a D-loop stem structure, the at least four contiguous guanosine-containing nucleotides are located at the 5' end of the neuroprotective molecule, and the neuroprotective molecule contains at least one deoxyribonucleotide. Also provided are neuroprotective molecules containing a sequence of 25-35 contiguous between nucleotide 1 and nucleotide 50 of a mature human tRNA$^{Cys}$; and at least four contiguous guanosine-containing nucleotides, where the sequence of 25-35 contiguous nucleotides contains a D-loop stem structure and the at least four contiguous guanosine-containing nucleotides are located at the 5' end of the neuroprotective molecule.

22 Claims, 17 Drawing Sheets

Specification includes a Sequence Listing.

(56) References Cited

OTHER PUBLICATIONS

Freier et al., The ups and downs of nucleic acid duplex stability: structure—stability studies on chemically-modified DNA:RNA duplexes, Nucleic Acid Res. 25: No. 22, pp. 4429-4443, 1997.
International Preliminary Report on Patentability for PCT/US/2011/043400 dated Jan. 8, 2013, 7 pages.
International Search Report and Written Opinion of the International Searching Authority, dated Feb. 9, 2012, in International Application No. PCT/US2011/043400, 12 pgs.
Junghee Lee et al., Mitochondrial nuclear receptors and transcription factors: Who's minding the cell?, J Neurosci. Res., vol. 86, pp. 961-971, 2008.
Kaminski et al., Translation of encephalomyocarditis virus RNA: parameters influencing the selection of the internal initiation site, EMBO J., vol. 13, pp. 1673-1681, 1998.
Kedersha et al., Real-time and quantitative imaging of mammalian stress granules and processing bodies, Methods Enzymol. vol. 448, pp. 521-552, 2008 (Abstract).
Phizicky et al. Roles of tRNA Modifications in tRNA Turnover. In Grosjean H. Ed., DNA and RNA Modification Enzymes: Structure, Mechanism, Function and Evolution. 2009. pp. 564-576.
United States Office Action in U.S. Appl. No. 13/808,863, dated Apr. 28, 2016, 21 pages.
Yamasaki et al., Angiogenin cleaves tRNA and promotes stress-induced translational repression, J Cell Biol., vol. 185, No. 1, pp. 35-42, 2009.
Yoshihiko Suzuki et al., "A Case of Diabetic Amyotrophy Associated with 3243 Mitochondrial tRNA (leu: UUR) Mutation and Successful Therapy with Coenzyme QIO," Endocrine Journal, vol. 42(2), pp. 141-145 (1995).

* cited by examiner (SEQ ID NO: 37)

G-rich ODNs

- 5' Ala tiDNA
  GGGGGTGTAGCTCAGTGGTAGAGCGCGTGC (SEQ ID NO: 32)
- Tel4
  TTAGGGTTAGGGTTAGGGTTAGGG (SEQ ID NO: 33)
- AS1411
  GGTGGTGGTGGTTGTGGTGGTGGTGG (SEQ ID NO: 34)
- GT-oligo
  TGTTTGTTTGTTTGTTTGTTTGTTTGT (SEQ ID NO: 35)
- C-myc-oligo
  GGGGAGGGTGGGGAGGGTGGGG (SEQ ID NO: 36)

FIG. 23

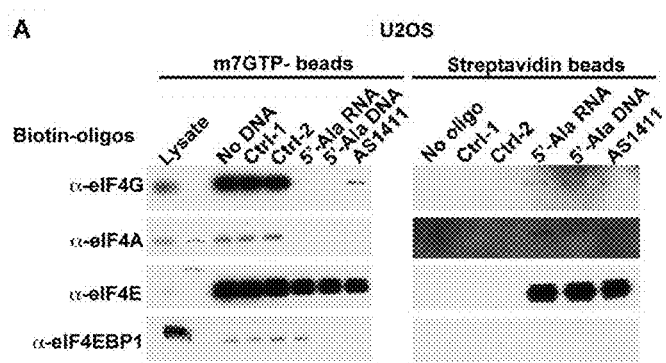
FIG. 26A
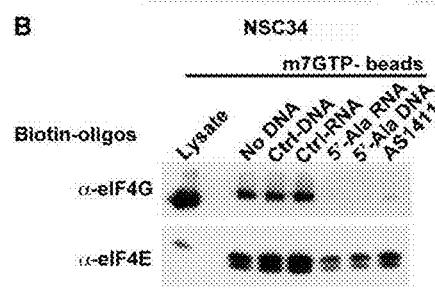
FIG. 26B
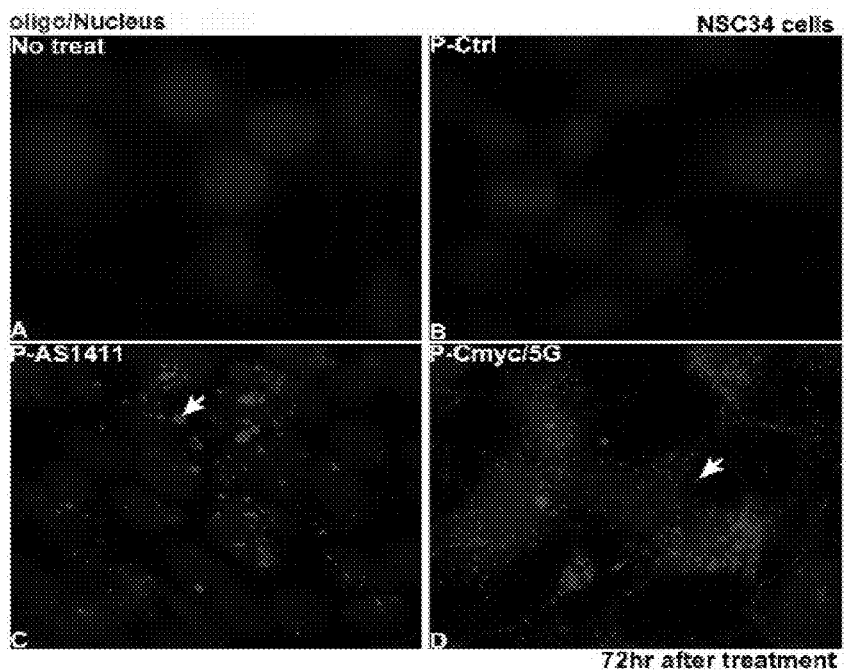
FIG. 27A
FIG. 27B
FIG. 27C
FIG. 27D

SEQUENCE LISTING

<160> NUMBER OF SEQ ID NOS: 796

<210> SEQ ID NO 1
<211> LENGTH: 30
<212> TYPE: RNA
<213> ORGANISM: Artificial Sequence
<220> FEATURE:
<223> OTHER INFORMATION: Description of Artificial Sequence: Synthetic
      Ctrl1 tiRNA oligonucleotide

<400> SEQUENCE: 1 ugaagggu̇uu uugugucuc uauuuccuuc                                          30

<210> SEQ ID NO 2
<211> LENGTH: 29
<212> TYPE: RNA
<213> ORGANISM: Artificial Sequence
<220> FEATURE:
<223> OTHER INFORMATION: Description of Artificial Sequence: Synthetic
      Ctrl2 tiRNA oligonucleotide

<400> SEQUENCE: 2
ugugagucac gugagggcag aaucugcuc                                           29

<210> SEQ ID NO 3
<211> LENGTH: 31
<212> TYPE: RNA
<213> ORGANISM: Artificial Sequence
<220> FEATURE:
<223> OTHER INFORMATION: Description of Artificial Sequence: Synthetic
      Ctrl3 tiRNA oligonucleotide

<400> SEQUENCE: 3
gcauucacuu ggauaguaaa uccaagcuga a                                        31

<210> SEQ ID NO 4
<211> LENGTH: 30
<212> TYPE: RNA
<213> ORGANISM: Artificial Sequence
<220> FEATURE:
<223> OTHER INFORMATION: Description of Artificial Sequence: Synthetic
      5' Ala tiRNA oligonucleotide

<400> SEQUENCE: 4
ggggguguag cucaguggua gagcgcgugc　　　　　　　　　　　　　　　　　　30

<210> SEQ ID NO 5
<211> LENGTH: 32
<212> TYPE: RNA
<213> ORGANISM: Artificial Sequence
<220> FEATURE:
<223> OTHER INFORMATION: Description of Artificial Sequence: Synthetic
      5' Val tiRNA oligonucleotide

<400> SEQUENCE: 5 guuccguag uguaguggu aucacguucg cc　　　　　　　　　　　　　　　　　32

<210> SEQ ID NO 6
<211> LENGTH: 30
<212> TYPE: RNA
<213> ORGANISM: Artificial Sequence
<220> FEATURE:
<223> OTHER INFORMATION: Description of Artificial Sequence: Synthetic
      5'-Gly-GCC tiRNA oligonucleotide

<400> SEQUENCE: 6
gcaugggugg uucaguggua gaauucucgc　　　　　　　　　　　　　　　　　　30

<210> SEQ ID NO 7
<211> LENGTH: 31
<212> TYPE: RNA
<213> ORGANISM: Artificial Sequence
<220> FEATURE:
<223> OTHER INFORMATION: Description of Artificial Sequence: Synthetic
      5'-GlyCCC tiRNA oligonucleotide

<400> SEQUENCE: 7
gcgccgcugg uguaguggua ucaugcaaga u　　　　　　　　　　　　　　　　31

<210> SEQ ID NO 8
<211> LENGTH: 30
<212> TYPE: RNA
<213> ORGANISM: Artificial Sequence
<220> FEATURE:
<223> OTHER INFORMATION: Description of Artificial Sequence: Synthetic
      5'-Pro tiRNA oligonucleotide

<400> SEQUENCE: 8
ggcucguugg ucuaggggua ugauucucgg　　　　　　　　　　　　　　　　　　30

<210> SEQ ID NO 9
<211> LENGTH: 29
<212> TYPE: RNA
<213> ORGANISM: Artificial Sequence
<220> FEATURE:
<223> OTHER INFORMATION: Description of Artificial Sequence: Synthetic
      5'-Gln tiRNA oligonucleotide

<400> SEQUENCE: 9
gguuccaugg uguaauggu agcacucug　　　　　　　　　　　　　　　　　　　29

<210> SEQ ID NO 10
<211> LENGTH: 30
<212> TYPE: RNA
<213> ORGANISM: Artificial Sequence
<220> FEATURE:
<223> OTHER INFORMATION: Description of Artificial Sequence: Synthetic
      5'-Cys tiRNA oligonucleotide

<400> SEQUENCE: 10
ggggguauag cucagugguagagcauuuga     30

<210> SEQ ID NO 11
<211> LENGTH: 31
<212> TYPE: RNA
<213> ORGANISM: Artificial Sequence
<220> FEATURE:
<223> OTHER INFORMATION: Description of Artificial Sequence: Synthetic
      5'-Met tiRNA oligonucleotide

<400> SEQUENCE: 11
gccucguuag cgcaguaggu agcgcgucag u     31

<210> SEQ ID NO 12
<211> LENGTH: 29
<212> TYPE: RNA
<213> ORGANISM: Artificial Sequence
<220> FEATURE:
<223> OTHER INFORMATION: Description of Artificial Sequence: Synthetic
      5'-Met-I tiRNA oligonucleotide

<400> SEQUENCE: 12
agcagagugg cgcagcggaa gcgugcugg     29

<210> SEQ ID NO 13
<211> LENGTH: 43
<212> TYPE: RNA
<213> ORGANISM: Artificial Sequence
<220> FEATURE:
<223> OTHER INFORMATION: Description of Artificial Sequence: Synthetic
      3'-Ala oligonucleotide

<400> SEQUENCE: 13
cuuagcaugc acgaggcccc ggguucaauc cccggcaccu cca     43

<210> SEQ ID NO 14
<211> LENGTH: 38
<212> TYPE: RNA
<213> ORGANISM: Artificial Sequence
<220> FEATURE:
<223> OTHER INFORMATION: Description of Artificial Sequence: Synthetic
      3'-Arg tiRNA oligonucleotide

<400> SEQUENCE: 14
ggaucagaag auugagggguu cggguccccuu cguggucg     38

<210> SEQ ID NO 15
<211> LENGTH: 38
<212> TYPE: RNA
<213> ORGANISM: Artificial Sequence
<220> FEATURE:
<223> OTHER INFORMATION: Description of Artificial Sequence: Synthetic
      3'-Gly tiRNA oligonucleotide

<400> SEQUENCE: 15
ccacgcggga ggcccggguu cgauucccgg ccaaugca     38

<210> SEQ ID NO 16
<211> LENGTH: 43
<212> TYPE: RNA
<213> ORGANISM: Artificial Sequence
<220> FEATURE:
<223> OTHER INFORMATION: Description of Artificial Sequence: Synthetic
      3'-Gln tiRNA oligonucleotide

<400> SEQUENCE: 16
gacucugaau ccagcgaucc gaguucaaau cucgguggaa ccu     43

<210> SEQ ID NO 17
<211> LENGTH: 42
<212> TYPE: RNA
<213> ORGANISM: Artificial Sequence
<220> FEATURE:
<223> OTHER INFORMATION: Description of Artificial Sequence: Synthetic
     3'-Pro tiRNA oligonucleotide

<400> SEQUENCE: 17
uuaggaugcg agagucccg gguucaaauc ccggacgagc cc                    42

<210> SEQ ID NO 18
<211> LENGTH: 30
<212> TYPE: RNA
<213> ORGANISM: Artificial Sequence
<220> FEATURE:
<223> OTHER INFORMATION: Description of Artificial Sequence: Synthetic
     U4G tiRNA oligonucleotide

<400> SEQUENCE: 18 uggggguguag cucagugguua gagcgcgugc                               30

<210> SEQ ID NO 19
<211> LENGTH: 29
<212> TYPE: RNA
<213> ORGANISM: Artificial Sequence
<220> FEATURE:
<223> OTHER INFORMATION: Description of Artificial Sequence: Synthetic
     4G tiRNA oligonucleotide

<400> SEQUENCE: 19
gggguguagc ucagugguag agcgcgugc                                  29

<210> SEQ ID NO 20
<211> LENGTH: 30
<212> TYPE: RNA
<213> ORGANISM: Artificial Sequence
<220> FEATURE:
<223> OTHER INFORMATION: Description of Artificial Sequence: Synthetic
     UU3G tiRNA oligonucleotide

<400> SEQUENCE: 20
uuggguguag cucaguggua gagcgcgugc                                 30

<210> SEQ ID NO 21
<211> LENGTH: 28
<212> TYPE: RNA
<213> ORGANISM: Artificial Sequence
<220> FEATURE:
<223> OTHER INFORMATION: Description of Artificial Sequence: Synthetic
     3G tiRNA oligonucleotide

<400> SEQUENCE: 21
ggguguagcu cagugguaga gcgcgugc                                   28

<210> SEQ ID NO 22
<211> LENGTH: 30
<212> TYPE: RNA
<213> ORGANISM: Artificial Sequence
<220> FEATURE:
<223> OTHER INFORMATION: Description of Artificial Sequence: Synthetic
     GG-UU tiRNA oligonucleotide

<400> SEQUENCE: 22
ggggguguag cucaguuuua gagcgcgugc                                 30

<210> SEQ ID NO 23
<211> LENGTH: 27
<212> TYPE: RNA
<213> ORGANISM: Artificial Sequence
<220> FEATURE:
<223> OTHER INFORMATION: Description of Artificial Sequence: Synthetic
      27-mer tiRNA oligonucleotide

<400> SEQUENCE: 23
ggggguguag cucaguggua gagcgcg                                            27

<210> SEQ ID NO 24
<211> LENGTH: 24
<212> TYPE: RNA
<213> ORGANISM: Artificial Sequence
<220> FEATURE:
<223> OTHER INFORMATION: Description of Artificial Sequence: Synthetic
      24-mer tiRNA oligonucleotide

<400> SEQUENCE: 24
ggggguguag cucaguggua gagc                                               24

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      21-mer tiRNA oligonucleotide

<400> SEQUENCE: 25
ggggguguag cucaguggua g                                                  21

<210> SEQ ID NO 26
<211> LENGTH: 31
<212> TYPE: RNA
<213> ORGANISM: Artificial Sequence
<220> FEATURE:
<223> OTHER INFORMATION: Description of Artificial Sequence: Synthetic
      Modified 5'-tiRNAMet oligonucleotide

<400> SEQUENCE: 26
gggggguuag cgcaguaggu agcgcgucag u                                       31

<210> SEQ ID NO 27
<211> LENGTH: 30
<212> TYPE: RNA
<213> ORGANISM: Artificial Sequence
<220> FEATURE:
<223> OTHER INFORMATION: Description of Artificial Sequence: Synthetic
      Ctrl1-biotinylated tiRNA oligonucleotide
<220> FEATURE:
<223> OTHER INFORMATION: 3' Biotin

<400> SEQUENCE: 27
ugaaggguuu uuugugucuc uauuuccuuc                                         30

<210> SEQ ID NO 28
<211> LENGTH: 29
<212> TYPE: RNA
<213> ORGANISM: Artificial Sequence
<220> FEATURE:
<223> OTHER INFORMATION: Description of Artificial Sequence: Synthetic
      Ctrl2-biotinylated tiRNA oligonucleotide
<220> FEATURE:
<223> OTHER INFORMATION: 3' Biotin

<400> SEQUENCE: 28
ugugagucac gugagggcag aaucugcuc                                    29

<210> SEQ ID NO 29
<211> LENGTH: 31
<212> TYPE: RNA
<213> ORGANISM: Artificial Sequence
<220> FEATURE:
<223> OTHER INFORMATION: Description of Artificial Sequence: Synthetic
      Ctrl3-biotinylated tiRNA oligonucleotide
<220> FEATURE:
<223> OTHER INFORMATION: 3' Biotin

<400> SEQUENCE: 29
gcauucacuu ggauaguaaa uccaagcuga a                                 31

<210> SEQ ID NO 30
<211> LENGTH: 30
<212> TYPE: RNA
<213> ORGANISM: Artificial Sequence
<220> FEATURE:
<223> OTHER INFORMATION: Description of Artificial Sequence: Synthetic
      5'-Ala-biotinylated tiRNA oligonucleotide
<220> FEATURE:
<223> OTHER INFORMATION: 3' Biotin

<400> SEQUENCE: 30 gggggguguag cucaguggua gagcgcgugc                                  30

<210> SEQ ID NO 31
<211> LENGTH: 43
<212> TYPE: RNA
<213> ORGANISM: Artificial Sequence
<220> FEATURE:
<223> OTHER INFORMATION: Description of Artificial Sequence: Synthetic
      3'-Ala-biotinylated tiRNA oligonucleotide
<220> FEATURE:
<223> OTHER INFORMATION: 3' Biotin

<400> SEQUENCE: 31
cuuagcaugc acgaggcccc ggguucaauc cccggcaccu cca                    43

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      5'-Ala tiDNA oligonucleotide

<400> SEQUENCE: 32
gggggtgtag ctcagtggta gagcgcgtgc                                   30

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      Tel4 oligonucleotide

<400> SEQUENCE: 33
ttagggttag ggttagggtt aggg                                         24

<210> SEQ ID NO 34
<211> LENGTH: 26
<212> TYPE: DNA
<213> ORGANISM: Artificial Sequence

```
<220> FEATURE:
<223> OTHER INFORMATION: Description of Artificial Sequence: Synthetic
      AS1411 oligonucleotide

<400> SEQUENCE: 34
ggtggtggtg gttgtggtgg tggtgg                                           26

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      GT-oligonucleotide

<400> SEQUENCE: 35
tgtttgtttg tttgtttgtt tgtttgt                                          27

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      C-myc oligonucleotide

<400> SEQUENCE: 36
ggggagggtg gggagggtgg gg                                               22

<210> SEQ ID NO 37
<211> LENGTH: 75
<212> TYPE: RNA
<213> ORGANISM: Artificial Sequence
<220> FEATURE:
<223> OTHER INFORMATION: Description of Artificial Sequence: Synthetic
      5'-tiRNAAla oligonucleotide

<400> SEQUENCE: 37 gggggugudag cucaguggua gagcgcgugc uuagcaugca cgaggccccg gguucaaucc     60
ccggcaccuc caccc                                                       75

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      Ctrl 25 oligonucleotide

<400> SEQUENCE: 38
aaaaaactcg agatggcgca cgctg                                            25

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
      CRO26 oligonucleotide

<400> SEQUENCE: 39
cctcctcctc cttctcctcc tcctcc                                           26

<210> SEQ ID NO 40
<211> LENGTH: 32
<212> TYPE: RNA
```

<213> ORGANISM: Homo sapiens

<400> SEQUENCE: 40 gggggguguag cucaguggua gagcgcgugc uu          32

<210> SEQ ID NO 41
<211> LENGTH: 31
<212> TYPE: RNA
<213> ORGANISM: Homo sapiens

<400> SEQUENCE: 41 gggggguguag cucaguggua gagcgcgugc u           31

<210> SEQ ID NO 42
<211> LENGTH: 32
<212> TYPE: RNA
<213> ORGANISM: Homo sapiens

<400> SEQUENCE: 42
ggggggugua gcucaguggu agagcgcgug cu           32

<210> SEQ ID NO 43
<211> LENGTH: 30
<212> TYPE: RNA
<213> ORGANISM: Homo sapiens

<400> SEQUENCE: 43 gggggguguag cucaguggua gagcgcgugc             30

<210> SEQ ID NO 44
<211> LENGTH: 31
<212> TYPE: RNA
<213> ORGANISM: Homo sapiens

<400> SEQUENCE: 44
ggggggugua gcucaguggu agagcgcgug c            31

<210> SEQ ID NO 45
<211> LENGTH: 32
<212> TYPE: RNA
<213> ORGANISM: Homo sapiens
<220> FEATURE:
<221> NAME/KEY: modified_base
<222> LOCATION: (7)..(7)
<223> OTHER INFORMATION: a, c, g or u

<400> SEQUENCE: 45 ggggggunuag cucaguggua gagcgcgugc uu          32

<210> SEQ ID NO 46
<211> LENGTH: 29
<212> TYPE: RNA
<213> ORGANISM: Homo sapiens

<400> SEQUENCE: 46 gggggguguag cucaguggua gagcgcgug              29

<210> SEQ ID NO 47
<211> LENGTH: 31
<212> TYPE: RNA
<213> ORGANISM: Homo sapiens

<400> SEQUENCE: 47
guguagcuca gugguagagc gcgugcuucg c            31

```
<210> SEQ ID NO 48
<211> LENGTH: 31
<212> TYPE: RNA
<213> ORGANISM: Homo sapiens
<220> FEATURE:
<221> NAME/KEY: modified_base
<222> LOCATION: (6)..(6)
<223> OTHER INFORMATION: a, c, g or u

<400> SEQUENCE: 48
ggggunuagc ucagugguag agcgcgugcu u                              31

<210> SEQ ID NO 49
<211> LENGTH: 32
<212> TYPE: RNA
<213> ORGANISM: Homo sapiens
<220> FEATURE:
<221> NAME/KEY: modified_base
<222> LOCATION: (8)..(8)
<223> OTHER INFORMATION: a, c, g or u

<400> SEQUENCE: 49 gggggunua gcucaguggu agagcgcgug cu                              32

<210> SEQ ID NO 50
<211> LENGTH: 31
<212> TYPE: RNA
<213> ORGANISM: Homo sapiens

<400> SEQUENCE: 50
gggguguagc ucagugguag agagcgugcu u                              31

<210> SEQ ID NO 51
<211> LENGTH: 30
<212> TYPE: RNA
<213> ORGANISM: Homo sapiens
<220> FEATURE:
<221> NAME/KEY: modified_base
<222> LOCATION: (7)..(7)
<223> OTHER INFORMATION: a, c, g or u

<400> SEQUENCE: 51 ggggunuag cucaguggua gagcgcgugc                                 30

<210> SEQ ID NO 52
<211> LENGTH: 31
<212> TYPE: RNA
<213> ORGANISM: Homo sapiens

<400> SEQUENCE: 52
ggggguguag cucaguggua gagagcgugc u                              31

<210> SEQ ID NO 53
<211> LENGTH: 31
<212> TYPE: RNA
<213> ORGANISM: Homo sapiens

<400> SEQUENCE: 53
ggggauguag cucaguggua gagcgcaugc u                              31

<210> SEQ ID NO 54
<211> LENGTH: 30
<212> TYPE: RNA
<213> ORGANISM: Homo sapiens
```

```
<400> SEQUENCE: 54
gggggauuag cucaaauggu agagcgcucg                              30

<210> SEQ ID NO 55
<211> LENGTH: 31
<212> TYPE: RNA
<213> ORGANISM: Homo sapiens
<220> FEATURE:
<221> NAME/KEY: modified_base
<222> LOCATION: (7)..(7)
<223> OTHER INFORMATION: a, c, g or u

<400> SEQUENCE: 55
ggggaunuag cucaguggua gagcgcaugc u                            31

<210> SEQ ID NO 56
<211> LENGTH: 27
<212> TYPE: RNA
<213> ORGANISM: Homo sapiens

<400> SEQUENCE: 56
ggcucuguug cgcaauggau agcgcau                                 27

<210> SEQ ID NO 57
<211> LENGTH: 28
<212> TYPE: RNA
<213> ORGANISM: Homo sapiens

<400> SEQUENCE: 57
uccucauuag uauaguggug aguauccc                                28

<210> SEQ ID NO 58
<211> LENGTH: 30
<212> TYPE: RNA
<213> ORGANISM: Homo sapiens

<400> SEQUENCE: 58
ggggguauag cucaguggua gagcauuuga                              30

<210> SEQ ID NO 59
<211> LENGTH: 29
<212> TYPE: RNA
<213> ORGANISM: Homo sapiens

<400> SEQUENCE: 59 gggggguauag cucaguggua gagcauuug                              29

<210> SEQ ID NO 60
<211> LENGTH: 28
<212> TYPE: RNA
<213> ORGANISM: Homo sapiens

<400> SEQUENCE: 60 gggguauag cucaguggua gagcauuu                                 28

<210> SEQ ID NO 61
<211> LENGTH: 27
<212> TYPE: RNA
<213> ORGANISM: Homo sapiens

<400> SEQUENCE: 61 gggguauag cucagugggu agagcau                                  27
```

```
<210> SEQ ID NO 62
<211> LENGTH: 30
<212> TYPE: RNA
<213> ORGANISM: Homo sapiens

<400> SEQUENCE: 62 gggggguguaa cucaguggua gagcauuuga                              30

<210> SEQ ID NO 63
<211> LENGTH: 29
<212> TYPE: RNA
<213> ORGANISM: Homo sapiens

<400> SEQUENCE: 63 gguccaugg uguaaugguu agcacucug                                 29

<210> SEQ ID NO 64
<211> LENGTH: 32
<212> TYPE: RNA
<213> ORGANISM: Homo sapiens

<400> SEQUENCE: 64
uuggugguuc aggguagaa uucucgccug cc                             32

<210> SEQ ID NO 65
<211> LENGTH: 31
<212> TYPE: RNA
<213> ORGANISM: Homo sapiens

<400> SEQUENCE: 65
uuggugguuc aggguagaa uucucgccug c                              31

<210> SEQ ID NO 66
<211> LENGTH: 30
<212> TYPE: RNA
<213> ORGANISM: Homo sapiens

<400> SEQUENCE: 66
uuggugguuc aggguagaa uucucgccug                                30

<210> SEQ ID NO 67
<211> LENGTH: 29
<212> TYPE: RNA
<213> ORGANISM: Homo sapiens

<400> SEQUENCE: 67
uggugguuca gugguagaau ucucgccug                                29

<210> SEQ ID NO 68
<211> LENGTH: 31
<212> TYPE: RNA
<213> ORGANISM: Homo sapiens

<400> SEQUENCE: 68
auuggugguu caggguaga auucucgccu g                              31

<210> SEQ ID NO 69
<211> LENGTH: 29
<212> TYPE: RNA
<213> ORGANISM: Homo sapiens

<400> SEQUENCE: 69
uuggugguuc aggguagaa uucucgccu                                 29
```

```
<210> SEQ ID NO 70
<211> LENGTH: 31
<212> TYPE: RNA
<213> ORGANISM: Homo sapiens

<400> SEQUENCE: 70
ggcauuggug guucaguggu agaauucucg c                              31

<210> SEQ ID NO 71
<211> LENGTH: 29
<212> TYPE: RNA
<213> ORGANISM: Homo sapiens

<400> SEQUENCE: 71
auuggugguu cagugguaga auucucgcc                                 29

<210> SEQ ID NO 72
<211> LENGTH: 31
<212> TYPE: RNA
<213> ORGANISM: Homo sapiens

<400> SEQUENCE: 72
agcauuggug guucaguggu agaauucucg c                              31

<210> SEQ ID NO 73
<211> LENGTH: 29
<212> TYPE: RNA
<213> ORGANISM: Homo sapiens

<400> SEQUENCE: 73
cauugguggu ucagugguag aauucucgc                                 29

<210> SEQ ID NO 74
<211> LENGTH: 32
<212> TYPE: RNA
<213> ORGANISM: Homo sapiens

<400> SEQUENCE: 74
gggaggcccg gguucguuuc ccggccaaug ca                             32

<210> SEQ ID NO 75
<211> LENGTH: 30
<212> TYPE: RNA
<213> ORGANISM: Homo sapiens

<400> SEQUENCE: 75
gcauuggugg uucaguggua gaauucucac                                30

<210> SEQ ID NO 76
<211> LENGTH: 32
<212> TYPE: RNA
<213> ORGANISM: Homo sapiens

<400> SEQUENCE: 76
cgggaggccc ggguucgguu cccggccaau gc                             32

<210> SEQ ID NO 77
<211> LENGTH: 27
<212> TYPE: RNA
<213> ORGANISM: Homo sapiens

<400> SEQUENCE: 77
uuggugguuc agugguagaa uucucgc                                   27
```

```
<210> SEQ ID NO 78
<211> LENGTH: 28
<212> TYPE: RNA
<213> ORGANISM: Homo sapiens

<400> SEQUENCE: 78
gacauuggug guucaguggu agaauucu                                          28

<210> SEQ ID NO 79
<211> LENGTH: 27
<212> TYPE: RNA
<213> ORGANISM: Homo sapiens

<400> SEQUENCE: 79
ugguucagug guagaauucu cgccucc                                           27

<210> SEQ ID NO 80
<211> LENGTH: 27
<212> TYPE: RNA
<213> ORGANISM: Homo sapiens

<400> SEQUENCE: 80
gcauugguau agugguauca ugcaaga                                           27

<210> SEQ ID NO 81
<211> LENGTH: 32
<212> TYPE: RNA
<213> ORGANISM: Homo sapiens

<400> SEQUENCE: 81
agcguuggug guauaguggu gagcauagcu gc                                     32

<210> SEQ ID NO 82
<211> LENGTH: 30
<212> TYPE: RNA
<213> ORGANISM: Homo sapiens

<400> SEQUENCE: 82
ggccgugauc guauaguggu uaguacucug                                        30

<210> SEQ ID NO 83
<211> LENGTH: 31
<212> TYPE: RNA
<213> ORGANISM: Homo sapiens

<400> SEQUENCE: 83
ucgccgugau cguauagugg uuaguacucu g                                      31

<210> SEQ ID NO 84
<211> LENGTH: 28
<212> TYPE: RNA
<213> ORGANISM: Homo sapiens

<400> SEQUENCE: 84
ggccgugauc guauaguggu uaguacuc                                          28

<210> SEQ ID NO 85
<211> LENGTH: 29
<212> TYPE: RNA
<213> ORGANISM: Homo sapiens

<400> SEQUENCE: 85
```
aggccgugau cguauagugg uuaguacuc                                29

<210> SEQ ID NO 86
<211> LENGTH: 27
<212> TYPE: RNA
<213> ORGANISM: Homo sapiens

<400> SEQUENCE: 86
ggccgugauc guauaguggu uaguacu                                  27

<210> SEQ ID NO 87
<211> LENGTH: 26
<212> TYPE: RNA
<213> ORGANISM: Homo sapiens

<400> SEQUENCE: 87
ggccgugauc guauaguggu uaguac                                   26

<210> SEQ ID NO 88
<211> LENGTH: 26
<212> TYPE: RNA
<213> ORGANISM: Homo sapiens

<400> SEQUENCE: 88
ggccgguuag cucaguuggu uagagc                                   26

<210> SEQ ID NO 89
<211> LENGTH: 26
<212> TYPE: RNA
<213> ORGANISM: Homo sapiens

<400> SEQUENCE: 89
ggccgguuag cucaguuggu cagagc                                   26

<210> SEQ ID NO 90
<211> LENGTH: 31
<212> TYPE: RNA
<213> ORGANISM: Homo sapiens

<400> SEQUENCE: 90
ggccgguuag cucaguuggu aagagcuugg u                             31

<210> SEQ ID NO 91
<211> LENGTH: 31
<212> TYPE: RNA
<213> ORGANISM: Homo sapiens

<400> SEQUENCE: 91
ggggcggccg guuagcucag uugguaagag c                             31

<210> SEQ ID NO 92
<211> LENGTH: 26
<212> TYPE: RNA
<213> ORGANISM: Homo sapiens

<400> SEQUENCE: 92
ggccgguuag cucaguuggu aagagc                                   26

<210> SEQ ID NO 93
<211> LENGTH: 26
<212> TYPE: RNA
<213> ORGANISM: Homo sapiens

<400> SEQUENCE: 93

```
gguagugugg ccgagcgguc uaaggc                                        26

<210> SEQ ID NO 94
<211> LENGTH: 31
<212> TYPE: RNA
<213> ORGANISM: Homo sapiens

<400> SEQUENCE: 94
guagucgugg ccgagugguu aaggcuaugg a                                  31

<210> SEQ ID NO 95
<211> LENGTH: 32
<212> TYPE: RNA
<213> ORGANISM: Homo sapiens

<400> SEQUENCE: 95
gacgaggugg ccgagugguu aaggcuaugg au                                 32

<210> SEQ ID NO 96
<211> LENGTH: 32
<212> TYPE: RNA
<213> ORGANISM: Homo sapiens

<400> SEQUENCE: 96
gacgaggugg ccgagugguu aaggcuaugg ac                                 32

<210> SEQ ID NO 97
<211> LENGTH: 31
<212> TYPE: RNA
<213> ORGANISM: Homo sapiens

<400> SEQUENCE: 97
gacgaggugg ccgagugguu aaggcuaugg a                                  31

<210> SEQ ID NO 98
<211> LENGTH: 30
<212> TYPE: RNA
<213> ORGANISM: Homo sapiens

<400> SEQUENCE: 98
gacgaggugg ccgagugguu aaggcuaugg                                    30

<210> SEQ ID NO 99
<211> LENGTH: 31
<212> TYPE: RNA
<213> ORGANISM: Homo sapiens

<400> SEQUENCE: 99
gacgaggugg ccgagugguu aaggcaaugg a                                  31

<210> SEQ ID NO 100
<211> LENGTH: 30
<212> TYPE: RNA
<213> ORGANISM: Homo sapiens

<400> SEQUENCE: 100
gacgaggugg ccgagugguu aaggcaaugg                                    30

<210> SEQ ID NO 101
<211> LENGTH: 26
<212> TYPE: RNA
<213> ORGANISM: Homo sapiens
```

```
<400> SEQUENCE: 101
uguagucgug gccgaguggu uaaggc                                          26

<210> SEQ ID NO 102
<211> LENGTH: 31
<212> TYPE: RNA
<213> ORGANISM: Homo sapiens

<400> SEQUENCE: 102
gccuggauag cucaguuggu agagcaucag a                                    31

<210> SEQ ID NO 103
<211> LENGTH: 29
<212> TYPE: RNA
<213> ORGANISM: Homo sapiens

<400> SEQUENCE: 103
gccuggauag cucaguuggu agagcauca                                       29

<210> SEQ ID NO 104
<211> LENGTH: 32
<212> TYPE: RNA
<213> ORGANISM: Homo sapiens

<400> SEQUENCE: 104
gccuggguag cucagucggu agagcaucag ac                                   32

<210> SEQ ID NO 105
<211> LENGTH: 31
<212> TYPE: RNA
<213> ORGANISM: Homo sapiens

<400> SEQUENCE: 105
gccuggguag cucagucggu agagcaucag a                                    31

<210> SEQ ID NO 106
<211> LENGTH: 30
<212> TYPE: RNA
<213> ORGANISM: Homo sapiens

<400> SEQUENCE: 106 gccugggguag cucagucggu agagcaucag                                     30

<210> SEQ ID NO 107
<211> LENGTH: 32
<212> TYPE: RNA
<213> ORGANISM: Homo sapiens

<400> SEQUENCE: 107
gcagaguggc gcagcggaag cgugcugggc cc                                   32

<210> SEQ ID NO 108
<211> LENGTH: 32
<212> TYPE: RNA
<213> ORGANISM: Homo sapiens

<400> SEQUENCE: 108
ggcagagugg cgcagcggaa gcgugcuggg cc                                   32

<210> SEQ ID NO 109
<211> LENGTH: 28
<212> TYPE: RNA
<213> ORGANISM: Homo sapiens
```

```
<400> SEQUENCE: 109
gcagaguggc gcagcggaag cgugcugg                                      28

<210> SEQ ID NO 110
<211> LENGTH: 29
<212> TYPE: RNA
<213> ORGANISM: Homo sapiens

<400> SEQUENCE: 110
ugcagagugg cgcagcggaa gcgugcugg                                     29

<210> SEQ ID NO 111
<211> LENGTH: 29
<212> TYPE: RNA
<213> ORGANISM: Homo sapiens

<400> SEQUENCE: 111
gcaguggcgc agcggaagcg ugcugggcc                                     29

<210> SEQ ID NO 112
<211> LENGTH: 27
<212> TYPE: RNA
<213> ORGANISM: Homo sapiens

<400> SEQUENCE: 112
gcagaguggc gcagcggaag cgugcug                                       27

<210> SEQ ID NO 113
<211> LENGTH: 32
<212> TYPE: RNA
<213> ORGANISM: Homo sapiens

<400> SEQUENCE: 113
cgcagagucg cgcagcggaa gcgugcuggg cc                                 32

<210> SEQ ID NO 114
<211> LENGTH: 31
<212> TYPE: RNA
<213> ORGANISM: Homo sapiens

<400> SEQUENCE: 114
cagagucgcg cagcggaagc gugcugggcc c                                  31

<210> SEQ ID NO 115
<211> LENGTH: 31
<212> TYPE: RNA
<213> ORGANISM: Homo sapiens

<400> SEQUENCE: 115
agaguugcgc agcggaagcg ugcugggccc a                                  31

<210> SEQ ID NO 116
<211> LENGTH: 27
<212> TYPE: RNA
<213> ORGANISM: Homo sapiens

<400> SEQUENCE: 116
gagauagcag aguggcgcag cggaagc                                       27

<210> SEQ ID NO 117
<211> LENGTH: 30
<212> TYPE: RNA
```

```
<213> ORGANISM: Homo sapiens

<400> SEQUENCE: 117
ggcucguugg ucuaggggua ugauucucgg                                    30

<210> SEQ ID NO 118
<211> LENGTH: 30
<212> TYPE: RNA
<213> ORGANISM: Homo sapiens

<400> SEQUENCE: 118
aggcucguug gucuaguggu augauucucg                                    30

<210> SEQ ID NO 119
<211> LENGTH: 30
<212> TYPE: RNA
<213> ORGANISM: Homo sapiens

<400> SEQUENCE: 119
gcccggauga uccucagugg ucugggugc                                     30

<210> SEQ ID NO 120
<211> LENGTH: 26
<212> TYPE: RNA
<213> ORGANISM: Homo sapiens

<400> SEQUENCE: 120
uguagucgug gccgaguggu uaaggc                                        26

<210> SEQ ID NO 121
<211> LENGTH: 32
<212> TYPE: RNA
<213> ORGANISM: Homo sapiens

<400> SEQUENCE: 121
gacgaggugg ccgagugguu aaggcuaugg ac                                 32

<210> SEQ ID NO 122
<211> LENGTH: 32
<212> TYPE: RNA
<213> ORGANISM: Homo sapiens

<400> SEQUENCE: 122
gacgaggugg ccgagugguu aaggcuaugg au                                 32

<210> SEQ ID NO 123
<211> LENGTH: 31
<212> TYPE: RNA
<213> ORGANISM: Homo sapiens

<400> SEQUENCE: 123
gacgaggugg ccgagugguu aaggcuaugg a                                  31

<210> SEQ ID NO 124
<211> LENGTH: 31
<212> TYPE: RNA
<213> ORGANISM: Homo sapiens

<400> SEQUENCE: 124
gacgaggugg ccgagugguu aaggcaaugg a                                  31

<210> SEQ ID NO 125
<211> LENGTH: 30
```

<212> TYPE: RNA
<213> ORGANISM: Homo sapiens

<400> SEQUENCE: 125
gacgaggugg ccgaguggtu aaggcuaugg                                30

<210> SEQ ID NO 126
<211> LENGTH: 30
<212> TYPE: RNA
<213> ORGANISM: Homo sapiens

<400> SEQUENCE: 126
gacgaggugg ccgagugguu aaggcaaugg                                30

<210> SEQ ID NO 127
<211> LENGTH: 31
<212> TYPE: RNA
<213> ORGANISM: Homo sapiens

<400> SEQUENCE: 127
gccuggauag cucaguuggu agagcaucag a                              31

<210> SEQ ID NO 128
<211> LENGTH: 29
<212> TYPE: RNA
<213> ORGANISM: Homo sapiens

<400> SEQUENCE: 128
gccuggauag cucaguuggu agagcauca                                 29

<210> SEQ ID NO 129
<211> LENGTH: 32
<212> TYPE: RNA
<213> ORGANISM: Homo sapiens

<400> SEQUENCE: 129
ggcagagugg cgcagcggaa gcgugcuggg cc                             32

<210> SEQ ID NO 130
<211> LENGTH: 32
<212> TYPE: RNA
<213> ORGANISM: Homo sapiens

<400> SEQUENCE: 130
gcagaguggc gcagcggaag cgugcugggc cc                             32

<210> SEQ ID NO 131
<211> LENGTH: 28
<212> TYPE: RNA
<213> ORGANISM: Homo sapiens

<400> SEQUENCE: 131
gcagaguggc gcagcggaag cgugcugg                                  28

<210> SEQ ID NO 132
<211> LENGTH: 28
<212> TYPE: RNA
<213> ORGANISM: Homo sapiens

<400> SEQUENCE: 132
cggaagcgug cugggcccau aacccaga                                  28

<210> SEQ ID NO 133

```
<211> LENGTH: 29
<212> TYPE: RNA
<213> ORGANISM: Homo sapiens

<400> SEQUENCE: 133
ugcagagugg cgcagcggaa gcgugcugg                                        29

<210> SEQ ID NO 134
<211> LENGTH: 29
<212> TYPE: RNA
<213> ORGANISM: Homo sapiens

<400> SEQUENCE: 134
gcaguggcgc agcggaagcg ugcugggcc                                        29

<210> SEQ ID NO 135
<211> LENGTH: 27
<212> TYPE: RNA
<213> ORGANISM: Homo sapiens

<400> SEQUENCE: 135
gcagaguggc gcagcggaag cgugcug                                          27

<210> SEQ ID NO 136
<211> LENGTH: 32
<212> TYPE: RNA
<213> ORGANISM: Homo sapiens

<400> SEQUENCE: 136
cgcagagucg cgcagcggaa gcgugcuggg cc                                    32

<210> SEQ ID NO 137
<211> LENGTH: 31
<212> TYPE: RNA
<213> ORGANISM: Homo sapiens

<400> SEQUENCE: 137
cagagucgcg cagcggaagc gugcugggcc c                                     31

<210> SEQ ID NO 138
<211> LENGTH: 31
<212> TYPE: RNA
<213> ORGANISM: Homo sapiens

<400> SEQUENCE: 138
agaguugcgc agcggaagcg ugcugggccc a                                     31

<210> SEQ ID NO 139
<211> LENGTH: 31
<212> TYPE: RNA
<213> ORGANISM: Homo sapiens

<400> SEQUENCE: 139
gccuggauag cucaguuggu agagcaucag a                                     31

<210> SEQ ID NO 140
<211> LENGTH: 29
<212> TYPE: RNA
<213> ORGANISM: Homo sapiens

<400> SEQUENCE: 140
gccuggauag cucaguuggu agagcauca                                        29
```

-continued

```
<210> SEQ ID NO 141
<211> LENGTH: 32
<212> TYPE: RNA
<213> ORGANISM: Homo sapiens

<400> SEQUENCE: 141
uuccguagug uagugguuau cacguucgcc uc                                     32

<210> SEQ ID NO 142
<211> LENGTH: 30
<212> TYPE: RNA
<213> ORGANISM: Homo sapiens

<400> SEQUENCE: 142
uuccguagug uagugguuau cacguucgcc                                        30

<210> SEQ ID NO 143
<211> LENGTH: 32
<212> TYPE: RNA
<213> ORGANISM: Homo sapiens

<400> SEQUENCE: 143
uccguagugu agugguuauc acguucgccu ga                                     32

<210> SEQ ID NO 144
<211> LENGTH: 31
<212> TYPE: RNA
<213> ORGANISM: Homo sapiens

<400> SEQUENCE: 144
uccguagugu agugguuauc acguucgccu g                                      31

<210> SEQ ID NO 145
<211> LENGTH: 32
<212> TYPE: RNA
<213> ORGANISM: Homo sapiens

<400> SEQUENCE: 145
uccguagugu agugguuauc acguucgccu ca                                     32

<210> SEQ ID NO 146
<211> LENGTH: 30
<212> TYPE: RNA
<213> ORGANISM: Homo sapiens

<400> SEQUENCE: 146
uccguagugu agugguuauc acguucgccu                                        30

<210> SEQ ID NO 147
<211> LENGTH: 32
<212> TYPE: RNA
<213> ORGANISM: Homo sapiens

<400> SEQUENCE: 147
guuuccguag uguagguguc aucacguucg cc                                     32

<210> SEQ ID NO 148
<211> LENGTH: 28
<212> TYPE: RNA
<213> ORGANISM: Homo sapiens

<400> SEQUENCE: 148
ccguagugua gugguuauca cguucgcc                                          28
```

```
<210> SEQ ID NO 149
<211> LENGTH: 30
<212> TYPE: RNA
<213> ORGANISM: Homo sapiens

<400> SEQUENCE: 149
guuuccguag uguagugguc aucacguucg                              30

<210> SEQ ID NO 150
<211> LENGTH: 27
<212> TYPE: RNA
<213> ORGANISM: Homo sapiens

<400> SEQUENCE: 150
cguaguguag ugguuaucac guucgcc                                 27

<210> SEQ ID NO 151
<211> LENGTH: 30
<212> TYPE: RNA
<213> ORGANISM: Homo sapiens

<400> SEQUENCE: 151
uccguagugu agugguuauc acuuucgccu                              30

<210> SEQ ID NO 152
<211> LENGTH: 31
<212> TYPE: RNA
<213> ORGANISM: Homo sapiens

<400> SEQUENCE: 152
uccguagugu acugguuauc acguucgccu g                            31

<210> SEQ ID NO 153
<211> LENGTH: 28
<212> TYPE: RNA
<213> ORGANISM: Homo sapiens

<400> SEQUENCE: 153
cguaguguag uggucaucac guucgccu                                28

<210> SEQ ID NO 154
<211> LENGTH: 32
<212> TYPE: RNA
<213> ORGANISM: Homo sapiens

<400> SEQUENCE: 154 gggggguguag cucaguggua gagcgcgugc uu                          32

<210> SEQ ID NO 155
<211> LENGTH: 31
<212> TYPE: RNA
<213> ORGANISM: Homo sapiens

<400> SEQUENCE: 155 gggggguguag cucaguggua gagcgcgugc u                           31

<210> SEQ ID NO 156
<211> LENGTH: 30
<212> TYPE: RNA
<213> ORGANISM: Homo sapiens

<400> SEQUENCE: 156 gggggguguag cucaguggua gagcgcgugc                             30
```

<210> SEQ ID NO 157
<211> LENGTH: 29
<212> TYPE: RNA
<213> ORGANISM: Homo sapiens

<400> SEQUENCE: 157 gggggguguag cucaguggua gagcgcgug                              29

<210> SEQ ID NO 158
<211> LENGTH: 32
<212> TYPE: RNA
<213> ORGANISM: Homo sapiens

<400> SEQUENCE: 158 gggggguguaa gcucaguggu agagcgcgug cu                          32

<210> SEQ ID NO 159
<211> LENGTH: 32
<212> TYPE: RNA
<213> ORGANISM: Homo sapiens

<400> SEQUENCE: 159
uuggugguuc agugguagaa uucucgccug cc                           32

<210> SEQ ID NO 160
<211> LENGTH: 31
<212> TYPE: RNA
<213> ORGANISM: Homo sapiens

<400> SEQUENCE: 160
uuggugguuc agugguagaa uucucgccug c                            31

<210> SEQ ID NO 161
<211> LENGTH: 30
<212> TYPE: RNA
<213> ORGANISM: Homo sapiens

<400> SEQUENCE: 161
uuggugguuc agugguagaa uucucgccug                              30

<210> SEQ ID NO 162
<211> LENGTH: 29
<212> TYPE: RNA
<213> ORGANISM: Homo sapiens

<400> SEQUENCE: 162
uuggugguuc agugguagaa uucucgccu                               29

<210> SEQ ID NO 163
<211> LENGTH: 29
<212> TYPE: RNA
<213> ORGANISM: Homo sapiens

<400> SEQUENCE: 163
uggugguuca gugguagaau ucucgccug                               29

<210> SEQ ID NO 164
<211> LENGTH: 31
<212> TYPE: RNA
<213> ORGANISM: Homo sapiens

<400> SEQUENCE: 164

-continued auuggugguu cagugguaga auucucgccu g                                    31

<210> SEQ ID NO 165
<211> LENGTH: 29
<212> TYPE: RNA
<213> ORGANISM: Homo sapiens

<400> SEQUENCE: 165
auuggugguu cagugguaga auucucgcc                                       29

<210> SEQ ID NO 166
<211> LENGTH: 31
<212> TYPE: RNA
<213> ORGANISM: Homo sapiens

<400> SEQUENCE: 166
ggcauuggug guucaguggu agaauucucg c                                    31

<210> SEQ ID NO 167
<211> LENGTH: 27
<212> TYPE: RNA
<213> ORGANISM: Homo sapiens

<400> SEQUENCE: 167
uuggugguuc agugguagaa uucucgc                                         27

<210> SEQ ID NO 168
<211> LENGTH: 27
<212> TYPE: RNA
<213> ORGANISM: Homo sapiens

<400> SEQUENCE: 168
ugguucagug guagaauucu cgccucc                                         27

<210> SEQ ID NO 169
<211> LENGTH: 29
<212> TYPE: RNA
<213> ORGANISM: Homo sapiens

<400> SEQUENCE: 169
cauuggaggu ucagugguag aauucucgc                                       29

<210> SEQ ID NO 170
<211> LENGTH: 31
<212> TYPE: RNA
<213> ORGANISM: Homo sapiens

<400> SEQUENCE: 170
agcauuggug guucaguggu agaauucucg c                                    31

<210> SEQ ID NO 171
<211> LENGTH: 30
<212> TYPE: RNA
<213> ORGANISM: Homo sapiens

<400> SEQUENCE: 171
gcauuggugg uucaguggua gaauucucac                                      30

<210> SEQ ID NO 172
<211> LENGTH: 40
<212> TYPE: DNA
<213> ORGANISM: Homo sapiens

<400> SEQUENCE: 172
gtctctgtgg cgcaatcggt tagcgcgttc ggctgttaac                     40

<210> SEQ ID NO 173
<211> LENGTH: 40
<212> TYPE: DNA
<213> ORGANISM: Homo sapiens

<400> SEQUENCE: 173
gccgaaatag ctcagttggg agagcgttag actgaagatc                     40

<210> SEQ ID NO 174
<211> LENGTH: 21
<212> TYPE: DNA
<213> ORGANISM: Homo sapiens

<400> SEQUENCE: 174
gggagggtgg ggagggtggg g                                         21

<210> SEQ ID NO 175
<211> LENGTH: 32
<212> TYPE: DNA
<213> ORGANISM: Artificial Sequence
<220> FEATURE:
<223> OTHER INFORMATION: Description of Artificial Sequence: Synthetic
      ME8 probe

<400> SEQUENCE: 175
ctttatgttt ttggcgtctt ccatctcgag gc                             32

<210> SEQ ID NO 176
<211> LENGTH: 73
<212> TYPE: DNA
<213> ORGANISM: Homo sapiens

<400> SEQUENCE: 176
ggggaattag ctcaagcggt agagcgctcc cttagcatgc gagaggtagc gggatcgacg     60
cccccattct cta                                                  73

<210> SEQ ID NO 177
<211> LENGTH: 73
<212> TYPE: DNA
<213> ORGANISM: Homo sapiens

<400> SEQUENCE: 177
gggggattag ctcaagcggt agggtgcctg cttagcatgc aagaggtagc aggatcgacg     60
cctgcattct cca                                                  73

<210> SEQ ID NO 178
<211> LENGTH: 71
<212> TYPE: DNA
<213> ORGANISM: Homo sapiens

<400> SEQUENCE: 178
gggggtgtag atcagtggta gggcgcacgc ttagcatgca tgaggccctg ggtcaatccc     60
cagcacctcc a                                                    71

<210> SEQ ID NO 179
<211> LENGTH: 73
<212> TYPE: DNA
<213> ORGANISM: Homo sapiens

<400> SEQUENCE: 179

```
gggggattag ctcaagcggt agagcgcctg cttagcatgc aagaggtagc aggatcgatg    60
cctgcattct cca                                                      73

<210> SEQ ID NO 180
<211> LENGTH: 73
<212> TYPE: DNA
<213> ORGANISM: Homo sapiens

<400> SEQUENCE: 180
ggggaattgg ctcaagcggt agagcgcttg cttagcatgc aagaggtagc aggatcgacg    60
cctgcactct cca                                                      73

<210> SEQ ID NO 181
<211> LENGTH: 73
<212> TYPE: DNA
<213> ORGANISM: Homo sapiens

<400> SEQUENCE: 181
ggggaattgg ctcaagcggt agagcgcttg cttagcatgc aagaggtagc aggatcgacg    60
cctgcactct cca                                                      73

<210> SEQ ID NO 182
<211> LENGTH: 73
<212> TYPE: DNA
<213> ORGANISM: Homo sapiens

<400> SEQUENCE: 182
ggggaattag cgcaagtggt agagtgcttg cttagcatgc aagaggtagt gggatcgatg    60
cccacattct cca                                                      73

<210> SEQ ID NO 183
<211> LENGTH: 73
<212> TYPE: DNA
<213> ORGANISM: Homo sapiens

<400> SEQUENCE: 183
ggggaattag cccaagtggt agagcgcttg cttagcatgc aagaggtagt gggatcgatg    60
cccacattct cca                                                      73

<210> SEQ ID NO 184
<211> LENGTH: 73
<212> TYPE: DNA
<213> ORGANISM: Homo sapiens

<400> SEQUENCE: 184
ggggaattag ctcaagtggt agagcgctcg cttagcatgc gagaggtagt gggatcgatg    60
cccgcattct cca                                                      73

<210> SEQ ID NO 185
<211> LENGTH: 73
<212> TYPE: DNA
<213> ORGANISM: Homo sapiens

<400> SEQUENCE: 185
ggggaattag ctcaagtggt agagcgcttg cttagcatgc aagaggtagt gggatcaatg    60
cccacattct cca                                                      73

<210> SEQ ID NO 186
```

```
<211> LENGTH: 73
<212> TYPE: DNA
<213> ORGANISM: Homo sapiens

<400> SEQUENCE: 186 gggggaattag ctcaagcggt agagcgcttg cttagcatgc aagaggtagt gggatcgatg    60
cccacattct cca                                                       73

<210> SEQ ID NO 187
<211> LENGTH: 73
<212> TYPE: DNA
<213> ORGANISM: Homo sapiens

<400> SEQUENCE: 187 gggggaattag ctcaagcggt agagcgcttg cttagcatgc aagaggtagt gggatcgatg    60
cccacattct cca                                                       73

<210> SEQ ID NO 188
<211> LENGTH: 73
<212> TYPE: DNA
<213> ORGANISM: Homo sapiens

<400> SEQUENCE: 188 gggggaattag ctcaagtggt agagcgcttg cttagcatgc aagaggtagt gggatcgatg    60
cccacattct cca                                                       73

<210> SEQ ID NO 189
<211> LENGTH: 73
<212> TYPE: DNA
<213> ORGANISM: Homo sapiens

<400> SEQUENCE: 189 gggggaattag ctcaagtggt agagcgcttg cttagcatgc aagaggtagt gggatcgatg    60
cccacattct cca                                                       73

<210> SEQ ID NO 190
<211> LENGTH: 73
<212> TYPE: DNA
<213> ORGANISM: Homo sapiens

<400> SEQUENCE: 190 gggggaattag ctcaagtggt agagcgcttg cttagcatgc aagaggtagt gggatcgatg    60
cccacattct cca                                                       73

<210> SEQ ID NO 191
<211> LENGTH: 73
<212> TYPE: DNA
<213> ORGANISM: Homo sapiens

<400> SEQUENCE: 191 gggggaattag ctcaaatggt agagcgctcg cttagcatgc gagaggtagc gggatcgatg    60
cccgcattct cca                                                       73

<210> SEQ ID NO 192
<211> LENGTH: 73
<212> TYPE: DNA
<213> ORGANISM: Homo sapiens

<400> SEQUENCE: 192 gggggaattag ctcaagtggt agagcgcttg cttagcacgc aagaggtagt gggatcgatg    60
```

```
cccacattct cca                                                          73

<210> SEQ ID NO 193
<211> LENGTH: 73
<212> TYPE: DNA
<213> ORGANISM: Homo sapiens

<400> SEQUENCE: 193
ggggaattag ctcaggcggt agagcgctcg cttagcatgc gagaggtagc gggatcgacg       60
cccgcattct cca                                                          73

<210> SEQ ID NO 194
<211> LENGTH: 73
<212> TYPE: DNA
<213> ORGANISM: Homo sapiens

<400> SEQUENCE: 194
ggggaattag ctcaggcggt agagcgctcg cttagcatgc gagaggtagc gggatcgacg       60
cccgcattct cca                                                          73

<210> SEQ ID NO 195
<211> LENGTH: 73
<212> TYPE: DNA
<213> ORGANISM: Homo sapiens

<400> SEQUENCE: 195
gggggattag ctcaaatggt agagcgctcg cttagcatgc gagaggtagc gggatcgatg       60
cccgcatcct cca                                                          73

<210> SEQ ID NO 196
<211> LENGTH: 73
<212> TYPE: DNA
<213> ORGANISM: Homo sapiens

<400> SEQUENCE: 196
gggggattag ctcaaatggt agagcgctcg cttagcatgc gagaggtagc gggatcgatg       60
cccgcatcct cca                                                          73

<210> SEQ ID NO 197
<211> LENGTH: 72
<212> TYPE: DNA
<213> ORGANISM: Homo sapiens

<400> SEQUENCE: 197
gggggtgtag ctcagtggta gagcgcgtgc ttagcatgca cgaggccccg ggttcaatcc       60
ctggcacctc ca                                                           72

<210> SEQ ID NO 198
<211> LENGTH: 72
<212> TYPE: DNA
<213> ORGANISM: Homo sapiens

<400> SEQUENCE: 198
gggggtatag ctcagcggta gagcgcgtgc ttagcatgca cgaggtcctg ggttcaatcc       60
ccaatacctc ca                                                           72

<210> SEQ ID NO 199
<211> LENGTH: 72
<212> TYPE: DNA
```

<213> ORGANISM: Homo sapiens

<400> SEQUENCE: 199
gggggtgtag ctcagtggta gagcgcgtgc ttagcatgca cgaggccctg ggttcaatcc    60
ccagcacctc ca    72

<210> SEQ ID NO 200
<211> LENGTH: 72
<212> TYPE: DNA
<213> ORGANISM: Homo sapiens

<400> SEQUENCE: 200
ggggatgtag ctcagtggta gagcgcatgc ttagcatgca tgaggtcccg ggttcgatcc    60
ccagcatctc ca    72

<210> SEQ ID NO 201
<211> LENGTH: 72
<212> TYPE: DNA
<213> ORGANISM: Homo sapiens

<400> SEQUENCE: 201
gggggtgtag ctcagtggta gagcgcgtgc ttagcatgta cgaggtcccg ggttcaatcc    60
ccggcacctc ca    72

<210> SEQ ID NO 202
<211> LENGTH: 72
<212> TYPE: DNA
<213> ORGANISM: Homo sapiens

<400> SEQUENCE: 202
gggggtgtag ctcagtggta gagcgcgtgc ttagcatgca cgaggccccg ggttcaatcc    60
ccggcacctc ca    72

<210> SEQ ID NO 203
<211> LENGTH: 72
<212> TYPE: DNA
<213> ORGANISM: Homo sapiens

<400> SEQUENCE: 203
gggggtgtag ctcagtggta gagcgcgtgc ttagcatgca cgaggccccg ggttcaatcc    60
ccggcacctc ca    72

<210> SEQ ID NO 204
<211> LENGTH: 72
<212> TYPE: DNA
<213> ORGANISM: Homo sapiens

<400> SEQUENCE: 204
gggggtatag ctcagtggta gagcgcgtgc ttagcatgca cgaggtcctg ggttcgatcc    60
ccagtacctc ca    72

<210> SEQ ID NO 205
<211> LENGTH: 72
<212> TYPE: DNA
<213> ORGANISM: Homo sapiens

<400> SEQUENCE: 205
gggggtgtag atcagtggta gagcgcatgc ttcgcatgta cgaggtccct ggttcaatcc    60
ctggtacctc ca    72

```
<210> SEQ ID NO 206
<211> LENGTH: 72
<212> TYPE: DNA
<213> ORGANISM: Homo sapiens

<400> SEQUENCE: 206
gggggtgtag ctcagtggta gagcgcgtgc ttcgcatgta cgaggccccg ggttcgaccc    60
ccggctcctc ca                                                       72

<210> SEQ ID NO 207
<211> LENGTH: 72
<212> TYPE: DNA
<213> ORGANISM: Homo sapiens

<400> SEQUENCE: 207
ggggatgtag ctcagtggta gagcgcgcgc ttcgcatgtg tgaggtcccg ggttcaatcc    60
ccggcatctc ca                                                       72

<210> SEQ ID NO 208
<211> LENGTH: 72
<212> TYPE: DNA
<213> ORGANISM: Homo sapiens

<400> SEQUENCE: 208
ggggatgtag ctcagtggta gagcgcatgc ttcgcatgta tgaggccccg ggttcgatcc    60
ccggcatctc ca                                                       72

<210> SEQ ID NO 209
<211> LENGTH: 72
<212> TYPE: DNA
<213> ORGANISM: Homo sapiens

<400> SEQUENCE: 209
ggggatgtag ctcagtggta gagcgcatgc ttcgcatgta tgaggtcccg ggttcgatcc    60
ccggcatctc ca                                                       72

<210> SEQ ID NO 210
<211> LENGTH: 72
<212> TYPE: DNA
<213> ORGANISM: Homo sapiens

<400> SEQUENCE: 210
gggggtgtag ctcagtggta gagcggatgc tttgcatgta tgagactttg ggttggatcc    60
ccagcacctc ca                                                       72

<210> SEQ ID NO 211
<211> LENGTH: 71
<212> TYPE: DNA
<213> ORGANISM: Homo sapiens

<400> SEQUENCE: 211
gggggtgtag ctcagtggta gagcgcatgc tttgcatgta tgaggcctcg gttcgatccc    60
cgacacctcc a                                                        71

<210> SEQ ID NO 212
<211> LENGTH: 72
<212> TYPE: DNA
<213> ORGANISM: Homo sapiens
```

-continued

<400> SEQUENCE: 212
gggggtgtag ctcagtggta gagcacatgc tttgcatgtg tgaggcccg ggttcgatcc        60 ccggcacctc ca        72

<210> SEQ ID NO 213
<211> LENGTH: 72
<212> TYPE: DNA
<213> ORGANISM: Homo sapiens

<400> SEQUENCE: 213
gggggtgtag ctcagtggta gagcgcatgc tttgcatgta tgaggcctcg ggttcgatcc        60
ccgacacctc ca        72

<210> SEQ ID NO 214
<211> LENGTH: 72
<212> TYPE: DNA
<213> ORGANISM: Homo sapiens

<400> SEQUENCE: 214
ggggatgtag ctcagtggta gagcgcatgc tttgcacgta tgaggcccg ggttcaatcc        60 ccggcatctc ca        72

<210> SEQ ID NO 215
<211> LENGTH: 72
<212> TYPE: DNA
<213> ORGANISM: Homo sapiens

<400> SEQUENCE: 215
ggggatgtag ctcagtggta gagcgcatgc tttgcatgta tgaggcccg ggttcgatcc        60 ccggcatctc ca        72

<210> SEQ ID NO 216
<211> LENGTH: 72
<212> TYPE: DNA
<213> ORGANISM: Homo sapiens

<400> SEQUENCE: 216
ggggatgtag ctcagtggta gagcgcatgc tttgcatgta tgaggcccg ggttcgatcc        60 ccggcatctc ca        72

<210> SEQ ID NO 217
<211> LENGTH: 72
<212> TYPE: DNA
<213> ORGANISM: Homo sapiens

<400> SEQUENCE: 217
ggggatgtag ctcagtggta gagcgcatgc tttgcatgta tgaggtcccg ggttcgatcc        60
ccggcatctc ca        72

<210> SEQ ID NO 218
<211> LENGTH: 72
<212> TYPE: DNA
<213> ORGANISM: Homo sapiens

<400> SEQUENCE: 218
gggggtgtag ctcagtggta gagcgcatgc tttgcatgta tgaggtcccg ggttcgatcc        60
ccggcacctc ca        72

-continued

```
<210> SEQ ID NO 219
<211> LENGTH: 73
<212> TYPE: DNA
<213> ORGANISM: Homo sapiens

<400> SEQUENCE: 219
gggccagtgg cgcaatggat aacgcgtctg actacggatc agaagattct aggttcgact    60
cctggctggc tcg                                                       73

<210> SEQ ID NO 220
<211> LENGTH: 73
<212> TYPE: DNA
<213> ORGANISM: Homo sapiens

<400> SEQUENCE: 220
gggccagtgg cgcaatggat aacgcgtctg actacggatc agaagattct aggttcgact    60
cctggctggc tcg                                                       73

<210> SEQ ID NO 221
<211> LENGTH: 73
<212> TYPE: DNA
<213> ORGANISM: Homo sapiens

<400> SEQUENCE: 221
gggccagtgg cgcaatggat aacgcgtctg actacggatc agaagattct aggttcgact    60
cctggctggc tcg                                                       73

<210> SEQ ID NO 222
<211> LENGTH: 73
<212> TYPE: DNA
<213> ORGANISM: Homo sapiens

<400> SEQUENCE: 222
gggccagtgg cgcaatggat aacgcgtctg actacggatc agaagattct aggttcgact    60
cctggctggc tcg                                                       73

<210> SEQ ID NO 223
<211> LENGTH: 73
<212> TYPE: DNA
<213> ORGANISM: Homo sapiens

<400> SEQUENCE: 223
gggccagtgg cgcaatggat aacgcgtctg actacggatc agaagattcc aggttcgact    60
cctggctggc tcg                                                       73

<210> SEQ ID NO 224
<211> LENGTH: 73
<212> TYPE: DNA
<213> ORGANISM: Homo sapiens

<400> SEQUENCE: 224
gggccagtgg cgcaatggat aacgcgtctg actacggatc agaagattcc aggttcgact    60
cctggctggc tcg                                                       73

<210> SEQ ID NO 225
<211> LENGTH: 73
<212> TYPE: DNA
<213> ORGANISM: Homo sapiens

<400> SEQUENCE: 225
```

```
gggccagtgg cgcaatggat aacgcgtctg actacggatc agaagattcc aggttcgact    60
cctggctggc tcg                                                      73

<210> SEQ ID NO 226
<211> LENGTH: 73
<212> TYPE: DNA
<213> ORGANISM: Homo sapiens

<400> SEQUENCE: 226
gacccagtgg cctaatggat aaggcatcag cctccggagc tggggattgt gggttcgagt    60
cccatctggg tcg                                                      73

<210> SEQ ID NO 227
<211> LENGTH: 73
<212> TYPE: DNA
<213> ORGANISM: Homo sapiens

<400> SEQUENCE: 227
gacccagtgg cctaatggat aaggcatcag cctccggagc tggggattgt gggttcgagt    60
cccatctggg tcg                                                      73

<210> SEQ ID NO 228
<211> LENGTH: 73
<212> TYPE: DNA
<213> ORGANISM: Homo sapiens

<400> SEQUENCE: 228
ggccgcgtgg cctaatggat aaggcgtctg attccggatc agaagattga gggttcgagt    60
cccttcgtgg tcg                                                      73

<210> SEQ ID NO 229
<211> LENGTH: 73
<212> TYPE: DNA
<213> ORGANISM: Homo sapiens

<400> SEQUENCE: 229
ggccgcgtgg cctaatggat aaggcgtctg attccggatc agaagattga gggttcgagt    60
cccttcgtgg tcg                                                      73

<210> SEQ ID NO 230
<211> LENGTH: 73
<212> TYPE: DNA
<213> ORGANISM: Homo sapiens

<400> SEQUENCE: 230
ggccgcgtgg cctaatggat aaggcgtctg attccggatc agaagattga gggttcgagt    60
cccttcgtgg tcg                                                      73

<210> SEQ ID NO 231
<211> LENGTH: 73
<212> TYPE: DNA
<213> ORGANISM: Homo sapiens

<400> SEQUENCE: 231
gccccagtgg cctgatggat aaggtactgg cctcctaagc cagggattgt gggttcgagt    60
tccacctggg gta                                                      73

<210> SEQ ID NO 232
<211> LENGTH: 73
```

-continued

<212> TYPE: DNA
<213> ORGANISM: Homo sapiens

<400> SEQUENCE: 232
gccccagtgg cctaatggat aaggcattgg cctcctaagc cagggattgt gggttcgagt    60
cccatctggg gtg                                                      73

<210> SEQ ID NO 233
<211> LENGTH: 73
<212> TYPE: DNA
<213> ORGANISM: Homo sapiens

<400> SEQUENCE: 233
gccccggtgg cctaatggat aaggcattgg cctcctaagc cagggattgt gggttcgagt    60
cccacccggg gta                                                      73

<210> SEQ ID NO 234
<211> LENGTH: 73
<212> TYPE: DNA
<213> ORGANISM: Homo sapiens

<400> SEQUENCE: 234
gccccagtgg cctaatggat aaggcactgg cctcctaagc cagggattgt gggttcgagt    60
cccacctggg gtg                                                      73

<210> SEQ ID NO 235
<211> LENGTH: 73
<212> TYPE: DNA
<213> ORGANISM: Homo sapiens

<400> SEQUENCE: 235
gccccagtgg cctaatggat aaggcactgg cctcctaagc cagggattgt gggttcgagt    60
cccacctggg gta                                                      73

<210> SEQ ID NO 236
<211> LENGTH: 73
<212> TYPE: DNA
<213> ORGANISM: Homo sapiens

<400> SEQUENCE: 236
ggccgtgtgg cctaatggat aaggcgtctg acttcggatc aaaagattgc aggtttgagt    60
tctgccacgg tcg                                                      73

<210> SEQ ID NO 237
<211> LENGTH: 73
<212> TYPE: DNA
<213> ORGANISM: Homo sapiens

<400> SEQUENCE: 237
gaccacgtgg cctaatggat aaggcgtctg acttcggatc agaagattga gggttcgaat    60
cccttcgtgg ttg                                                      73

<210> SEQ ID NO 238
<211> LENGTH: 73
<212> TYPE: DNA
<213> ORGANISM: Homo sapiens

<400> SEQUENCE: 238
gaccacgtgg cctaatggat aaggcgtctg acttcggatc agaagattga gggttcgaat    60

```
cccttcgtgg tta                                                        73

<210> SEQ ID NO 239
<211> LENGTH: 73
<212> TYPE: DNA
<213> ORGANISM: Homo sapiens

<400> SEQUENCE: 239
gaccgcgtgg cctaatggat aaggcgtctg acttcggatc agaagattga gggttcgagt    60
cccttcgtgg tcg                                                        73

<210> SEQ ID NO 240
<211> LENGTH: 73
<212> TYPE: DNA
<213> ORGANISM: Homo sapiens

<400> SEQUENCE: 240
gaccacgtgg cctaatggat aaggcgtctg acttcggatc agaagattga gggttcgaat    60
ccctccgtgg tta                                                        73

<210> SEQ ID NO 241
<211> LENGTH: 73
<212> TYPE: DNA
<213> ORGANISM: Homo sapiens

<400> SEQUENCE: 241
ggccgcgtgg cctaatggat aaggcgtctg acttcggatc agaagattgc aggttcgagt    60
cctgccgcgg tcg                                                        73

<210> SEQ ID NO 242
<211> LENGTH: 74
<212> TYPE: DNA
<213> ORGANISM: Homo sapiens

<400> SEQUENCE: 242
gtctctgtgg cgcaatggac gagcgcgctg gacttctaat ccagaggttc cgggttcgag    60
tcccggcaga gatg                                                       74

<210> SEQ ID NO 243
<211> LENGTH: 91
<212> TYPE: DNA
<213> ORGANISM: Homo sapiens

<400> SEQUENCE: 243
ggctctgtgg cgcaatggat agcgcattgg acttctagct gagcctagtg tggtcattca    60
aaggttgtgg gttcgagtcc caccagagtc g                                    91

<210> SEQ ID NO 244
<211> LENGTH: 87
<212> TYPE: DNA
<213> ORGANISM: Homo sapiens

<400> SEQUENCE: 244
ggctctgtgg cgcaatggat agcgcattgg acttctagcc taaatcaaga gattcaaagg    60
ttgcgggttc gagtccctcc agagtcg                                         87

<210> SEQ ID NO 245
<211> LENGTH: 86
<212> TYPE: DNA
<213> ORGANISM: Homo sapiens
```

```
<400> SEQUENCE: 245
ggctctgtgg cgcaatggat agcgcattgg acttctagat agttagagaa attcaaaggt    60
tgtgggttcg agtcccacca gagtcg                                         86

<210> SEQ ID NO 246
<211> LENGTH: 88
<212> TYPE: DNA
<213> ORGANISM: Homo sapiens

<400> SEQUENCE: 246
ggctctgtgg cgcaatggat agcgcattgg acttctagtg acgaatagag caattcaaag    60
gttgtgggtt cgaatcccac cagagtcg                                       88

<210> SEQ ID NO 247
<211> LENGTH: 85
<212> TYPE: DNA
<213> ORGANISM: Homo sapiens

<400> SEQUENCE: 247
ggctccgtgg cgcaatggat agcgcattgg acttctagag gctgaaggca ttcaaaggtt    60
ccgggttcga gtcccggcgg agtcg                                          85

<210> SEQ ID NO 248
<211> LENGTH: 74
<212> TYPE: DNA
<213> ORGANISM: Homo sapiens

<400> SEQUENCE: 248
gtctctgtgg cgcaatcggt cagagcgttc ggctattaac cgaacggtga gtagttcaag    60
accacccagg gacg                                                      74

<210> SEQ ID NO 249
<211> LENGTH: 76
<212> TYPE: DNA
<213> ORGANISM: Homo sapiens

<400> SEQUENCE: 249
gtctctgtgg cgccatcggt tagtgccttc ggctgtttga accgaaaggc tggtggttca    60
agcccaccca gagatg                                                    76

<210> SEQ ID NO 250
<211> LENGTH: 74
<212> TYPE: DNA
<213> ORGANISM: Homo sapiens

<400> SEQUENCE: 250
atctccgtgg agcaattggt tagcgcgttc ggccgttaac cggaaagttg gtggttcgag    60
cctacccagg gacg                                                      74

<210> SEQ ID NO 251
<211> LENGTH: 74
<212> TYPE: DNA
<213> ORGANISM: Homo sapiens

<400> SEQUENCE: 251
gtctctgtgg tgcaatcggt tagcgcgttc ggctgttaac cataaggttg gtggttacag    60
accacccagg gacg                                                      74
```

<210> SEQ ID NO 252
<211> LENGTH: 74
<212> TYPE: DNA
<213> ORGANISM: Homo sapiens

<400> SEQUENCE: 252
gtttctgtag cgcgatcggt tagcgccttc ggctgttaaa cgaaaggttg gtggttcgtt    60
cccaccccgg gaca    74

<210> SEQ ID NO 253
<211> LENGTH: 74
<212> TYPE: DNA
<213> ORGANISM: Homo sapiens

<400> SEQUENCE: 253
gtctctgtgg cgcaatcggt tagcgcgttt gactgttaac tgaaaggttg gtggtgcaag    60
cccatccagg gatg    74

<210> SEQ ID NO 254
<211> LENGTH: 74
<212> TYPE: DNA
<213> ORGANISM: Homo sapiens

<400> SEQUENCE: 254
gtctctgtgg cgcaatcggt tagcgcgttt gactgttaac tgaaaggttg gtggtgcaag    60
cccatccagg gatg    74

<210> SEQ ID NO 255
<211> LENGTH: 74
<212> TYPE: DNA
<213> ORGANISM: Homo sapiens

<400> SEQUENCE: 255
gtctctgtgg cgcaatcggt tagcgcgttt gactgttaac tgaaaggttg gtggtgcaag    60
cccatccagg gatg    74

<210> SEQ ID NO 256
<211> LENGTH: 74
<212> TYPE: DNA
<213> ORGANISM: Homo sapiens

<400> SEQUENCE: 256
gtctctgtgg cgcaatcggt tagcgcgttt gactgttaac tgaaaggttg gtggtgcaag    60
cccatccagg gatg    74

<210> SEQ ID NO 257
<211> LENGTH: 74
<212> TYPE: DNA
<213> ORGANISM: Homo sapiens

<400> SEQUENCE: 257
gtctctgtgg cgcaatcggt tagcgcgttt gactgttaac tgaaaggttg gtggtgcaag    60
cccatccagg gatg    74

<210> SEQ ID NO 258
<211> LENGTH: 74
<212> TYPE: DNA
<213> ORGANISM: Homo sapiens

<400> SEQUENCE: 258

```
atctccgtgg agcaattggt tagcgcgttc ggctgttaac cggaaagttg gtggttcgag    60
cctacccagg gacg                                                     74

<210> SEQ ID NO 259
<211> LENGTH: 74
<212> TYPE: DNA
<213> ORGANISM: Homo sapiens

<400> SEQUENCE: 259
gtctctgtgg tgcaatcggt tagcgcgttc cgctgttaac cgaaagcttg gtggtttgag    60
cccacccagg gatg                                                     74

<210> SEQ ID NO 260
<211> LENGTH: 74
<212> TYPE: DNA
<213> ORGANISM: Homo sapiens

<400> SEQUENCE: 260
gtctctgtgg tgcaatcggt tagcgcgttc ggctgttaac cataaggttg gtggttagag    60
accacccagg gacg                                                     74

<210> SEQ ID NO 261
<211> LENGTH: 74
<212> TYPE: DNA
<213> ORGANISM: Homo sapiens

<400> SEQUENCE: 261
gtctctgtgg cgcaatcggc tagcgcgttt ggctgttaac taaaaagttg gtggttcgaa    60
cacacccaga ggcg                                                     74

<210> SEQ ID NO 262
<211> LENGTH: 74
<212> TYPE: DNA
<213> ORGANISM: Homo sapiens

<400> SEQUENCE: 262
gtctctgtgg tgcaatcggt tagcgcgttc cgctgttaac cgaaagcttg gtggttcgag    60
cccacccagg gatg                                                     74

<210> SEQ ID NO 263
<211> LENGTH: 74
<212> TYPE: DNA
<213> ORGANISM: Homo sapiens

<400> SEQUENCE: 263
gtctctgtgg tgcaatcggt tagcgcgttc cgctgttaac cgaaagcttg gtggttcgag    60
cccacccagg gatg                                                     74

<210> SEQ ID NO 264
<211> LENGTH: 74
<212> TYPE: DNA
<213> ORGANISM: Homo sapiens

<400> SEQUENCE: 264
gtctctgtgg cgcaatcggc tagcgcgttt ggctgttaac taaaaggttg gcggttcgaa    60
cccacccaga ggcg                                                     74

<210> SEQ ID NO 265
```

```
<211> LENGTH: 74
<212> TYPE: DNA
<213> ORGANISM: Homo sapiens

<400> SEQUENCE: 265
gtctctgtgg cgcaatcggt tagcgcgttc ggctgttaac tgaaaggtta gtggttcgag      60
cccacccggg gacg                                                       74

<210> SEQ ID NO 266
<211> LENGTH: 74
<212> TYPE: DNA
<213> ORGANISM: Homo sapiens

<400> SEQUENCE: 266
gtctctgtgg cgcaatcggt tagcgcgttc ggctgttaac tgaaaggtta gtggttcgag      60
cccacccggg gacg                                                       74

<210> SEQ ID NO 267
<211> LENGTH: 74
<212> TYPE: DNA
<213> ORGANISM: Homo sapiens

<400> SEQUENCE: 267
gtctctgtgg cgcaatcggc tagcgcgttt ggctgttaac taaaaggttg gtggttcgaa      60
cccacccaga ggcg                                                       74

<210> SEQ ID NO 268
<211> LENGTH: 74
<212> TYPE: DNA
<213> ORGANISM: Homo sapiens

<400> SEQUENCE: 268
gtctctgtgg cgtagtcggt tagcgcgttc ggctgttaac cgaaaagttg gtggttcgag      60
cccacccagg aacg                                                       74

<210> SEQ ID NO 269
<211> LENGTH: 74
<212> TYPE: DNA
<213> ORGANISM: Homo sapiens

<400> SEQUENCE: 269
gtctctgtgg cgcaatgggt tagcgcgttc ggctgttaac cgaaaggttg gtggttcgag      60
cccatccagg gacg                                                       74

<210> SEQ ID NO 270
<211> LENGTH: 74
<212> TYPE: DNA
<213> ORGANISM: Homo sapiens

<400> SEQUENCE: 270
gtctctgtgg cgcaatcggt tagcgcgttc ggctgttaac tgaaaggttg gtggttcgag      60
cccacccagg gacg                                                       74

<210> SEQ ID NO 271
<211> LENGTH: 74
<212> TYPE: DNA
<213> ORGANISM: Homo sapiens

<400> SEQUENCE: 271
gtctctgtgg cgcaatcggt tagcgcgttc ggctgttaac cgaaagattg gtggttcgag      60
```

-continued

```
cccacccagg gacg                                                           74

<210> SEQ ID NO 272
<211> LENGTH: 74
<212> TYPE: DNA
<213> ORGANISM: Homo sapiens

<400> SEQUENCE: 272
gtctctgtgg cgcaatcggt tagcgcattc ggctgttaac cgaaaggttg gtggttcgag         60
cccacccagg gacg                                                           74

<210> SEQ ID NO 273
<211> LENGTH: 74
<212> TYPE: DNA
<213> ORGANISM: Homo sapiens

<400> SEQUENCE: 273
gtctctgtgg cgcaatcggt tagcgcattc ggctgttaac cgaaaggttg gtggttcgag         60
cccacccagg gacg                                                           74

<210> SEQ ID NO 274
<211> LENGTH: 74
<212> TYPE: DNA
<213> ORGANISM: Homo sapiens

<400> SEQUENCE: 274
gtctctgtgg cgcaatcggt tagcgcgttc ggctgttaac cgaaaggttg gtggttcgag         60
cccacccagg gacg                                                           74

<210> SEQ ID NO 275
<211> LENGTH: 74
<212> TYPE: DNA
<213> ORGANISM: Homo sapiens

<400> SEQUENCE: 275
gtctctgtgg cgcaatcggt tagcgcgttc ggctgttaac cgaaaggttg gtggttcgag         60
cccacccagg gacg                                                           74

<210> SEQ ID NO 276
<211> LENGTH: 74
<212> TYPE: DNA
<213> ORGANISM: Homo sapiens

<400> SEQUENCE: 276
gtctctgtgg cgcaatcggt tagcgcgttc ggctgttaac cgaaaggttg gtggttcgag         60
cccacccagg gacg                                                           74

<210> SEQ ID NO 277
<211> LENGTH: 74
<212> TYPE: DNA
<213> ORGANISM: Homo sapiens

<400> SEQUENCE: 277
gtctctgtgg cgcaatcggt tagcgcgttc ggctgttaac cgaaaggttg gtggttcgag         60
cccacccagg gacg                                                           74

<210> SEQ ID NO 278
<211> LENGTH: 74
<212> TYPE: DNA
```

<213> ORGANISM: Homo sapiens

<400> SEQUENCE: 278
gtctctgtgg cgcaatcggt tagcgcgttc ggctgttaac cgaaaggttg gtggttcgag    60
cccacccagg gacg                                                     74

<210> SEQ ID NO 279
<211> LENGTH: 74
<212> TYPE: DNA
<213> ORGANISM: Homo sapiens

<400> SEQUENCE: 279
gtctctgtgg cgcaatcggt tagcgcgttc ggctgttaac cgaaaggttg gtggttcgag    60
cccacccagg gacg                                                     74

<210> SEQ ID NO 280
<211> LENGTH: 74
<212> TYPE: DNA
<213> ORGANISM: Homo sapiens

<400> SEQUENCE: 280
gtctctgtgg cgcaatcggt tagcgcgttc ggctgttaac cgaaaggttg gtggttcgat    60
cccacccagg gacg                                                     74

<210> SEQ ID NO 281
<211> LENGTH: 72
<212> TYPE: DNA
<213> ORGANISM: Homo sapiens

<400> SEQUENCE: 281
tccttgttac tatagtggta agtatctctg cctgtcatgc atgagagagg gggtcgattc    60
cctgacgggg ag                                                       72

<210> SEQ ID NO 282
<211> LENGTH: 71
<212> TYPE: DNA
<213> ORGANISM: Homo sapiens

<400> SEQUENCE: 282
tccttgttag tatagtggtg agtgtttctg cctgtcatgt ggagactgga gtttgagtcc    60
ccaacaggga g                                                        71

<210> SEQ ID NO 283
<211> LENGTH: 72
<212> TYPE: DNA
<213> ORGANISM: Homo sapiens

<400> SEQUENCE: 283
tactcgttag tatagtggtg cgtatccccg tctgtcacgc gggagagcgg ggttcgctct    60
cccgacgggg ag                                                       72

<210> SEQ ID NO 284
<211> LENGTH: 71
<212> TYPE: DNA
<213> ORGANISM: Homo sapiens

<400> SEQUENCE: 284
ttcttgttaa tatagtggtg agtattccca cctgtcatgc gggagacggg gttcaattcc    60
ctgatgggga g                                                        71

<210> SEQ ID NO 285
<211> LENGTH: 72
<212> TYPE: DNA
<213> ORGANISM: Homo sapiens

<400> SEQUENCE: 285
tcctcatcag tatagtggtg agtatccccg cctgtcacgc gggagactgg ggttcgattc    60
cctgaggagg ag                                                        72

<210> SEQ ID NO 286
<211> LENGTH: 72
<212> TYPE: DNA
<213> ORGANISM: Homo sapiens

<400> SEQUENCE: 286
tcctcgttag tatggtggtg agtatccctg cctgtcacgc gggagaccgg ggttcgattc    60
cccaacgggg ag                                                        72

<210> SEQ ID NO 287
<211> LENGTH: 72
<212> TYPE: DNA
<213> ORGANISM: Homo sapiens

<400> SEQUENCE: 287
tcctcgttag tatagtggtg agtgtccccg tctgtcacgc gggagaccgg ggttcgattc    60
cccgacgggg ag                                                        72

<210> SEQ ID NO 288
<211> LENGTH: 72
<212> TYPE: DNA
<213> ORGANISM: Homo sapiens

<400> SEQUENCE: 288
tcctcgttag tatagtggtg agtatccccg cctgtcacgc gggagaccgg ggttcgattc    60
cccgacgggg ag                                                        72

<210> SEQ ID NO 289
<211> LENGTH: 72
<212> TYPE: DNA
<213> ORGANISM: Homo sapiens

<400> SEQUENCE: 289
tcctcgttag tatagtggtg agtatccccg cctgtcacgc gggagaccgg ggttcgattc    60
cccgacgggg ag                                                        72

<210> SEQ ID NO 290
<211> LENGTH: 72
<212> TYPE: DNA
<213> ORGANISM: Homo sapiens

<400> SEQUENCE: 290
tcctcgttag tatagtggtg agtatccccg cctgtcacgc gggagaccgg ggttcgattc    60
cccgacgggg ag                                                        72

<210> SEQ ID NO 291
<211> LENGTH: 72
<212> TYPE: DNA
<213> ORGANISM: Homo sapiens

```
<400> SEQUENCE: 291
tcctcgttag tatagtggtg agtatccccg cctgtcacgc gggagaccgg ggttcgattc      60
cccgacgggg ag                                                         72

<210> SEQ ID NO 292
<211> LENGTH: 72
<212> TYPE: DNA
<213> ORGANISM: Homo sapiens

<400> SEQUENCE: 292
tcctcgttag tatagtggtg agtatccccg cctgtcacgc gggagaccgg ggttcgattc      60
cccgacgggg ag                                                         72

<210> SEQ ID NO 293
<211> LENGTH: 72
<212> TYPE: DNA
<213> ORGANISM: Homo sapiens

<400> SEQUENCE: 293
tcctcgttag tatagtggtg agtatccccg cctgtcacgc gggagaccgg ggttcgattc      60
cccgacgggg ag                                                         72

<210> SEQ ID NO 294
<211> LENGTH: 72
<212> TYPE: DNA
<213> ORGANISM: Homo sapiens

<400> SEQUENCE: 294
tcctcgttag tatagtggtg agtatccccg cctgtcacgc gggagaccgg ggttcgattc      60
cccgacgggg ag                                                         72

<210> SEQ ID NO 295
<211> LENGTH: 72
<212> TYPE: DNA
<213> ORGANISM: Homo sapiens

<400> SEQUENCE: 295
tcctcgttag tatagtggtg agtatccccg cctgtcacgc gggagaccgg ggttcgattc      60
cccgacgggg ag                                                         72

<210> SEQ ID NO 296
<211> LENGTH: 72
<212> TYPE: DNA
<213> ORGANISM: Homo sapiens

<400> SEQUENCE: 296
tcctcgttag tatagtggtg agtatccccg cctgtcacgc gggagaccgg ggttcgattc      60
cccgacgggg ag                                                         72

<210> SEQ ID NO 297
<211> LENGTH: 72
<212> TYPE: DNA
<213> ORGANISM: Homo sapiens

<400> SEQUENCE: 297
tcctcgttag tatagtggtg agtatccccg cctgtcacgc gggagaccgg ggttcgattc      60
cccgacgggg ag                                                         72
```

-continued

```
<210> SEQ ID NO 298
<211> LENGTH: 72
<212> TYPE: DNA
<213> ORGANISM: Homo sapiens

<400> SEQUENCE: 298
tcctcgttag tatagtggtg agtatccccg cctgtcacgc gggagaccgg ggttcgattc      60
cccgacgggg ag                                                          72

<210> SEQ ID NO 299
<211> LENGTH: 72
<212> TYPE: DNA
<213> ORGANISM: Homo sapiens

<400> SEQUENCE: 299
tcctcgttag tatagtggtt agtatccccg cctgtcacgc gggagaccgg ggttcaattc      60
cccgacgggg ag                                                          72

<210> SEQ ID NO 300
<211> LENGTH: 72
<212> TYPE: DNA
<213> ORGANISM: Homo sapiens

<400> SEQUENCE: 300
gggggtaggg ctcagggata gagcatttga ctgcagatca agaggtcccc ggttcgaatc      60
taggtgcccc ct                                                          72

<210> SEQ ID NO 301
<211> LENGTH: 72
<212> TYPE: DNA
<213> ORGANISM: Homo sapiens

<400> SEQUENCE: 301
gggggtatag ctcacaggta gagcatttga ctgcagatca agaggtcccc ggttcaaatc      60
cggttactcc ct                                                          72

<210> SEQ ID NO 302
<211> LENGTH: 72
<212> TYPE: DNA
<213> ORGANISM: Homo sapiens

<400> SEQUENCE: 302
gggcgtatag ctcaggggta gagcatttga ctgcagatca agaggtcccc agttcaaatc      60
tgggtgccca ct                                                          72

<210> SEQ ID NO 303
<211> LENGTH: 72
<212> TYPE: DNA
<213> ORGANISM: Homo sapiens

<400> SEQUENCE: 303
gggggtatag ctcacaggta gagcatttga ctgcagatca agaggtcccc ggttcaaatc      60
tgggtgcccc ct                                                          72

<210> SEQ ID NO 304
<211> LENGTH: 72
<212> TYPE: DNA
<213> ORGANISM: Homo sapiens

<400> SEQUENCE: 304
```

```
gggcgtatag ctcaggggta gagcatttga ctgcagatca agaggtcccc agttcaaatc    60
tgggtgcccc ct                                                        72

<210> SEQ ID NO 305
<211> LENGTH: 72
<212> TYPE: DNA
<213> ORGANISM: Homo sapiens

<400> SEQUENCE: 305
gggggtatag ctcaggggta gagcatttga ctgcaaatca agaggtccct gattcaaatc    60
caggtgcccc ct                                                        72

<210> SEQ ID NO 306
<211> LENGTH: 72
<212> TYPE: DNA
<213> ORGANISM: Homo sapiens

<400> SEQUENCE: 306
gggggtatag ttcaggggta gagcatttga ctgcagatca agaggtccct ggttcaaatc    60
caggtgcccc ct                                                        72

<210> SEQ ID NO 307
<211> LENGTH: 72
<212> TYPE: DNA
<213> ORGANISM: Homo sapiens

<400> SEQUENCE: 307
ggggatatag ctcaggggta gagcatttga ctgcagatca agaggtcccc ggttcaaatc    60
cgggtgcccc cc                                                        72

<210> SEQ ID NO 308
<211> LENGTH: 72
<212> TYPE: DNA
<213> ORGANISM: Homo sapiens

<400> SEQUENCE: 308
gggggtatag ctcaggggta gagcacttga ctgcagatca agaagtcctt ggttcaaatc    60
caggtgcccc ct                                                        72

<210> SEQ ID NO 309
<211> LENGTH: 72
<212> TYPE: DNA
<213> ORGANISM: Homo sapiens

<400> SEQUENCE: 309
gggggtatag ctcaggggta gagcatttga ctgcagatca agaggtctct ggttcaaatc    60
caggtgcccc ct                                                        72

<210> SEQ ID NO 310
<211> LENGTH: 72
<212> TYPE: DNA
<213> ORGANISM: Homo sapiens

<400> SEQUENCE: 310
gggggtatag ctcaggggta gagcatttga ctgcagatca agaagtcccc ggttcaaatc    60
cgggtgcccc ct                                                        72

<210> SEQ ID NO 311
<211> LENGTH: 72
```

```
<212> TYPE: DNA
<213> ORGANISM: Homo sapiens

<400> SEQUENCE: 311
gggggtatag ctcaggggta gagcatttga ctgcagatca agaggtcccc agttcaaatc    60
tgggtgcccc ct                                                       72

<210> SEQ ID NO 312
<211> LENGTH: 72
<212> TYPE: DNA
<213> ORGANISM: Homo sapiens

<400> SEQUENCE: 312
gggggtatag cttaggggta gagcatttga ctgcagatca aaaggtccct ggttcaaatc    60
caggtgcccc tt                                                       72

<210> SEQ ID NO 313
<211> LENGTH: 72
<212> TYPE: DNA
<213> ORGANISM: Homo sapiens

<400> SEQUENCE: 313
gggggtatag cttagcggta gagcatttga ctgcagatca agaggtcccc ggttcaaatc    60
cgggtgcccc ct                                                       72

<210> SEQ ID NO 314
<211> LENGTH: 72
<212> TYPE: DNA
<213> ORGANISM: Homo sapiens

<400> SEQUENCE: 314
gggggtatag ctcaggggta gagcatttga ctgcagatca agaggtccct ggttcaaatc    60
caggtgcccc cc                                                       72

<210> SEQ ID NO 315
<211> LENGTH: 72
<212> TYPE: DNA
<213> ORGANISM: Homo sapiens

<400> SEQUENCE: 315
gggggtatag ctcaggggta gagcatttga ctgcagatca agaggtccct ggttcaaatc    60
caggtgcccc ct                                                       72

<210> SEQ ID NO 316
<211> LENGTH: 72
<212> TYPE: DNA
<213> ORGANISM: Homo sapiens

<400> SEQUENCE: 316
gggggtatag ctcaggggta gagcatttga ctgcagatca agaggtccct ggttcaaatc    60
caggtgcccc ct                                                       72

<210> SEQ ID NO 317
<211> LENGTH: 72
<212> TYPE: DNA
<213> ORGANISM: Homo sapiens

<400> SEQUENCE: 317
gggggtatag ctcaggggta gagcatttga ctgcagatca agaggtccct ggttcaaatc    60
```
caggtgcccc ct                                                          72

<210> SEQ ID NO 318
<211> LENGTH: 72
<212> TYPE: DNA
<213> ORGANISM: Homo sapiens

<400> SEQUENCE: 318
gggggtatag ctcaggggta gagcatttga ctgcagatca agaggtccct ggttcaaatc      60
caggtgcccc ct                                                          72

<210> SEQ ID NO 319
<211> LENGTH: 72
<212> TYPE: DNA
<213> ORGANISM: Homo sapiens

<400> SEQUENCE: 319
gggggtatag ctcaggggta gagcatttga ctgcagatca agaggtcccc ggttcaaatc      60
cgggtgcccc ct                                                          72

<210> SEQ ID NO 320
<211> LENGTH: 73
<212> TYPE: DNA
<213> ORGANISM: Homo sapiens

<400> SEQUENCE: 320
gggggtatag ctcaggtggt agagcatttg actgcagatc aagaggtccc cggttcaaat      60
ccgggtgccc cct                                                         73

<210> SEQ ID NO 321
<211> LENGTH: 72
<212> TYPE: DNA
<213> ORGANISM: Homo sapiens

<400> SEQUENCE: 321
gggggtgtag ctcagtggta gagcatttga ctgcagatca agaggtccct ggttcaaatc      60
caggtgcccc ct                                                          72

<210> SEQ ID NO 322
<211> LENGTH: 73
<212> TYPE: DNA
<213> ORGANISM: Homo sapiens

<400> SEQUENCE: 322
gggggtatag ctcagtgggt agagcatttg actgcagatc aagaggtccc cggttcaaat      60
ccgggtgccc cct                                                         73

<210> SEQ ID NO 323
<211> LENGTH: 72
<212> TYPE: DNA
<213> ORGANISM: Homo sapiens

<400> SEQUENCE: 323
gggggtatag ctcagtggta gagcatttga ctgcagatca agaggtccct ggttcaaatc      60
cgggtgcccc ct                                                          72

<210> SEQ ID NO 324
<211> LENGTH: 72
<212> TYPE: DNA
<213> ORGANISM: Homo sapiens

```
<400> SEQUENCE: 324
gggggtatag ctcaggggta gagcacttga ctgcagatca agaggtccct ggttcaaatc      60
caggtgcccc ct                                                         72

<210> SEQ ID NO 325
<211> LENGTH: 72
<212> TYPE: DNA
<213> ORGANISM: Homo sapiens

<400> SEQUENCE: 325
gggggtatag ctcagtggta gagcatttga ctgcagatca agaggtcccc ggttcaaatc      60
cgggtgcccc ct                                                         72

<210> SEQ ID NO 326
<211> LENGTH: 72
<212> TYPE: DNA
<213> ORGANISM: Homo sapiens

<400> SEQUENCE: 326
gggggtatag ctcagtggta gagcatttga ctgcagatca agaggtcccc ggttcaaatc      60
cgggtgcccc ct                                                         72

<210> SEQ ID NO 327
<211> LENGTH: 72
<212> TYPE: DNA
<213> ORGANISM: Homo sapiens

<400> SEQUENCE: 327
gggggtatag ctcagtggta gagcatttga ctgcagatca agaggtcccc ggttcaaatc      60
cgggtgcccc ct                                                         72

<210> SEQ ID NO 328
<211> LENGTH: 72
<212> TYPE: DNA
<213> ORGANISM: Homo sapiens

<400> SEQUENCE: 328
gggggtatag ctcagtggta gagcatttga ctgcagatca agaggtcccc ggttcaaatc      60
cgggtgcccc ct                                                         72

<210> SEQ ID NO 329
<211> LENGTH: 72
<212> TYPE: DNA
<213> ORGANISM: Homo sapiens

<400> SEQUENCE: 329
gggggcatag ctcagtggta gagcatttga ctgcagatca agaggtccct ggttcaaatc      60
caggtgcccc ct                                                         72

<210> SEQ ID NO 330
<211> LENGTH: 74
<212> TYPE: DNA
<213> ORGANISM: Homo sapiens

<400> SEQUENCE: 330
ggcagtatgg tagagtggtt aagatcatga actctgaagt cagagatact tgaatttgaa      60
tgctggttct gtca                                                       74
```

```
<210> SEQ ID NO 331
<211> LENGTH: 78
<212> TYPE: DNA
<213> ORGANISM: Homo sapiens

<400> SEQUENCE: 331
ggcagtgtag cccagaggtt caagggcatt cgctctggta tcagaagggt ctgggttcaa    60
atcccttgtg cactgctt                                                 78

<210> SEQ ID NO 332
<211> LENGTH: 73
<212> TYPE: DNA
<213> ORGANISM: Homo sapiens

<400> SEQUENCE: 332
gagctgtagc atagtgatta gggacatgga ctctggagcc aaatctgcct gggttctagt    60
cccagctgtc tca                                                      73

<210> SEQ ID NO 333
<211> LENGTH: 73
<212> TYPE: DNA
<213> ORGANISM: Homo sapiens

<400> SEQUENCE: 333
ggttccatgg tgtaatggta agcaccctgg actctgaatc cagcaaccag agttccagtc    60
tcagcgtgga cct                                                      73

<210> SEQ ID NO 334
<211> LENGTH: 72
<212> TYPE: DNA
<213> ORGANISM: Homo sapiens

<400> SEQUENCE: 334
ggttccatgg tgtaatggtg accactttgg actctgaata cagtgatcag agttcaagtc    60
tcactggaac ct                                                       72

<210> SEQ ID NO 335
<211> LENGTH: 72
<212> TYPE: DNA
<213> ORGANISM: Homo sapiens

<400> SEQUENCE: 335
ggttccatgg tgtaatggtg agcactttgg actctgaata cagtgatcag agttcaagtc    60
tcactgggac ct                                                       72

<210> SEQ ID NO 336
<211> LENGTH: 72
<212> TYPE: DNA
<213> ORGANISM: Homo sapiens

<400> SEQUENCE: 336
ggttccatgg tgtaatggtg agcactttgg actctgaata cagtgatcag agttcaagtc    60
tcactgggac ct                                                       72

<210> SEQ ID NO 337
<211> LENGTH: 72
<212> TYPE: DNA
<213> ORGANISM: Homo sapiens

<400> SEQUENCE: 337
```
ggttccatgg tgtaatggtg agcactttgg actctgaata cagtgatcag agttcaagtc      60
tcactgggac ct                                                          72

<210> SEQ ID NO 338
<211> LENGTH: 72
<212> TYPE: DNA
<213> ORGANISM: Homo sapiens

<400> SEQUENCE: 338
ggttccatgg tgtaatggta agcactctgg actctgaatc cagccatctg agttcgagtc      60
tctgtggaac ct                                                          72

<210> SEQ ID NO 339
<211> LENGTH: 72
<212> TYPE: DNA
<213> ORGANISM: Homo sapiens

<400> SEQUENCE: 339
ggccccatgg tgtaatggtc agcactctgg actctgaatc cagcgatccg agttcaaatc      60
tcggtgggac cc                                                          72

<210> SEQ ID NO 340
<211> LENGTH: 72
<212> TYPE: DNA
<213> ORGANISM: Homo sapiens

<400> SEQUENCE: 340
ggttccatgg tgtaatggtt agcactctgg actctgaatc cggtaatccg agttcaaatc      60
tcggtggaac ct                                                          72

<210> SEQ ID NO 341
<211> LENGTH: 72
<212> TYPE: DNA
<213> ORGANISM: Homo sapiens

<400> SEQUENCE: 341
ggttccatgg tgtaatggta agcactctgg actctgaatc cagcgatccg agttcgagtc      60
tcggtggaac ct                                                          72

<210> SEQ ID NO 342
<211> LENGTH: 72
<212> TYPE: DNA
<213> ORGANISM: Homo sapiens

<400> SEQUENCE: 342
ggttccatgg tgtaatggta agcactctgg actctgaatc cagcgatccg agttcgagtc      60
tcggtggaac ct                                                          72

<210> SEQ ID NO 343
<211> LENGTH: 72
<212> TYPE: DNA
<213> ORGANISM: Homo sapiens

<400> SEQUENCE: 343
ggttccatgg tgtaatggtg agcactctgg actctgaatc cagcgatccg agttcgagtc      60
tcggtggaac ct                                                          72

<210> SEQ ID NO 344

```
<211> LENGTH: 72
<212> TYPE: DNA
<213> ORGANISM: Homo sapiens

<400> SEQUENCE: 344
ggttccatgg tgtaatggtg agcactctgg actctgaatc cagcgatccg agttcgagtc    60
tcggtggaac ct                                                        72

<210> SEQ ID NO 345
<211> LENGTH: 72
<212> TYPE: DNA
<213> ORGANISM: Homo sapiens

<400> SEQUENCE: 345
ggttccatgg tgtaatggtt agcactctgg actctgaatc cagcgatccg agttcaagtc    60
tcggtggaac ct                                                        72

<210> SEQ ID NO 346
<211> LENGTH: 72
<212> TYPE: DNA
<213> ORGANISM: Homo sapiens

<400> SEQUENCE: 346
ggttccatgg tgtaatggtt agcactctgg actctgaatc cagcgatccg agttcaaatc    60
tcggtggaac ct                                                        72

<210> SEQ ID NO 347
<211> LENGTH: 72
<212> TYPE: DNA
<213> ORGANISM: Homo sapiens

<400> SEQUENCE: 347
ggttccatgg tgtaatggtt agcactctgg actctgaatc cagcgatccg agttcaaatc    60
tcggtggaac ct                                                        72

<210> SEQ ID NO 348
<211> LENGTH: 72
<212> TYPE: DNA
<213> ORGANISM: Homo sapiens

<400> SEQUENCE: 348
ggttccatgg tgtaatggtt agcactctgg actctgaatc cagcgatccg agttcaaatc    60
tcggtggaac ct                                                        72

<210> SEQ ID NO 349
<211> LENGTH: 72
<212> TYPE: DNA
<213> ORGANISM: Homo sapiens

<400> SEQUENCE: 349
ggttccatgg tgtaatggtt agcactctgg actctgaatc cagcgatccg agttcaaatc    60
tcggtggaac ct                                                        72

<210> SEQ ID NO 350
<211> LENGTH: 72
<212> TYPE: DNA
<213> ORGANISM: Homo sapiens

<400> SEQUENCE: 350
ggttccatgg tgtaatggtt agcactctgg actctgaatc cagcgatccg agttcaaatc    60
```
tcggtggaac ct                                                            72

<210> SEQ ID NO 351
<211> LENGTH: 73
<212> TYPE: DNA
<213> ORGANISM: Homo sapiens

<400> SEQUENCE: 351
gtgcagagta gtacagtggt taaaccatgg tctttggagc cagactgcct ggggtcggat    60
cccagctctc aca                                                           73

<210> SEQ ID NO 352
<211> LENGTH: 72
<212> TYPE: DNA
<213> ORGANISM: Homo sapiens

<400> SEQUENCE: 352
taggacttgg tgtaatgggt agcacagaga attttggatt ctcaggggtg ggttcaattc    60
ctttcgtcct ag                                                            72

<210> SEQ ID NO 353
<211> LENGTH: 73
<212> TYPE: DNA
<213> ORGANISM: Homo sapiens

<400> SEQUENCE: 353
gaccatgtgg cctaagggaa aagacatctc actttgggtc agaagattga gggttcaagt    60
cctttcatgg tca                                                           73

<210> SEQ ID NO 354
<211> LENGTH: 72
<212> TYPE: DNA
<213> ORGANISM: Homo sapiens

<400> SEQUENCE: 354
taggacatgg tgtaataggt agaatggaga attttgaatt ctcaggggta ggttcaattc    60
ctatagttct ag                                                            72

<210> SEQ ID NO 355
<211> LENGTH: 72
<212> TYPE: DNA
<213> ORGANISM: Homo sapiens

<400> SEQUENCE: 355
ggtcccatgg tgtaatggtt agcactctgg gctttgaatc cagcaatccg agttcgaatc    60
ttggtgggac ct                                                            72

<210> SEQ ID NO 356
<211> LENGTH: 72
<212> TYPE: DNA
<213> ORGANISM: Homo sapiens

<400> SEQUENCE: 356
ggccccatgg tgtaatggtt agcactctgg actttgaatc cagcgatccg agttcaaatc    60
tcggtgggac ct                                                            72

<210> SEQ ID NO 357
<211> LENGTH: 72
<212> TYPE: DNA

<213> ORGANISM: Homo sapiens

<400> SEQUENCE: 357
ggccccatgg tgtaatggtt agcactctgg actttgaatc cagcgatccg agttcaaatc    60
tcggtgggac ct    72

<210> SEQ ID NO 358
<211> LENGTH: 72
<212> TYPE: DNA
<213> ORGANISM: Homo sapiens

<400> SEQUENCE: 358
ggccccatgg tgtaatggtt agcactctgg actttgaatc cagcgatccg agttcaaatc    60
tcggtgggac ct    72

<210> SEQ ID NO 359
<211> LENGTH: 72
<212> TYPE: DNA
<213> ORGANISM: Homo sapiens

<400> SEQUENCE: 359
ggtcccatgg tgtaatggtt agcactctgg actttgaatc cagcgatccg agttcaaatc    60
tcggtgggac ct    72

<210> SEQ ID NO 360
<211> LENGTH: 69
<212> TYPE: DNA
<213> ORGANISM: Homo sapiens

<400> SEQUENCE: 360
tccctggtag tctagtggct aaagtttggc gctctcaccg ccgggactgg ttgattccag    60
atcagggga    69

<210> SEQ ID NO 361
<211> LENGTH: 72
<212> TYPE: DNA
<213> ORGANISM: Homo sapiens

<400> SEQUENCE: 361
cccctggtgg tctatcggtt aggattcaga cctctcacca ctgctaccca tgctcgattc    60
ctggtcaggg aa    72

<210> SEQ ID NO 362
<211> LENGTH: 72
<212> TYPE: DNA
<213> ORGANISM: Homo sapiens

<400> SEQUENCE: 362
ccccgggtgg tgtagtggat gggatttggc gctctcacca ccatggcccg gatttgattc    60
ccggtcaggg aa    72

<210> SEQ ID NO 363
<211> LENGTH: 71
<212> TYPE: DNA
<213> ORGANISM: Homo sapiens

<400> SEQUENCE: 363
tccttgatgt ctagtggtta ggatttggtg ctctcactgc agcagcctgg gttcatttct    60
cagtcaggga a    71

<210> SEQ ID NO 364
<211> LENGTH: 72
<212> TYPE: DNA
<213> ORGANISM: Homo sapiens

<400> SEQUENCE: 364
cccctggtgg tctagtgctt aggattcggt gctctcaccg ctgctgcctg cgttcgattc    60
ccggtcaggg aa                                                       72

<210> SEQ ID NO 365
<211> LENGTH: 72
<212> TYPE: DNA
<213> ORGANISM: Homo sapiens

<400> SEQUENCE: 365
tccctggtgg tctagtggtt aggattcggc gctctcaccg ccgcggcccg ggttcgattc    60
ccggtcagga aa                                                       72

<210> SEQ ID NO 366
<211> LENGTH: 72
<212> TYPE: DNA
<213> ORGANISM: Homo sapiens

<400> SEQUENCE: 366
tccctggtgg tctagtggtt aggattcggc gctctcaccg ccgcggcccg ggttcgattc    60
ccggtcaggg aa                                                       72

<210> SEQ ID NO 367
<211> LENGTH: 72
<212> TYPE: DNA
<213> ORGANISM: Homo sapiens

<400> SEQUENCE: 367
tccctggtgg tctagtggtt aggattcggc gctctcaccg ccgcggcccg ggttcgattc    60
ccggtcaggg aa                                                       72

<210> SEQ ID NO 368
<211> LENGTH: 72
<212> TYPE: DNA
<213> ORGANISM: Homo sapiens

<400> SEQUENCE: 368
tccctggtgg tctagtggtt aggattcggc gctctcaccg ccgcggcccg ggttcgattc    60
ccggtcaggg aa                                                       72

<210> SEQ ID NO 369
<211> LENGTH: 72
<212> TYPE: DNA
<213> ORGANISM: Homo sapiens

<400> SEQUENCE: 369
tccctggtgg tctagtggtt aggattcggc gctctcaccg ccgcggcccg ggttcgattc    60
ccggtcaggg aa                                                       72

<210> SEQ ID NO 370
<211> LENGTH: 72
<212> TYPE: DNA
<213> ORGANISM: Homo sapiens

<400> SEQUENCE: 370
tccctggtgg tctagtggtt aggattcggc gctctcaccg ccgcggcccg ggttcgattc    60
ccggtcaggg aa    72

<210> SEQ ID NO 371
<211> LENGTH: 72
<212> TYPE: DNA
<213> ORGANISM: Homo sapiens

<400> SEQUENCE: 371
tccctggtgg tctagtggtt aggattcggc gctctcaccg ccgcggcccg ggttcgattc    60
ccggtcaggg aa    72

<210> SEQ ID NO 372
<211> LENGTH: 72
<212> TYPE: DNA
<213> ORGANISM: Homo sapiens

<400> SEQUENCE: 372
tccctggtgg tctagtggtt aggattcggc gctctcaccg ccgcggcccg ggttcgattc    60
ccggtcaggg aa    72

<210> SEQ ID NO 373
<211> LENGTH: 69
<212> TYPE: DNA
<213> ORGANISM: Homo sapiens

<400> SEQUENCE: 373
tccctggtag tctagtggct aaagtttggc gctttcaccg ccgggactgg ttgattccag    60
atcagggga    69

<210> SEQ ID NO 374
<211> LENGTH: 69
<212> TYPE: DNA
<213> ORGANISM: Homo sapiens

<400> SEQUENCE: 374
gcctgtggtc tagtggttag aattcagtgt tttcagtgct ctagtccagg ttcaattcct    60
ggtcaggga    69

<210> SEQ ID NO 375
<211> LENGTH: 69
<212> TYPE: DNA
<213> ORGANISM: Homo sapiens

<400> SEQUENCE: 375
ccctgtggtc tagtggttag gagttggtgc tttcgtcatg acagcccagg ttcaattcct    60
ggttagaga    69

<210> SEQ ID NO 376
<211> LENGTH: 71
<212> TYPE: DNA
<213> ORGANISM: Homo sapiens

<400> SEQUENCE: 376
accctgtggt ctagtggcta agactttgtg ctttcattgc tgcatcctag gttcaattcc    60
cagtcaggga a    71

```
<210> SEQ ID NO 377
<211> LENGTH: 73
<212> TYPE: DNA
<213> ORGANISM: Homo sapiens

<400> SEQUENCE: 377
tccctggtgg tctagtggct aggattcggc gctttcaccg cctgcagctc gagttcgatt      60
cctggtcagg gaa                                                        73

<210> SEQ ID NO 378
<211> LENGTH: 72
<212> TYPE: DNA
<213> ORGANISM: Homo sapiens

<400> SEQUENCE: 378
gcgttggtgg tgtagtggtg agcacagctg cctttcaagc agttaacgcg ggttcgattc      60
ccgggtaacg aa                                                         72

<210> SEQ ID NO 379
<211> LENGTH: 72
<212> TYPE: DNA
<213> ORGANISM: Homo sapiens

<400> SEQUENCE: 379
tccctggtgg tctagtggct aggattcggc gctttcaccg ccgcggcccg ggttcgattc      60
ccggtcaggg aa                                                         72

<210> SEQ ID NO 380
<211> LENGTH: 72
<212> TYPE: DNA
<213> ORGANISM: Homo sapiens

<400> SEQUENCE: 380
tccctggtgg tctagtggct aggattcggc gctttcaccg ccgcggcccg ggttcgattc      60
ccggtcaggg aa                                                         72

<210> SEQ ID NO 381
<211> LENGTH: 72
<212> TYPE: DNA
<213> ORGANISM: Homo sapiens

<400> SEQUENCE: 381
tccctggtgg tctagtggct aggattcggc gctttcaccg ccgcggcccg ggttcgattc      60
ccggccaggg aa                                                         72

<210> SEQ ID NO 382
<211> LENGTH: 72
<212> TYPE: DNA
<213> ORGANISM: Homo sapiens

<400> SEQUENCE: 382
tcccacatgg tctagcggtt aggattcctg gttttcaccc aggcggcccg ggttcgactc      60
ccggtgtggg aa                                                         72

<210> SEQ ID NO 383
<211> LENGTH: 72
<212> TYPE: DNA
<213> ORGANISM: Homo sapiens

<400> SEQUENCE: 383
```

```
tcccacatgg tctagcggtt aggattcctg gttttcaccc aggcggcccg ggttcgactc    60
ccggtgtggg aa                                                        72

<210> SEQ ID NO 384
<211> LENGTH: 72
<212> TYPE: DNA
<213> ORGANISM: Homo sapiens

<400> SEQUENCE: 384
tcccatatgg tctagcggtt aggattcctg gttttcaccc aggtggcccg ggttcgactc    60
ccggtatggg aa                                                        72

<210> SEQ ID NO 385
<211> LENGTH: 72
<212> TYPE: DNA
<213> ORGANISM: Homo sapiens

<400> SEQUENCE: 385
tcccatatgg tctagcggtt aggattcctg gttttcaccc aggtggcccg ggttcgactc    60
ccggtatggg aa                                                        72

<210> SEQ ID NO 386
<211> LENGTH: 71
<212> TYPE: DNA
<213> ORGANISM: Homo sapiens

<400> SEQUENCE: 386
gccttggtgg tgcagtggta gaattctcgc ctcccacgtg ggagacccgg gttcaattcc    60
cggccaatgc a                                                         71

<210> SEQ ID NO 387
<211> LENGTH: 71
<212> TYPE: DNA
<213> ORGANISM: Homo sapiens

<400> SEQUENCE: 387
gcgttggtgg tttagtggta gaattctcgc ctcccatgcg ggagacccgg gttcaattcc    60
cggccactgc a                                                         71

<210> SEQ ID NO 388
<211> LENGTH: 71
<212> TYPE: DNA
<213> ORGANISM: Homo sapiens

<400> SEQUENCE: 388
gcattggtgg ttcaatggta gaattctcgc ctcccacgca ggagacccag gttcgattcc    60
tggccaatgc a                                                         71

<210> SEQ ID NO 389
<211> LENGTH: 71
<212> TYPE: DNA
<213> ORGANISM: Homo sapiens

<400> SEQUENCE: 389
gcgccgctgg tgtagtggta tcatgcaaga ttcccattct tgcgacccgg gttcgattcc    60
cgggcggcgc a                                                         71

<210> SEQ ID NO 390
<211> LENGTH: 71
```

```
<212> TYPE: DNA
<213> ORGANISM: Homo sapiens

<400> SEQUENCE: 390
gcgccgctgg tgtagtggta tcatgcaaga ttcccattct tgcgacccgg gttcgattcc      60
cgggcggcgc a                                                          71

<210> SEQ ID NO 391
<211> LENGTH: 71
<212> TYPE: DNA
<213> ORGANISM: Homo sapiens

<400> SEQUENCE: 391
gcattggtgg ttcagtggta gaattctcgc ctcccacgcg ggagacccgg gttcaattcc      60
cggccaatgc a                                                          71

<210> SEQ ID NO 392
<211> LENGTH: 71
<212> TYPE: DNA
<213> ORGANISM: Homo sapiens

<400> SEQUENCE: 392
gcattggtgg ttcagtggta gaattctcgc ctcccacgcg ggagacccgg gttcaattcc      60
cggccaatgc a                                                          71

<210> SEQ ID NO 393
<211> LENGTH: 71
<212> TYPE: DNA
<213> ORGANISM: Homo sapiens

<400> SEQUENCE: 393
gcatgggtga ttcagtggta gaattttcac ctgccatgca ggaggtccag gttcatttcc      60
tggcctatgc a                                                          71

<210> SEQ ID NO 394
<211> LENGTH: 71
<212> TYPE: DNA
<213> ORGANISM: Homo sapiens

<400> SEQUENCE: 394
gcattggtgg ttcagtggta gaattctcgc ctgccatgcg ggcggccggg cttcgattcc      60
tggccaatgc a                                                          71

<210> SEQ ID NO 395
<211> LENGTH: 71
<212> TYPE: DNA
<213> ORGANISM: Homo sapiens

<400> SEQUENCE: 395
gcataggtgg ttcagtggta gaattcttgc ctgccacgca ggaggcccag gtttgattcc      60
tggcccatgc a                                                          71

<210> SEQ ID NO 396
<211> LENGTH: 71
<212> TYPE: DNA
<213> ORGANISM: Homo sapiens

<400> SEQUENCE: 396
gcattggtgg ttcagtggta gaattctcgc ctgccacgcg ggaggcccgg gtttgattcc      60
```
cggccagtgc a                                                          71

<210> SEQ ID NO 397
<211> LENGTH: 71
<212> TYPE: DNA
<213> ORGANISM: Homo sapiens

<400> SEQUENCE: 397
gcattggtgg ttcagtggta gaattctcgc ctgccacgcg ggaggcccgg gttcgattcc      60
cggccaatgc a                                                          71

<210> SEQ ID NO 398
<211> LENGTH: 71
<212> TYPE: DNA
<213> ORGANISM: Homo sapiens

<400> SEQUENCE: 398
gcattggtgg ttcagtggta gaattctcgc ctgccacgcg ggaggcccgg gttcgattcc      60
cggccaatgc a                                                          71

<210> SEQ ID NO 399
<211> LENGTH: 71
<212> TYPE: DNA
<213> ORGANISM: Homo sapiens

<400> SEQUENCE: 399
gcattggtgg ttcagtggta gaattctcgc ctgccacgcg ggaggcccgg gttcgattcc      60
cggccaatgc a                                                          71

<210> SEQ ID NO 400
<211> LENGTH: 71
<212> TYPE: DNA
<213> ORGANISM: Homo sapiens

<400> SEQUENCE: 400
gcattggtgg ttcagtggta gaattctcgc ctgccacgcg ggaggcccgg gttcgattcc      60
cggccaatgc a                                                          71

<210> SEQ ID NO 401
<211> LENGTH: 71
<212> TYPE: DNA
<213> ORGANISM: Homo sapiens

<400> SEQUENCE: 401
gcattggtgg ttcagtggta gaattctcgc ctgccacgcg ggaggcccgg gttcgattcc      60
cggccaatgc a                                                          71

<210> SEQ ID NO 402
<211> LENGTH: 71
<212> TYPE: DNA
<213> ORGANISM: Homo sapiens

<400> SEQUENCE: 402
gcattggtgg ttcagtggta gaattctcgc ctgccacgcg ggaggcccgg gttcgattcc      60
cggccaatgc a                                                          71

<210> SEQ ID NO 403
<211> LENGTH: 71
<212> TYPE: DNA
<213> ORGANISM: Homo sapiens

<400> SEQUENCE: 403
gcatgggtgg ttcagtggta gaattctcgc ctgccacgcg ggaggcccgg gttcgattcc    60
cggcccatgc a                                                        71

<210> SEQ ID NO 404
<211> LENGTH: 71
<212> TYPE: DNA
<213> ORGANISM: Homo sapiens

<400> SEQUENCE: 404
gcatgggtgg ttcagtggta gaattctcgc ctgccacgcg ggaggcccgg gttcgattcc    60
cggcccatgc a                                                        71

<210> SEQ ID NO 405
<211> LENGTH: 71
<212> TYPE: DNA
<213> ORGANISM: Homo sapiens

<400> SEQUENCE: 405
gcatgggtgg ttcagtggta gaattctcgc ctgccacgcg ggaggcccgg gttcgattcc    60
cggcccatgc a                                                        71

<210> SEQ ID NO 406
<211> LENGTH: 71
<212> TYPE: DNA
<213> ORGANISM: Homo sapiens

<400> SEQUENCE: 406
gcatgggtgg ttcagtggta gaattctcgc ctgccacgcg ggaggcccgg gttcgattcc    60
cggcccatgc a                                                        71

<210> SEQ ID NO 407
<211> LENGTH: 71
<212> TYPE: DNA
<213> ORGANISM: Homo sapiens

<400> SEQUENCE: 407
gcatgggtgg ttcagtggta gaattctcgc ctgccacgcg ggaggcccgg gttcgattcc    60
cggcccatgc a                                                        71

<210> SEQ ID NO 408
<211> LENGTH: 72
<212> TYPE: DNA
<213> ORGANISM: Homo sapiens

<400> SEQUENCE: 408
gcgttggtgg tatagtggtg agcatagttg ccttccaagc agttgacccg ggctcgattc    60
ccgcccaacg ca                                                       72

<210> SEQ ID NO 409
<211> LENGTH: 72
<212> TYPE: DNA
<213> ORGANISM: Homo sapiens

<400> SEQUENCE: 409
gcgttggtgg tatagtggta agcatagctg ccttccaagc agttgacccg ggttcgattc    60
ccggccaacg ca                                                       72

<210> SEQ ID NO 410
<211> LENGTH: 72
<212> TYPE: DNA
<213> ORGANISM: Homo sapiens

<400> SEQUENCE: 410
gcgttggtgg tatagtggtg agcatagctg ccttccaagc agttgacccg ggttcgattc    60
ccggccaacg ca                                                        72

<210> SEQ ID NO 411
<211> LENGTH: 72
<212> TYPE: DNA
<213> ORGANISM: Homo sapiens

<400> SEQUENCE: 411
gcgttggtgg tatagtggtg agcatagctg ccttccaagc agttgacccg ggttcgattc    60
ccggccaacg ca                                                        72

<210> SEQ ID NO 412
<211> LENGTH: 72
<212> TYPE: DNA
<213> ORGANISM: Homo sapiens

<400> SEQUENCE: 412
gcgttggtgg tatagtggtg agcatagctg ccttccaagc agttgacccg ggttcgattc    60
ccggccaacg ca                                                        72

<210> SEQ ID NO 413
<211> LENGTH: 72
<212> TYPE: DNA
<213> ORGANISM: Homo sapiens

<400> SEQUENCE: 413
gcgttggtgg tatagtggtg agcatagctg ccttccaagc agttgacccg ggttcgattc    60
ccggccaacg ca                                                        72

<210> SEQ ID NO 414
<211> LENGTH: 72
<212> TYPE: DNA
<213> ORGANISM: Homo sapiens

<400> SEQUENCE: 414
gcgttggtgg tatagtggtg agcatagctg ccttccaagc agttgacccg ggttcgattc    60
ccggccaacg ca                                                        72

<210> SEQ ID NO 415
<211> LENGTH: 72
<212> TYPE: DNA
<213> ORGANISM: Homo sapiens

<400> SEQUENCE: 415
gcgttggtgg tatagtggtg agcatagctg ccttccaagc agttgacccg ggttcgattc    60
ccggccaacg ca                                                        72

<210> SEQ ID NO 416
<211> LENGTH: 72
<212> TYPE: DNA
<213> ORGANISM: Homo sapiens

<400> SEQUENCE: 416
gcgttggtgg tatagtggtt agcatagctg ccttccaagc agttgacccg ggttcgattc    60
ccggccaacg ca    72

<210> SEQ ID NO 417
<211> LENGTH: 72
<212> TYPE: DNA
<213> ORGANISM: Homo sapiens

<400> SEQUENCE: 417
gcagtgactg tatagtggtt agcactctgt gttgtggcca cagcaaccat ggttcaaatc    60
tgagtcatga ca    72

<210> SEQ ID NO 418
<211> LENGTH: 72
<212> TYPE: DNA
<213> ORGANISM: Homo sapiens

<400> SEQUENCE: 418
gccatgatcg tatagtggtt agtactctgc gctgtggccg cagcaacctc ggttcgaatc    60
cgagtcacgg ca    72

<210> SEQ ID NO 419
<211> LENGTH: 72
<212> TYPE: DNA
<213> ORGANISM: Homo sapiens

<400> SEQUENCE: 419
gccgtgatcg tatagtggtt agtactctgc gttgtggccg cagcaacctc ggttcgaatc    60
cgagtcacgg ca    72

<210> SEQ ID NO 420
<211> LENGTH: 72
<212> TYPE: DNA
<213> ORGANISM: Homo sapiens

<400> SEQUENCE: 420
gccgtgatcg tatagtggtt agtactctgc gttgtggccg cagcaacctc ggttcgaatc    60
cgagtcacgg ca    72

<210> SEQ ID NO 421
<211> LENGTH: 72
<212> TYPE: DNA
<213> ORGANISM: Homo sapiens

<400> SEQUENCE: 421
gccgtgatcg tatagtggtt agtactctgc gttgtggccg cagcaacctc ggttcgaatc    60
cgagtcacgg ca    72

<210> SEQ ID NO 422
<211> LENGTH: 72
<212> TYPE: DNA
<213> ORGANISM: Homo sapiens

<400> SEQUENCE: 422
gccgtgatcg tatagtggtt agtactctgc gttgtggccg cagcaacctc ggttcgaatc    60
cgagtcacgg ca    72

<210> SEQ ID NO 423

```
<211> LENGTH: 72
<212> TYPE: DNA
<213> ORGANISM: Homo sapiens

<400> SEQUENCE: 423
gccgtgatcg tatagtggtt agtactctgc gttgtggccg cagcaacctc ggttcgaatc    60
cgagtcacgg ca                                                       72

<210> SEQ ID NO 424
<211> LENGTH: 72
<212> TYPE: DNA
<213> ORGANISM: Homo sapiens

<400> SEQUENCE: 424
gccgtgatcg tatagtggtt agtactctgc gttgtggccg cagcaacctc ggttcgaatc    60
cgagtcacgg ca                                                       72

<210> SEQ ID NO 425
<211> LENGTH: 72
<212> TYPE: DNA
<213> ORGANISM: Homo sapiens

<400> SEQUENCE: 425
gccgtgatcg tatagtggtt agtactctgc gttgtggccg cagcaacctc ggttcgaatc    60
cgagtcacgg ca                                                       72

<210> SEQ ID NO 426
<211> LENGTH: 72
<212> TYPE: DNA
<213> ORGANISM: Homo sapiens

<400> SEQUENCE: 426
gccgtgatcg tatagtggtt agtactctgc gttgtggccg cagcaacctc ggttcgaatc    60
cgagtcacgg ca                                                       72

<210> SEQ ID NO 427
<211> LENGTH: 72
<212> TYPE: DNA
<213> ORGANISM: Homo sapiens

<400> SEQUENCE: 427
gccgtgatcg tatagtggtt agtactctgc gttgtggccg cagcaacctc ggttcgaatc    60
cgagtcacgg ca                                                       72

<210> SEQ ID NO 428
<211> LENGTH: 74
<212> TYPE: DNA
<213> ORGANISM: Homo sapiens

<400> SEQUENCE: 428
ggctggttag ttcagttggt tagagcgtgg tgctaataac gccaaggtcg tgggttcgat    60
ccccatatcg gcca                                                     74

<210> SEQ ID NO 429
<211> LENGTH: 74
<212> TYPE: DNA
<213> ORGANISM: Homo sapiens

<400> SEQUENCE: 429
ggccggttag ctcagtcggc tagagcgtgg tgctaataac gccaaggtcg cgggttcgat    60
``` cccgtacgg gcca 74

<210> SEQ ID NO 430
<211> LENGTH: 74
<212> TYPE: DNA
<213> ORGANISM: Homo sapiens

<400> SEQUENCE: 430
ggccggttag ctcagttggt cagagcgtgg tgctaataac gccaaggtcg cgggttcgat   60
ccccgtacgg gcca   74

<210> SEQ ID NO 431
<211> LENGTH: 74
<212> TYPE: DNA
<213> ORGANISM: Homo sapiens

<400> SEQUENCE: 431
ggccggttag ctcagttggt cagagcgtgg tgctaataac gccaaggtcg cgggttcgat   60
ccccgtacgg gcca   74

<210> SEQ ID NO 432
<211> LENGTH: 74
<212> TYPE: DNA
<213> ORGANISM: Homo sapiens

<400> SEQUENCE: 432
ggccggttag ctcagttggt tagagcgtgg tgctaataac gctaaggtcg cgggttcgat   60
ccccgtactg gcca   74

<210> SEQ ID NO 433
<211> LENGTH: 74
<212> TYPE: DNA
<213> ORGANISM: Homo sapiens

<400> SEQUENCE: 433
ggccggttag ctcagttggt tagagcgtgg tgctaataac gccaaggtcg cgggttcgat   60
ccccgtacgg gcca   74

<210> SEQ ID NO 434
<211> LENGTH: 74
<212> TYPE: DNA
<213> ORGANISM: Homo sapiens

<400> SEQUENCE: 434
ggccggttag ctcagttggt tagagcgtgg tgctaataac gccaaggtcg cgggttcgat   60
ccccgtacgg gcca   74

<210> SEQ ID NO 435
<211> LENGTH: 74
<212> TYPE: DNA
<213> ORGANISM: Homo sapiens

<400> SEQUENCE: 435
ggccggttag ctcagttggt tagagcgtgg tgctaataac gccaaggtcg cgggttcgat   60
ccccgtacgg gcca   74

<210> SEQ ID NO 436
<211> LENGTH: 74
<212> TYPE: DNA

<213> ORGANISM: Homo sapiens

<400> SEQUENCE: 436

```
ggccggttag ctcagttggt tagagcgtgg tgctaataac gccaaggtcg cgggttcgat    60
ccccgtacgg gcca                                                      74
```

<210> SEQ ID NO 437
<211> LENGTH: 74
<212> TYPE: DNA
<213> ORGANISM: Homo sapiens

<400> SEQUENCE: 437

```
ggccggttag ctcagttggt tagagcgtgg tgctaataac gccaaggtcg cgggttcgat    60
ccccgtacgg gcca                                                      74
```

<210> SEQ ID NO 438
<211> LENGTH: 74
<212> TYPE: DNA
<213> ORGANISM: Homo sapiens

<400> SEQUENCE: 438

```
ggccggttag ctcagttggt tagagcgtgg tgctaataac gccaaggtcg cgggttcgaa    60
ccccgtacgg gcca                                                      74
```

<210> SEQ ID NO 439
<211> LENGTH: 74
<212> TYPE: DNA
<213> ORGANISM: Homo sapiens

<400> SEQUENCE: 439

```
ggctggttag ctcagttggt tagagcgtgg tgctaataac gccaaggtcg cgggttcgat    60
ccccgtactg gcca                                                      74
```

<210> SEQ ID NO 440
<211> LENGTH: 74
<212> TYPE: DNA
<213> ORGANISM: Homo sapiens

<400> SEQUENCE: 440

```
ggccggttag ctcagttggt tagagcgtgg tgctaataac gccaaggtcg cgggttcgat    60
ccccgtactg gcca                                                      74
```

<210> SEQ ID NO 441
<211> LENGTH: 74
<212> TYPE: DNA
<213> ORGANISM: Homo sapiens

<400> SEQUENCE: 441

```
ggccggttag ctcagttggt tagagcgtgg cgctaataac gccaaggtcg cgggttcgat    60
ccccgtacgg gcca                                                      74
```

<210> SEQ ID NO 442
<211> LENGTH: 74
<212> TYPE: DNA
<213> ORGANISM: Homo sapiens

<400> SEQUENCE: 442

```
ggccggttag ctcagttggt aagagcgtgg tgctgataac accaaggtcg cgggctcgac    60
tcccgcaccg gcca                                                      74
```

-continued

<210> SEQ ID NO 443
<211> LENGTH: 74
<212> TYPE: DNA
<213> ORGANISM: Homo sapiens

<400> SEQUENCE: 443
ggccggttag ctcagttggt aagagcgtgg tgctgataac accaaggtcg cgggctcgac    60
tcccgcaccg gcca                                                      74

<210> SEQ ID NO 444
<211> LENGTH: 74
<212> TYPE: DNA
<213> ORGANISM: Homo sapiens

<400> SEQUENCE: 444
ggccggttag ctcagttggt aagagcgtgg tgctgataac accaaggtcg cgggctcgac    60
tcccgcaccg gcca                                                      74

<210> SEQ ID NO 445
<211> LENGTH: 74
<212> TYPE: DNA
<213> ORGANISM: Homo sapiens

<400> SEQUENCE: 445
ggccggttag ctcagttggt aagagcgtgg tgctgataac accaaggtcg cgggctcgac    60
tcccgcaccg gcca                                                      74

<210> SEQ ID NO 446
<211> LENGTH: 74
<212> TYPE: DNA
<213> ORGANISM: Homo sapiens

<400> SEQUENCE: 446
ggccggttag ctcagttggt aagagcgtgg tgctgataac accaaggtcg cgggctcgac    60
tcccgcaccg gcca                                                      74

<210> SEQ ID NO 447
<211> LENGTH: 74
<212> TYPE: DNA
<213> ORGANISM: Homo sapiens

<400> SEQUENCE: 447
ggccggttag ctcagttggt aagagcgtgg tgctgataac accaaggtcg cgggctcgac    60
tcccgcaccg gcca                                                      74

<210> SEQ ID NO 448
<211> LENGTH: 74
<212> TYPE: DNA
<213> ORGANISM: Homo sapiens

<400> SEQUENCE: 448
ggccggttag ctcagttggt aagagcgtgg tgctgataac accaaggtcg cgggctcgac    60
tcccgcaccg gcca                                                      74

<210> SEQ ID NO 449
<211> LENGTH: 74
<212> TYPE: DNA
<213> ORGANISM: Homo sapiens

<400> SEQUENCE: 449
ggccggttag ctcagttggt aagagcgtgg tgctgataac accaaggtcg cgggctcgac    60
tcccgcaccg gcca                                                      74

<210> SEQ ID NO 450
<211> LENGTH: 94
<212> TYPE: DNA
<213> ORGANISM: Homo sapiens

<400> SEQUENCE: 450
gctccagtgg cgcaatcggt tagcgcgcgg tacttatatg gcagtatgtg tgcgagtgat    60
gccgaggttg tgagttcgag cctcacctgg agca                                94

<210> SEQ ID NO 451
<211> LENGTH: 94
<212> TYPE: DNA
<213> ORGANISM: Homo sapiens

<400> SEQUENCE: 451
gctccagtgg cgcaatcggt tagcgcgcgg tacttataca acagtatatg tgcgggtgat    60
gccgaggttg tgagttcgag cctcacctgg agca                                94

<210> SEQ ID NO 452
<211> LENGTH: 94
<212> TYPE: DNA
<213> ORGANISM: Homo sapiens

<400> SEQUENCE: 452
gctccagtgg cgcaatcggt tagcgcgcgg tacttataag acagtgcacc tgtgagcaat    60
gccgaggttg tgagttcaag cctcacctgg agca                                94

<210> SEQ ID NO 453
<211> LENGTH: 93
<212> TYPE: DNA
<213> ORGANISM: Homo sapiens

<400> SEQUENCE: 453
gctccagtgg cgcaatcggt tagcgcgcgg tacttataca gcagtacatg cagagcaatg    60
ccgaggttgt gagttcgagc ctcacctgga gca                                 93

<210> SEQ ID NO 454
<211> LENGTH: 93
<212> TYPE: DNA
<213> ORGANISM: Homo sapiens

<400> SEQUENCE: 454
gctccagtgg cgcaatcggt tagcgcgcgg tacttatatg acagtgcgag cggagcaatg    60
ccgaggttgt gagttcgatc ctcacctgga gca                                 93

<210> SEQ ID NO 455
<211> LENGTH: 82
<212> TYPE: DNA
<213> ORGANISM: Homo sapiens

<400> SEQUENCE: 455
ggtagcatgg ctgagtggtc taagattctg aattaagtct ccagtctctt tgggggcgtg    60
gttttcaatc ccaccgctgc ta                                             82

```
<210> SEQ ID NO 456
<211> LENGTH: 82
<212> TYPE: DNA
<213> ORGANISM: Homo sapiens

<400> SEQUENCE: 456
ggtagggtgg ccgagcggtc taaggcactg tattaagact ccagtctctt cagaggcatg    60 ggttttgaatc ccactgctgc ca                                            82

<210> SEQ ID NO 457
<211> LENGTH: 73
<212> TYPE: DNA
<213> ORGANISM: Homo sapiens

<400> SEQUENCE: 457
gggccagtgg ctcaatggat aatgcgtctg actaagaatc agaagattcc agccttgact    60
cctggctggc tca                                                       73

<210> SEQ ID NO 458
<211> LENGTH: 82
<212> TYPE: DNA
<213> ORGANISM: Homo sapiens

<400> SEQUENCE: 458
ggtagcgtgg ccgagtggtc taagacgctg gattaaggct ccagtctctt cggggcgtg     60 ggtttgaatc ccaccgctgc ca                                             82

<210> SEQ ID NO 459
<211> LENGTH: 82
<212> TYPE: DNA
<213> ORGANISM: Homo sapiens

<400> SEQUENCE: 459
ggtagcgtgg ccgagcggtc taaggcgctg gattaaggct ccagtctctt cggggcgtg     60 ggttcaaatc ccaccgctgc ca                                             82

<210> SEQ ID NO 460
<211> LENGTH: 82
<212> TYPE: DNA
<213> ORGANISM: Homo sapiens

<400> SEQUENCE: 460
ggtagcgtgg ccgagcggtc taaggcgctg gattaaggct ccagtctctt cggggcgtg     60 ggttcgaatc ccaccgctgc ca                                             82

<210> SEQ ID NO 461
<211> LENGTH: 82
<212> TYPE: DNA
<213> ORGANISM: Homo sapiens

<400> SEQUENCE: 461
ggtagcgtgg ccgagcggtc taaggcgctg gattaaggct ccagtctctt cggggcgtg     60 ggttcgaatc ccaccgctgc ca                                             82

<210> SEQ ID NO 462
<211> LENGTH: 82
<212> TYPE: DNA
<213> ORGANISM: Homo sapiens

<400> SEQUENCE: 462
```

```
ggtagcgtgg ccgagcggtc taaggcgctg gattaaggct ccagtctctt cggggcgtg      60 ggttcgaatc ccaccgctgc ca                                              82
```

<210> SEQ ID NO 463
<211> LENGTH: 82
<212> TYPE: DNA
<213> ORGANISM: Homo sapiens

<400> SEQUENCE: 463

```
ggtagcgtgg ccgagcggtc taaggcgctg gattaaggct ccagtctctt cggggcgtg      60 ggttcgaatc ccaccgctgc ca                                              82
```

<210> SEQ ID NO 464
<211> LENGTH: 82
<212> TYPE: DNA
<213> ORGANISM: Homo sapiens

<400> SEQUENCE: 464

```
ggtagcgtgg ccgagcggtc taaggcgctg gattaaggct ccagtctctt cggaggcgtg      60
ggttcgaatc ccaccgctgc ca                                              82
```

<210> SEQ ID NO 465
<211> LENGTH: 82
<212> TYPE: DNA
<213> ORGANISM: Homo sapiens

<400> SEQUENCE: 465

```
ggtagcgtgg ccgagcggtc taaggcgctg gattaaggct ccagtctctt cggaggcgtg      60
ggttcgaatc ccaccgctgc ca                                              82
```

<210> SEQ ID NO 466
<211> LENGTH: 82
<212> TYPE: DNA
<213> ORGANISM: Homo sapiens

<400> SEQUENCE: 466

```
ggtagcgtgg ccgagcggtc taaggcgctg gattaaggct ccagtctctt cggaggcgtg      60
ggttcgaatc ccaccgctgc ca                                              82
```

<210> SEQ ID NO 467
<211> LENGTH: 84
<212> TYPE: DNA
<213> ORGANISM: Homo sapiens

<400> SEQUENCE: 467

```
gtcaggatgg ccgagcagtc ttaaggcgct gcgttcaaat cgcaccctcc gctggaggcg      60
tgggttcgaa tcccactttt gaca                                            84
```

<210> SEQ ID NO 468
<211> LENGTH: 74
<212> TYPE: DNA
<213> ORGANISM: Homo sapiens

<400> SEQUENCE: 468

```
gcctccttag tgcagtaggt agcgcatcag tctcaaaatc tgaatggtcc tgagttcaag      60
cctcagaggg ggca                                                       74
```

<210> SEQ ID NO 469
<211> LENGTH: 106

```
<212> TYPE: DNA
<213> ORGANISM: Homo sapiens

<400> SEQUENCE: 469
gtcaggatgg ccgagtggtc taaggcgcca gactcaaggt aagcaccttg cctgcgggct      60
ttctggtctc cggatggagg cgtgggttcg aatcccactt ctgaca                   106

<210> SEQ ID NO 470
<211> LENGTH: 107
<212> TYPE: DNA
<213> ORGANISM: Homo sapiens

<400> SEQUENCE: 470
gtcaggatgg ccgagtggtc taaggcgcca gactcaagtt gctacttccc aggtttgggg      60
cttctggtct ccgcatggag gcgtgggttc gaatcccact tctgaca                  107

<210> SEQ ID NO 471
<211> LENGTH: 108
<212> TYPE: DNA
<213> ORGANISM: Homo sapiens

<400> SEQUENCE: 471
gtcaggatgg ccgagtggtc taaggcgcca gactcaagct tactgcttcc tgtgttcggg      60
tcttctggtc tccgtatgga ggcgtgggtt cgaatcccac ttctgaca                 108

<210> SEQ ID NO 472
<211> LENGTH: 106
<212> TYPE: DNA
<213> ORGANISM: Homo sapiens

<400> SEQUENCE: 472
gtcaggatgg ccgagtggtc taaggcgcca gactcaagct aagcttcctc cgcggtgggg      60
attctggtct ccaatggagg cgtgggttcg aatcccactt ctgaca                   106

<210> SEQ ID NO 473
<211> LENGTH: 105
<212> TYPE: DNA
<213> ORGANISM: Homo sapiens

<400> SEQUENCE: 473
gtcaggatgg ccgagtggtc taaggcgcca gactcaagct tggcttcctc gtgttgagga      60
ttctggtctc caatggaggc gtgggttcga atcccacttc tgaca                    105

<210> SEQ ID NO 474
<211> LENGTH: 78
<212> TYPE: DNA
<213> ORGANISM: Homo sapiens

<400> SEQUENCE: 474
ggcagtggag tttagtggtt aaggacctgc tcagacatca caggtaggta gatctgggtt      60
caaaccctag ccctggca                                                   78

<210> SEQ ID NO 475
<211> LENGTH: 83
<212> TYPE: DNA
<213> ORGANISM: Homo sapiens

<400> SEQUENCE: 475
gtcaggatgg ccgagcggtc taaggcgctg cgttcaggtc gcagtctccc ctggaggcgt      60
```

```
gggttcgaat cccacttctg aca                                            83
```

<210> SEQ ID NO 476
<211> LENGTH: 83
<212> TYPE: DNA
<213> ORGANISM: Homo sapiens

<400> SEQUENCE: 476

```
gtcaggatgg ccgagcggtc taaggcgctg cgttcaggtc gcagtctccc ctggaggcgt    60
gggttcgaat cccacttctg aca                                            83
```

<210> SEQ ID NO 477
<211> LENGTH: 83
<212> TYPE: DNA
<213> ORGANISM: Homo sapiens

<400> SEQUENCE: 477

```
gtcaggatgg ccgagcggtc taaggcgctg cgttcaggtc gcagtctccc ctggaggcgt    60
gggttcgaat cccactcctg aca                                            83
```

<210> SEQ ID NO 478
<211> LENGTH: 83
<212> TYPE: DNA
<213> ORGANISM: Homo sapiens

<400> SEQUENCE: 478

```
gtcaggatgg ccgagcggtc taaggcgctg cgttcaggtc gcagtctccc ctggaggcgt    60
gggttcgaat cccactcctg aca                                            83
```

<210> SEQ ID NO 479
<211> LENGTH: 83
<212> TYPE: DNA
<213> ORGANISM: Homo sapiens

<400> SEQUENCE: 479

```
gtcaggatgg ccgagcggtc taaggcgctg cgttcaggtc gcagtctccc ctggaggcgt    60
gggttcgaat cccactcctg aca                                            83
```

<210> SEQ ID NO 480
<211> LENGTH: 83
<212> TYPE: DNA
<213> ORGANISM: Homo sapiens

<400> SEQUENCE: 480

```
gtcaggatgg ccgagcggtc taaggcgctg cgttcaggtc gcagtctccc ctggaggcgt    60
gggttcgaat cccactcctg aca                                            83
```

<210> SEQ ID NO 481
<211> LENGTH: 83
<212> TYPE: DNA
<213> ORGANISM: Homo sapiens

<400> SEQUENCE: 481

```
gtcaggatgg ccgagcggtc taaggcgctg cgttcaggtc gcagtctccc ctggaggcgt    60
gggttcgaat cccactcctg aca                                            83
```

<210> SEQ ID NO 482
<211> LENGTH: 83
<212> TYPE: DNA
<213> ORGANISM: Homo sapiens

```
<400> SEQUENCE: 482
gtcaggatgg ccgagcggtc taaggcgctg cgttcaggtc gcagtctccc ctggaggcgt     60
gggttcgaat cccactcctg aca                                             83

<210> SEQ ID NO 483
<211> LENGTH: 83
<212> TYPE: DNA
<213> ORGANISM: Homo sapiens

<400> SEQUENCE: 483
gtcaggatgg ccgagcggtc taaggcgctg cgttcaggtc gcagtctccc ctggaggcgt     60
gggttcgaat cccactcctg aca                                             83

<210> SEQ ID NO 484
<211> LENGTH: 75
<212> TYPE: DNA
<213> ORGANISM: Homo sapiens

<400> SEQUENCE: 484
gttaagatgg cagagcccgg caattgcata agacttaaaa ctttataatc agaggttcaa     60
ctcctctcat taaca                                                      75

<210> SEQ ID NO 485
<211> LENGTH: 83
<212> TYPE: DNA
<213> ORGANISM: Homo sapiens

<400> SEQUENCE: 485
actcatttgg ctgagtggtt aaggcattgg acttaagatc caatggagta gtggctgtgt     60 gggttttaaac cccactactg gta                                            83

<210> SEQ ID NO 486
<211> LENGTH: 75
<212> TYPE: DNA
<213> ORGANISM: Homo sapiens

<400> SEQUENCE: 486
gttaagatgg cagagcctgg taattgcata aaacttaaaa ttttataatc agaggttcaa     60
ctcctcttct taaca                                                      75

<210> SEQ ID NO 487
<211> LENGTH: 83
<212> TYPE: DNA
<213> ORGANISM: Homo sapiens

<400> SEQUENCE: 487
accgggatgg ctgagtggtt aaggcgttgg acttaagatc caatggacag gtgtccgcgt     60
gggttcgagc cccactcccg gta                                             83

<210> SEQ ID NO 488
<211> LENGTH: 83
<212> TYPE: DNA
<213> ORGANISM: Homo sapiens

<400> SEQUENCE: 488
accagaatgg ccgagtggtt aaggcgttgg acttaagatc caatggattc atatccgcgt     60
gggttcgaac cccacttctg gta                                             83
```

<210> SEQ ID NO 489
<211> LENGTH: 83
<212> TYPE: DNA
<213> ORGANISM: Homo sapiens

<400> SEQUENCE: 489
accgggatgg ccgagtggtt aaggcgttgg acttaagatc caatgggctg gtgcccgcgt    60
gggttcgaac cccactctcg gta                                            83

<210> SEQ ID NO 490
<211> LENGTH: 83
<212> TYPE: DNA
<213> ORGANISM: Homo sapiens

<400> SEQUENCE: 490
accaggatgg ccgagtggtt aaggcgttgg acttaagatc caatggacat atgtccgcgt    60
gggttcgaac cccactcctg gta                                            83

<210> SEQ ID NO 491
<211> LENGTH: 82
<212> TYPE: DNA
<213> ORGANISM: Homo sapiens

<400> SEQUENCE: 491
ggtagcgtgg ccgagtggtc taaggcgctg gatttaggct ccagtcattt cgatggcgtg    60
ggttcgaatc ccaccgctgc ca                                             82

<210> SEQ ID NO 492
<211> LENGTH: 82
<212> TYPE: DNA
<213> ORGANISM: Homo sapiens

<400> SEQUENCE: 492
ggtagtgtgg ccgagcggtc taaggcgctg gatttaggct ccagtctctt cggggcgtg    60 ggttcgaatc ccaccactgc ca                                             82

<210> SEQ ID NO 493
<211> LENGTH: 82
<212> TYPE: DNA
<213> ORGANISM: Homo sapiens

<400> SEQUENCE: 493
ggtagcgtgg ccgagcggtc taaggcgctg gatttaggct ccagtctctt cggaggcgtg    60
ggttcgaatc ccaccgctgc ca                                             82

<210> SEQ ID NO 494
<211> LENGTH: 73
<212> TYPE: DNA
<213> ORGANISM: Homo sapiens

<400> SEQUENCE: 494
aaccgaatag cttagttgat gaagcgtgag actcttaatc tcagggtagt gggttcaagc    60
cccacattgg aca                                                       73

<210> SEQ ID NO 495
<211> LENGTH: 73
<212> TYPE: DNA
<213> ORGANISM: Homo sapiens

<400> SEQUENCE: 495
ctgcagctag ctcagtcggt agagcatgag actcttaatc tcagggtcat gggttcgtgc    60
cccatgttgg gtg                                                       73

<210> SEQ ID NO 496
<211> LENGTH: 73
<212> TYPE: DNA
<213> ORGANISM: Homo sapiens

<400> SEQUENCE: 496
gcccagctag ctcagtcggt agagcataag actcttaatc tcagggttgt ggattcgtgc    60
cccatgctgg gtg                                                       73

<210> SEQ ID NO 497
<211> LENGTH: 73
<212> TYPE: DNA
<213> ORGANISM: Homo sapiens

<400> SEQUENCE: 497
gcccgactac ctcagtcggt ggagcatggg actcttcatc ccagggttgt gggttcgagc    60
cccacattgg gca                                                       73

<210> SEQ ID NO 498
<211> LENGTH: 73
<212> TYPE: DNA
<213> ORGANISM: Homo sapiens

<400> SEQUENCE: 498
gcctggctag ctcagtcggc aaagcatgag actcttaatc tcagggtcgt gggctcgagc    60
tccatgttgg gcg                                                       73

<210> SEQ ID NO 499
<211> LENGTH: 73
<212> TYPE: DNA
<213> ORGANISM: Homo sapiens

<400> SEQUENCE: 499
gcccagctag ctcagtcggt agagcatgag actcttaatc tcagggtcat gggtttgagc    60
cccacgtttg gtg                                                       73

<210> SEQ ID NO 500
<211> LENGTH: 73
<212> TYPE: DNA
<213> ORGANISM: Homo sapiens

<400> SEQUENCE: 500
gacgagctag ctcagtcggt agagcatggg actcttaatc ccagggtcgt gggtttgagc    60
cccatgttgg gca                                                       73

<210> SEQ ID NO 501
<211> LENGTH: 73
<212> TYPE: DNA
<213> ORGANISM: Homo sapiens

<400> SEQUENCE: 501
gcccggctag ctcagtcgat agagcatgag actcttaatc tcagggtcgt gggttcgagc    60
cgcacgttgg gcg                                                       73

<210> SEQ ID NO 502

<211> LENGTH: 73
<212> TYPE: DNA
<213> ORGANISM: Homo sapiens

<400> SEQUENCE: 502
gcccggctag ctcagtcggt agagcatggg actcttaatc tcagggtcgt gggttcgagc    60
cccacgttgg gcg                                                      73

<210> SEQ ID NO 503
<211> LENGTH: 73
<212> TYPE: DNA
<213> ORGANISM: Homo sapiens

<400> SEQUENCE: 503
gcccggctag ctcagtcggt agagcatgag acccttaatc tcagggtcgt gggttcgagc    60
cccacgttgg gcg                                                      73

<210> SEQ ID NO 504
<211> LENGTH: 73
<212> TYPE: DNA
<213> ORGANISM: Homo sapiens

<400> SEQUENCE: 504
gcccggctag ctcagtcggt agagcatgag actcttaatc tcagggtcgt gggttcgagc    60
cccacgttgg gcg                                                      73

<210> SEQ ID NO 505
<211> LENGTH: 73
<212> TYPE: DNA
<213> ORGANISM: Homo sapiens

<400> SEQUENCE: 505
gcccggctag ctcagtcggt agagcatgag actcttaatc tcagggtcgt gggttcgagc    60
cccacgttgg gcg                                                      73

<210> SEQ ID NO 506
<211> LENGTH: 73
<212> TYPE: DNA
<213> ORGANISM: Homo sapiens

<400> SEQUENCE: 506
gcccggctag ctcagtcggt agagcatgag actcttaatc tcagggtcgt gggttcgagc    60
cccacgttgg gcg                                                      73

<210> SEQ ID NO 507
<211> LENGTH: 73
<212> TYPE: DNA
<213> ORGANISM: Homo sapiens

<400> SEQUENCE: 507
gcccggctag ctcagtcggt agagcatgag actcttaatc tcagggtcgt gggttcgagc    60
cccacgttgg gcg                                                      73

<210> SEQ ID NO 508
<211> LENGTH: 73
<212> TYPE: DNA
<213> ORGANISM: Homo sapiens

<400> SEQUENCE: 508
gcccggctag ctcagtcggt agagcatgag actcttaatc tcagggtcgt gggttcgagc    60

-continued

```
cccacgttgg gcg                                                        73

<210> SEQ ID NO 509
<211> LENGTH: 73
<212> TYPE: DNA
<213> ORGANISM: Homo sapiens

<400> SEQUENCE: 509
gcccggctag ctcagtcggt agagcatggg actcttaatc ccagggtcgt gggttcgagc    60
cccacgttgg gcg                                                        73

<210> SEQ ID NO 510
<211> LENGTH: 73
<212> TYPE: DNA
<213> ORGANISM: Homo sapiens

<400> SEQUENCE: 510
gcccggctag ctcagtcggt agagcatggg actcttaatc ccagggtcgt gggttcgagc    60
cccacgttgg gcg                                                        73

<210> SEQ ID NO 511
<211> LENGTH: 71
<212> TYPE: DNA
<213> ORGANISM: Homo sapiens

<400> SEQUENCE: 511
accctgtggt acaggggcta atatgctggg cctttaccac ttcagcccag gttcgattcc    60
tggtcaggga a                                                          71

<210> SEQ ID NO 512
<211> LENGTH: 73
<212> TYPE: DNA
<213> ORGANISM: Homo sapiens

<400> SEQUENCE: 512
acctgggtag cttagttggt agagcattgg acttttaatt tgagggccca ggtttcaagt    60
ccctgtttgg gtg                                                        73

<210> SEQ ID NO 513
<211> LENGTH: 73
<212> TYPE: DNA
<213> ORGANISM: Homo sapiens

<400> SEQUENCE: 513
acccagatag ctcagtcagt agagcatcag acttttaatc tgagggtcca aggttcatgt    60
ccctttttgg gtg                                                        73

<210> SEQ ID NO 514
<211> LENGTH: 73
<212> TYPE: DNA
<213> ORGANISM: Homo sapiens

<400> SEQUENCE: 514
acctgggtag ctcagtaggt agaacatcag acttttaatc tgagggtcta gggttcaagt    60
ccctgtccag gcg                                                        73

<210> SEQ ID NO 515
<211> LENGTH: 73
<212> TYPE: DNA
```

<213> ORGANISM: Homo sapiens

<400> SEQUENCE: 515
gcccggagag ctcagtgggt agagcatcag acttttaatc tgagggtcca gggttcaagt    60
cctcgttcgg gca    73

<210> SEQ ID NO 516
<211> LENGTH: 77
<212> TYPE: DNA
<213> ORGANISM: Homo sapiens

<400> SEQUENCE: 516
gcccacgtag ctcaatggtc agagcgtgcg gcttttaacc gcaaggaagg ctgcgagttc    60
gaccctcgcc gtgggct    77

<210> SEQ ID NO 517
<211> LENGTH: 73
<212> TYPE: DNA
<213> ORGANISM: Homo sapiens

<400> SEQUENCE: 517
gcctggatag ctcagttggt agaacatcag acttttaatc tgacggtgca gggttcaagt    60
ccctgttcag gcg    73

<210> SEQ ID NO 518
<211> LENGTH: 73
<212> TYPE: DNA
<213> ORGANISM: Homo sapiens

<400> SEQUENCE: 518
gcctgggtag ctcagtcggt agagcatcag acttttaatc tgagggtcca gggttcaagt    60
ccctgtccag gcg    73

<210> SEQ ID NO 519
<211> LENGTH: 73
<212> TYPE: DNA
<213> ORGANISM: Homo sapiens

<400> SEQUENCE: 519
gcccggatag ctcagtcggt agagcatcag acttttaatc tgagggtccg gggttcaagt    60
ccctgttcgg gcg    73

<210> SEQ ID NO 520
<211> LENGTH: 73
<212> TYPE: DNA
<213> ORGANISM: Homo sapiens

<400> SEQUENCE: 520
gcctggatag ctcagtcggt agagcatcag acttttaatc tgagggtcca gggttcaagt    60
ccctgttcag gcg    73

<210> SEQ ID NO 521
<211> LENGTH: 73
<212> TYPE: DNA
<213> ORGANISM: Homo sapiens

<400> SEQUENCE: 521
gcccggatag ctcagtcggt agagcatcag acttttaatc tgagggtcca gggttcaagt    60
ccctgttcgg gcg    73

<210> SEQ ID NO 522
<211> LENGTH: 73
<212> TYPE: DNA
<213> ORGANISM: Homo sapiens

<400> SEQUENCE: 522
gcccggatag ctcagtcggt agagcatcag acttttaatc tgagggtcca gggttcaagt    60
ccctgttcgg gcg                                                        73

<210> SEQ ID NO 523
<211> LENGTH: 73
<212> TYPE: DNA
<213> ORGANISM: Homo sapiens

<400> SEQUENCE: 523
gcccggatag ctcagtcggt agagcatcag acttttaatc tgagggtcca gggttcaagt    60
ccctgttcgg gcg                                                        73

<210> SEQ ID NO 524
<211> LENGTH: 73
<212> TYPE: DNA
<213> ORGANISM: Homo sapiens

<400> SEQUENCE: 524
gcccggatag ctcagtcggt agagcatcag acttttaatc tgagggtcca gggttcaagt    60
ccctgttcgg gcg                                                        73

<210> SEQ ID NO 525
<211> LENGTH: 73
<212> TYPE: DNA
<213> ORGANISM: Homo sapiens

<400> SEQUENCE: 525
gcccggatag ctcagtcggt agagcatcag acttttaatc tgagggtcca gggttcaagt    60
ccctgttcgg gcg                                                        73

<210> SEQ ID NO 526
<211> LENGTH: 73
<212> TYPE: DNA
<213> ORGANISM: Homo sapiens

<400> SEQUENCE: 526
gcctggatag ctcagttggt agagcatcag acttttaatc tgagggtcca gggttcaagt    60
ccctgttcag gcg                                                        73

<210> SEQ ID NO 527
<211> LENGTH: 73
<212> TYPE: DNA
<213> ORGANISM: Homo sapiens

<400> SEQUENCE: 527
gcctggatag ctcagttggt agagcatcag acttttaatc tgagggtcca gggttcaagt    60
ccctgttcag gca                                                        73

<210> SEQ ID NO 528
<211> LENGTH: 75
<212> TYPE: DNA
<213> ORGANISM: Homo sapiens

<400> SEQUENCE: 528
agcagagtgg tgcagtggaa gcatacctat gggcccataa cccagaggtt gatggatgga    60
aaccatcctc tgcta    75

<210> SEQ ID NO 529
<211> LENGTH: 72
<212> TYPE: DNA
<213> ORGANISM: Homo sapiens

<400> SEQUENCE: 529
agcagagtgg cgcagcggaa gcgtgctggg cccataaccc agaggtcgat ggatctaaac    60
catcctctgc ta    72

<210> SEQ ID NO 530
<211> LENGTH: 73
<212> TYPE: DNA
<213> ORGANISM: Homo sapiens

<400> SEQUENCE: 530
gccctcttag tgcagctggc agcgcgtcag tttcataatc tgaaagtcct gagttcaagc    60
ctcagagagg gca    73

<210> SEQ ID NO 531
<211> LENGTH: 72
<212> TYPE: DNA
<213> ORGANISM: Homo sapiens

<400> SEQUENCE: 531
agcagagtgg cgcagcggaa gcgtgctggg cccataaccc agaggtcgat ggatcgaaac    60
catcctctgc ta    72

<210> SEQ ID NO 532
<211> LENGTH: 72
<212> TYPE: DNA
<213> ORGANISM: Homo sapiens

<400> SEQUENCE: 532
agcagagtgg cgcagcggaa gcgtgctggg cccataaccc agaggtcgat ggatcgaaac    60
catcctctgc ta    72

<210> SEQ ID NO 533
<211> LENGTH: 72
<212> TYPE: DNA
<213> ORGANISM: Homo sapiens

<400> SEQUENCE: 533
agcagagtgg cgcagcggaa gcgtgctggg cccataaccc agaggtcgat ggatcgaaac    60
catcctctgc ta    72

<210> SEQ ID NO 534
<211> LENGTH: 72
<212> TYPE: DNA
<213> ORGANISM: Homo sapiens

<400> SEQUENCE: 534
agcagagtgg cgcagcggaa gcgtgctggg cccataaccc agaggtcgat ggatcgaaac    60
catcctctgc ta    72

```
<210> SEQ ID NO 535
<211> LENGTH: 72
<212> TYPE: DNA
<213> ORGANISM: Homo sapiens

<400> SEQUENCE: 535
agcagagtgg cgcagcggaa gcgtgctggg cccataaccc agaggtcgat ggatcgaaac      60
catcctctgc ta                                                         72

<210> SEQ ID NO 536
<211> LENGTH: 72
<212> TYPE: DNA
<213> ORGANISM: Homo sapiens

<400> SEQUENCE: 536
agcagagtgg cgcagcggaa gcgtgctggg cccataaccc agaggtcgat ggatcgaaac      60
catcctctgc ta                                                         72

<210> SEQ ID NO 537
<211> LENGTH: 72
<212> TYPE: DNA
<213> ORGANISM: Homo sapiens

<400> SEQUENCE: 537
agcagagtgg cgcagcggaa gcgtgctggg cccataaccc agaggtcgat ggatcgaaac      60
catcctctgc ta                                                         72

<210> SEQ ID NO 538
<211> LENGTH: 72
<212> TYPE: DNA
<213> ORGANISM: Homo sapiens

<400> SEQUENCE: 538
agcagagtgg cgcagcggaa gcgtgctggg cccataaccc agaggtcgat ggatcgaaac      60
catcctctgc ta                                                         72

<210> SEQ ID NO 539
<211> LENGTH: 73
<212> TYPE: DNA
<213> ORGANISM: Homo sapiens

<400> SEQUENCE: 539
gcctcgttag cgcagtaggc agcgcgtcag tctcataatc tgaaggtcgt gagttcgagc      60
ctcacacggg gca                                                        73

<210> SEQ ID NO 540
<211> LENGTH: 73
<212> TYPE: DNA
<213> ORGANISM: Homo sapiens

<400> SEQUENCE: 540
gccctcttag cgcagctggc agcgcgtcag tctcataatc tgaaggtcct gagttcaagc      60
ctcagagagg gca                                                        73

<210> SEQ ID NO 541
<211> LENGTH: 73
<212> TYPE: DNA
<213> ORGANISM: Homo sapiens

<400> SEQUENCE: 541
```

```
gccctcttag cgcagcgggc agcgcgtcag tctcataatc tgaaggtcct gagttcgagc    60
ctcagagagg gca                                                       73

<210> SEQ ID NO 542
<211> LENGTH: 73
<212> TYPE: DNA
<213> ORGANISM: Homo sapiens

<400> SEQUENCE: 542
gccctcttag cgcagcgggc agcgcgtcag tctcataatc tgaaggtcct gagttcgagc    60
ctcagagagg gca                                                       73

<210> SEQ ID NO 543
<211> LENGTH: 73
<212> TYPE: DNA
<213> ORGANISM: Homo sapiens

<400> SEQUENCE: 543
gccctcttag cgcagcgggc agcgcgtcag tctcataatc tgaaggtcct gagttcgagc    60
ctcagagagg gca                                                       73

<210> SEQ ID NO 544
<211> LENGTH: 73
<212> TYPE: DNA
<213> ORGANISM: Homo sapiens

<400> SEQUENCE: 544
gcctccttag cgcagtaggc agcgcgtcag tctcataatc tgaaggtcct gagttcgaac    60
ctcagagggg gca                                                       73

<210> SEQ ID NO 545
<211> LENGTH: 73
<212> TYPE: DNA
<213> ORGANISM: Homo sapiens

<400> SEQUENCE: 545
gcctccttag cgcagtaggc agcgcgtcag tctcataatc tgaaggtcct gagttcgaac    60
ctcagagggg gca                                                       73

<210> SEQ ID NO 546
<211> LENGTH: 73
<212> TYPE: DNA
<213> ORGANISM: Homo sapiens

<400> SEQUENCE: 546
gccctcttag cgcagtgggc agcgcgtcag tctcataatc tgaaggtcct gagttcgagc    60
ctcagagagg gca                                                       73

<210> SEQ ID NO 547
<211> LENGTH: 73
<212> TYPE: DNA
<213> ORGANISM: Homo sapiens

<400> SEQUENCE: 547
gcctcgttag cgcagtaggt agcgcgtcag tctcataatc tgaaggtcgt gagttcgatc    60
ctcacacggg gca                                                       73

<210> SEQ ID NO 548
<211> LENGTH: 76
```

```
<212> TYPE: DNA
<213> ORGANISM: Homo sapiens

<400> SEQUENCE: 548
gccgaaatag ctcaattggg agagtgttag actgaagatc ttctgcaggt ctctggttca    60
attccgggtt tcgaca                                                    76

<210> SEQ ID NO 549
<211> LENGTH: 74
<212> TYPE: DNA
<213> ORGANISM: Homo sapiens

<400> SEQUENCE: 549
gctgaaatag ctcagttggg agagcgttag actgaagatc ttaaagttcc ctggttcaac    60
cctgggtttc agcc                                                      74

<210> SEQ ID NO 550
<211> LENGTH: 73
<212> TYPE: DNA
<213> ORGANISM: Homo sapiens

<400> SEQUENCE: 550
gccaaaattg ctcagttggg agagcgttag actgaagatc taaaggtccc tggttcgatc    60
ccgggtttca cca                                                       73

<210> SEQ ID NO 551
<211> LENGTH: 74
<212> TYPE: DNA
<213> ORGANISM: Homo sapiens

<400> SEQUENCE: 551
gccgaaatag ctcagttggg agagcgttag accgaagatc ttaaaggtcc ctggttcaat    60
cccgggtttc ggca                                                      74

<210> SEQ ID NO 552
<211> LENGTH: 73
<212> TYPE: DNA
<213> ORGANISM: Homo sapiens

<400> SEQUENCE: 552
gccgagatag ctcagttggg agagcgttag actgaagatc taaaggtccc tggttcaatc    60
ccgggtttcg gca                                                       73

<210> SEQ ID NO 553
<211> LENGTH: 73
<212> TYPE: DNA
<213> ORGANISM: Homo sapiens

<400> SEQUENCE: 553
gccgaaatag ctcagttggg agagcgttag actgaagatc taaaggtccc tggttcaatc    60
ccgggtttcg gca                                                       73

<210> SEQ ID NO 554
<211> LENGTH: 73
<212> TYPE: DNA
<213> ORGANISM: Homo sapiens

<400> SEQUENCE: 554
gccgaaatag ctcagttggg agagcgttag actgaagatc taaaggtccc tggttcgatc    60
```
ccgggtttcg gca 73

<210> SEQ ID NO 555
<211> LENGTH: 73
<212> TYPE: DNA
<213> ORGANISM: Homo sapiens

<400> SEQUENCE: 555
gccgaaatag ctcagttggg agagcgttag actgaagatc taaaggtccc tggttcgatc 60
ccgggtttcg gca 73

<210> SEQ ID NO 556
<211> LENGTH: 73
<212> TYPE: DNA
<213> ORGANISM: Homo sapiens

<400> SEQUENCE: 556
gccgaaatag ctcagttggg agagcgttag actgaagatc taaaggtccc tggttcgatc 60
ccgggtttcg gca 73

<210> SEQ ID NO 557
<211> LENGTH: 73
<212> TYPE: DNA
<213> ORGANISM: Homo sapiens

<400> SEQUENCE: 557
gccgaaatag ctcagttggg agagcgttag actgaagatc taaaggtccc tggttcgatc 60
ccgggtttcg gca 73

<210> SEQ ID NO 558
<211> LENGTH: 73
<212> TYPE: DNA
<213> ORGANISM: Homo sapiens

<400> SEQUENCE: 558
gccgaaatag ctcagttggg agagcgttag actgaagatc taaaggtccc tggttcgatc 60
ccgggtttcg gca 73

<210> SEQ ID NO 559
<211> LENGTH: 73
<212> TYPE: DNA
<213> ORGANISM: Homo sapiens

<400> SEQUENCE: 559
gccgaaatag ctcagttggg agagcgttag actgaagatc taaaggtccc tggttcgatc 60
ccgggtttcg gca 73

<210> SEQ ID NO 560
<211> LENGTH: 72
<212> TYPE: DNA
<213> ORGANISM: Homo sapiens

<400> SEQUENCE: 560
ggctcgttgg tctaggggta tgattctcgc ttagggtgcg agaggtcccg ggttcaaatc 60
ccggacgagc cc 72

<210> SEQ ID NO 561
<211> LENGTH: 72
<212> TYPE: DNA
<213> ORGANISM: Homo sapiens

<400> SEQUENCE: 561
ggctcgttgg tctaggggta tgattctcgc ttagggtgcg agaggtcccg ggttcaaatc    60
ccggacgagc cc                                                        72

<210> SEQ ID NO 562
<211> LENGTH: 72
<212> TYPE: DNA
<213> ORGANISM: Homo sapiens

<400> SEQUENCE: 562
ggctcgttgg tctaggggta tgattctcgc ttagggtgcg agaggtcccg ggttcaaatc    60
ccggacgagc cc                                                        72

<210> SEQ ID NO 563
<211> LENGTH: 72
<212> TYPE: DNA
<213> ORGANISM: Homo sapiens

<400> SEQUENCE: 563
ggctcgttgg tctaggggta tgattctcgc ttagggtgcg agaggtcccg ggttcaaatc    60
ccggacgagc cc                                                        72

<210> SEQ ID NO 564
<211> LENGTH: 72
<212> TYPE: DNA
<213> ORGANISM: Homo sapiens

<400> SEQUENCE: 564
ggctcgttgg tctaggggta tgattctcgc ttagggtgcg agaggtcccg ggttcaaatc    60
ccggacgagc cc                                                        72

<210> SEQ ID NO 565
<211> LENGTH: 72
<212> TYPE: DNA
<213> ORGANISM: Homo sapiens

<400> SEQUENCE: 565
ggctcgttgg tctaggggta tgattctcgc ttagggtgcg agaggtcccg ggttcaaatc    60
ccggacgagc cc                                                        72

<210> SEQ ID NO 566
<211> LENGTH: 72
<212> TYPE: DNA
<213> ORGANISM: Homo sapiens

<400> SEQUENCE: 566
ggctcgttgg tctaggggta tgattctcgc ttagggtgcg agaggtcccg ggttcaaatc    60
ccggacgagc cc                                                        72

<210> SEQ ID NO 567
<211> LENGTH: 72
<212> TYPE: DNA
<213> ORGANISM: Homo sapiens

<400> SEQUENCE: 567
ggctcgttgg tctaggggta tgattctcgc ttagggtgcg agaggtcccg ggttcaaatc    60
ccggacgagc cc                                                        72

<210> SEQ ID NO 568
<211> LENGTH: 72
<212> TYPE: DNA
<213> ORGANISM: Homo sapiens

<400> SEQUENCE: 568
ggctcgttgg tctaggggta tgattctcgc ttaggatgcg agaggtcccg ggttcaaatc    60
ccggacgagc cc                                                       72

<210> SEQ ID NO 569
<211> LENGTH: 95
<212> TYPE: DNA
<213> ORGANISM: Homo sapiens

<400> SEQUENCE: 569
ggctcgttgg tctaggggtg tggttctcgc ttagggacca cagggacaag cccgggagac    60
ccaagaggtc ccgggttcaa atcccggacg agccc                              95

<210> SEQ ID NO 570
<211> LENGTH: 72
<212> TYPE: DNA
<213> ORGANISM: Homo sapiens

<400> SEQUENCE: 570
ggctcgttgg tctaggggta tgattctcgc ttcgggtgtg agaggtcccg ggttcaaatc    60
ccggacgagc cc                                                       72

<210> SEQ ID NO 571
<211> LENGTH: 72
<212> TYPE: DNA
<213> ORGANISM: Homo sapiens

<400> SEQUENCE: 571
ggctcgttgg tctaggggta tgattctcgc ttcgggtgcg agaggtcccg ggttcaaatc    60
ccggacgagc cc                                                       72

<210> SEQ ID NO 572
<211> LENGTH: 72
<212> TYPE: DNA
<213> ORGANISM: Homo sapiens

<400> SEQUENCE: 572
ggctcgttgg tctaggggta tgattctcgc ttcgggtgcg agaggtcccg ggttcaaatc    60
ccggacgagc cc                                                       72

<210> SEQ ID NO 573
<211> LENGTH: 72
<212> TYPE: DNA
<213> ORGANISM: Homo sapiens

<400> SEQUENCE: 573
ggctcgttgg tctaggggta tgattctcgc ttcgggtgcg agaggtcccg ggttcaaatc    60
ccggacgagc cc                                                       72

<210> SEQ ID NO 574
<211> LENGTH: 72
<212> TYPE: DNA
<213> ORGANISM: Homo sapiens

<400> SEQUENCE: 574
ggctcgttgg tctaggggta tgattctcgc tttgggtgcg agaggtcccg ggttcaaatc    60
ccggacgagc cc                                                        72

<210> SEQ ID NO 575
<211> LENGTH: 72
<212> TYPE: DNA
<213> ORGANISM: Homo sapiens

<400> SEQUENCE: 575
ggctcgttgg tctaggggta tgattctcgc tttgggtgcg agaggtcccg ggttcaaatc    60
ccggacgagc cc                                                        72

<210> SEQ ID NO 576
<211> LENGTH: 72
<212> TYPE: DNA
<213> ORGANISM: Homo sapiens

<400> SEQUENCE: 576
ggctcgttgg tctaggggta tgattctcgc tttgggtgcg agaggtcccg ggttcaaatc    60
ccggacgagc cc                                                        72

<210> SEQ ID NO 577
<211> LENGTH: 72
<212> TYPE: DNA
<213> ORGANISM: Homo sapiens

<400> SEQUENCE: 577
ggctcgttgg tctaggggta tgattctcgc tttgggtgcg agaggtcccg ggttcaaatc    60
ccggacgagc cc                                                        72

<210> SEQ ID NO 578
<211> LENGTH: 72
<212> TYPE: DNA
<213> ORGANISM: Homo sapiens

<400> SEQUENCE: 578
ggctcgttgg tctaggggta tgattctcgc tttgggtgcg agaggtcccg ggttcaaatc    60
ccggacgagc cc                                                        72

<210> SEQ ID NO 579
<211> LENGTH: 72
<212> TYPE: DNA
<213> ORGANISM: Homo sapiens

<400> SEQUENCE: 579
ggctcgttgg tctaggggta tgattctcgg tttgggtccg agaggtcccg ggttcaaatc    60
ccggacgagc cc                                                        72

<210> SEQ ID NO 580
<211> LENGTH: 72
<212> TYPE: DNA
<213> ORGANISM: Homo sapiens

<400> SEQUENCE: 580
ggctcgttgg tctagtggta tgattctcgc tttgggtgcg agaggtcccg ggttcaaatc    60
ccggacgagc cc                                                        72

<210> SEQ ID NO 581

```
<211> LENGTH: 82
<212> TYPE: DNA
<213> ORGANISM: Homo sapiens

<400> SEQUENCE: 581
gatagcaagg ccgagcggtc taaggctccg gattaaggcg ccggtgtctt cggaggcatg      60
ggttcgaatt ccacctctgc ca                                              82

<210> SEQ ID NO 582
<211> LENGTH: 78
<212> TYPE: DNA
<213> ORGANISM: Homo sapiens

<400> SEQUENCE: 582
gaccaattag caagcacagt tggctagaac atggtgctaa taaggccacg gtcagggggtt     60 caattccctt atgggctg                                                   78

<210> SEQ ID NO 583
<211> LENGTH: 75
<212> TYPE: DNA
<213> ORGANISM: Homo sapiens

<400> SEQUENCE: 583
tggctgatga gctcagctgg tgggagcatg gtgttaatga ggctgaggtc gtgggttcaa      60
tccccaccgg gctat                                                      75

<210> SEQ ID NO 584
<211> LENGTH: 74
<212> TYPE: DNA
<213> ORGANISM: Homo sapiens

<400> SEQUENCE: 584
ggccggttaa cttaattggt tagagcgtgg tgctaataat gtcaaggttg cgggttggat      60
ccccgaacgg gcca                                                       74

<210> SEQ ID NO 585
<211> LENGTH: 176
<212> TYPE: DNA
<213> ORGANISM: Homo sapiens

<400> SEQUENCE: 585
ggctgtatag ctcagtggta gagcatttga ctacagaatc ctatactcag gggaaggaga      60
actgggggtt tctcagtggg tcaaaggact tgtagtggta aatcaaaagc aactctataa     120
gctatgtaac aaactttaaa gtcatatgta gctgggttca aatcctgttt ctgcca         176

<210> SEQ ID NO 586
<211> LENGTH: 74
<212> TYPE: DNA
<213> ORGANISM: Homo sapiens

<400> SEQUENCE: 586
ggccggttag ctcagttggt tagagcgtgc tgctactaat gccagggtcg aggtttcgat      60
ccccgtacgg gcct                                                       74

<210> SEQ ID NO 587
<211> LENGTH: 72
<212> TYPE: DNA
<213> ORGANISM: Homo sapiens

<400> SEQUENCE: 587
```

```
ggtaatgtag cctcgtggtt aggggctgca ttctagagct atgctgccca ggttcaaatt    60
ctggtgccac tc                                                         72

<210> SEQ ID NO 588
<211> LENGTH: 72
<212> TYPE: DNA
<213> ORGANISM: Homo sapiens

<400> SEQUENCE: 588
gggggtatag ctcagggaca gagcacgtgg ttagcatgcg tgaggtcctg cgttcaactt    60
ccagtatttc ca                                                         72

<210> SEQ ID NO 589
<211> LENGTH: 72
<212> TYPE: DNA
<213> ORGANISM: Homo sapiens

<400> SEQUENCE: 589
cgctctttgg tctaggggta tgatcttcgc ttagggtgcg agaggtgcct ggatcaactc    60
cttcacaagc cg                                                         72

<210> SEQ ID NO 590
<211> LENGTH: 71
<212> TYPE: DNA
<213> ORGANISM: Homo sapiens

<400> SEQUENCE: 590
ggctggttgg tctagggcta tgattctcac ttagggtgca agaggtcctg gttcaaatcc    60
cagaggagcc c                                                          71

<210> SEQ ID NO 591
<211> LENGTH: 72
<212> TYPE: DNA
<213> ORGANISM: Homo sapiens

<400> SEQUENCE: 591
ggctggttgg tctagggcta tgattctcac ttagggtgca aaaggtcctg ggttcaaatc    60
ccagaggagc cc                                                         72

<210> SEQ ID NO 592
<211> LENGTH: 68
<212> TYPE: DNA
<213> ORGANISM: Homo sapiens

<400> SEQUENCE: 592
catagggtag tggctaagaa cctaaactct aaatttagat gtcctgagtt caaatcccag    60
ctgtatgc                                                              68

<210> SEQ ID NO 593
<211> LENGTH: 73
<212> TYPE: DNA
<213> ORGANISM: Homo sapiens

<400> SEQUENCE: 593
gcttctgtaa tgtagtggtt atcacattcg cctcacacat gaaggtcac cagtttgaga    60 ccgggccaaa aca                                                        73

<210> SEQ ID NO 594
```

```
<211> LENGTH: 73
<212> TYPE: DNA
<213> ORGANISM: Homo sapiens

<400> SEQUENCE: 594
gtttctgtag tatagtggtt atcatgtttg cctcacatgt gaaagaccct tggctcgaga      60
ctggagggaa aca                                                        73

<210> SEQ ID NO 595
<211> LENGTH: 73
<212> TYPE: DNA
<213> ORGANISM: Homo sapiens

<400> SEQUENCE: 595
gtttctgtgg tgtagtggtt attatgttcg cttcacatat gaaaggtctc tggttcgaga      60
ctgcgtggga aca                                                        73

<210> SEQ ID NO 596
<211> LENGTH: 73
<212> TYPE: DNA
<213> ORGANISM: Homo sapiens

<400> SEQUENCE: 596
gtttctgtgg tgtagtggtt attatgttcg cttcacatat gaaaggtctc tggttcgaga      60
ctgcgtggga aca                                                        73

<210> SEQ ID NO 597
<211> LENGTH: 72
<212> TYPE: DNA
<213> ORGANISM: Homo sapiens

<400> SEQUENCE: 597
tactcagtgg tctagtggtt aggattcagc gctcccaccg ccgcagcccg ggttcgattc      60
ccggtcatgg aa                                                         72

<210> SEQ ID NO 598
<211> LENGTH: 71
<212> TYPE: DNA
<213> ORGANISM: Homo sapiens

<400> SEQUENCE: 598
gcactggtgg ttcagtggta gaattctcgc ctcccacgcg ggagacccgg gtttaattcc      60
cggtcaagat a                                                          71

<210> SEQ ID NO 599
<211> LENGTH: 69
<212> TYPE: DNA
<213> ORGANISM: Homo sapiens

<400> SEQUENCE: 599
gcattcgtag ttcagcggca gaaatttcgt ctcctacgcg ggagactcgg gttcgacttc      60
ggccatgca                                                             69

<210> SEQ ID NO 600
<211> LENGTH: 71
<212> TYPE: DNA
<213> ORGANISM: Homo sapiens

<400> SEQUENCE: 600
ggatttgtgg tccagtggta gaattctcac cgcctgcata ggagaccctg gtttaattcc      60
```
tggccaatgc a                                                          71

<210> SEQ ID NO 601
<211> LENGTH: 71
<212> TYPE: DNA
<213> ORGANISM: Homo sapiens

<400> SEQUENCE: 601
ggattggtgg tccagtggta gaattctcac cgcctgcata ggagaccctg gtttaattcc     60
tggccaatgc a                                                          71

<210> SEQ ID NO 602
<211> LENGTH: 71
<212> TYPE: DNA
<213> ORGANISM: Homo sapiens

<400> SEQUENCE: 602
gcattggtag ttcagcggtg gcattctccc cacctacgcg ggagacctgg gttcaactcc     60
cggccaaagc a                                                          71

<210> SEQ ID NO 603
<211> LENGTH: 71
<212> TYPE: DNA
<213> ORGANISM: Homo sapiens

<400> SEQUENCE: 603
gcattggtag ttcagcggtg gcattctccc cacctacgcg ggagacctgg gttcaactcc     60
cggccaaagc a                                                          71

<210> SEQ ID NO 604
<211> LENGTH: 73
<212> TYPE: DNA
<213> ORGANISM: Homo sapiens

<400> SEQUENCE: 604
ggcgggataa tgtagtggtt aaaggcatgg gctctagagc cagacttcct gggttcaaat     60
ctcagacctg cta                                                        73

<210> SEQ ID NO 605
<211> LENGTH: 68
<212> TYPE: DNA
<213> ORGANISM: Homo sapiens

<400> SEQUENCE: 605
ggcagggtag ggtagaggtt aaaaccatgg attctagagc cagatgggtt caaatcccgg     60
ctctgccg                                                              68

<210> SEQ ID NO 606
<211> LENGTH: 72
<212> TYPE: DNA
<213> ORGANISM: Homo sapiens

<400> SEQUENCE: 606
tccctggtgt tccggtggtt aggatttggc attctcactg ttgtggtgcg gattcaatcc     60
tggcttaggg ta                                                         72

<210> SEQ ID NO 607
<211> LENGTH: 73
<212> TYPE: DNA

-continued

<213> ORGANISM: Homo sapiens

<400> SEQUENCE: 607
ccgtggatag cccagcggct atgggagccg ggctctcact ctgacgtcct gggttcaagt    60
cccagtgtgc aca    73

<210> SEQ ID NO 608
<211> LENGTH: 73
<212> TYPE: DNA
<213> ORGANISM: Homo sapiens

<400> SEQUENCE: 608
cccctggcgg tctagtggtt aggattcggc gctctcatcc accgcggcct gggttcgact    60
cgtggtcaga gtg    73

<210> SEQ ID NO 609
<211> LENGTH: 75
<212> TYPE: DNA
<213> ORGANISM: Homo sapiens

<400> SEQUENCE: 609
ctctggtggt ttagtggcta ggattcacct ctctcactgc tgcagcccag ggttccattc    60
cctgggagtc agatg    75

<210> SEQ ID NO 610
<211> LENGTH: 72
<212> TYPE: DNA
<213> ORGANISM: Homo sapiens

<400> SEQUENCE: 610 cccctttgtag tctagtggtt agaattctgc ggtctcacag ccgcggcccg ggttcgattc    60
ccattccggg aa    72

<210> SEQ ID NO 611
<211> LENGTH: 72
<212> TYPE: DNA
<213> ORGANISM: Homo sapiens

<400> SEQUENCE: 611
ttattattat acctgtggtt aggattcggc gctctcaccg ccacgacccg ggttcaattc    60
ccggtcaggg aa    72

<210> SEQ ID NO 612
<211> LENGTH: 72
<212> TYPE: DNA
<213> ORGANISM: Homo sapiens

<400> SEQUENCE: 612
cccctggtag tctagtggtt aggctttgcc gctctcagtg ccgctgcctg ggttggattc    60
ccagtcatgt ga    72

<210> SEQ ID NO 613
<211> LENGTH: 72
<212> TYPE: DNA
<213> ORGANISM: Homo sapiens

<400> SEQUENCE: 613
tccctgcttg tctagtggtt agaattcagc actctcactg ccacagccca ggttcaattc    60
cctgtcagag aa    72

```
<210> SEQ ID NO 614
<211> LENGTH: 73
<212> TYPE: DNA
<213> ORGANISM: Homo sapiens

<400> SEQUENCE: 614
ttccccttgg tctagtggtt aggattcaac actctcaccg ccgcagcccg ggtttgattc    60
ccaggcaggg aag                                                      73

<210> SEQ ID NO 615
<211> LENGTH: 72
<212> TYPE: DNA
<213> ORGANISM: Homo sapiens

<400> SEQUENCE: 615
cccctggtgg tctagtgctt aggatttggc actctcgcca ccgcagcctg cgttcaattc    60
ccggtcaggg aa                                                       72

<210> SEQ ID NO 616
<211> LENGTH: 72
<212> TYPE: DNA
<213> ORGANISM: Homo sapiens

<400> SEQUENCE: 616
tccctggtgg tctaatggtt aggagtcggc actctcaccg ccgcggctgg ggtttgattc    60
ccagtcatgt aa                                                       72

<210> SEQ ID NO 617
<211> LENGTH: 76
<212> TYPE: DNA
<213> ORGANISM: Homo sapiens

<400> SEQUENCE: 617
gtgagactgc acagcccagt ggtgcagggc atggctctga cacctggcgg cctgggttca    60
aatcccagct tctaca                                                   76

<210> SEQ ID NO 618
<211> LENGTH: 72
<212> TYPE: DNA
<213> ORGANISM: Homo sapiens

<400> SEQUENCE: 618
ggttccatga tgtaatggtg agcgctttgg actctgagta cggtgatcag cgttcaagtc    60
tcagtgggac ct                                                       72

<210> SEQ ID NO 619
<211> LENGTH: 72
<212> TYPE: DNA
<213> ORGANISM: Homo sapiens

<400> SEQUENCE: 619
ggtagtgtag tctactggtt aaacgcttgg gctctgacat taacgtcctg ggttcaaatc    60
ccagctttgt ca                                                       72

<210> SEQ ID NO 620
<211> LENGTH: 75
<212> TYPE: DNA
<213> ORGANISM: Homo sapiens
```

<400> SEQUENCE: 620
ctaggacgtg gtgtaatagg tagcacagag aattctggat tctcaggggt aggttcaatt    60
cctatagaac ctagg                                                     75

<210> SEQ ID NO 621
<211> LENGTH: 72
<212> TYPE: DNA
<213> ORGANISM: Homo sapiens

<400> SEQUENCE: 621
ggttccatgg tgtaatggtg agggctttgg actctgacta cagtgatcag agttcaagtc    60
tcagtgggac ct                                                        72

<210> SEQ ID NO 622
<211> LENGTH: 72
<212> TYPE: DNA
<213> ORGANISM: Homo sapiens

<400> SEQUENCE: 622
ggttccatgg gttaatggtg agcaccctgg actctgaatc aagcgatccg agttcaaatc    60
tcggtggtac ct                                                        72

<210> SEQ ID NO 623
<211> LENGTH: 74
<212> TYPE: DNA
<213> ORGANISM: Homo sapiens

<400> SEQUENCE: 623
gcctggctac ctcagttggt agagcatggg actcttaatc ccagagtcag tgggttcaag    60
cctcacattg agtg                                                      74

<210> SEQ ID NO 624
<211> LENGTH: 73
<212> TYPE: DNA
<213> ORGANISM: Homo sapiens

<400> SEQUENCE: 624
gcccagctag ctcagccggt agagcacaag actcttaatc tcagggtcgt gggtttgagc    60
cctgtgttga gca                                                       73

<210> SEQ ID NO 625
<211> LENGTH: 73
<212> TYPE: DNA
<213> ORGANISM: Homo sapiens

<400> SEQUENCE: 625
gtctagctag atcagttggt agagcataag actcttaatc tcagggtcat gggtttgagc    60
cctacgttgg gcg                                                       73

<210> SEQ ID NO 626
<211> LENGTH: 73
<212> TYPE: DNA
<213> ORGANISM: Homo sapiens

<400> SEQUENCE: 626
accagcatgt ctcagtcggt atagtgtgag actcttaatc tcagggtcgt gggttcaagc    60
cccacattgg gcg                                                       73

```
<210> SEQ ID NO 627
<211> LENGTH: 73
<212> TYPE: DNA
<213> ORGANISM: Homo sapiens

<400> SEQUENCE: 627
gccaaaatag ctcagctggg agagtattag gttgaagata caaagttcct tggctcaatc    60
cagagtttgg ggg                                                       73

<210> SEQ ID NO 628
<211> LENGTH: 73
<212> TYPE: DNA
<213> ORGANISM: Homo sapiens

<400> SEQUENCE: 628
gctgagatag ctcggttggg agggcatcag cctgaagatc taaaggagac tggttcaatt    60
ctgggttttg gca                                                       73

<210> SEQ ID NO 629
<211> LENGTH: 72
<212> TYPE: DNA
<213> ORGANISM: Homo sapiens

<400> SEQUENCE: 629
tgcatggttg tctagtggct aggattcggt gctgaaagcg tcacggcccg ggttcgattc    60
ccggtcaggg aa                                                        72

<210> SEQ ID NO 630
<211> LENGTH: 72
<212> TYPE: DNA
<213> ORGANISM: Homo sapiens

<400> SEQUENCE: 630
tgcatggttg tctagtggct aggattcggt gctgaaagag ccacggcccg ggttcgattc    60
ccggtcaggg aa                                                        72

<210> SEQ ID NO 631
<211> LENGTH: 73
<212> TYPE: DNA
<213> ORGANISM: Homo sapiens

<400> SEQUENCE: 631
gccaaaatag ctcagctggg agagcattag actgaagatc taaaggtctc tggtttgatc    60
ctgggtttca gaa                                                       73

<210> SEQ ID NO 632
<211> LENGTH: 73
<212> TYPE: DNA
<213> ORGANISM: Homo sapiens

<400> SEQUENCE: 632
gggggtatat ctcaggggc agagcatttg actgcagatc aagaggtccc cggttgaaat     60
ccgggtgctg gat                                                       73

<210> SEQ ID NO 633
<211> LENGTH: 73
<212> TYPE: DNA
<213> ORGANISM: Homo sapiens

<400> SEQUENCE: 633
```

```
ggcagtgtgg catagtggtt agaaatgtgc gctctggggc tgctgatccc aggctcaaac    60
cctggcgctg tca                                                       73

<210> SEQ ID NO 634
<211> LENGTH: 73
<212> TYPE: DNA
<213> ORGANISM: Homo sapiens

<400> SEQUENCE: 634
gtcagtgttg cacaacggtt aagtgaagag gctgtaaacc cagactggat gggttcaatt    60
cccatctctg ccg                                                       73

<210> SEQ ID NO 635
<211> LENGTH: 76
<212> TYPE: DNA
<213> ORGANISM: Homo sapiens

<400> SEQUENCE: 635
tcaattatag ctcagtggta gagcatttaa ctgtagatca agaggtccct ggatcaactc    60
tgggtgcccc cttttaa                                                   76

<210> SEQ ID NO 636
<211> LENGTH: 72
<212> TYPE: DNA
<213> ORGANISM: Homo sapiens

<400> SEQUENCE: 636
tccttgttac tatagtggtg agtatctctg cctgtcatgc gtgagagagg gggtcgattc    60
cccgacgggg ag                                                        72

<210> SEQ ID NO 637
<211> LENGTH: 74
<212> TYPE: DNA
<213> ORGANISM: Homo sapiens

<400> SEQUENCE: 637
gtctctgtgg cacaatcggt tagcttgttc ggctgttaat ctagaggttg gtggttagag    60
cccactgagg gatg                                                      74

<210> SEQ ID NO 638
<211> LENGTH: 74
<212> TYPE: DNA
<213> ORGANISM: Homo sapiens

<400> SEQUENCE: 638
gtctctgtgg cacaatcggt tagagcgttc ggctgttaat ctaaaggttg gtggctagaa    60
cccactgagg gacg                                                      74

<210> SEQ ID NO 639
<211> LENGTH: 74
<212> TYPE: DNA
<213> ORGANISM: Homo sapiens

<400> SEQUENCE: 639
gtctctgtgg cacaatcggt tagcgcgttc ggctgttaat ctagaggttg gtggttagag    60
cccactgagg gatg                                                      74

<210> SEQ ID NO 640
<211> LENGTH: 75
```

```
<212> TYPE: DNA
<213> ORGANISM: Homo sapiens

<400> SEQUENCE: 640
gttaagatgg catagcccag caattgcata aaacttaaga ctttataatt agaagttcaa    60
cacctcttct taaca                                                     75

<210> SEQ ID NO 641
<211> LENGTH: 75
<212> TYPE: DNA
<213> ORGANISM: Homo sapiens

<400> SEQUENCE: 641
gttaagatgg cagagcccag cgattgcata aaacttaaca ctttataatc agaggttcaa    60
ctcctcttct taaca                                                     75

<210> SEQ ID NO 642
<211> LENGTH: 75
<212> TYPE: DNA
<213> ORGANISM: Homo sapiens

<400> SEQUENCE: 642
gttaagatgg cagagcccag caattgcata aaacttaaaa ctttacaatc agaggttcaa    60
ctcctcttct taaca                                                     75

<210> SEQ ID NO 643
<211> LENGTH: 75
<212> TYPE: DNA
<213> ORGANISM: Homo sapiens

<400> SEQUENCE: 643
gttaagatgg cagagcccag caattgcata aatcttaaaa ctttataatc agaggttcga    60
ctcctcttct taaca                                                     75

<210> SEQ ID NO 644
<211> LENGTH: 75
<212> TYPE: DNA
<213> ORGANISM: Homo sapiens

<400> SEQUENCE: 644
gttaagacgg cagagcccgg caattgcgta aaatttacaa ctttatgggc agaggttcaa    60
ttcctcttct taaca                                                     75

<210> SEQ ID NO 645
<211> LENGTH: 82
<212> TYPE: DNA
<213> ORGANISM: Homo sapiens

<400> SEQUENCE: 645
ggtagtgtgg ttgaatggtc taaggcactg aatttaggct ccagtctctt tggggacgtg    60
ggtttaaatc ccactgctgc aa                                             82

<210> SEQ ID NO 646
<211> LENGTH: 72
<212> TYPE: DNA
<213> ORGANISM: Homo sapiens

<400> SEQUENCE: 646
gtgttgatgg tatagtggtg agcatagctg ccttccaagc aattgacccg acttcaattc    60
```

```
ccagccaacg ca                                                       72

<210> SEQ ID NO 647
<211> LENGTH: 72
<212> TYPE: DNA
<213> ORGANISM: Homo sapiens

<400> SEQUENCE: 647
gtgttgatgg tatagtggtg agcatagctg ccttccaagc aattgacccg acttcgattc    60
ccagccaatg ca                                                       72

<210> SEQ ID NO 648
<211> LENGTH: 69
<212> TYPE: DNA
<213> ORGANISM: Homo sapiens

<400> SEQUENCE: 648
gaaaaagtca tagggttat gaggctggct tgaaaccagc cttaggaggt tcaattcctt     60
cctttttttg                                                          69

<210> SEQ ID NO 649
<211> LENGTH: 70
<212> TYPE: DNA
<213> ORGANISM: Homo sapiens

<400> SEQUENCE: 649
gagaaggtca tagaggttat gggattggct tgaaaccagt ctctgggggg ttcgattccc    60 tccttttttca                                                         70

<210> SEQ ID NO 650
<211> LENGTH: 70
<212> TYPE: DNA
<213> ORGANISM: Homo sapiens

<400> SEQUENCE: 650
gggggagtgg tgtggttacg aatgtggcct ctgcaagcag acagcctggg ttcaattccc    60
agcttggcca                                                          70

<210> SEQ ID NO 651
<211> LENGTH: 72
<212> TYPE: DNA
<213> ORGANISM: Homo sapiens

<400> SEQUENCE: 651
gtggatgtag tttagtggta gaacgcgcgc tttgcatgta tgaggtcccg gtttcgatcc    60
ctggcgtttc ca                                                       72

<210> SEQ ID NO 652
<211> LENGTH: 77
<212> TYPE: DNA
<213> ORGANISM: Homo sapiens

<400> SEQUENCE: 652
gccaggagag ctcagtggtg atgggatgag atctggactc acacctctag gcctgggttc    60
aaatcccagg tctagcg                                                  77

<210> SEQ ID NO 653
<211> LENGTH: 72
<212> TYPE: DNA
<213> ORGANISM: Homo sapiens
```

<400> SEQUENCE: 653
taggacttgg tgtaataggt agcacgaaga gatttggatt ctcaggggta ggttcaattc    60
ctatagttct gg                                                        72

<210> SEQ ID NO 654
<211> LENGTH: 71
<212> TYPE: DNA
<213> ORGANISM: Homo sapiens

<400> SEQUENCE: 654
ggcctgttgg tctagaggta tgattctcgc tttgggtgcg agaggcccccg gtgcgagtcc    60 cagaggagcc c                                                         71

<210> SEQ ID NO 655
<211> LENGTH: 72
<212> TYPE: DNA
<213> ORGANISM: Homo sapiens

<400> SEQUENCE: 655
ggcagcctgg cttagtggaa agggaatagg ctttagagcc agactgcctg ggtttgaatc    60
ccagccccgc ca                                                        72

<210> SEQ ID NO 656
<211> LENGTH: 69
<212> TYPE: DNA
<213> ORGANISM: Homo sapiens

<400> SEQUENCE: 656
tccctggtct agtggttagg atttattatt ttcatggctg tggcctgagt tcaatttcca    60
atcagggaa                                                            69

<210> SEQ ID NO 657
<211> LENGTH: 72
<212> TYPE: DNA
<213> ORGANISM: Homo sapiens

<400> SEQUENCE: 657
tccctggtgg tctggtggct agaatttagc gctttcaccg ccgcagctcg ggttggatta    60
ccagtcaggg aa                                                        72

<210> SEQ ID NO 658
<211> LENGTH: 73
<212> TYPE: DNA
<213> ORGANISM: Homo sapiens

<400> SEQUENCE: 658
tccgtggtgg tctagtggct aggattcggc gctttcaccg cctgcagctc gagttcgatt    60
cctggtcagg gaa                                                       73

<210> SEQ ID NO 659
<211> LENGTH: 71
<212> TYPE: DNA
<213> ORGANISM: Homo sapiens

<400> SEQUENCE: 659
gcaatggtgg ttcagtggta gaattctcgc ctttcacaca ggagacccgg gttcaattcc    60
tgacccatgt a                                                         71

```
<210> SEQ ID NO 660
<211> LENGTH: 72
<212> TYPE: DNA
<213> ORGANISM: Homo sapiens

<400> SEQUENCE: 660
tgtctggtgg tcaagtggct aggatttggc gctttcactg ccgcggcccg cgttcgattc      60
ccggtcaggg aa                                                         72

<210> SEQ ID NO 661
<211> LENGTH: 72
<212> TYPE: DNA
<213> ORGANISM: Homo sapiens

<400> SEQUENCE: 661
tccttggtgg tctagtggct aggattcggt gctttcacct gtgcggcccg ggttcaattc      60
ccgatgaagg aa                                                         72

<210> SEQ ID NO 662
<211> LENGTH: 72
<212> TYPE: DNA
<213> ORGANISM: Homo sapiens

<400> SEQUENCE: 662
taggacgtgg tgtgataggt agcacagaga attttggatt ctcaggggta ggttaaattc      60
ctatagtact ag                                                         72

<210> SEQ ID NO 663
<211> LENGTH: 72
<212> TYPE: DNA
<213> ORGANISM: Homo sapiens

<400> SEQUENCE: 663
taggacgtgg tgtgataggt agcatgggga attttggatt ctcaggggtg ggttcaattc      60
ctatagttct ag                                                         72

<210> SEQ ID NO 664
<211> LENGTH: 74
<212> TYPE: DNA
<213> ORGANISM: Homo sapiens

<400> SEQUENCE: 664
ggcaatgtag cattgtggct aagtgcacag gctttggaaa ctggcaggcc tgggttcaaa      60
tcccagctta ttca                                                       74

<210> SEQ ID NO 665
<211> LENGTH: 72
<212> TYPE: DNA
<213> ORGANISM: Homo sapiens

<400> SEQUENCE: 665
taggatgtgg tgtaataggt ggcatggaga attttggatt atcagggta ggttcaattc       60 ctatagttct ag                                                         72

<210> SEQ ID NO 666
<211> LENGTH: 72
<212> TYPE: DNA
<213> ORGANISM: Homo sapiens

<400> SEQUENCE: 666
```
tagtacatag tgtaataggt agcacagata attttggatt ctcagggta ggttcaattc    60 ttatagttct ag    72

<210> SEQ ID NO 667
<211> LENGTH: 73
<212> TYPE: DNA
<213> ORGANISM: Homo sapiens

<400> SEQUENCE: 667
agcagtgtag cctagtggct aggtcctctg actttgaaac cacgtggtct gggtttaagt    60
ctcagctgtg cta    73

<210> SEQ ID NO 668
<211> LENGTH: 72
<212> TYPE: DNA
<213> ORGANISM: Homo sapiens

<400> SEQUENCE: 668
taggatgtgg tgtgacaggt agcatggaga attttggatt ctcagggtta ggttcaattc    60
ctatagttct ag    72

<210> SEQ ID NO 669
<211> LENGTH: 73
<212> TYPE: DNA
<213> ORGANISM: Homo sapiens

<400> SEQUENCE: 669
agctgtatat tatagtggaa taaatgtgga ctttgaagtt agatacacct gggttcaaat    60
cccagtgctg tca    73

<210> SEQ ID NO 670
<211> LENGTH: 72
<212> TYPE: DNA
<213> ORGANISM: Homo sapiens

<400> SEQUENCE: 670
taggacgtgg tgtgataggt agcacggaga attttggatt ctcagggatg ggttcaattc    60
ctgtagttct ag    72

<210> SEQ ID NO 671
<211> LENGTH: 75
<212> TYPE: DNA
<213> ORGANISM: Homo sapiens

<400> SEQUENCE: 671
tttaggacgt ggtgtaatag gtagcacaga gaattttgga ttctcaggtg caggttcaat    60
tcctatattc tagag    75

<210> SEQ ID NO 672
<211> LENGTH: 72
<212> TYPE: DNA
<213> ORGANISM: Homo sapiens

<400> SEQUENCE: 672
taggacgtgg tgtgataggt agcatggaga attttggatt ctcagggatg ggttcaattc    60
ctatagtcct ag    72

<210> SEQ ID NO 673

```
<211> LENGTH: 75
<212> TYPE: DNA
<213> ORGANISM: Homo sapiens

<400> SEQUENCE: 673
tctaggatgt ggtgtgatag gtagcatgga gaattttgga ttctcagggg taggttcaat      60
tcctatattc tagaa                                                      75

<210> SEQ ID NO 674
<211> LENGTH: 72
<212> TYPE: DNA
<213> ORGANISM: Homo sapiens

<400> SEQUENCE: 674
taggatgtgg tgtattaggt agcacagaga attttggatt ctcagggta ggttcgattc       60 ctataattct ac                                                         72

<210> SEQ ID NO 675
<211> LENGTH: 72
<212> TYPE: DNA
<213> ORGANISM: Homo sapiens

<400> SEQUENCE: 675
taggacgtgg tgtagtaggt agcatggaga atgttgaatt ctcagggta ggttcaattc       60 ctatagttct ag                                                         72

<210> SEQ ID NO 676
<211> LENGTH: 72
<212> TYPE: DNA
<213> ORGANISM: Homo sapiens

<400> SEQUENCE: 676
taggacatgg tgtgataggt agcatggaga attttggatt ctcagggta ggttcaattc       60 ctacagttct ag                                                         72

<210> SEQ ID NO 677
<211> LENGTH: 73
<212> TYPE: DNA
<213> ORGANISM: Homo sapiens

<400> SEQUENCE: 677
ggctgtgtac ctcagtgggc aagggtatgg actttgaagc cagactattt gggttcaaat     60
cccagcttgg cct                                                        73

<210> SEQ ID NO 678
<211> LENGTH: 70
<212> TYPE: DNA
<213> ORGANISM: Homo sapiens

<400> SEQUENCE: 678
tcctatagcc cagtgattag gattctttgc ttttactacc atgacctggg ttcaataccc      60
agtcaggaa                                                             70

<210> SEQ ID NO 679
<211> LENGTH: 73
<212> TYPE: DNA

<400> SEQUENCE: 679
gttggggtaa ctcagttggt agagtagcag acttttcatc tgagggtcca gggtttaagt     60
```
ccatgtccag gca                                                            73

<210> SEQ ID NO 680
<211> LENGTH: 73
<212> TYPE: DNA
<213> ORGANISM: Homo sapiens

<400> SEQUENCE: 680
acccagatag ctcagttgat agagcatcag acttttaatc tgagggtcca gggttcatgt         60
ccctgttcct taa                                                            73

<210> SEQ ID NO 681
<211> LENGTH: 74
<212> TYPE: DNA
<213> ORGANISM: Homo sapiens

<400> SEQUENCE: 681
gcctgggtag ctcagtcggt agagctatca gacttttagc ctgaggattc agggttcaat         60
cccttgctgg ggcg                                                           74

<210> SEQ ID NO 682
<211> LENGTH: 73
<212> TYPE: DNA
<213> ORGANISM: Homo sapiens

<400> SEQUENCE: 682
gccaggatag ttcaggtggt agagcatcag acttttaacc tgagggttca gggttcaagt         60
ctctgtttgg gcg                                                            73

<210> SEQ ID NO 683
<211> LENGTH: 74
<212> TYPE: DNA
<213> ORGANISM: Homo sapiens

<400> SEQUENCE: 683
gaccgtgtgg ccttaatgga taaggtgtct gacttcagat cagaagattg agggtttgag         60
tccctttgtg gtca                                                           74

<210> SEQ ID NO 684
<211> LENGTH: 86
<212> TYPE: DNA
<213> ORGANISM: Homo sapiens

<400> SEQUENCE: 684
gctcggatga tcctcagtgg tctggggtgc aggcttcaaa cctgtagctg tctagtgaca         60
gagtggttca attccacctt tgtagg                                              86

<210> SEQ ID NO 685
<211> LENGTH: 86
<212> TYPE: DNA
<213> ORGANISM: Homo sapiens

<400> SEQUENCE: 685
gcccggatga tcctcagtgg tctggggtgc aggcttcaaa cctgtagctg tctagcgaca         60
gagtggttca attccacctt tcgggc                                              86

<210> SEQ ID NO 686
<211> LENGTH: 82
<212> TYPE: DNA

<213> ORGANISM: Homo sapiens

<400> SEQUENCE: 686
tgagttgtag ctgagtggtt aaggcaacga gctagaaatt cgttggtttc tctctgtgca    60
ggtttgaatc ctgctaatta tg                                              82

<210> SEQ ID NO 687
<211> LENGTH: 72
<212> TYPE: DNA
<213> ORGANISM: Homo sapiens

<400> SEQUENCE: 687
gggtgtatgg ctcaggggta gagaatttga ctagagatca agaggtccct ggttcaaatc    60
caggtgcccc ct                                                         72

<210> SEQ ID NO 688
<211> LENGTH: 82
<212> TYPE: DNA
<213> ORGANISM: Homo sapiens

<400> SEQUENCE: 688
gtagtcgtgg ccgagtggtt aaggtgatgg actagaaacc cattggggtc tccccgcgca    60
ggttcgaatc ctgccgacta cg                                              82

<210> SEQ ID NO 689
<211> LENGTH: 82
<212> TYPE: DNA
<213> ORGANISM: Homo sapiens

<400> SEQUENCE: 689
gtagtcgtgg ccgagtggtt aaggcgatgg actagaaatc cattggggtt tccccacgca    60
ggttcgaatc ctgccgacta cg                                              82

<210> SEQ ID NO 690
<211> LENGTH: 82
<212> TYPE: DNA
<213> ORGANISM: Homo sapiens

<400> SEQUENCE: 690
gtagtcgtgg ccgagtggtt aaggcgatgg actagaaatc cattggggtc tccccgcgca    60
ggttcgaatc ctgccgacta cg                                              82

<210> SEQ ID NO 691
<211> LENGTH: 82
<212> TYPE: DNA
<213> ORGANISM: Homo sapiens

<400> SEQUENCE: 691
gtagtcgtgg ccgagtggtt aaggcgatgg actagaaatc cattggggtc tccccgcgca    60
ggttcgaatc ctgccgacta cg                                              82

<210> SEQ ID NO 692
<211> LENGTH: 82
<212> TYPE: DNA
<213> ORGANISM: Homo sapiens

<400> SEQUENCE: 692
gtagtcgtgg ccgagtggtt aaggcgatgg actagaaatc cattggggtc tccccgcgca    60
ggttcgaatc ctgccgacta cg                                              82

<210> SEQ ID NO 693
<211> LENGTH: 82
<212> TYPE: DNA
<213> ORGANISM: Homo sapiens

<400> SEQUENCE: 693
gtagtcgtgg ccgagtggtt aaggcgatgg actagaaatc cattggggtc tccccgcgca    60
ggttcgaatc ctgccgacta cg    82

<210> SEQ ID NO 694
<211> LENGTH: 82
<212> TYPE: DNA
<213> ORGANISM: Homo sapiens

<400> SEQUENCE: 694
gtagtcgtgg ccgagtggtt aaggcgatgg actagaaatc cattggggtc tccccgcgca    60
ggttcgaatc ctgccgacta cg    82

<210> SEQ ID NO 695
<211> LENGTH: 82
<212> TYPE: DNA
<213> ORGANISM: Homo sapiens

<400> SEQUENCE: 695
gtagtcgtgg ccgagtggtt aaggcgatgg actagaaatc cattggggtc tccccgcgca    60
ggttcgaatc ctgccgacta cg    82

<210> SEQ ID NO 696
<211> LENGTH: 82
<212> TYPE: DNA
<213> ORGANISM: Homo sapiens

<400> SEQUENCE: 696
gtagtcgtgg ccgagtggtt aaggcgatgg actagaaatc cattgggggtt tccccgcgca    60 ggttcgaatc ctgccgacta cg    82

<210> SEQ ID NO 697
<211> LENGTH: 82
<212> TYPE: DNA
<213> ORGANISM: Homo sapiens

<400> SEQUENCE: 697
gtcacggtgg ccgagtggtt aaggcgttgg actcgaaatc caatggggtt tccccgcaca    60
ggttcgaatc ctgttcgtga cg    82

<210> SEQ ID NO 698
<211> LENGTH: 82
<212> TYPE: DNA
<213> ORGANISM: Homo sapiens

<400> SEQUENCE: 698
gctgtgatgg ccgagtggtt aaggtgttgg actcgaaatc caatgggggt tccccgcgca    60
ggttcaaatc ctgctcacag cg    82

<210> SEQ ID NO 699
<211> LENGTH: 82
<212> TYPE: DNA
<213> ORGANISM: Homo sapiens

```
<400> SEQUENCE: 699
gctgtgatgg ccgagtggtt aaggcgttgg actcgaaatc caatggggtc tccccgcgca      60
ggttcaaatc ctgctcacag cg                                               82

<210> SEQ ID NO 700
<211> LENGTH: 82
<212> TYPE: DNA
<213> ORGANISM: Homo sapiens

<400> SEQUENCE: 700
gctgtgatgg ccgagtggtt aaggcgttgg actcgaaatc caatggggtc tccccgcgca      60
ggttcgaatc ctgctcacag cg                                               82

<210> SEQ ID NO 701
<211> LENGTH: 84
<212> TYPE: DNA
<213> ORGANISM: Homo sapiens

<400> SEQUENCE: 701
ggagaggcct ggccgagtgg ttaaggcgat ggactgctaa tccattgtgc tctgcacgcg      60
tgggttcgaa tcccatcctc gtcg                                             84

<210> SEQ ID NO 702
<211> LENGTH: 82
<212> TYPE: DNA
<213> ORGANISM: Homo sapiens

<400> SEQUENCE: 702
gacgaggtgg ccgagtggtt aaggcgatgg actgctaatc cattgtgctc tgcacacgtg      60
ggttcgaatc ccatcctcgt cg                                               82

<210> SEQ ID NO 703
<211> LENGTH: 82
<212> TYPE: DNA
<213> ORGANISM: Homo sapiens

<400> SEQUENCE: 703
gacgaggtgg ccgagtggtt aaggcgatgg actgctaatc cattgtgctc tgcacgcgtg      60
ggttcgaatc ccatcctcgt cg                                               82

<210> SEQ ID NO 704
<211> LENGTH: 82
<212> TYPE: DNA
<213> ORGANISM: Homo sapiens

<400> SEQUENCE: 704
gacgaggtgg ccgagtggtt aaggcgatgg actgctaatc cattgtgctc tgcacgcgtg      60
ggttcgaatc ccatcctcgt cg                                               82

<210> SEQ ID NO 705
<211> LENGTH: 82
<212> TYPE: DNA
<213> ORGANISM: Homo sapiens

<400> SEQUENCE: 705
gacgaggtgg ccgagtggtt aaggcgatgg actgctaatc cattgtgctc tgcacgcgtg      60
ggttcgaatc ccatcctcgt cg                                               82
```

```
<210> SEQ ID NO 706
<211> LENGTH: 82
<212> TYPE: DNA
<213> ORGANISM: Homo sapiens

<400> SEQUENCE: 706
gacgaggtgg ccgagtggtt aaggcgatgg actgctaatc cattgtgctt tgcacgcgtg      60
ggttcgaatc ccatcctcgt cg                                               82

<210> SEQ ID NO 707
<211> LENGTH: 82
<212> TYPE: DNA
<213> ORGANISM: Homo sapiens

<400> SEQUENCE: 707
gacgaggtgg ccgagtggtt aaggcgatgg actgctaatc cattgtgctc tgcacgcgtg      60
ggttcgaatc ccaccttcgt cg                                               82

<210> SEQ ID NO 708
<211> LENGTH: 82
<212> TYPE: DNA
<213> ORGANISM: Homo sapiens

<400> SEQUENCE: 708
gacgaggtgg ccgagtggtt aaggcgatgg actgctaatc cattgtgctc tgcacgcgtg      60
ggttcgaatc ccaccctcgt cg                                               82

<210> SEQ ID NO 709
<211> LENGTH: 70
<212> TYPE: DNA
<213> ORGANISM: Homo sapiens

<400> SEQUENCE: 709
gagaaggtca cagaggttat gggattggct tgaaaccagt ctgtgggggg ttcgattccc      60 tccttttttca                                                            70

<210> SEQ ID NO 710
<211> LENGTH: 82
<212> TYPE: DNA
<213> ORGANISM: Homo sapiens

<400> SEQUENCE: 710
gtagtcgtgg ccgagtggtt aaggcgatgg acttgaaatc cattggggtt tccccgcgca      60
ggttcgaatc ctgtcggcta cg                                               82

<210> SEQ ID NO 711
<211> LENGTH: 82
<212> TYPE: DNA
<213> ORGANISM: Homo sapiens

<400> SEQUENCE: 711
gtagtcgtgg ccgagtggtt aaggcgatgg acttgaaatc cattggggtc tccccgcgca      60
ggttcgaatc ctgccgacta cg                                               82

<210> SEQ ID NO 712
<211> LENGTH: 82
<212> TYPE: DNA
<213> ORGANISM: Homo sapiens

<400> SEQUENCE: 712
```

```
gtagtcgtgg ccgagtggtt aaggcgatgg acttgaaatc cattggggtt tccccgcgca    60
ggttcgaatc ctgccgacta cg                                             82

<210> SEQ ID NO 713
<211> LENGTH: 82
<212> TYPE: DNA
<213> ORGANISM: Homo sapiens

<400> SEQUENCE: 713
gcagcgatgg ccgagtggtt aaggcgttgg acttgaaatc caatggggtc tccccgcgca    60
ggttcgaacc ctgctcgctg cg                                             82

<210> SEQ ID NO 714
<211> LENGTH: 74
<212> TYPE: DNA
<213> ORGANISM: Homo sapiens

<400> SEQUENCE: 714
ggcagtgacg cctactggtt tagagcacag attctagatc gagacattcc tgggttcaaa    60
tcccagcact gttg                                                      74

<210> SEQ ID NO 715
<211> LENGTH: 71
<212> TYPE: DNA
<213> ORGANISM: Homo sapiens

<400> SEQUENCE: 715
ggcagtgaca tgtaatggtt atgagggtgg actttaacca cactgcctag gttcaaatcc    60
tgactctgtc a                                                         71

<210> SEQ ID NO 716
<211> LENGTH: 71
<212> TYPE: DNA
<213> ORGANISM: Homo sapiens

<400> SEQUENCE: 716
gcccggatag ttcagttggt agagcatcag acttaatcag agggtccagg gttcaagtcc    60
ctgtttgggt g                                                         71

<210> SEQ ID NO 717
<211> LENGTH: 74
<212> TYPE: DNA
<213> ORGANISM: Homo sapiens

<400> SEQUENCE: 717
agcaccatgg cttagctggt taaagcacct gtctagtaaa caggagatcc tgagtttcaa    60
ttccaatggt gcct                                                      74

<210> SEQ ID NO 718
<211> LENGTH: 74
<212> TYPE: DNA
<213> ORGANISM: Homo sapiens

<400> SEQUENCE: 718
ggccctgtgg cttagctggt caaagcgcct gtctagtaaa caggagatcc tgggttcgaa    60
tcccagcggg gcct                                                      74

<210> SEQ ID NO 719
<211> LENGTH: 74
```

```
<212> TYPE: DNA
<213> ORGANISM: Homo sapiens

<400> SEQUENCE: 719
ggcttcgtgg cttagctggt taaagcgcct gtctagtaaa caggagatcc tgggttcgaa    60
tcccagcgag gcct                                                      74

<210> SEQ ID NO 720
<211> LENGTH: 74
<212> TYPE: DNA
<213> ORGANISM: Homo sapiens

<400> SEQUENCE: 720
ggcgccgtgg cttagctggt taaagcgcct gtctagtaaa caggagatcc tgggttcgaa    60
tcccagcggt gcct                                                      74

<210> SEQ ID NO 721
<211> LENGTH: 74
<212> TYPE: DNA
<213> ORGANISM: Homo sapiens

<400> SEQUENCE: 721
ggctccgtag cttagttggt taaagcgcct gtctagtaaa caggagatcc tgggttcgac    60
tcccagcggg gcct                                                      74

<210> SEQ ID NO 722
<211> LENGTH: 74
<212> TYPE: DNA
<213> ORGANISM: Homo sapiens

<400> SEQUENCE: 722
ggctccgtgg cttagctggt taaagcgcct gtctagtaaa caggagatcc tgggttcgaa    60
tcccagcggg gcct                                                      74

<210> SEQ ID NO 723
<211> LENGTH: 74
<212> TYPE: DNA
<213> ORGANISM: Homo sapiens

<400> SEQUENCE: 723
ggctccgtgg cttagctggt taaagcgcct gtctagtaaa caggagatcc tgggttcgaa    60
tcccagcggg gcct                                                      74

<210> SEQ ID NO 724
<211> LENGTH: 74
<212> TYPE: DNA
<213> ORGANISM: Homo sapiens

<400> SEQUENCE: 724
ggcgccgtgg cttagttggt taaagcgcct gtctagtaaa caggagatcc tgggttcgaa    60
tcccagcggt gcct                                                      74

<210> SEQ ID NO 725
<211> LENGTH: 74
<212> TYPE: DNA
<213> ORGANISM: Homo sapiens

<400> SEQUENCE: 725
ggcgccgtgg cttagttggt taaagcgcct gtctagtaaa caggagatcc tgggttcgaa    60
```

```
tcccagcggt gcct                                                         74

<210> SEQ ID NO 726
<211> LENGTH: 74
<212> TYPE: DNA
<213> ORGANISM: Homo sapiens

<400> SEQUENCE: 726
ggcgccgtgg cttagttggt taaagcgcct gtctagtaaa caggagatcc tgggttcgaa      60
tcccagcggt gcct                                                         74

<210> SEQ ID NO 727
<211> LENGTH: 72
<212> TYPE: DNA
<213> ORGANISM: Homo sapiens

<400> SEQUENCE: 727
ggcagagtgg tgcagcggaa gcgtgctggg cccgtaaccc agaggtcaat ggatcgaagc      60
catccttggc ta                                                           72

<210> SEQ ID NO 728
<211> LENGTH: 74
<212> TYPE: DNA
<213> ORGANISM: Homo sapiens

<400> SEQUENCE: 728
ggccctgtag ctcagcggtt ggagcgctgg tctcgtaaac ctaggggtcg tgagttcaaa      60
tctcaccagg gcct                                                         74

<210> SEQ ID NO 729
<211> LENGTH: 72
<212> TYPE: DNA
<213> ORGANISM: Homo sapiens

<400> SEQUENCE: 729
ggcgcggtgg ccaagtggta aggcgtcggt ctcgtaaacc gaagatcgcg ggttcgaacc      60
ccgtccgtgc ct                                                           72

<210> SEQ ID NO 730
<211> LENGTH: 74
<212> TYPE: DNA
<213> ORGANISM: Homo sapiens

<400> SEQUENCE: 730
ggctctgtgg cttagttggc taaagcgcct gtctcgtaaa caggagatcc tgggttcgaa      60
tcccagcggg gcct                                                         74

<210> SEQ ID NO 731
<211> LENGTH: 72
<212> TYPE: DNA
<213> ORGANISM: Homo sapiens

<400> SEQUENCE: 731
ggcgcggtgg ccaagtggta aggcgtcggt ctcgtaaacc gaagatcacg ggttcgaacc      60
ccgtccgtgc ct                                                           72

<210> SEQ ID NO 732
<211> LENGTH: 74
<212> TYPE: DNA
<213> ORGANISM: Homo sapiens
```

<400> SEQUENCE: 732
ggctctatgg cttagttggt taaagcgcct gtctcgtaaa caggagatcc tgggttcgac    60
tcccagtggg gcct    74

<210> SEQ ID NO 733
<211> LENGTH: 72
<212> TYPE: DNA
<213> ORGANISM: Homo sapiens

<400> SEQUENCE: 733
ggctccatag ctcaggggtt agagcactgg tcttgtaaac cagggtcgcg agttcaaatc    60
tcgctggggc ct    72

<210> SEQ ID NO 734
<211> LENGTH: 73
<212> TYPE: DNA
<213> ORGANISM: Homo sapiens

<400> SEQUENCE: 734
ggccctatag ctcaggggtt agagcactgg tcttgtaaac caggggtcgc gagttcaaat    60
ctcgctgggg cct    73

<210> SEQ ID NO 735
<211> LENGTH: 73
<212> TYPE: DNA
<213> ORGANISM: Homo sapiens

<400> SEQUENCE: 735
ggctccatag ctcaggggtt agagcactgg tcttgtaaac caggggtcgc gagttcaaat    60
ctcgctgggg cct    73

<210> SEQ ID NO 736
<211> LENGTH: 73
<212> TYPE: DNA
<213> ORGANISM: Homo sapiens

<400> SEQUENCE: 736
ggctccatag ctcaggggtt agagcgctgg tcttgtaaac caggggtcgc gagttcaatt    60
ctcgctgggg cct    73

<210> SEQ ID NO 737
<211> LENGTH: 73
<212> TYPE: DNA
<213> ORGANISM: Homo sapiens

<400> SEQUENCE: 737
ggctccatag ctcagtggtt agagcactgg tcttgtaaac caggggtcgc gagttcgatc    60
ctcgctgggg cct    73

<210> SEQ ID NO 738
<211> LENGTH: 74
<212> TYPE: DNA
<213> ORGANISM: Homo sapiens

<400> SEQUENCE: 738
ggctctatgg cttagttggt taaagcgcct gtcttgtaaa caggagatcc tgggttcgaa    60
tcccagtaga gcct    74

<210> SEQ ID NO 739
<211> LENGTH: 74
<212> TYPE: DNA
<213> ORGANISM: Homo sapiens

<400> SEQUENCE: 739
ggaaggatgg ggccaagctg gaaagcctgt gggctccaca gtcatgtgcc tgggttcaat    60
tcccagttct gcat    74

<210> SEQ ID NO 740
<211> LENGTH: 72
<212> TYPE: DNA
<213> ORGANISM: Homo sapiens

<400> SEQUENCE: 740
gacctcgtgg cgcaacggca gcgcgtctga ctccagatca gaaggttgcg tgttcaaatc    60
acgtcggggt ca    72

<210> SEQ ID NO 741
<211> LENGTH: 72
<212> TYPE: DNA
<213> ORGANISM: Homo sapiens

<400> SEQUENCE: 741
gacctcgtgg cgcaacggta gcgcgtctga ctccagatca gaaggctgcg tgttcgaatc    60
acgtcggggt ca    72

<210> SEQ ID NO 742
<211> LENGTH: 72
<212> TYPE: DNA
<213> ORGANISM: Homo sapiens

<400> SEQUENCE: 742
gacctcgtgg cgcaacggta gcgcgtctga ctccagatca gaaggttgcg tgttcaaatc    60
acgtcggggt ca    72

<210> SEQ ID NO 743
<211> LENGTH: 72
<212> TYPE: DNA
<213> ORGANISM: Homo sapiens

<400> SEQUENCE: 743
gacctcgtgg cgcaacggta gcgcgtctga ctccagatca gaaggttgcg tgttcaaatc    60
acgtcggggt ca    72

<210> SEQ ID NO 744
<211> LENGTH: 72
<212> TYPE: DNA
<213> ORGANISM: Homo sapiens

<400> SEQUENCE: 744
gacctcgtgg cgcaacggta gcgcgtctga ctccagatca gaaggttgcg tgttcaaatc    60
acgtcggggt ca    72

<210> SEQ ID NO 745
<211> LENGTH: 72
<212> TYPE: DNA
<213> ORGANISM: Homo sapiens

<400> SEQUENCE: 745

```
gacctcgtgg cgcaatggta gcgcgtctga ctccagatca gaaggttgcg tgttcaagtc    60
acgtcggggt ca                                                        72

<210> SEQ ID NO 746
<211> LENGTH: 72
<212> TYPE: DNA
<213> ORGANISM: Homo sapiens

<400> SEQUENCE: 746
ggcctcgtgg cgcaacggta gcgcgtctga ctccagatca gaaggttgcg tgttcaaatc    60
acgtcggggt ca                                                        72

<210> SEQ ID NO 747
<211> LENGTH: 99
<212> TYPE: DNA
<213> ORGANISM: Homo sapiens

<400> SEQUENCE: 747
ggcagaggag ggtgcagttg gcagcctgtc caagtccagc acggttggag cacaggattt    60
agaatgggat ggtcctgggt tcaaacccca gctgcgccc                           99

<210> SEQ ID NO 748
<211> LENGTH: 93
<212> TYPE: DNA
<213> ORGANISM: Homo sapiens

<400> SEQUENCE: 748
ccttcaatag ttcagctggt agagcagagg actatagcta cttcctcagt aggagacgtc    60
cttaggttgc tggttcgatt ccagcttgaa gga                                 93

<210> SEQ ID NO 749
<211> LENGTH: 73
<212> TYPE: DNA
<213> ORGANISM: Homo sapiens

<400> SEQUENCE: 749
gggggtatag ctcagggcta gagcttttg actgtagagc aagaggtccc tggttcaaat     60
ccaggttctc cct                                                       73

<210> SEQ ID NO 750
<211> LENGTH: 94
<212> TYPE: DNA
<213> ORGANISM: Homo sapiens

<400> SEQUENCE: 750
ccttcgatag ctcagctggt agagcggagg actgtagcct gtagaaacat ttgtggacat    60
ccttaggtcg ctggttcgat tccggctcga agga                                94

<210> SEQ ID NO 751
<211> LENGTH: 94
<212> TYPE: DNA
<213> ORGANISM: Homo sapiens

<400> SEQUENCE: 751
ccttcgatag ctcagctggt agagcggagg actgtagatt gtatagacat ttgcggacat    60
ccttaggtcg ctggttcgat tccagctcga agga                                94

<210> SEQ ID NO 752
```

```
<211> LENGTH: 94
<212> TYPE: DNA
<213> ORGANISM: Homo sapiens

<400> SEQUENCE: 752
ccttcgatag ctcagctggt agagcggagg actgtagact gcggaaacgt ttgtggacat    60
ccttaggtcg ctggttcaat tccggctcga agga                                94

<210> SEQ ID NO 753
<211> LENGTH: 94
<212> TYPE: DNA
<213> ORGANISM: Homo sapiens

<400> SEQUENCE: 753
ccttcgatag ctcagctggt agagcggagg actgtagatt gtacagacat ttgcggacat    60
ccttaggtcg ctggttcgat tccggctcga agga                                94

<210> SEQ ID NO 754
<211> LENGTH: 89
<212> TYPE: DNA
<213> ORGANISM: Homo sapiens

<400> SEQUENCE: 754
ccttcgatag ctcagctggt agagcggagg actgtagtac ttaatgtgtg gtcatcctta    60
ggtcgctggt tcgattccgg ctcgaagga                                      89

<210> SEQ ID NO 755
<211> LENGTH: 91
<212> TYPE: DNA
<213> ORGANISM: Homo sapiens

<400> SEQUENCE: 755
ccttcgatag ctcagttggt agagcggagg actgtagttg gctgtgtcct tagacatcct    60
taggtcgctg gttcgaatcc ggctcgaagg a                                   91

<210> SEQ ID NO 756
<211> LENGTH: 90
<212> TYPE: DNA
<213> ORGANISM: Homo sapiens

<400> SEQUENCE: 756
ctttcgatag ctcagttggt agagcggagg actgtaggtt cattaaacta aggcatcctt    60
aggtcgctgg ttcgaatccg gctcgaagga                                     90

<210> SEQ ID NO 757
<211> LENGTH: 89
<212> TYPE: DNA
<213> ORGANISM: Homo sapiens

<400> SEQUENCE: 757
ccttcgatag ctcagttggt agagcggagg actgtaggct cattaagcaa ggtatcctta    60
ggtcgctggt tcgaatccgg ctcggagga                                      89

<210> SEQ ID NO 758
<211> LENGTH: 89
<212> TYPE: DNA
<213> ORGANISM: Homo sapiens

<400> SEQUENCE: 758
ccttcgatag ctcagctggt agagcggagg actgtagggg tttgaatgtg gtcatcctta    60
```

```
ggtcgctggt tcgaatccgg ctcggagga                                       89

<210> SEQ ID NO 759
<211> LENGTH: 89
<212> TYPE: DNA
<213> ORGANISM: Homo sapiens

<400> SEQUENCE: 759
ccttcgatag ctcagttggt agagcggagg actgtagtgg atagggcgtg gcaatcctta    60
ggtcgctggt tcgattccgg ctcgaagga                                       89

<210> SEQ ID NO 760
<211> LENGTH: 88
<212> TYPE: DNA
<213> ORGANISM: Homo sapiens

<400> SEQUENCE: 760
tcttcaatag ctcagctggt agagcggagg actgtaggtg cacgcccgtg gccattctta    60
ggtgctggtt tgattccgac ttggagag                                        88

<210> SEQ ID NO 761
<211> LENGTH: 93
<212> TYPE: DNA
<213> ORGANISM: Homo sapiens

<400> SEQUENCE: 761
ccttcgatag ctcagctggt agagcggagg actgtagcta cttcctcagc aggagacatc    60
cttaggtcgc tggttcgatt ccggctcgaa gga                                  93

<210> SEQ ID NO 762
<211> LENGTH: 89
<212> TYPE: DNA
<213> ORGANISM: Homo sapiens

<400> SEQUENCE: 762
ccttcgatag ctcagctggt agagcggagg actgtaggcg cgcgcccgtg gccatcctta    60
ggtcgctggt tcgattccgg ctcgaagga                                       89

<210> SEQ ID NO 763
<211> LENGTH: 73
<212> TYPE: DNA
<213> ORGANISM: Homo sapiens

<400> SEQUENCE: 763
gtttccatag tgtactggtt atcacattca cctaacacgc gaaaggtcct tggtttgaaa    60
ccaggcagaa aca                                                        73

<210> SEQ ID NO 764
<211> LENGTH: 72
<212> TYPE: DNA
<213> ORGANISM: Homo sapiens

<400> SEQUENCE: 764
gggggtgtag ctcagtggta gagcgtatgc ttaacattca tgaggctctg ggttcgatcc    60
ccagcacttc ca                                                         72

<210> SEQ ID NO 765
<211> LENGTH: 73
<212> TYPE: DNA
```

```
<213> ORGANISM: Homo sapiens

<400> SEQUENCE: 765
gtttccgtag tgtagtggtt atcacgtttg cctaacacgc gaaaggtccc cggttcgaaa    60
ccgggcagaa aca                                                       73

<210> SEQ ID NO 766
<211> LENGTH: 73
<212> TYPE: DNA
<213> ORGANISM: Homo sapiens

<400> SEQUENCE: 766
gtttccgtag tgtagtggtt atcacgttcg cctaacacgc gaaaggtccg cggttcgaaa    60
ccgggcggaa aca                                                       73

<210> SEQ ID NO 767
<211> LENGTH: 73
<212> TYPE: DNA
<213> ORGANISM: Homo sapiens

<400> SEQUENCE: 767
gtttccgtag tgtagtggtt atcacgttcg cctaacacgc gaaaggtccc tggatcaaaa    60
ccaggcggaa aca                                                       73

<210> SEQ ID NO 768
<211> LENGTH: 73
<212> TYPE: DNA
<213> ORGANISM: Homo sapiens

<400> SEQUENCE: 768
gtttccgtag tgtagtggtc atcacgttcg cctaacacgc gaaaggtccc cggttcgaaa    60
ccgggcggaa aca                                                       73

<210> SEQ ID NO 769
<211> LENGTH: 73
<212> TYPE: DNA
<213> ORGANISM: Homo sapiens

<400> SEQUENCE: 769
gtttccgtag tgtagtggtt atcacgttcg cctaacacgc gaaaggtccc cggttcgaaa    60
ccgggcggaa aca                                                       73

<210> SEQ ID NO 770
<211> LENGTH: 73
<212> TYPE: DNA
<213> ORGANISM: Homo sapiens

<400> SEQUENCE: 770
gtttccgtag tgtagtggtt atcacgttcg cctaacacgc gaaaggtccc cggttcgaaa    60 ccgggcgaa aca                                                        73

<210> SEQ ID NO 771
<211> LENGTH: 73
<212> TYPE: DNA
<213> ORGANISM: Homo sapiens

<400> SEQUENCE: 771
gtttccgtag tgtagtggtt atcacgttcg cctaacacgc gaaaggtccc cggttcgaaa    60
ccgggcggaa aca                                                       73
```

<210> SEQ ID NO 772
<211> LENGTH: 73
<212> TYPE: DNA
<213> ORGANISM: Homo sapiens

<400> SEQUENCE: 772
gtttccgtag tgtagtggtt atcacgttcg cctaacacgc gaaaggtccc cggttcgaaa    60
ccgggcggaa aca                                                       73

<210> SEQ ID NO 773
<211> LENGTH: 73
<212> TYPE: DNA
<213> ORGANISM: Homo sapiens

<400> SEQUENCE: 773
gtttccgtag tgtagtggtt atcacgttcg cctaacacgc gaaaggtccc cggttcgaaa    60
ccgggcggaa aca                                                       73

<210> SEQ ID NO 774
<211> LENGTH: 74
<212> TYPE: DNA
<213> ORGANISM: Homo sapiens

<400> SEQUENCE: 774
ttttctgtag tgtagttgtt aacacgttcg cctcacacgc ttaaagttct ctggttggat    60
accagatgga aatg                                                      74

<210> SEQ ID NO 775
<211> LENGTH: 73
<212> TYPE: DNA
<213> ORGANISM: Homo sapiens

<400> SEQUENCE: 775
gtttctgtgg tgtagtggtt atcatgttcg cctcacacga gaaaagtccc tgattcgaga    60
ctgggtggga acg                                                       73

<210> SEQ ID NO 776
<211> LENGTH: 73
<212> TYPE: DNA
<213> ORGANISM: Homo sapiens

<400> SEQUENCE: 776
gtttctgtag tatggtggtt atcacgttag tctcacacgt gaaaggtccc tggttcgaaa    60
ccaggtggaa aca                                                       73

<210> SEQ ID NO 777
<211> LENGTH: 71
<212> TYPE: DNA
<213> ORGANISM: Homo sapiens

<400> SEQUENCE: 777
gcactggtgg ttcagtggta gaattctcgc ctcacacgcg ggacacccgg gttcaattcc    60
cggtcaaggc a                                                         71

<210> SEQ ID NO 778
<211> LENGTH: 73
<212> TYPE: DNA
<213> ORGANISM: Homo sapiens

<400> SEQUENCE: 778
gtttccgtag tgtagtggtt attatgttcg cctcacacgc gaaaagtccc cggttcgaaa    60
tcaggcggga aca    73

<210> SEQ ID NO 779
<211> LENGTH: 73
<212> TYPE: DNA
<213> ORGANISM: Homo sapiens

<400> SEQUENCE: 779
gtttccgtag tggagtggtt atcacgttcg cctcacacgc gaaaggtccc cggtttgaaa    60
ccaggcggaa aca    73

<210> SEQ ID NO 780
<211> LENGTH: 74
<212> TYPE: DNA
<213> ORGANISM: Homo sapiens

<400> SEQUENCE: 780
gtttccgtag tgtagtggtt atcacgttcg cctcacacgc gtaaaggtcc ccggttcgaa    60
accgggcgga aaca    74

<210> SEQ ID NO 781
<211> LENGTH: 73
<212> TYPE: DNA
<213> ORGANISM: Homo sapiens

<400> SEQUENCE: 781
gtttccgtag tgtagtggtt atcacgttcg cctcacacgc gaaaggtccc cggttcgaaa    60
ctgggcggaa aca    73

<210> SEQ ID NO 782
<211> LENGTH: 73
<212> TYPE: DNA
<213> ORGANISM: Homo sapiens

<400> SEQUENCE: 782
gtttccgtag tgtagcggtt atcacattcg cctcacacgc gaaaggtccc cggttcgatc    60
ccgggcggaa aca    73

<210> SEQ ID NO 783
<211> LENGTH: 73
<212> TYPE: DNA
<213> ORGANISM: Homo sapiens

<400> SEQUENCE: 783
gcttctgtag tgtagtggtt atcacgttcg cctcacacgc gaaaggtccc cggttcgaaa    60
ccgggcagaa gca    73

<210> SEQ ID NO 784
<211> LENGTH: 73
<212> TYPE: DNA
<213> ORGANISM: Homo sapiens

<400> SEQUENCE: 784
gtttccgtag tgtagtggtt atcacgttcg cctcacacgc gaaaggtccc cggttcgaaa    60
ccgggcggaa aca    73

```
<210> SEQ ID NO 785
<211> LENGTH: 73
<212> TYPE: DNA
<213> ORGANISM: Homo sapiens

<400> SEQUENCE: 785
gtttccgtag tgtagtggtt atcacgttcg cctcacacgc gaaaggtccc cggttcgaaa      60
ccgggcggaa aca                                                        73

<210> SEQ ID NO 786
<211> LENGTH: 73
<212> TYPE: DNA
<213> ORGANISM: Homo sapiens

<400> SEQUENCE: 786
gtttccgtag tgtagtggtt atcacgttcg cctcacacgc gaaaggtccc cggttcgaaa      60
ccgggcggaa aca                                                        73

<210> SEQ ID NO 787
<211> LENGTH: 73
<212> TYPE: DNA
<213> ORGANISM: Homo sapiens

<400> SEQUENCE: 787
gtttccgtag tgtagtggtt atcacgttcg cctcacacgc gaaaggtccc cggttcgaaa      60
ccgggcggaa aca                                                        73

<210> SEQ ID NO 788
<211> LENGTH: 73
<212> TYPE: DNA
<213> ORGANISM: Homo sapiens

<400> SEQUENCE: 788
gtttccgtag tgtagtggtt atcacgttcg cctcacacgc gaaaggtccc cggttcgaaa      60
ccgggcggaa aca                                                        73

<210> SEQ ID NO 789
<211> LENGTH: 73
<212> TYPE: DNA
<213> ORGANISM: Homo sapiens

<400> SEQUENCE: 789
gtttccgtag tgtagtggtt atcacgttcg cctcacacgc gaaaggtccc cggttcgaaa      60
ccgggcggaa aca                                                        73

<210> SEQ ID NO 790
<211> LENGTH: 73
<212> TYPE: DNA
<213> ORGANISM: Homo sapiens

<400> SEQUENCE: 790
gtttccgtgg tgtagtggtt atcacattcg ccttacacgc gaaaggtcct cgggtcgaaa      60
ccgagcggaa aca                                                        73

<210> SEQ ID NO 791
<211> LENGTH: 73
<212> TYPE: DNA
<213> ORGANISM: Homo sapiens

<400> SEQUENCE: 791
```

-continued

```
ggttccatag tgtagtggtt atcacatctg ctttacacgc agaaggtcct gggttcaagc     60
cccagtggaa cca                                                        73

<210> SEQ ID NO 792
<211> LENGTH: 73
<212> TYPE: DNA
<213> ORGANISM: Homo sapiens

<400> SEQUENCE: 792
ggttccatag tgtagcggtt atcacgtctg ctttacacgc agaaggtcct gggttcgagc     60
cccagtggaa cca                                                        73

<210> SEQ ID NO 793
<211> LENGTH: 73
<212> TYPE: DNA
<213> ORGANISM: Homo sapiens

<400> SEQUENCE: 793
ggttccatag tgtagtggtt atcacgtctg ctttacacgc agaaggtcct gggttcgagc     60
cccagtggaa cca                                                        73

<210> SEQ ID NO 794
<211> LENGTH: 73
<212> TYPE: DNA
<213> ORGANISM: Homo sapiens

<400> SEQUENCE: 794
ggttccatag tgtagtggtt atcacgtctg ctttacacgc agaaggtcct gggttcgagc     60
cccagtggaa cca                                                        73

<210> SEQ ID NO 795
<211> LENGTH: 72
<212> TYPE: DNA
<213> ORGANISM: Homo sapiens

<400> SEQUENCE: 795
taggatatgg tttaataggt agcatggaga attttggagt ctcagggata ggttcaattc     60
ctatagttcc ag                                                         72

<210> SEQ ID NO 796
<211> LENGTH: 72
<212> TYPE: DNA
<213> ORGANISM: Homo sapiens

<400> SEQUENCE: 796
ggtcccatgg tgtaatggtt agcactctgg actttgaatc cagcaatccg agttcgaatc     60
tcggtgggac ct                                                         72
```

NEUROPROTECTIVE MOLECULES AND METHODS OF TREATING NEUROLOGICAL DISORDERS AND INDUCING STRESS GRANULES

CLAIM OF PRIORITY

This application is a continuation of U.S. patent application Ser. No. 13/808,863, with a 371 filing date of Mar. 29, 2013, which is a 35 U.S.C. § 371 national phase application of International Application No. PCT/US2011/043400, filed Jul. 8, 2011, which claims the benefit of U.S. Provisional Application Ser. No. 61/362,526, filed Jul. 8, 2010, the entire contents of each of which are incorporated by reference herein.

STATEMENT AS TO FEDERALLY-SPONSORED RESEARCH

This invention was made with government support under federal research grant AI0658568 awarded by the National Institutes of Health. The government has certain rights in the invention.

TECHNICAL FIELD

This invention relates to neuroprotective molecules and methods of treating neurological diseases associated with neuron death, inducing stress granule formation in a cell, inhibiting translation in a cell, and decreasing stress-induced cell death.

BACKGROUND

Amyotrophic lateral sclerosis (ALS) is a progressive neurodegenerative disease distinguished by a specific loss of motor neurons in the brain, brain stem, and spinal cord. Initial symptoms of loss of motor neuron activity, including distal muscle weakness and wasting, increased muscle tone with hyperreflexia, and diaphragmatic and/or bulbar weakness are first noticed at an average age of 55. Death occurs from respiratory failure at an average of 4 years after disease onset. The only recognized treatment for ALS is riluzole which extends survival by only about 3 months with no improvement in motor muscular function.

Although ALS is a rare disease (~1-2 persons per 100,000 population), an understanding of its pathogenesis is likely to impact other neurological diseases that share some pathological features (e.g., frontotemporal lobal degeneration, Alzheimer's disease, Huntington's disease, spinal motor atrophy and fragilexmental retardation). Approximately 10% of ALS cases are familial and the rest are sporadic. Mutations in the Cu,Zn superoxide dismutase 1 gene (ALS1; SOD1) have been identified in ~20% of familial and in ~3% of sporadic ALS patients, making SOD1 mutations the most common cause of this disease. The RNA-binding proteins TDP-43 and FUS/TLS are the next most commonly mutated genes, each of which is responsible for ~4% of familial cases. A number of dominantly-inherited genes associated with atypical ALS phenotypes are each responsible for 1-3% of ALS cases (e.g., ALS with dementia/parkinsonism: microtubule-associated protein tau (MAPT); progressive lower motor neuron disease: dynactin subunit 1 (DCTN1); ALS8: vesicle-associated membrane protein-associated protein B/C (VAPB); juvenile onset autosomal dominant ALS: senataxin (SETX)).

ALS genes involved in RNA metabolism include TDP-43 and FUS/TLS: two RNA-binding proteins implicated in transcription, splicing, and translation. Both of these proteins are components of stress granules: cytoplasmic foci that are characterized as signaling centers assembled from proteins and untranslated mRNAs in cells exposed to adverse conditions. ALS-linked genes associated with RNA/ stress response pathways include: mutant SOD1 which inactivates a retrograde transport pathway that causes proteins to accumulate in the endoplasmic reticulum and trigger the unfolded protein response (UPR), a pro-survival program; vesicle-associated membrane protein (VAPB), an endoplasmic reticulum protein that interacts with ATF6, a UPR-activated transcription factor; senataxin, a DNA/RNA helicase associated with tRNA metabolism and the oxidative stress response; and angiogenin (ANG), a stress-activated ribonuclease that promotes motor neuron survival and extends the survival of SOD1$^{G93A}$ mice in a murine model of ALS. These genes indicate an association between mutations in proteins involved in stress granule formation and ALS, a neurological disorder associated with neuron death.

SUMMARY

Provided herein are neuroprotective molecules that contain a sequence of 25-35 contiguous nucleotides that is at least 80% identical to a contiguous sequence between nucleotide 1 and nucleotide 50 of a mature human tRNA that are useful for inducing or increasing stress granule formation in a cell, decreasing protein translation in a cell, reducing stress-induced cell death, and treating a neurological disorder associated with neuron death in a subject. The invention is based on the discovery that these neuroprotective molecules are taken up by motor neurons in the absence of transfection agents, induce stress granule formation in motor neurons, and confer protection against stress-induced motor neuron death.

Provided herein are neuroprotective molecules containing a sequence of 25-35 contiguous nucleotides that is at least 80% identical to a contiguous sequence between nucleotide 1 and nucleotide 50 of a mature human RNA, and at least four (e.g., at least five or six) contiguous guanosine-containing nucleotides, where the sequence of 25-35 contiguous nucleotides contains a D-loop stem structure, the at least four contiguous guanosine-containing nucleotides are located at the 5' end of the neuroprotective molecule, and the neuroprotective molecule contains at least one (e.g., at least two, three, or four) deoxyribonucleotide. In some embodiments, the sequence of 25-35 contiguous nucleotides is at least 80% identical to a contiguous sequence between nucleotide 1 and nucleotide 50 of a mature human tRNA having a sequence selected from the group consisting of: SEQ ID NOS: 4, 5, 8-11, 13-17, 32, 37, and 40-173.

Also provided are neuroprotective molecules containing a sequence of 25-35 contiguous nucleotides that is at least 80% identical to a contiguous sequence between nucleotide 1 and nucleotide 50 of a mature human tRNA selected from the group of: tRNA$^{Arg}$, tRNA$^{Asp}$, tRNA$^{Glu}$, tRNA$^{Gln}$, tRNA$^{Gly}$, tRNA$^{His}$, tRNA$^{Ile}$, tRNA$^{Leu}$, tRNA$^{Lys}$, tRNA$^{Met}$, tRNA$^{Pro}$, tRNA$^{SeC}$, tRNA$^{Ser}$, tRNA$^{Sup}$, tRNA$^{Thr}$, tRNA$^{Trp}$, tRNA$^{Tyr}$, tRNA$^{Val}$, tRNA$^{Asn}$, and tRNA$^{Phe}$; and at least four (e.g., at least five or six) contiguous guanosine-containing nucleotides, where the sequence of 25-35 contiguous nucleotides contains a D-loop stem structure and the at least four contiguous guanosine-containing nucleotides are located at the 5' end of the neuroprotective molecule. In some embodiments, the sequence of 25-35 contiguous nucleotides is at least 80% identical to a contiguous sequence between nucleotide 1 and nucleotide 50 of a mature human tRNA having a sequence selected from the group of SEQ ID NOS: 5, 8, 9, 11, 14-17, 32, 37, 56, 57, and 63-173. In some embodiments, the sequence of 25-35 contiguous nucleotides is at least 80% identical to a contiguous sequence between nucleotide 1 and nucleotide 50 of a mature human tRNA having a sequence selected from the group of SEQ ID NOS: 11 and 107-116.

In some embodiments, the neuroprotective molecule further comprises a 5'-monophosphate. In some embodiments, the neuroprotective molecule contains at least one modified nucleotide (e.g., a nucleotide containing a modified base and/or a modified sugar). In some embodiments, the neuroprotective molecule contains at least one modification in the phosphate backbone. In some embodiments, the neuroprotective molecule contains a 5' and/or a 3' protective group. In some embodiments, the neuroprotective molecule has a total length of between 39 to 60 nucleotides (e.g., 39 to 50 nucleotides or 50 to 60 nucleotides).

Also provided are pharmaceutical compositions that contain at least one neuroprotective molecule described herein (e.g., any of the neuroprotective molecules described herein).

Also provided are methods of inducing or increasing stress granule formation in a cell that include administering to a cell a neuroprotective molecule (e.g., any of the neuroprotective molecules described herein) or an isolated C-myc oligonucleotide containing the sequence of SEQ ID NO: 174, where the neuroprotective molecule or the isolated C-myc oligonucleotide is administered in an amount sufficient to induce or increase stress granule formation in the cell.

Also provided are methods of decreasing protein translation in a cell that include administering to a cell a neuroprotective molecule (e.g., any of the neuroprotective molecules described herein) or an isolated C-myc oligonucleotide containing the sequence of SEQ ID NO: 174, where the neuroprotective molecule or the isolated C-myc oligonucleotide is administered in an amount sufficient to decrease protein translation in the cell.

Also provided are methods of decreasing stress-induced cell death that include administering to the cell a neuroprotective molecule (e.g., any of the neuroprotective molecules described herein) or an isolated C-myc oligonucleotide containing the sequence of SEQ ID NO: 174, where the neuroprotective molecule or the isolated C-myc oligonucleotide is administered in an amount sufficient to decrease stress-induced cell death.

In some embodiments, the cell is in vitro. In some embodiments, the cell is in vivo. In some embodiments, the cell is a neuron (e.g., a motor neuron).

Also provided are methods of treating a neurological disorder associated with neuron death (necrosis and/or apoptosis, or stress-induced cell death) in a subject that include administering a neuroprotective molecule (e.g., any of the neuroprotective molecules described herein) or an isolated C-myc oligonucleotide containing the sequence of SEQ ID NO: 174, where the neuroprotective molecule or the isolated C-myc oligonucleotide is administered in an amount sufficient to treat the neurological disorder associated with neuron death in the subject.

In some embodiments, the neurological disorder associated with neuron death is selected from the group of: amyotrophic lateral sclerosis, Alzheimer's disease, Parkinson's disease, Huntington's disease, muscular dystrophy, multiple sclerosis, and stroke. In some embodiments, the neuroprotective molecule or the isolated C-myc oligonucleotide is administered intravenously, intraarterially, intracranially, ocularly, intraperitoneally, subcutaneously, or intramuscularly. In some embodiments, the subject is administered at least one additional therapeutic agent.

Also provided are methods of identifying a candidate translation inhibitor nucleic acid that include (a) attaching to the 5' end of a nucleic acid sequence of between 20-50 nucleotides at least four (e.g., at least five or six) guanosine-containing nucleotides, and (b) determining the level of protein translation in the presence of the molecule produced in (a), where a decrease in the level of protein translation in the presence of the molecule produced in (a) relative to the level of protein translation in the absence of the molecule produced in (a) identifies the molecule produced in (a) as a candidate translation inhibitory nucleic acid.

In some embodiments, the nucleic acid sequence of between 20-50 nucleotides contains at least 50% (e.g., at least 55%, 60%, 65%, or 70%) guanosine-containing/cytosine-containing nucleotides. In some embodiments, the nucleic acid sequence of between 20-50 nucleotides is at least 80% identical to a contiguous sequence in a mature human tRNA sequence. In some embodiments, the level of protein translation is determined in a cell. In some embodiments, the cell is a fibroblast or a motor neuron. In some embodiments, the cell is human. In some embodiments, the level of protein translation is determined in a cell lysate (e.g., a rabbit reticulocyte lysate).

By the phrase "mature human tRNA" is meant a human transfer RNA molecule in which the intron sequences have been removed.

By the phrase "D-loop stem structure" is meant a secondary loop structure present in mature human tRNAs that is formed by approximately nucleotides 5 to 28 of a mature human tRNA or a significantly similar stem-loop structure. Several exemplary three-dimensional structures of mature human tRNAs have been described and modeled by those skilled in the art.

By the phrase "deoxyribonucleotide" is meant a nucleotide that contains a 2'-deoxyribose. This term also includes nucleotides that contain modifications at other positions within the deoxyribose sugar or in the attached base.

By the phrase "guanosine-containing nucleotide" is meant a nucleotide that contains a guanosine or a modified guanosine. In some embodiments, the guanosine-containing nucleotide has the ability to form a G-quadruplex.

By the phrase "cytosine-containing nucleotide" is meant a nucleotide that contains a cytosine or a modified cytosine.

By the term "G-quadraplex" is meant a square structural arrangement of four guanines that is stabilized by Hoogsteen hydrogen bonds. A G-quadraplex can also be stabilized by the presence of a monovalent cation (e.g., potassium) in the center of the tetrad. A G-quadraplex can be formed by a DNA, a RNA, an LNA, or a PNA molecule (or any combination thereof). In some embodiments, the G-quadraplex is formed by four guanines that are present in the same molecule (e.g., any of the neuroprotective molecules or C-myc oligonucleotides described herein).

By the term "modified nucleotide" is meant a nucleotide that has a modification in its sugar and/or in its base. Non-limiting examples of modified nucleotides are described herein. Additional examples of modified nucleotides are known in the art.

By the phrase "5' or 3' protective group" is meant a moiety that is attached to the 5'- or the 3'-end of an oligonucleotide that prevents nuclease degradation or decreases (e.g., significantly decreases) the rate of nuclease degradation of the oligonucleotide. In some embodiments, the neuroprotective molecules or the C-myc oligonucleotides described herein contain a 5' and/or 3' protective group. Non-limiting examples of 5' and 3' protective groups are described herein. Additional examples of 5' and 3' protective groups are known in the art.

By the term "stress granule formation" is meant the formation or detection of at least one stress granule in a cell. Stress granule formation in a cell can be detected, for example, by microscopy (e.g., immunofluorescence microscopy) or the detection of phosphorylated eIF2α. Additional methods for detecting stress granule formation in a cell are described herein and are known in the art.

By the term "stress granule" is meant an aggregate of proteins and mRNAs that form in a cell under stress conditions. The poly(A)-mRNAs in a stress granule are present in stalled pre-initiation complexes. A stress granule can contain one or more (e.g., two, three, four, or five) of the following proteins/complexes, including but not limited to: 40S ribosomal subunits, eIF4E, eIF4G, eIF4A, eIF4B, poly (A) binding protein (Pabp), eIF3, and eIF2. Additional examples of proteins that can be found in stress granules are described herein. Additional examples of proteins that can be found in stress granules are known in the art (see, for example, Buchan et al., *Mol. Cell* 36:932, 2009).

By the term "protein translation" is meant the synthesis of a polypeptide from a messenger ribonucleic acid (RNA) molecule (e.g., a capped or uncapped mRNA molecule). The mRNA molecule typically contains a polyA 3'-tail. Protein translation can be performed in a cell or in a cellular lysate. Methods for detecting protein translation or the rate of protein translation are described herein. Additional methods for detecting protein translation or the rate of protein translation are known in the art.

By the term "neurological disorder associated with neuron death" is meant a neurological disease that is characterized by neuron death (e.g., motor neuron death) or has an etiology that involves neuron death (e.g., motor neuron death). Neuron death (apoptosis or necrosis) in these disorders can occur by a variety of different means (e.g., oxidative stress, excitotoxicity, and neuroinflammation). Methods for detecting neuron death in vivo or in vitro are described herein and are known in the art. Non-limiting examples of neurological disorders associated with neuron death are described herein. Additional examples of neurological disorders associated with neuron death are known in the art. In general, the methods do not require that cell death be detected in a subject prior to treatment, if the subject has a disorder known in the art to be associated with neuron death.

By the term "treating" is meant decreasing the number of symptoms or decreasing (e.g., a significant or detectable decrease) the severity, frequency, or duration of one or more symptoms of a disease in a subject. The term "treating" can also include decreasing (e.g., a significant or detectable decrease) the rate of neuron death in a subject having a neurological disorder associated with neuron death (e.g., compared to the rate of neuron death in the same subject prior to treatment or compared to the rate of neuron death in a control subject having the same disease but not receiving treatment or receiving a different treatment). A decrease in neuron death or the rate of neuron death in a subject can be assessed in a subject by a decrease in the rate of the development of one or more symptoms of a neurological disease associated with neuron death or a decrease in the worsening or exacerbation of one of more symptoms of a neurological disease associated with neuron death in a subject.

By the term "stress-induced cell death" is meant cell death that is triggered by or occurs in response to a cellular stress condition (e.g., oxidative stress, neuroexicitotoxicity, and neuroinflammation). Methods for detecting stress-induced cell death are described herein. Additional methods of detecting stress-induced cell death are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

in the RRL using uncapped (dark bars) or capped (light bars) pF/R bicistronic transcripts in the presence of 5'-tiRNA$^{Ala}$ (left panel).

Figure 6:
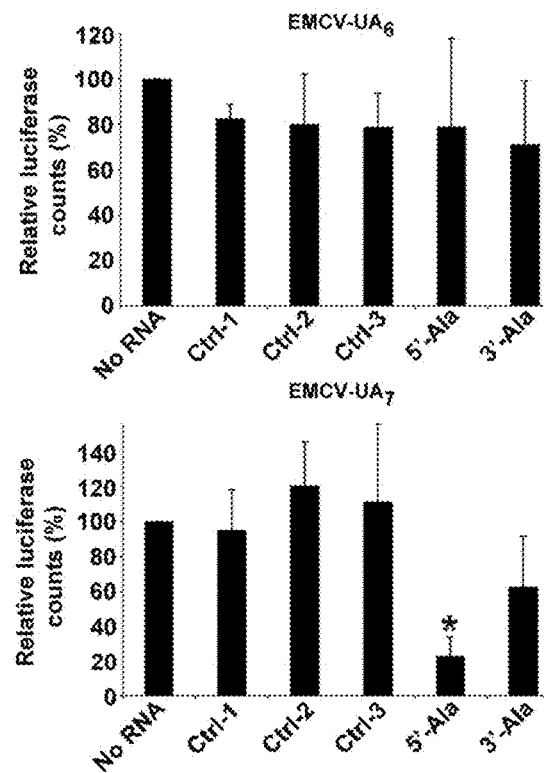

FIG. 6 is two graphs showing the luciferase expression in RRL assays using monocistronic transcripts encoding *Renilla* luciferase under the control of different EMCV IRES variants (WT EMCV-UA$_6$ (upper graph) and EMVC-UA$_7$ (lower graph)) in the presence of control RNAs (ctrl-1, -2, and -3), 5'-tiRNA$^{Ala}$, or 3'-tiRNA$^{Ala}$ (*p<0.05 compared to no RNA and three control RNAs (ctrl-1, -2, and -3), Student's t-test, n=3).

Figure 7:
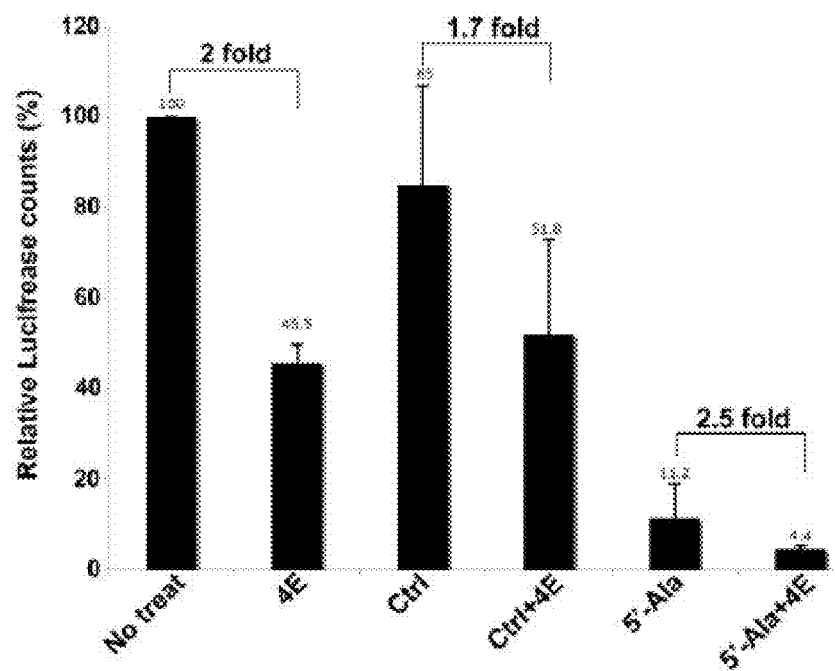

FIG. 7 is a graph showing the luciferase expression in RRL assays using uncapped Firefly luciferase RNA in the presence of control RNA or synthetic 5'-tiRNA$^{Ala}$ (5'-Ala) supplemented with a two-molar excess of recombinant eIF4E protein (+4E). Translation of the reporter in the absence of any RNA (no RNA) is assigned a relative value of 100%. The error bars reflect standard deviations of the mean.

Figure 8:
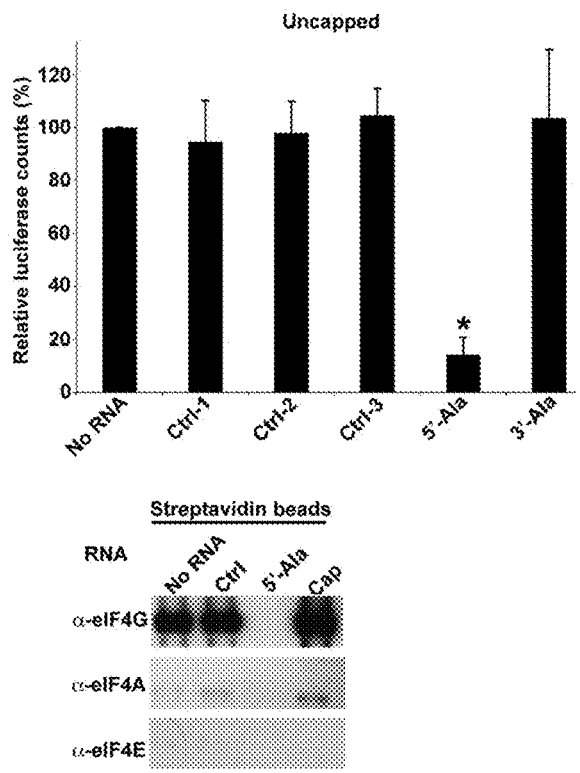

FIG. 8 is a graph showing luciferase expression in translation assays using uncapped polyA-biotinylated *Renilla* luciferase transcript in RRL supplemented with U2OS extract in the presence of the indicated control RNAs or tiRNAs (*p<0.05, compared to no RNA and three control RNAs (ctrl-1, -2, and -3), Student's t-test, n=3) (top), and an immunoblot of the streptavidin pull-down of uncapped polyA-biotinylated transcripts (bottom). In vitro translation was performed in the presence of control RNA (Ctrl), 5'-tiRNA$^{Ala}$, or cap analogue (Cap, m$^7$GpppG, 0.1 mM). Streptavidin beads were used to pull down reporter RNA-protein complexes. The bound proteins were identified by Western blotting using the indicated antibodies.

Figure 9:
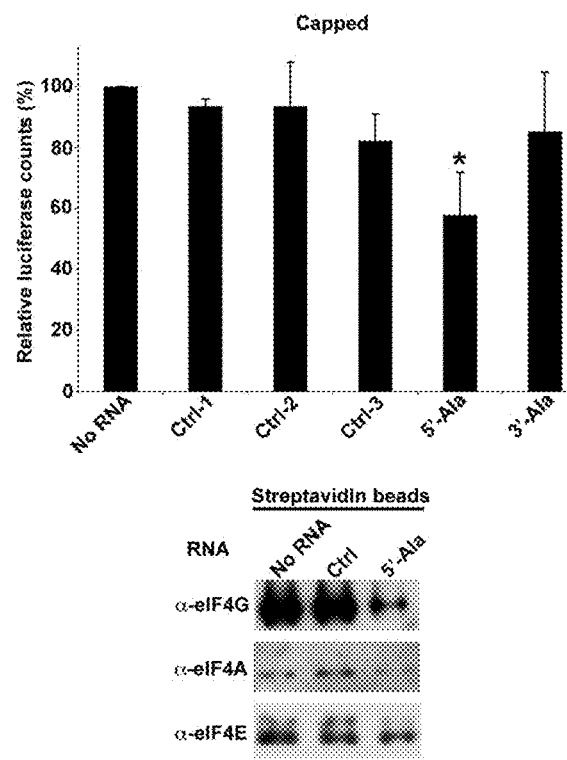

FIG. 9 is a graph showing luciferase expression in translation assays using capped polyA-biotinylated *Renilla* luciferase transcript in RRL supplemented with U2OS extract in the presence of the indicated control RNAs or tiRNAs (*p<0.05, compared to no RNA and three control RNAs (ctrl-1, -2, and -3), Student's t-test, n=3), and an immunoblot of the streptavidin pull-down of capped polyA-biotinylated transcripts (bottom). In vitro translation was performed in the presence of control RNA (Ctrl), 5'-tiRNA$^{Ala}$, or without any RNA (No RNA). Streptavidin beads were used to pull down reporter RNA-protein complexes. The bound proteins were identified by Western blotting using the indicated antibodies.

Figure 10:
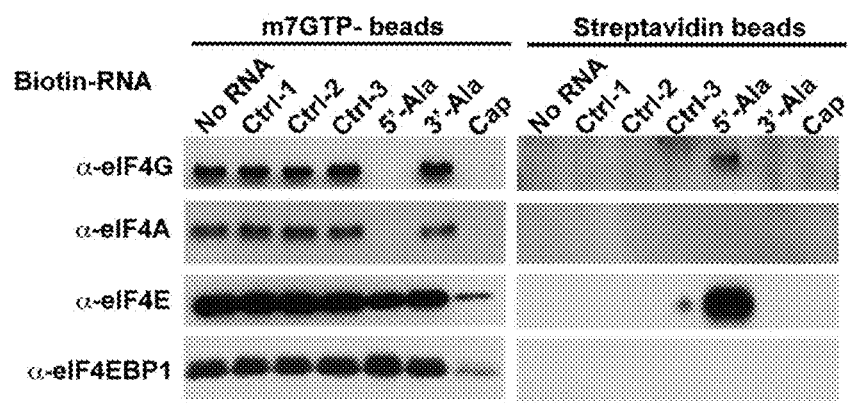

FIG. 10 is two Western blots showing the displaced components following incubation of eIF4E complexes (assembled on m$^7$GTP-Sepharose using U2OS lysates) with various components. The right blot shows the displaced components following incubation of the complexes with the indicated 3'-end biotinylated RNAs or cap analogue (Cap, m$^7$GpppG, 0.1 mM). Streptavidin beads were used to pull down displaced RNA-bound proteins and were identified by Western blotting (left blot).

Figure 11:
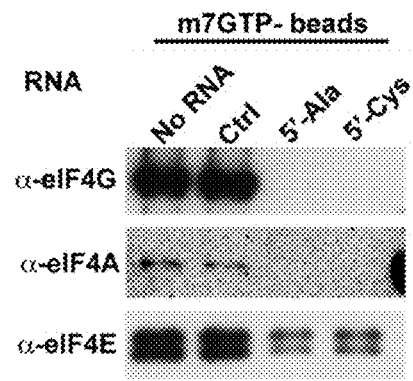

FIG. 11 is an immunoblot showing the displaced components following incubation of eIF4E complexes (assembled on m$^7$GTP-Sepharose using RRL supplemented U2OS extract) with no RNA, control RNA (ctrl), 5'-tiRNA$^{Ala}$, or 5'-tiRNA$^{Cys}$. The integrity of the eIF4F complex was monitored by Western blotting using anti-eIF4E, anti-eIF4G, and anti-eIF4A antibodies.

Figure 12:
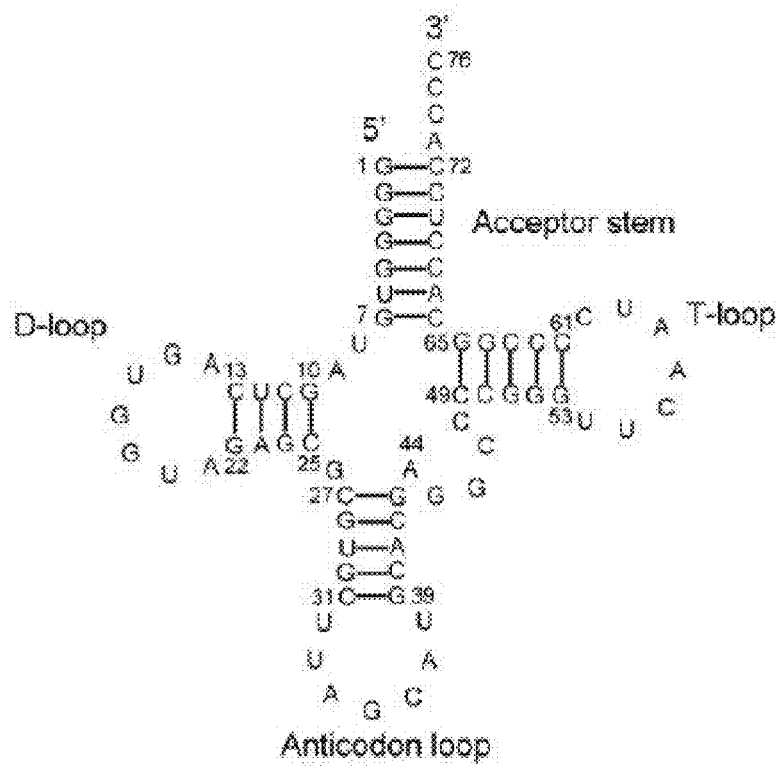

FIG. 12 is the secondary structure of 5'-tiRNA$^{Ala}$.

Figure 13:
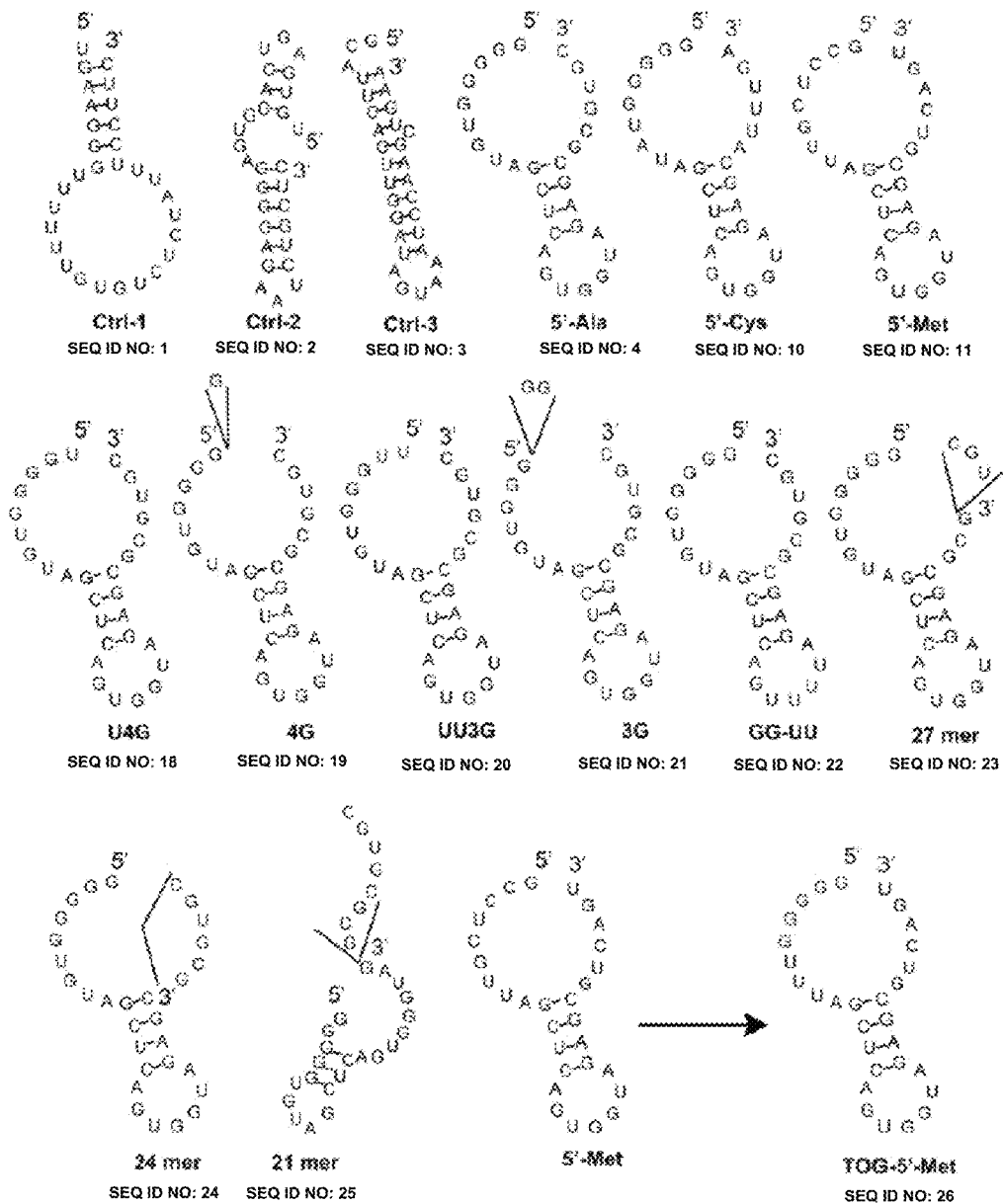

FIG. 13 is the predicted secondary structures of the control RNAs and 5'-tiRNA$^{Ala}$, 5'-tiRNA$^{Cys}$, 5'-tiRNA$^{Met}$, the mutants of 5'-tiRNA$^{Ala}$, and the modified 5'-tiRNA$^{Met}$.

Figure 14:
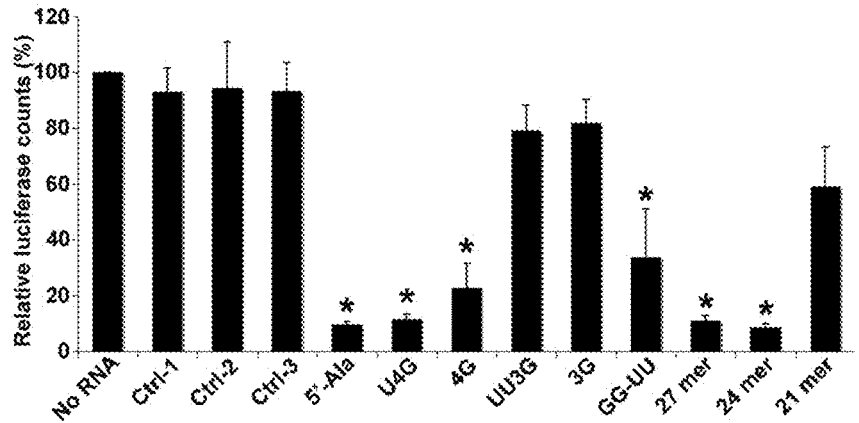

FIG. 14 is a graph of the relative luciferase expression in RRL in the presence of synthetic control RNAs (ctrl-1, -2, and -3), 5'-tiRNA$^{Ala}$, or the indicated mutants relative to the luciferase expression that is observed in the absence of any RNA (No RNA=100%) (*p<0.05, Student's t-test, n=4).

Figure 15:
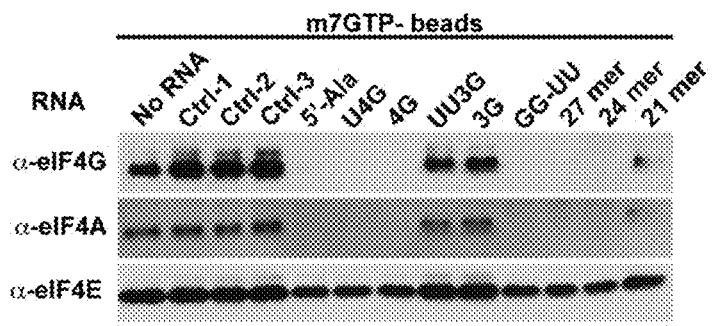

FIG. 15 is a Western blot showing the displacement of eIF4F complexes from m$^7$GTP-Sepharose in U2OS lysates following the addition of the indicated RNAs to the beads.

Figure 16:
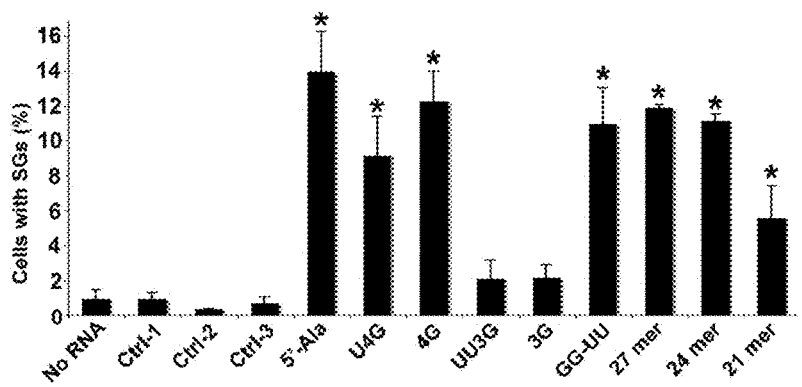

FIG. 16 is a graph showing the percentage of cells with stress granules following transfection with the control and synthetic RNAs shown (200 cells/experiment; *p<0.05, compared to a control without any RNA, Student's t-test, n=3).

Figure 17:
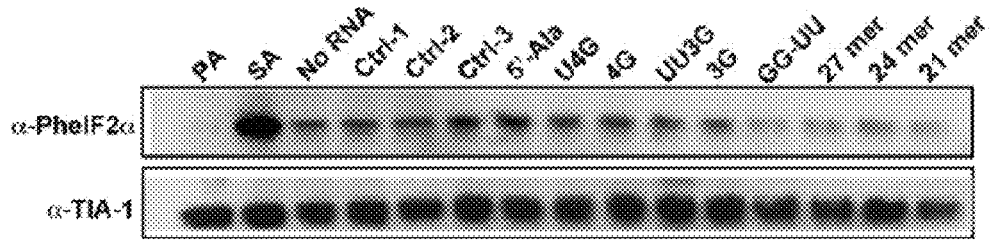

FIG. 17 is a Western blot showing the level of phospho-eIF2α in U2OS cells treated with pateamine A (PA; 15 nM) or sodium arsenite (SA; 70 μM), or transfected with no RNA, control RNA (ctrl-1, -2, or -3), 5'-tiRNA$^{Ala}$, and its mutants. Phospho-eIF2α was detected with polyclonal antibodies specific for eIF2α phosphorylated at S52 (Assay Designs) (upper panels). Detection of TIA-1 (lower panels) was used as a loading control.

Figure 18:
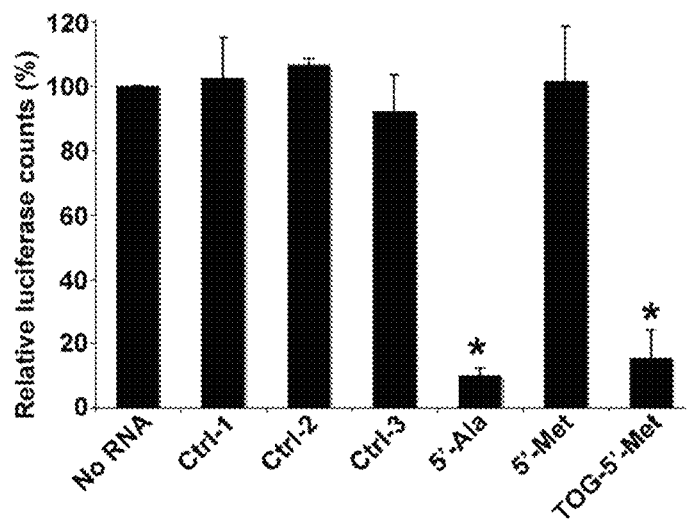

FIG. 18 is a graph of the relative luciferase expression in RRL in the presence of synthetic control RNAs (ctrl-1, -2, and -3) or the indicated 5'-tiRNAs relative to the luciferase expression that is produced in the absence of any RNA (No RNA=100%) (*p<0.05, Student's t-test, n=3).

Figure 19:
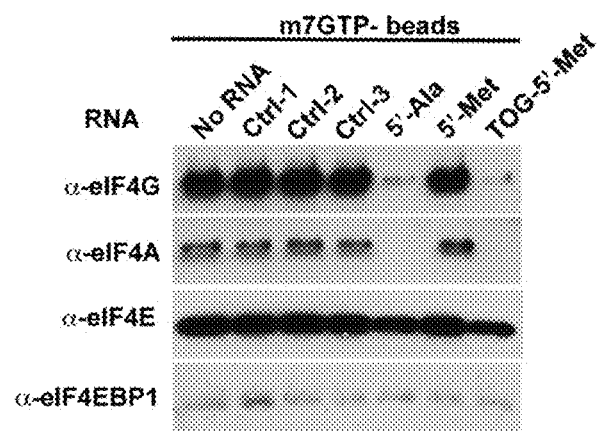

FIG. 19 is a Western blot showing the displacement of eIF4F complexes from m$^7$GTP-Sepharose in U2OS lysates following addition of the indicated RNAs to the beads. The Western blot was developed to detect eIF4F complexes and eIF4E-BP1.

Figure 20:
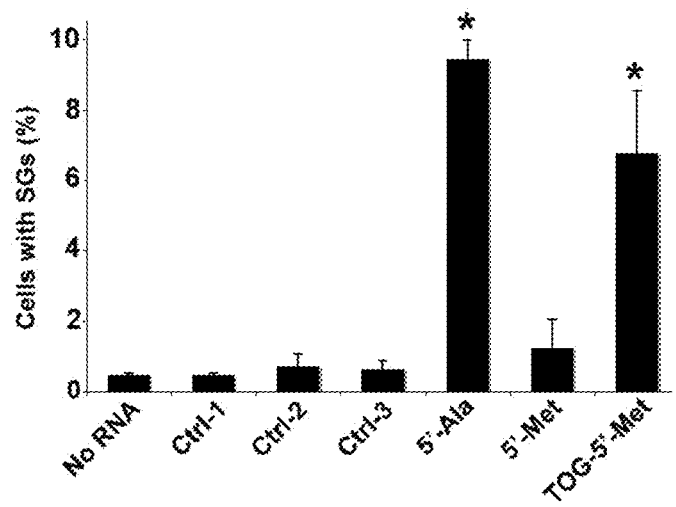

FIG. 20 is a graph showing the percentage of cells with stress granules following transfection with the indicated RNAs (200 cells/experiment; *p<0.05, Student's t-test, n=3).

Figure 21:
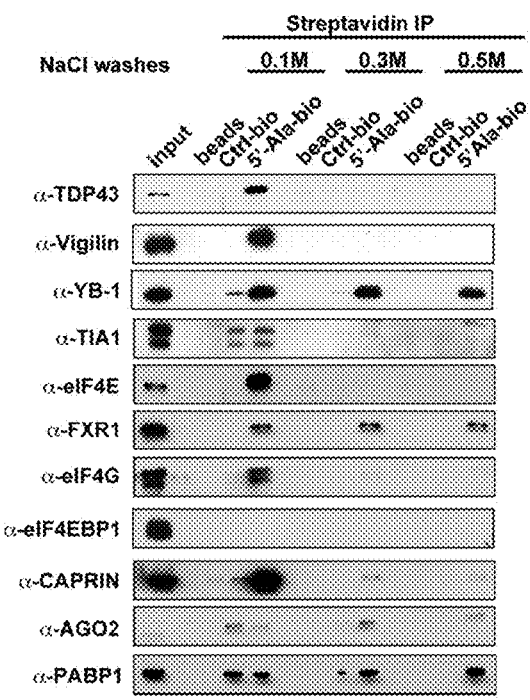

FIG. 21 is an immunoblot showing proteins bound to biotinylated control RNA and 5'-tiRNA$^{Ala}$ that were purified using streptavidin beads, subjected to the indicated salt washes (0.1 M, 0.3 M, or 0.5 M NaCl), and eluted.

Figure 22:
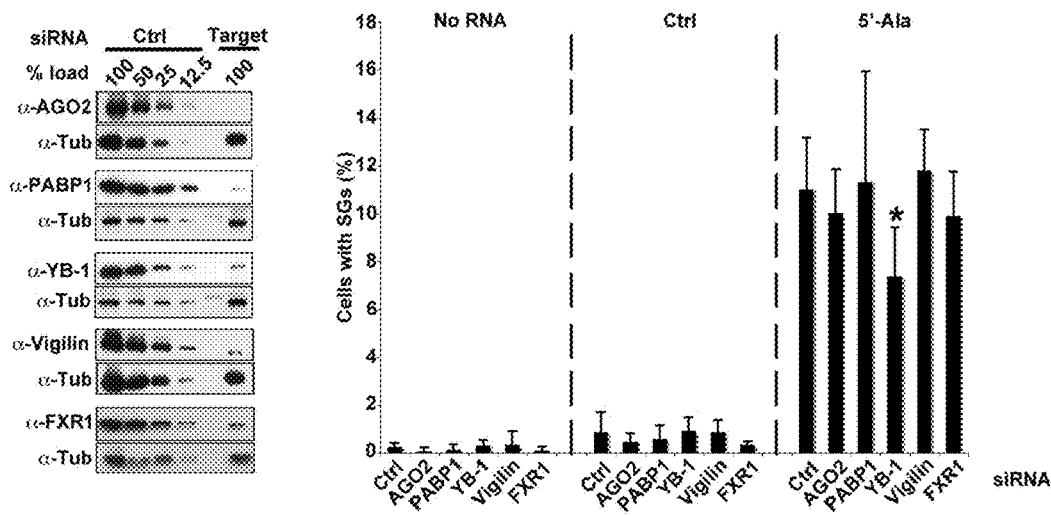

FIG. 22 is an immunoblot showing the expression of specific binding proteins following transfection with a control (Ctrl) or the different siRNAs shown (Target) (left panel) (tubulin was used as a specificity and loading control), and a graph showing the percentage of cells having stress granules following treatment with the indicated siRNAs, followed by mock transfection or transfection with control RNA (Ctrl) or 5'-tiRN$^{Ala}$ (200 cells/experiment; AGO2 siRNA, n=7; PABP1 siRNA, n=3; YB-1 siRNA, n=9; Vigilin siRNA, n=3; FXR1 siRNA, n=3) (*p<0.0001 when comparing the percentage of cells with stress granules in control and YB-1 siRNA treated cells; no other treatment reached statistical significance).

FIG. 23 shows the nucleotide sequences of the G-rich oligodeoxynucleotides used in some experiments described herein. The 5'-terminal guanines are indicated in bold.

Figure 24A:
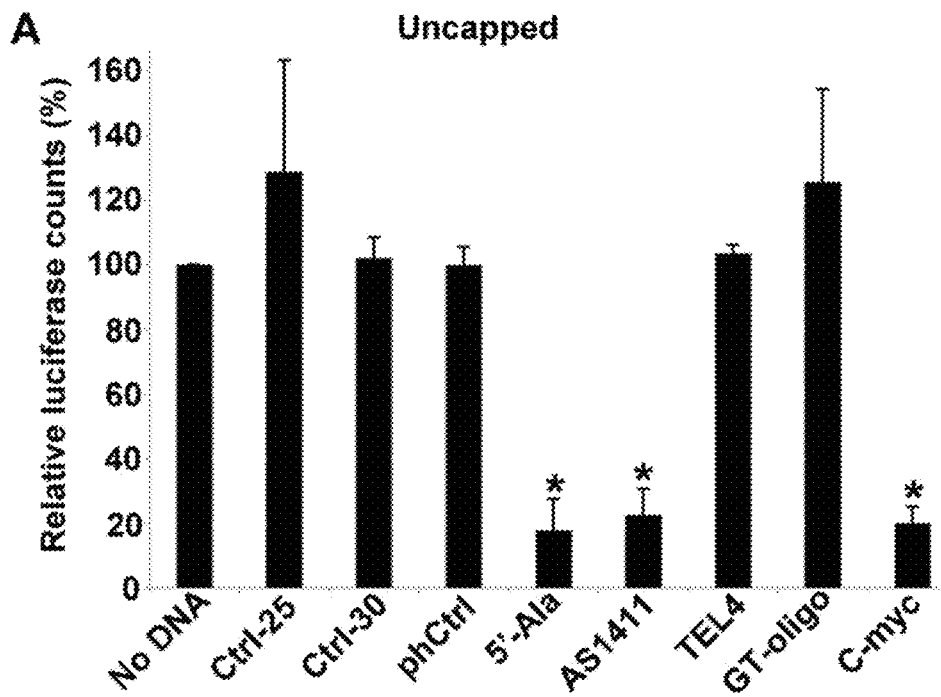
Figure 24B:
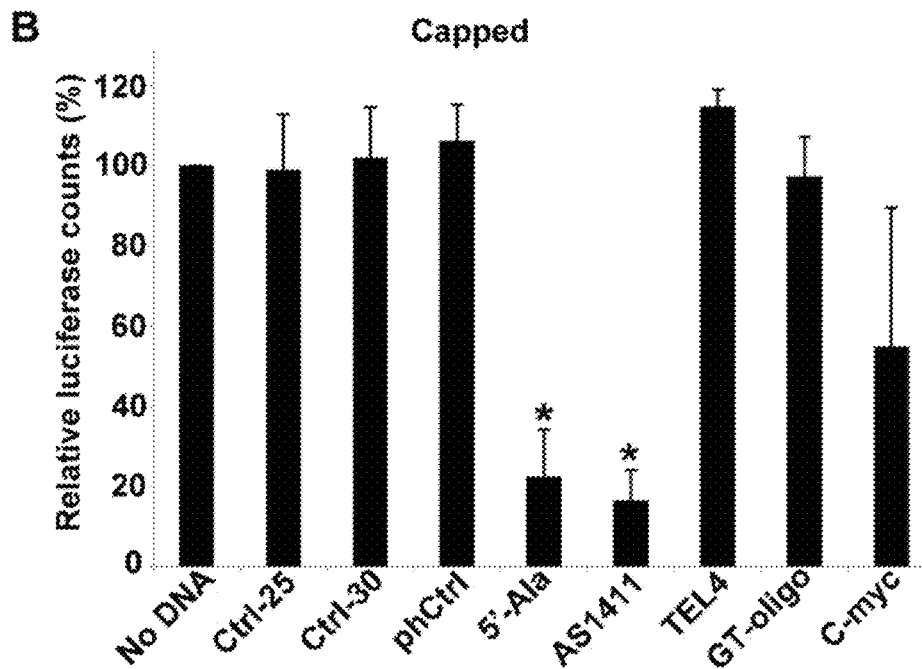

FIGS. 24A-B are two graphs showing the relative luciferase count from translation assays performed using uncapped (A) or capped (B) Firefly luciferase mRNA and RRL lysate in the presence of control G-rich oligonucleotides (Ctrl 25, Ctrl 30, and phCtrl) or the indicated G-rich oligodeoxynucleotides. The percentage luciferase expression shown is relative to the luciferase expression observed in the absence of any DNA oligonucleotide (No DNA=100%). The means and standard deviations from at least three independent experiments are shown (*p<0.05).

Figure 25:
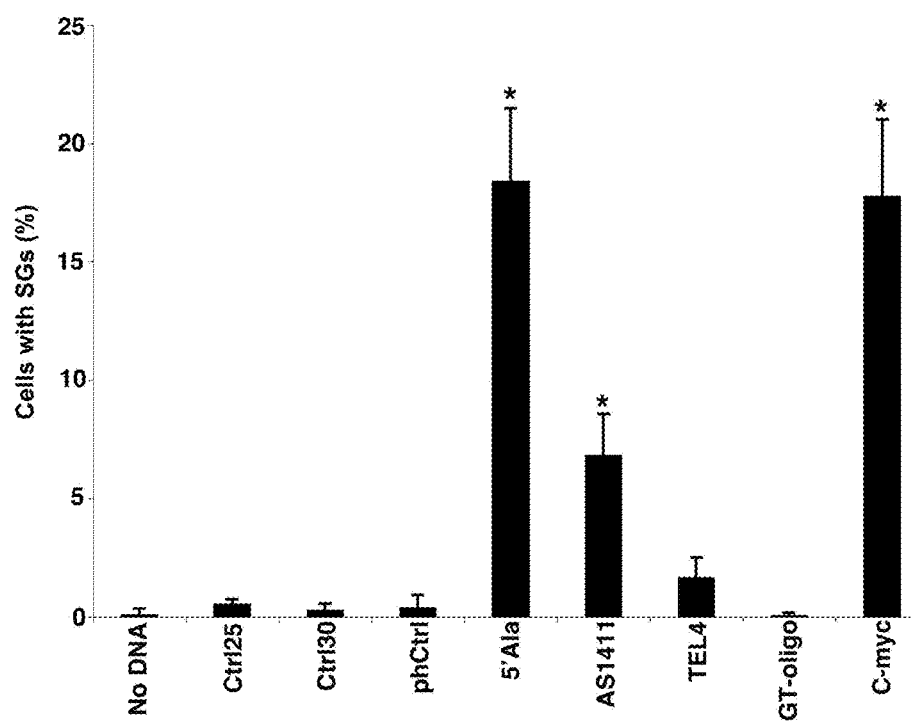

FIG. 25 shows the percentage of U2OS cells having stress granules following transfection with the indicated control or G-rich oligodeoxynucleotides (0.75 μM) using Lipofectamine. After 24 hours, the cells were processed for immunofluorescence microscopy using antibodies reactive with the stress granule components eIF3, G3BP, and TIA-1. The percentage of cells with stress granules is depicted as the mean±standard error (n=3) (*p<0.05, compared with control oligodeoxynucleotides).

FIGS. 26A-B show two immunoblots showing the displacement of eIF4F from eIF4F:m7GTP-Sepharose complexes formed in U2OS (A) or NSC34 (B) lysates upon co-incubation with the indicated 3'-biotinylated control or G-rich oligodeoxynucleotides. Synthetic 5'-tiRNA$^{Ala}$ served as a positive control for displacement of eIF4F complex from m7GTP beads (A; left panel). Streptavidin beads were used to pull down displaced DNA-bound proteins that were identified by immunoblotting (A; right panel).

FIGS. 27A-D are four photomicrographs of NSC34 cells treated with no DNA (A; upper left panel) or 1.5 μM of biotin-labeled control DNA (p-ctrl) (B; upper right panel), AS1411 (p-PS1411) (C; lower left panel), or C-myc oligodeoxynucleotide (D; lower right panel), and then stained with Cy3-streptavidin 72 hours after oligodeoxynucleotide treatment. White arrows indicate the presence of the biotin-labeled oligodeoxynucleotides in the cell.

Figure 28:
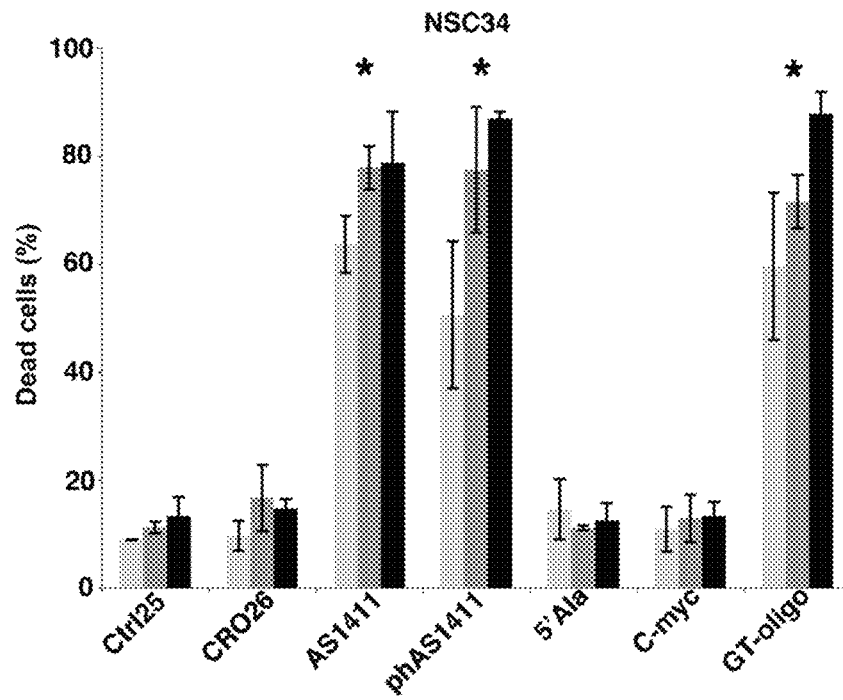

FIG. 28 is a graph showing the percent dead NSC34 cells (percent Trypan Blue-positive NSC34 cells) following treatment with the indicated G-rich deoxyoligonucleotides for 72 hours. The means and standard deviations are from four independent experiments (*p<0.05 compared to controls). The increased shading of the bars indicates an increased concentration of the G-rich deoxyoligonucleotide.

Figure 29:
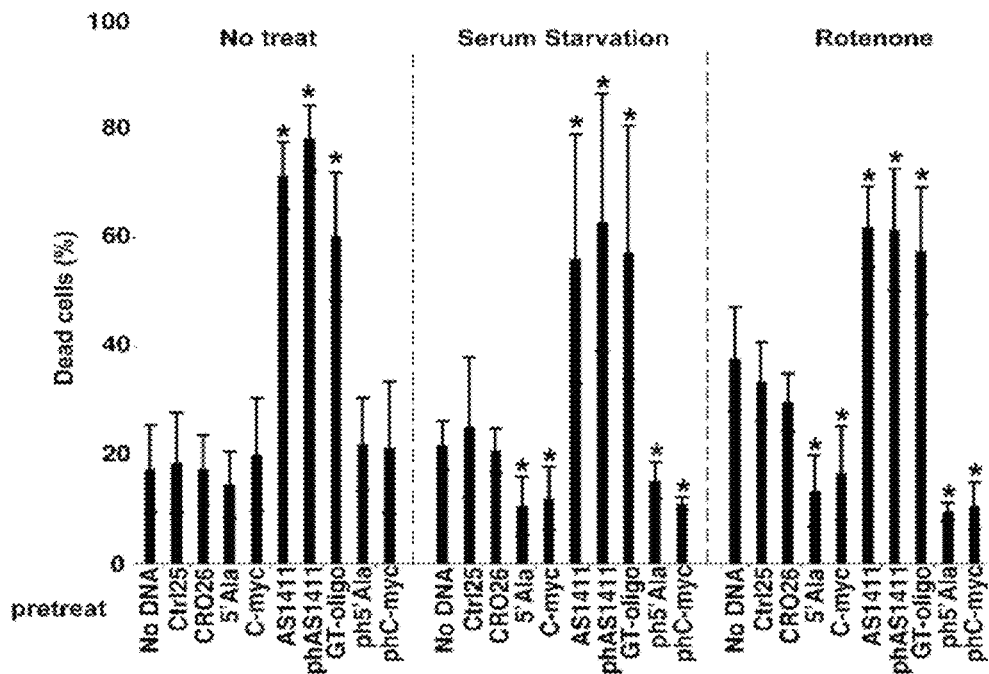

FIG. 29 is a graph showing the percent dead NSC34 cells following pretreatment for 72 hours with the indicated G-rich oligodeoxynucleotides and subsequent exposure to serum starvation or rotenone treatment (10 μM) for 24 hours. No treatment (No treat) served as a control. The percentage of dead cells was determined by Trypan Blue staining. The means and standard deviations are from four independent experiments (*p<0.05 compared to controls).

DETAILED DESCRIPTION

Neuroprotective molecules that are capable of inhibiting protein translation, inducing or increasing stress granule formation in a cell (e.g., a motor neuron), and decreasing stress-induced cell death (e.g., motor neuron death) have been discovered. These neuroprotective molecules are based, in part, on sequences present within mature human tRNAs. Some of these neuroprotective molecules have been shown to be taken up by motor neurons in the absence of transfection agents. The structural features of the neuroprotective molecules are described below, as well as their use in methods of inhibiting protein translation in a cell, inducing or increasing stress granule formation in a cell, reducing stress-induced cell death, and treating a neurological disorder associated with neuron death. Also provided herein are methods of identifying a candidate translation inhibitory nucleic acid.

Compositions

Provided herein are neuroprotective molecules containing a sequence of 25-35 contiguous nucleotides (e.g., 25-30 nucleotides or 30-35 nucleotides) that is at least 80% identical (e.g., at least 81%, 82%, 83%, 84%, 85%, 86%, 87%, 88%, 89%, 90%, 91%, 92%, 93%, 94%, 95%, 96%, 97%, 98%, 99%, or 100% identical) to a contiguous sequence between nucleotide 1 and nucleotide 50 (e.g., between nucleotide 1 to nucleotide 30) of a mature human tRNA (e.g., any of the mature human tRNA sequences described herein or known in the art), and at least four (e.g., five, six, seven, or eight) guanosine-containing nucleotides, where the sequence of 25-35 contiguous nucleotides contains a D-loop stem structure, the at least four contiguous guanosine-containing nucleotides are located at the 5'-end of the neuroprotective molecule, and the neuroprotective molecule contains at least one (e.g., two, three, four, five, six, seven, eight, nine, or ten) deoxyribonucleotide. In some embodiments, the sequence of 25-35 contiguous nucleotides is at least 80% identical to a contiguous sequence of between nucleotide 1 and nucleotide 50 of a mature human tRNA having a sequence selected from: SEQ ID NOS: 4, 5, 8-11, 13-17, 32, 37, and 40-173.

Also provided are neuroprotective molecules containing a sequence of 25-35 contiguous nucleotides (e.g., 25-30 nucleotides or 30-35 nucleotides) that is at least 80% identical (e.g., at least 81%, 82%, 83%, 84%, 85%, 86%, 87%, 88%, 89%, 90%, 91%, 92%, 93%, 94%, 95%, 96%, 97%, 98%, 99%, or 100% identical) to a contiguous sequence between nucleotide 1 and nucleotide 50 (e.g., between nucleotide 1 to nucleotide 30) of a mature human tRNA selected from the group of: tRNA$^{Arg}$, tRNA$^{Asp}$, tRNA$^{Glu}$, tRNA$^{Gln}$, tRNA$^{Gly}$, tRNA$^{His}$, tRNA$^{Ile}$, tRNA$^{Leu}$, tRNA$^{Lys}$, tRNA$^{Met}$, tRNA$^{Pro}$, tRNA$^{SeC}$, tRNA$^{Ser}$, tRNA$^{Sup}$, tRNA$^{Thr}$, tRNA$^{Trp}$, tRNA$^{Tyr}$, tRNA$^{Val}$, tRNA$^{Asn}$, and tRNA$^{Phe}$ (e.g., any of the sequences described herein or known in the art), and at least four (e.g., five, six, seven, or eight) contiguous guanosine-containing nucleotides, where the sequence of 25-35 contiguous nucleotides contains a D-loop stem structure and the at least four contiguous guanosine-containing nucleotides are located at the 5' end of the neuroprotective molecule. In some embodiments, the sequence of 25-35 contiguous nucleotides is at least 80% identical to a contiguous sequence between nucleotide 1 and nucleotide 50 of a mature human tRNA having a sequence selected from the group of SEQ ID NOS: 5, 8, 9, 11, 14-17, 32, 37, 56, 57, and 63-173. In some embodiments, the sequence of 25-35 contiguous nucleotides is at least 80% identical to a contiguous sequence between nucleotide 1 and nucleotide 50 of a mature human tRNA having a sequence selected from the group of SEQ ID NOS: 11 and 107-116.

The comparison of sequences and determination of percent identity between two sequences can be accomplished using a mathematical algorithm. The percent identity between two amino acid sequences is determined using the Needleman and Wunsch J. Mol. Biol. 48:444-453, 1970) algorithm, which has been incorporated into the GAP program in the GCG software package (available at gcg.com), using either a Blossum 62 matrix or a PAM250 matrix, and a gap weight of 16 and a length weight of 1. The percent identity between two nucleotide sequences is determined using the GAP program in the GCG software package (available the Accelrys Inc. website), using a NWSgapdna.CMP matrix and a gap weight of 40 and a length weight of 1. The calculation of percent identity as described herein, recognizes a uracil-containing nucleotide (deoxyuracil and ribouracil) as being the same as a "T" (deoxythymine or ribothymine).

In some embodiments, the neuroprotective molecules can contain a sequence of 25, 26, 27, 28, 29, 30, 31, 32, 33, 34, or 35 contiguous nucleotides that is at least 80% identical to a contiguous sequence present between nucleotide 1 and nucleotide 50 of a mature human tRNA. In some embodiments, the contiguous sequence between nucleotide 1 and nucleotide 50 of a mature human tRNA starts at nucleotide number 1, 2, 3, 4, 5, 6, or 7 of the mature human tRNA sequence.

Non-limiting examples of mature human tRNAs are listed below. Any of the human tRNA molecules described herein or known in the art can be used to design the neuroprotective molecules described herein.

Non-limiting exemplary Ala tRNA sequences are listed below.

```
Ala tRNA
                                        (SEQ ID NO: 40)
gggggguguag cucaguggua gagcgcgugc uu (SEQ ID NO: 41)
gggggguguag cucaguggua gagcgcgugc u (SEQ ID NO: 42)
ggggggugua gcucagugguu agagcgcgug cu (SEQ ID NO: 43)
gggggguguag cucaguggua gagcgcgugc (SEQ ID NO: 44)
ggggggugua gcucagugguu agagcgcgug c (n is a, c, g, or u; SEQ ID NO: 45)
gggggunuag cucaguggua gagcgcgugc uu (SEQ ID NO: 46)
gggggguguag cucaguggua gagcgcgug (SEQ ID NO: 47)
guguagcuca gugguagagc gcgugcuucg c (n is a, c, g, or u; SEQ ID NO: 48)
ggggunuagc ucaguggguag agcgcgugcu u (n is a, c, g, or u; SEQ ID NO: 49)
gggggggunua gcucaguggu agagcgcgug cu (SEQ ID NO: 50)
ggggguguagc ucaguggguag agcgcgugcu u (SEQ ID NO: 51)
gggggunuag cucaguggua gagcgcgugc (SEQ ID NO: 52)
gggggguguag cucaguggua gagagcgugc u (SEQ ID NO: 53)
ggggauguag cucaguggua gagcgcaugc u (SEQ ID NO: 54)
gggggauuag cucaaauggu agagcgcucg (SEQ ID NO: 55)
ggggaunuag cucaguggua gagcgcaugc u A non-limiting exemplary Arg tRNA sequence is
                                        (SEQ ID NO: 56)
ggcucuguug cgcaauggau agcgcau
and a non-limiting exemplary Asp tRNA sequence is
                                        (SEQ ID NO: 57)
uccucauuag uauaguggug aguauccc.
```

Non-limiting exemplary Cys tRNA sequences are listed below.

```
Cys tRNA
                                        (SEQ ID NO: 58)
gggggguauag cucaguggua gagcauuuga (SEQ ID NO: 59)
gggggguauag cucaguggua gagcauuug (SEQ ID NO: 60)
gggggguauag cucaguggua gagcauuu (SEQ ID NO: 61)
gggggguauag cucagugggu agagcau (SEQ ID NO: 62)
ggggguguaa cucaguggua gagcauuuga A non-limiting exemplary Gln tRNA sequence is
                                        (SEQ ID NO: 63)
gguuccaugg uguaaugguu agcacucu.
```

Non-limiting exemplary Gly tRNA sequences are listed below.

```
Gly tRNA
                                        (SEQ ID NO: 64)
uuggugguuc aguggaagaa uucucgccug cc (SEQ ID NO: 65)
uuggugguuc aguggaagaa uucucgccug c (SEQ ID NO: 66)
uuggugguuc aguggaagaa uucucgccug (SEQ ID NO: 67)
uggugguuca gugguagaau ucucgccug (SEQ ID NO: 68)
auuggugguu cagugguaga auucucgccu g (SEQ ID NO: 69)
uuggugguuc aguggaagaa uucucgccu (SEQ ID NO: 70)
ggcauuggug guucaguggu agaauucucg c (SEQ ID NO: 71)
auuggugguu cagugguaga auucucgcc (SEQ ID NO: 72)
agcauuggug guucaguggu agaauucucg c (SEQ ID NO: 73)
cauugguggu ucaguggugg aauucucgc (SEQ ID NO: 74)
gggaggcccg gguucguuuc ccggccaaug ca (SEQ ID NO: 75)
gcauuggugg uucaguggua gaauucucac (SEQ ID NO: 76)
cgggaggccc ggguucgguu cccggccaau gc (SEQ ID NO: 77)
uuggugguuc aguggaagaa uucucgc (SEQ ID NO: 78)
gacauuggug guucaguggu agaauucu (SEQ ID NO: 79)
ugguucagug guagaauucu cgccucc (SEQ ID NO: 80)
gcauugguau aguggauca ugcaaga (SEQ ID NO: 81)
agcguuggug guauaguggu gagcauagcu gc
```

Non-limiting examples of His tRNA sequences are listed below.

```
His tRNA
                                        (SEQ ID NO: 82)
ggccgugauc guauaguggu uaguacucug (SEQ ID NO: 83)
ucgccgugau cguauagugg uuaguacucu g
```

```
                                        (SEQ ID NO: 84)
ggccgugauc guauaguggu uaguacuc (SEQ ID NO: 85)
aggccgugau cguauagugg uuaguacuc (SEQ ID NO: 86)
ggccgugauc guauaguggu uaguacu (SEQ ID NO: 87)
ggccgugauc guauaguggu uaguac
```

Non-limiting examples of Ile tRNA sequences are listed below.

```
Ile tRNA
                                        (SEQ ID NO: 88)
ggccgguuag cucaguuggu uagagc (SEQ ID NO: 89)
ggccgguuag cucaguuggu cagagc (SEQ ID NO: 90)
ggccgguuag cucaguuggu aagagcuugg u (SEQ ID NO: 91)
ggggcggccg guuagcucag uugguaagag c (SEQ ID NO: 92)
ggccgguuag cucaguuggu aagagc
```

Non-limiting examples of Leu tRNA sequences are listed below.

```
Leu tRNA
                                        (SEQ ID NO: 93)
gguagugugg ccgagcgguc uaaggc (SEQ ID NO: 94)
guagucgugg ccgagugguu aaggcuaugg a (SEQ ID NO: 95)
gacgaggugg ccgagugguu aaggcuaugg au (SEQ ID NO: 96)
gacgaggugg ccgaguggu aaggcuaugg ac (SEQ ID NO: 97)
gacgaggugg ccgagugguu aaggcuaugg a (SEQ ID NO: 98)
gacgaggugg ccgagugguu aaggcuaugg (SEQ ID NO: 99)
gacgaggugg ccgagugguu aaggcaaugg a (SEQ ID NO: 100)
gacgaggugg ccgaguggu aaggcaaugg (SEQ ID NO: 101)
uguagucgug gccgaguggu uaaggc
```

Non-limiting examples of Lys tRNA sequences are listed below.

```
Lys tRNA
                                        (SEQ ID NO: 102)
gccuggauag cucaguuggu agagcaucag a (SEQ ID NO: 103)
gccuggauag cucaguuggu agagcauca (SEQ ID NO: 104)
gccuggguag cucagucggu agagcaucag ac (SEQ ID NO: 105)
gccuggguag cucagucggu agagcaucag a (SEQ ID NO: 106)
gccuggguag cucagucggu agagcaucag
```

Non-limiting examples of Met tRNA sequences are listed below.

```
Met tRNA
                                        (SEQ ID NO: 107)
gcagaguggc gcagcggaag cgugcugggc cc (SEQ ID NO: 108)
ggcagagugg cgcagcggaa gcgugcuggg cc (SEQ ID NO: 109)
gcagaguggc gcagcggaag cgugcugg (SEQ ID NO: 110)
ugcagagugg cgcagcggaa gcgugcugg (SEQ ID NO: 111)
gcaguggcgc agcggaagcg ugcugggcc (SEQ ID NO: 112)
gcagaguggc gcagcggaag cgugcug (SEQ ID NO: 113)
cgcagagucg cgcagcggaa gcgugcuggg cc (SEQ ID NO: 114)
cagagucgcg cagcggaagc gugcugggcc c (SEQ ID NO: 115)
agaguugcgc agcggaagcg ugcugggccc a (SEQ ID NO: 116)
gagauagcag aguggcgcag cggaagc
```

Non-limiting examples of Pro tRNA sequences are

```
                                        (SEQ ID NO: 117)
ggcucguugg ucuaggggua ugauucucgg
and
                                        (SEQ ID NO: 118)
aggcucguug gucuaguggu augauucucg.
```

A non-limiting example of a SeC (selenocysteine) tRNA sequence is

```
                                        (SEQ ID NO: 119)
gcccggauga uccucagugg ucugggguge.
```

Non-limiting examples of Ser tRNA sequences are listed below.

```
Ser tRNA
                                        (SEQ ID NO: 120)
uguagucgug gccgaguggu uaaggc (SEQ ID NO: 121)
gacgaggugg ccgaguggu aaggcuaugg ac (SEQ ID NO: 122)
gacgaggugg ccgaguggu aaggcuaugg au (SEQ ID NO: 123)
gacgaggugg ccgaguggu aaggcuaugg a (SEQ ID NO: 124)
gacgaggugg ccgaguggu aaggcaaugg a (SEQ ID NO: 125)
gacgaggugg ccgaguggu aaggcuaugg
```

Non-limiting examples of Sup (suppressor) tRNA sequences are (SEQ ID NO: 127)
gccuggauag cucaguuggu agagcaucaga and (SEQ ID NO: 128)
gccuggauag cucaguuggu agagcauca.

Non-limiting examples of Thr tRNA sequences are listed below.

Thr tRNA
(SEQ ID NO: 129)
ggcagagugg cgcagcggaa gcgugcuggg cc (SEQ ID NO: 130)
gcagaguggc gcagcggaag cgugcugggc cc (SEQ ID NO: 131)
gcagaguggc gcagcggaag cgugcugg (SEQ ID NO: 132)
cggaagcgug cugggcccau aacccaga (SEQ ID NO: 133)
ugcagagugg cgcagcggaa gcgugcugg (SEQ ID NO: 134)
gcaguggcgc agcggaagcg ugcugggcc (SEQ ID NO: 135)
gcagaguggc gcagcggaag cgugcug (SEQ ID NO: 136)
cgcagagucg cgcagcggaa gcgugcuggg cc (SEQ ID NO: 137)
cagagucgcg cagcggaagc gugcugggcc c (SEQ ID NO: 138)
agaguugcgc agcggaagcg ugcugggccc a Non-limiting examples of Tyr tRNA sequences include
(SEQ ID NO: 139)
gccuggauag cucaguuggu agagcaucaga and
(SEQ ID NO: 140)
gccuggauag cucaguuggu agagcauca.

Non-limiting examples of Val tRNA sequences are listed below.

Val tRNA
(SEQ ID NO: 141)
uuccguagug uagugguuau cacguucgcc uc (SEQ ID NO: 142)
uuccguagug uagugguuau cacguucgcc (SEQ ID NO: 143)
uccguagugu agugguuauc acguucgccu ga (SEQ ID NO: 144)
uccguagugu agugguuauc acguucgccu g (SEQ ID NO: 145)
uccguagugu agugguuauc acguucgccu ca (SEQ ID NO: 146)
uccguagugu agugguuauc acguucgccu (SEQ ID NO: 147)
guuccguag uguagguguc aucacguucg cc (SEQ ID NO: 148)
ccguagugua gugguuauca cguucgcc (SEQ ID NO: 149)
guuccguag uguagguguc aucacguucg (SEQ ID NO: 150)
cguaguguag ugguuaucac guucgcc (SEQ ID NO: 151)
uccguagugu agugguuauc acuuucgccu (SEQ ID NO: 152)
uccguagugu acugguuauc acguucgccu g (SEQ ID NO: 153)
cguaguguag uggucaucac guucgccu (SEQ ID NO: 154)
ggggguguag cucaguggua gagcgcgugc uu (SEQ ID NO: 155)
ggggguguag cucaguggua gagcgcgugc u (SEQ ID NO: 156)
ggggguguag cucaguggua gagcgcgugc (SEQ ID NO: 157)
ggggguguag cucaguggua gagcgcgug (SEQ ID NO: 158)
gggggugua gcucaguggu agagcgcgug Cu (SEQ ID NO: 159)
uuggugguuc aguguagaa uucucgccug cc (SEQ ID NO: 160)
uuggugguuc aguguagaa uucucgccug c (SEQ ID NO: 161)
uuggugguuc aguguagaa uucucgccug (SEQ ID NO: 162)
uuggugguuc aguguagaa uucucgccu (SEQ ID NO: 163)
ugguguuca guguagaau ucucgccug (SEQ ID NO: 164)
auuggugguu caguguaga auucucgccu g (SEQ ID NO: 165)
auuggugguu caguguaga auucucgcc (SEQ ID NO: 166)
ggcauuggug guucaguggu agaauucucg c (SEQ ID NO: 167)
uuggugguuc aguguagaa uucucgc (SEQ ID NO: 168)
ugguucagug guagaauucu cgccucc (SEQ ID NO: 169)
cauuggguggu ucagugguag aauucucgc (SEQ ID NO: 170)
agcauuggug guucaguggu agaauucucg c -continued A non-limiting example of a Asn tRNA sequence is
(SEQ ID NO: 172)
gtctctgtgg cgcaatcggt tagcgcgttc ggctgttaac.

(SEQ ID NO: 171)
gcauuggugg uucaguggua gaauucucac

A non-limiting example of a Phe tRNA sequence is
(SEQ ID NO: 173)
gccgaaatag ctcagttggg agagcgttag actgaagatc.

Additional non-limiting examples of human mature tRNA sequences that can be used to generate any of the neuroprotective molecules described herein are listed in the Sequence Appendix and are described in U.S. Patent Application Publication No. 20110046209 (herein incorporated by reference). Additional examples of human mature tRNA sequences that can be used to generate any of the neuroprotective molecules described herein are known in the art (see, NCBI website, the UCSC genomic tRNA database website (address: gtrnadb.ucsc.edu), and the Unversitat Leipzig tRNAdb website (address:trandb.bioinf.uni-leipzig.edu).

The sequence of 25-35 contiguous nucleotides that is at least 80% identical to a contiguous sequence present between nucleotide 1 and nucleotide 50 of a mature human tRNA incorporated in the neuroprotective molecules described herein should be sufficient to allow the formation of a D-stem loop structure in the neuroprotective molecule. The D-stem loop structure of mature human tRNAs is typically comprised of a region extending from about nucleotide 6 to about nucleotide 27. The formation of a D-loop stem structure within the neuroprotective molecules described herein can be assessed by its gel migration (e.g., in the presence or absence of denaturing agents) or by circular dichroism. Additional methods for the detection of the D-loop stem structure within a nucleic acid are known in the art.

In some embodiments, the guanosine-containing nucleotide can contain a ribose. In some embodiments, the guanosine-containing nucleotide can contain a deoxyribose. In some embodiments, the guanosine-containing nucleotide can contain a modified sugar (e.g., any of the modified sugars described herein). In some embodiments, the guanosine-containing nucleotide can contain modified guanosine (e.g., 7-methyl guanosine or 6-thioguanosine). In preferred embodiments, the at least four contiguous guanosine-containing nucleotides form a G-quadraplex (e.g., a G-quadraplex with guanosines within the neuroprotective molecule).

The neuroprotective molecules described herein can contain one or more (e.g., two, three, four, of five) modified nucleotides. The modified nucleotides can contain a modified base or a modified sugar. Non-limiting examples of modified bases include: xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methyl-cytosine, 5-($C^3$-$C^6$)-alkynyl-cytosine, 5-fluorouracil, 5-bromouracil, pseudoisocytosine, 2-hydroxy-5-methyl-4-triazolopyridin, isocytosine, isoguanine, and inosine. Additional non-limiting examples of modified bases include those nucleobases described in U.S. Pat. Nos. 5,432,272 and 3,687,808 (herein incorporated by reference), Freier et al., *Nucleic Acid Res.* 25:4429-4443, 1997; Sanghvi, Antisense Research and Application, Chapter 15, Ed. S. T. Crooke and B. Lebleu, CRC Press, 1993; Englisch, et al., *Angewandte Chemie* 30:613-722, 1991, Kroschwitz, Concise Encyclopedia of Polymer Science and Engineering, John Wiley & Sons, pp. 858-859, 1990; and Cook, *Anti-Cancer Drug Design* 6:585-607, 1991. Additional non-limiting examples of modified bases include universal bases (e.g., 3-nitropyrrole and 5-nitroindole). Other modified bases include pyrene and pyridyloxazole derivatives, pyrenyl, pyrenylmethyl-glycerol derivatives, and the like. Other preferred universal bases include pyrrole, diazole, or triazole derivatives, including those universal bases known in the art.

In some embodiments, the modified nucleotide can contain a modification in its sugar moiety. A non-limiting examples of modified nucleotides that contains a modified sugar are locked nucleic acids (LNAs). LNA monomers are described in WO 99/14226 and U.S. Patent Application Publications Nos. 20110076675, 20100286044, 20100279895, 20100267018, 20100261175, 20100035968, 20090286753, 20090023594, 20080096191, 20030092905, 20020128381, and 20020115080 (herein incorporated by reference). Additional non-limiting examples of LNAs are disclosed in U.S. Pat. No. 6,043,060, U.S. Pat. No. 6,268,490, WO 01/07455, WO 01/00641, WO 98/39352, WO 00/56746, WO 00/56748, and WO 00/66604 (herein incorporated by reference), as well as in Morita et al., *Bioorg. Med. Chem. Lett.* 12(1):73-76, 2002; Hakansson et al., *Bioorg. Med. Chem. Lett.* 11(7):935-938, 2001; Koshkin et al., *J. Org. Chem.* 66(25):8504-8512, 2001; Kvaerno et al., *J. Org. Chem.* 66(16):5498-5503, 2001; Hakansson et al., *J. Org. Chem.* 65(17):5161-5166, 2000; Kvaerno et al., *J. Org. Chem.* 65(17):5167-5176, 2000; Pfundheller et al., *Nucleosides Nucleotides* 18(9):2017-2030, 1999; and Kumar et al., *Bioorg. Med. Chem. Lett.* 8(16):2219-2222, 1998. In some embodiments, the modified nucleotide is an oxy-LNA monomer, such as those described in WO 03/020739.

The neuroprotective molecules described herein can also contain a modification in the phosphodiester backbone. For example, at least one linkage between any two contiguous (adjoining) nucleotides in the neuroprotective molecule can be connected by a moiety containing 2 to 4 groups/atoms selected from the group of: —$CH_2$—, —O—, —S—, —$NR^H$—, >C=, >C=$NR^H$, >C=S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where $R^H$ is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—O—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—, —O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N= (including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH= (including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—S(O)$_2$—O—, —O—S(O)$_2$—$CH_2$—, —O—S(O)$_2$—

$NR^H$, —$NR_H$—S(O)$_2$—CH$_2$—, —O—S(O)$_2$—CH$_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO—(OCH$_2$CH$_3$)—O—, —O—PO(OCH$_2$S—R)—O—, —O—PO(BH$_3$)—O—, —O—PO(NHR$^N$)—O—, —O—P(O)$_2$—NR$^H$—, —NR$^H$—P(O)$_2$—O—, —O—P(O,NR$^H$)2-O—, —CH$_2$—P(O)$_2$—O—, —O—P(O)$_2$—CH$_2$—, and —O—Si(R")$_2$—O—; among which —CH$_2$—CO—NR$^H$, —CH$_2$—NR$^H$—O—, —S—CH$_2$—O—, —O—P(O)$_2$—O—, —O—P(O,S)—O—, —O—P(S)$_2$—O—, —NR$^H$—P(O)$_2$O—, —O—P(O,NR$^H$)O—, —O—PO(R")—O—, —O—PO(CH$_3$)—O—, and —O—PO(NHR$^N$)—O—, where R$^H$ is selected form hydrogen and C$_{1-4}$-alkyl, and R" is selected from C$_{1-6}$-alkyl and phenyl. Further illustrative examples are given in Mesmaeker et. al., *Curr. Opin. Struct. Biol.* 5:343-355, 1995; and Freier et al., *Nucleic Acids Research* 25:4429-43, 1997. The left-hand side of the inter-nucleoside linkage is bound to the 5-membered ring as substituent P* at the 3'-position, whereas the right-hand side is bound to the 5'-position of a preceding monomer.

In some embodiments, any of the neuroprotective molecules described herein can be modified at either the 3' and/or 5' end by any type of modification known in the art. For example, either or both ends may be capped with a protecting group, attached to a flexible linking group, attached to a reactive group to aid in attachment to the substrate surface. Non-limiting examples of 3' and/or 5' blocking groups include: 2-amino-2-oxyethyl, 2-aminobenzoyl, 4-aminobenzoyl, acetyl, acetyloxy, (acetylamino)methyl, 3-(9-acridinyl), tricyclo[3.3.1.1 (3,7)]dec-1-yloxy, 2-aminoethyl, propenyl, (9-anthracenylmethoxy)carbonyl, (1,1-dmimethylpropoxy)carbonyl, (1,1-dimethylpropoxy) carbonyl, [1-methyl-1-[4-(phenylazo)phenyl]ethoxy]carbonyl, bromoacetyl, (benzoylamino)methyl, (2-bromoethoxy) carbonyl, (diphenylmethoxy)carbonyl, 1-methyl-3-oxo-3-phenyl-1-propenyl, (3-bromo-2-nitrophenyl)thio, (1,1-dimethylethoxy)carbonyl, [[(1,1-dimethylethoxy)carbonyl] amino]ethyl, 2-(phenylmethoxy)phenoxy, (1=[1,1'-biphenyl]-4-yl-1-methylethoxy) carbonyl, bromo, (4-bromophenyl)sulfonyl, 1H-benzotriazol-1-yl, [(phenylmethyl)thio]carbonyl, [(phenylmetyl)thio]methyl, 2-methyl-propyl, 1,1-dimethylethyl, benzoyl, diphenylmethyl, phenylmethyl, carboxyacetyl, aminocarbonyl, chlorodifluoroacetyl, trifluoromethyl, cyclohexylcarbonyl, cycloheptyl, cyclohexyl, cyclohexylacetyl, chloro, carboxymethyl, cyclopentylcarbonyl, cyclopentyl, cyclopropylmethyl, ethoxycarbonyl, ethyl, fluoro, formyl, 1-oxohexyl, iodo, methyl, 2-methoxy-2-oxoethyl, nitro, azido, phenyl, 2-carboxybenzoyl, 4-pyridinylmethyl, 2-piperidinyl, propyl, 1-methylethyl, sulfo, and ethenyl. Additional examples of 5' and 3' blocking groups are known in the art. In some embodiments, the 5' and/or 3' blocking groups prevent nuclease degradation of the neuroprotective molecule.

The neurorprotective molecules described herein can be synthesized using any methods known in the art for synthesizing nucleic acids (see, e.g., Usman et al., *J. Am. Chem. Soc.* 109:7845, 1987; Scaringe et al., *Nucleic Acid Res.* 18:5433, 1990; Wincott et al., *Methods Mol. Biol.* 74:59, 1997; and Milligan, *Nucleic Acid Res.* 21:8783, 1987). These typically make use of common nucleic acid protecting and coupling groups. Synthesis can be performed on commercial equipment designed for this purpose, e.g., a 394 Applied Biosystems, Inc synthesizer, using protocols supplied by the manufacturer. Additional methods for synthesizing the neuroprotective molecules described herein are known in the art. Alternatively, neuroprotective molecules of the invention can be specially ordered from commercial vendors that synthesize oligonucleotides.

Any of the neuroprotective molecules described herein can be tested for activity (e.g., ability to inhibit or decrease protein translation, the ability to induce or increase stress granule formation in a cell, the ability to translocate into a cell in the absence of cell transfection reagents, the ability to treat a neurological disorder associated with neuron death, or the ability to confer upon cells (e.g., neurons) resistance to stress-induced cell death). Methods for detecting or assessing protein translation (e.g., the amount of translation over a specific period of time or rate of protein translation), methods for detecting or assessing the formation of at least one stress granule in a cell, methods of detecting or assessing the cellular uptake, methods of determining treatment of a neurological disorder associated with neuron death in a subject, and methods of determining whether a neuroprotective molecule confers protection against stress-induced cell death are described herein. Additional methods for assessing these activities are known in the art.

Pharmaceutical Compositions

Also provided herein are pharmaceutical compositions that contain at least one (e.g., one, two, three, or four) of the neuroprotective molecules (e.g., any of the neuroprotective molecules described herein) or C-myc oligonucleotides described herein. Two or more (e.g., two, three, or four) of any of the neuroprotective molecules or C-myc oligonucleotides described herein can be present in a pharmaceutical composition in any combination. The pharmaceutical compositions may be formulated in any manner known in the art.

Pharmaceutical compositions are formulated to be compatible with their intended route of administration (e.g., intravenous, intracranial, ocular, intraarterial, intramuscular, intradermal, subcutaneous, or intraperitoneal). The compositions can include a sterile diluent (e.g., sterile water or saline), a fixed oil, polyethylene glycol, glycerine, propylene glycol or other synthetic solvents, antibacterial or antifungal agents such as benzyl alcohol or methyl parabens, chlorobutanol, phenol, ascorbic acid, thimerosal, and the like, antioxidants such as ascorbic acid or sodium bisulfite, chelating agents such as ethylenediaminetetraacetic acid, buffers such as acetates, citrates, or phosphates, and isotonic agents such as sugars (e.g., dextrose), polyalcohols (e.g., manitol or sorbitol), or salts (e.g., sodium chloride), or any combination thereof. Liposomal suspensions can also be used as pharmaceutically acceptable carriers (see, e.g., U.S. Pat. No. 4,522,811). Preparations of the compositions can be formulated and enclosed in ampules, disposable syringes, or multiple dose vials. Where required (as in, for example, injectable formulations), proper fluidity can be maintained by, for example, the use of a coating such as lecithin, or a surfactant. Absorption of the neuroprotective molecule or C-myc oligonucleotide can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Compositions containing one or more of any of the neuroprotective molecules or C-myc oligonucleotides described herein can be formulated for parenteral (e.g., intravenous, intraarterial, intramuscular, intradermal, subcutaneous, or intraperitoneal), intracranial, or ocular administration in dosage unit form (i.e., physically discrete units containing a predetermined quantity of active compound for ease of administration and uniformity of dosage).

Toxicity and therapeutic efficacy of compositions can be determined by standard pharmaceutical procedures in cell cultures or experimental animals (e.g., monkeys). One can, for example, determine the LD50 (the dose lethal to 50% of the population) and the ED50 (the dose therapeutically effective in 50% of the population): the therapeutic index being the ratio of LD50:ED50. Agents that exhibit high therapeutic indices are preferred. Where an agent exhibits an undesirable side effect, care should be taken to minimize potential damage (i.e., reduce unwanted side effects). Toxicity and therapeutic efficacy can be determined by other standard pharmaceutical procedures.

Data obtained from cell culture assays and animal studies can be used in formulating an appropriate dosage of any given agent for use in a subject (e.g., a human). A therapeutically effective amount of the one or more (e.g., one, two, three, or four) neuroprotective molecules or C-myc oligonucleotides (e.g., any of the neuroprotective molecules or C-myc oligonucleotides described herein) will be an amount that treats a neurological disorder associated with neuron death (e.g., amyotrophic lateral sclerosis) in a subject (e.g., a human), decreases the severity, frequency, and/or duration of one or more symptoms of a neurological disorder associated with neuron death (e.g., amyotrophic lateral sclerosis) in a subject (e.g., a human), decreases the rate of neuron death (apoptosis and/or necrosis) in a subject (e.g., a human) having a neurological disorder associated with neuron death, induces or increases stress granule formation in a neuron (e.g., a motor neuron) in a subject having a neurological disorder associated with neuron death (e.g., amyotrophic lateral sclerosis), and/or decreases or inhibits protein translation in a neuron (e.g, a motor neuron) in a subject (e.g., a human) having a neurological disorder associated with neuron death (e.g., as compared to a control subject having the same disease but not receiving treatment or a different treatment, or the same subject prior to treatment). The effectiveness and dosing of any of the neuroprotective molecules or C-myc oligonucleotides described herein can be determined by a health care professional using methods known in the art, as well as by the observation of one or more symptoms of a neurological disorder associated with neuron death in a subject (e.g., a human). Certain factors may influence the dosage and timing required to effectively treat a subject (e.g., the severity of the disease or disorder, previous treatments, the general health and/or age of the subject, and the presence of other diseases).

Exemplary doses include milligram or microgram amounts of any of the neuroprotective molecules or C-myc oligonucleotides described herein per kilogram of the subject's weight (e.g., about 100 ng/kg to about 500 mg/kg; 500 ng/kg to about 1 μg/kg; 1 μg/kg to about 500 mg/kg; about 100 μg/kg to about 500 mg/kg; about 100 μg/kg to about 50 mg/kg; about 10 μg/kg to about 5 mg/kg; about 10 μg/kg to about 0.5 mg/kg; or about 1 μg/kg to about 50 μg/kg). While these doses cover a broad range, one of ordinary skill in the art will understand that therapeutic agents, including the neuroprotective molecules and the C-myc oligonucleotides, vary in their potency, and effective amounts can be determined by methods known in the art. Typically, relatively low doses are administered at first, and the attending health care professional (in the case of therapeutic application) or a researcher (when still working at the development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, and the half-life of the neuroprotective molecule or C-myc oligonucleotide in vivo.

The pharmaceutical compositions can be included in a container, pack, or dispenser together with instructions for administration.

Methods of Inducing/Increasing Stress Granule Formation in a Cell Provided herein are methods of inducing or increasing stress granule formation in a cell that include administering to a cell a neuroprotective molecule (e.g., any of the neuroprotective molecules described herein) or an isolated C-myc oligonucleotide containing the sequence of GGGAGGGTGG GGAGGGTGGGG (SEQ ID NO: 174) (e.g., any of the C-myc oligonucleotides described herein), wherein the neuroprotective molecule or isolated C-myc oligonucleotide is administered in an amount sufficient to induce or increase (e.g., a significant or detectable increase) stress granule formation in the cell. In some embodiments, the increase in stress granule formation is the formation of at least one stress granule in a cell that does not contain stress granules prior to treatment.

Stress granules are formed in the cytosol and nucleus of mammalian cells (e.g., neurons) in response to stress stimuli (e.g., oxidative stress). Stress granules contain both proteins and messenger RNAs (e.g., polyA mRNAs) that are stalled in translation pre-initiation complexes. Stress granules range between 100 nm to 200 nm in size and are not surrounded by a cellular membrane. A variety of proteins have been identified as being present within stress granules and the presence of stress granules can be identified by the localization of one or more (e.g., two, three, or four) of the following proteins/complexes in distinct foci within a cell (e.g., within the cytoplasm or nucleus of a cell): 40S ribosomal subunit, Ago2, AKAP350, APOBEC3G, Ataxin-2/Pbp1, BRF1, Calreticulin, Caprin1, CCAR1, Ccr4, CIRP, CPEB, CUG-BP1, Dcp1/Dcp1a, Dcp2; DDX1, DDX3/Ded1, DIC1/DHC1, DIS1, Eap1, Ebs1, Edc1-2, Edc3, eIF2, eIF2B, eIF3, eIF4A, eIF4E, eIF4E-T, eIF4G, eRF1, eRF3, FAK, FAST, FBP/KSRP, FMRP, FXR1P, FXR2P, G3BP, Gbp2, Ge-1/Hedls, Grb7, GW182, hMex3A, hMex3B, hnRNP A1, hnRNP A3, hnRNP K, hnRNP Q, Hrp1, Htt, Hsp27, HuD, HuR, IP5K, Importin-8, KHC/KLC, Lin28, LINE1 ORF1p, Lsm1, MBNL1, MEX67, MLN51, Musahi, Nrp1, NXF7, p97/NAT1, PABP/Pab1, Pan2/3, Pat1, PCBP2, Plakophilin 1/3, PMR1, Pop2/Caf1, Prohibitin 2, PRTB, Pum1, Pum2, RACK1, RBM42, Rap55/Sed6, RCK/Dhh1, RHAU, Roquin, Rpm2, RSK2, Sam68, SERBP1, SGNP, Smaug 1, Staufen, SMN, TDP-43, TDRD3, TIA-1/Pub1, TIA-R/Ngr1, TNRC6B, TRAF2, TTP, Upf1, Upf2, Upf3, Vts1, Xm1, YB-1, Ygr250c, and ZBP1. Typically, the presence of stress granules in a cell are detected using microscopy (e.g., immunofluorescence microscopy) using one or more antibodies that recognize the localization one or more of the following proteins in discrete foci in the cell: 40S ribosomal subunit, eIF4E, eIF4G, eIF4A, eIF4B, poly(A) binding protein (Pabp), eIF3, and eIF2. The presence of a stress granule can also be detected by assessment of the level of phosphorylated eIF2α present in the cell (e.g., an increased level of phospho-eIF2α indicates the presence of stress granules in the cell). Additional methods for detecting the formation or presence of stress granules in the cell are known in the art.

The formation of stress granule formation in a cell can be compared to the same cell prior to treatment or can be compared to at least one second cell or a population of cells not receiving treatment or receiving a different treatment. In some embodiments, the cell is treated with the at least one neuroprotective molecule or the C-myc oligonucleotide for at least 2 hours (e.g., at least 6 hours, 12 hours, 16 hours, 20 hours, or 24 hours) before the formation of stress granules is determined in the cell.

An increase in stress granule formation in a cell (e.g., a motor neuron) can be indirectly observed in a subject having a neurological disorder associated with neuron death (e.g., stress-induced motor neuron death) by a decrease (e.g., a detectable decrease) in the rate of the development of at least one symptom of a neurological disorder associated with neuron death or a decrease in the rate of the worsening or exacerbation of at least one symptom (e.g., an increase in the intensity, duration, or frequency of at least one symptom over time) of a neurological disorder associated with neuron death in a subject.

In some embodiments, a C-myc oligonucleotide containing the sequence of SEQ ID NO: 174 is administered to the cell. The C-myc oligonucleotides that can be used in these methods can include at least one modified nucleotide (e.g., any of the modified oligonucleotides described herein). In addition, the C-myc oligonucleotides can contain at least one modification in the phosphate backbone (the phosphodiester linkage between two adjoining nucleotides) (e.g., any of linkages described herein). The C-myc oligonucleotides described herein can also include a 5' and/or a 3' blocking group (e.g., a 5' and/or 3' blocking group that decreases or inhibits nuclease degradation) (e.g., any of the 5' and/or 3' blocking groups described herein or known in the art). In some embodiments, the C-myc oligonucleotides have a total length of between 21 to 50 nucleotides (e.g., 21-30 nucleotides, 30-40 nucleotides, or 40-50 nucleotides).

In various embodiments of these methods, the cell can be a neuron (e.g., a motor neuron), a fibroblast, an epithelial cell, an endothelial cell, or a muscle cell. In any of the methods described herein, the cell is a human cell. In some embodiments of these methods, the cell is in vitro (in tissue culture). In some embodiments of these methods, the cell is in vivo (in a human). In some embodiments, the cell is ex vivo (e.g., a primary human neuron or a primary rat neuron).

The neuroprotective molecule or C-myc oligonucleotide can be administered to the cell by a laboratory worker (a research scientist), a health care professional (e.g., a physician, a physician's assistant, or a nurse), or a subject (e.g., self-administration). In instances where the neuroprotective molecule or C-myc oligonucleotide are administered to a to a cell in vivo (in a subject), the dosing and administration of the neuroprotective molecule or C-myc oligonucleotide can be performed as described below.

Methods of Decreasing Protein Translation in a Cell

The data in the Examples show that the neuroprotective molecules and the C-myc oligonucleotides described herein inhibit protein translation of mRNA (capped and uncapped mRNAs) by displacing eIF4G/eIF4A from uncapped RNAs and by displacing eIF4F from the m$^7$G cap of mRNAs. Accordingly, provided herein are methods of decreasing protein translation in a cell that include administering to a cell a neuroprotective molecule (e.g., any of the neuroprotective molecules described herein) or an isolated C-myc oligonucleotide (e.g., any of the C-myc oligonucleotides described herein), where the neuroprotective molecule or the isolated C-myc oligonucleotide is administered in an amount sufficient to decrease (e.g., a significant or detectable decrease) protein translation in the cell.

In some embodiments, the decrease in protein translation is detected by the amount of protein translation (new proteins translated) over a specific period of time (e.g., at least 1 hour, 2 hours, 4 hours, or 6 hours). In some embodiments, the decrease is protein translation is a decrease in the rate of protein translation in the cell (e.g., as measured by radioisotope labeling ($^{35}$S) of newly translated proteins or by detection of the biological activity of a newly expressed protein). The decrease in protein translation in a cell can be compared to a control cell or population of cells not receiving the treatment or receiving a different treatment. Additional methods for detecting protein translation are described herein and are known in the art.

An decrease in protein translation in a cell (e.g., a motor neuron) can be indirectly observed in a subject having a neurological disorder associated with neuron death (e.g., stress-induced motor neuron death) by a decrease (e.g., a detectable decrease) in the rate of the development of at least one symptom of a neurological disorder associated with neuron death or a decrease in the rate of the worsening or exacerbation of at least one symptom (e.g., an increase in the intensity, duration, or frequency of at least one symptom over time) of a neurological disorder associated with neuron death in a subject.

In various embodiments of these methods, the cell can be a neuron (e.g., a motor neuron), a fibroblast, an epithelial cell, an endothelial cell, or a muscle cell. In any of the methods described herein, the cell is a human cell. In some embodiments of these methods, the cell is in vitro (in tissue culture). In some embodiments of these methods, the cell is in vivo (in a human). In some embodiments the cell is ex vivo (e.g., a primary human neuron or a primary rat neuron).

The neuroprotective molecule or C-myc oligonucleotide can be administered to the cell by a laboratory worker (a research scientist), a health care professional (e.g., a physician, a physician's assistant, or a nurse), or a subject (e.g., self-administration). In instances where the neuroprotective molecule or C-myc oligonucleotide are administered to a cell in vivo (administered to a subject), the dosing and administration of the neuroprotective molecule or C-myc oligonucleotide can be performed as described below.

Methods of Treating Neurological Disorders Associated with Neuron Death

Also provided herein are methods of treating neurological disorders associated with neuron death (apoptosis and/or necrosis, or stress-induced neuron death). These methods include administering a neuroprotective molecule (e.g., any of the neuroprotective molecules described herein) or an isolated C-myc oligonucleotide (e.g., any of the C-myc oligonucleotides described herein), where the neuroprotective molecule or C-myc oligonucleotide are administered in an amount sufficient to treat the neurological disorder associated with neuron death in the subject.

Neurological disorders associated with neuron death are a group of diseases that are characterized by neuron death (e.g., motor neuron death or stress-induced motor neuron death) and/or have an etiology that involves neuron death (e.g., motor neuron death or stress-induced motor neuron death). Non-limiting examples of neurological disorders associated with neuron death include amyotrophic lateral sclerosis, Alzheimer's disease, Parkinson's disease, Huntington's disease, muscular dystrophy, multiple sclerosis, and stroke. Neuronal death in this group of disorders can be induced by a variety of stress stimuli, including, for example, oxidative stress, excitotoxicity, and neuroinflammation. The data in the Examples herein show that induction of stress granules (e.g., by administration of any of the neuroprotective molecules or C-myc oligonucleotides described herein) mediates an increase in resistance to stress-induced neuronal death. Thus, by virtue of their ability to induce an increase in stress granule formation in neurons (e.g., motor neurons) in a subject, administration of the neuroprotective molecules and the C-myc oligonucleotides described herein can treat a neurological disorder associated with neuron death in a subject. Some of the same neuroprotective molecules and C-myc oligonucleotides described herein have the further advantage that they are taken up by neurons (e.g., motor neurons) without the addition of a transfection agent.

Non-limiting symptoms of neurological disorders associated with neuron death include: hyperflexia, weak muscles, twitching, speech problems, breathing problems, swallowing difficulties, loss of memory, confusion, disorientation, difficulty writing, depression, anxiety, social withdrawal, mood swings, aggressiveness, changes in sleeping habits, tremors, bradykinesia, rigid muscles, impaired balance, involuntary facial movements, numbness or weakness in limbs, partial or complete loss of vision, fatigue, dizziness, paralysis on one side of body or face, and headache. A neurological disorder associated with neuronal death can be diagnosed by a health care professional by detecting or observing one or more (e.g., two, three, or four) symptoms (any of the above listed symptoms) in a subject.

In some embodiments, the administering results in a decrease in the number of symptoms of a neurological disorder associated with neuron death (e.g., as compared to the number of symptoms in a subject prior to treatment or to a subject having the same neurological disorder and not receiving treatment or receiving a different treatment). In some embodiments, the administering results in a decrease (e.g., a detectable or observable decrease) in the severity, frequency, or duration of one or more symptoms of a neurological disorder associated with neuron death (e.g., those symptoms listed herein) (e.g., as compared to a subject having the same neurological disorder and not receiving treatment or receiving a different treatment).

In some embodiments, the administering results in a decrease (e.g., a detectable or observable decrease) in the rate of the development of one or more new symptoms of a neurological disorder associated with neuron death in a subject having a neurological disorder associated with neuron death (e.g., as compared to the rate of the development of one or more new symptoms of a neurological disorder associated with neuron death in a subject having the same neurological disorder and not receiving treatment or receiving a different treatment). In some embodiments, the administering results in a decrease (e.g., a detectable or observable decrease) in the rate of worsening or exacerbation of one or more symptoms of a neurological disorder associated with neuron death (e.g., an increase in the severity, frequency, or duration of one or more symptoms of a neurological disorder associated with neuron death over time) (e.g., any of those symptoms described herein) (e.g., as compared to a subject having the same neurological disorder and not receiving treatment or receiving a different treatment).

In some embodiments, the administering results in an increase in stress granule formation in a neuron (e.g., a motor neuron) in a subject that has a neurological disorder associated with neuron death (e.g., as compared to a subject having the same neurological disorder and not receiving treatment or receiving a different treatment). In some embodiments, the administering results in a decrease or inhibition in protein translation in a cell (e.g., a motor neuron) in a subject that has a neurological disorder associated with neuron death (e.g., as compared to a subject having the same neurological disorder and not receiving treatment or receiving a different treatment). In some embodiments, the administering results in a decrease in neuron death or a decrease in the rate of neuron death (e.g., stress-induced motor neuron death) over a period of time (e.g., at least one month, at least one year, or at least five years) (e.g., as compared to a subject having the same neurological disorder and not receiving treatment or receiving a different treatment). A decrease in protein translation in a neuron (e.g., a motor neuron), an increase in stress granule in a neuron (e.g., a motor neuron), or a decrease in the amount or rate of neuron death over time can be indirectly observed by a physician by a decrease (e.g., a detectable or observable decrease) in the rate of the development of at least one new symptom of a neurological disorder associated with neuron death in a subject (e.g., a decrease in further development of at least one additional symptom of the disorder) or a decrease in the rate of exacerbation of at least one symptom (e.g., a decreased rate of increasing frequency, severity, and/or duration of at least one symptom of the neurological disorder associated with neuron death) (e.g., as compared to a subject having the same neurological disorder and not receiving treatment or receiving a different treatment).

Any of the neuroprotective molecules or C-myc oligonucleotides described herein can be used in these methods. In preferred embodiments, the neuroprotective molecule or C-myc oligonucleotide is taken up by a neuron in the subject in the absence of a transfection agent. In some embodiments, the neuroprotective molecule or the C-myc oligonucleotide contains a modified nucleotide (e.g., any of the modified bases and/or sugars described herein). In some embodiments, the neuroprotective molecule or the C-myc oligonucleotide contains at least one modification in its phosphate (phosphodiester) backbone (e.g., any of the moieties described herein that can be used to link two adjoining nucleotides).

The neuroprotective molecule or C-myc oligonucleotide can be administered by a health care professional (e.g., a physician, a physician's assistant, a nurse, or a laboratory or clinic worker), the subject (i.e., self-administration), or a friend or family member of the subject. The administering can be performed in a clinical setting (e.g., at a clinic or a hospital), in an assisted living facility, or at a pharmacy.

The neuroprotective molecule or C-myc oligonucleotide can be administered to a subject that has been diagnosed as having a neurological disorder associated with neuron death. In some non-limiting embodiments, the subject is a man or a woman, an adult, or an adolescent. The subject can have experienced one or more symptoms of the neurological disorder associated with neuron death for at least one year, two years, three years, four years, or five years. The subject can also be diagnosed as having a later or severe form (an advanced stage) of the neurological disorder associated with neuron death.

In some embodiments of any of the methods described herein, the subject is administered at least one (e.g., at least 1, 2, 3, 4, 5, 6, 7, 8, 9, 10, 15, 20, 25, or 30) dose of a composition containing at least one (e.g., one, two, three, or four) of any of the neuroprotective molecules, C-myc oligonucleotides, or pharmaceutical compositions described herein. In any of the methods described herein, the neuroprotective molecule, C-myc oligonucleotide, or pharmaceutical composition (e.g., any of the neuroprotective molecules, C-myc oligonucleotides, or pharmaceutical compositions described herein) can be administered intravenously, intaarterially, subcutaneously, intraperitoneally, intracranially, ocularly, or intramuscularly to the subject. In some embodiments, the neuroprotective molecule, C-myc oligonucleotide, or pharmaceutical composition is administered intracranially, ocularly, or to the spinal fluid.

In some embodiments, the subject is administered the neuroprotective molecule, C-myc oligonucleotide, or pharmaceutical composition (e.g., any of the neuroprotective molecules, C-myc oligonucleotides, or pharmaceutical compositions described herein) and at least one additional therapeutic agent. The at least one additional therapeutic agent can be selected from the group consisting of: mexiletine, phenytoin, baclofen, dantrolene, carbamazepine, corticosteroids, β-interferons, glatiramer, fingolimod, natalizumab, mitoxantrone, aspirin, tissue plasminogen activator, anticholinergics (e.g., benzotropine and trihexyphenidyl), glutamate (NMDA) blocking drugs (e.g., amantadine), riluzole, cholesterase inhibitors (e.g., donepezil, galactamine, and rivastigmine), memantine, levodopa, carbidopa, dopamine agonists (e.g., pramipexole, ropinicole, and apomorphine), monoamine oxidase B inhibitors (e.g., selegiline and vasagiline), catechol O-methyl transferase inhibitors (e.g., tolcapone and entracapone), tetrabenazine, and anti-psychotic drugs (e.g., haloperidol and clozapine). In some embodiments, at least one additional therapeutic agent and at least one neuroprotective molecule or C-myc oligonucleotide (e.g., any of the neuroprotective molecules or C-myc oligonucleotides described herein) are administered in the same composition (e.g., the same pharmaceutical composition). In some embodiments, the at least one additional therapeutic agent and the neuroprotective molecule or C-myc oligonucleotide are administered to the subject using different routes of administration (e.g., at least one additional therapeutic agent delivered by oral administration and the neuroprotective molecule or C-myc oligonucleotide delivered by intravenous administration).

In any of the methods described herein, the neuroprotective molecule, C-myc oligonucleotide, or pharmaceutical composition (e.g., any of the neuroprotective molecules, C-myc oligonucleotides, or pharmaceutical compositions described herein) and, optionally, at least one additional therapeutic agent can be administered to the subject at least once a week (e.g., once a week, twice a week, three times a week, four times a week, once a day, twice a day, or three times a day). In some embodiments, at least two different neuroprotective molecules and/or C-myc oligonucleotides are administered in the same composition (e.g., a liquid composition). In some embodiments, the neuroprotective molecule or C-myc oligonucleotide and at least one additional therapeutic agent are administered in the same composition (e.g., a liquid composition). In some embodiments, the neuroprotective molecule or C-myc oligonucleotide and the at least one additional therapeutic agent are administered in two different compositions (e.g., a liquid composition containing the neuroprotective molecule or C-myc oligonucleotide and a solid oral composition containing at least one additional therapeutic agent). In some embodiments, the at least one additional therapeutic agent is administered as a pill, tablet, or capsule. In some embodiments, the at least one additional therapeutic agent is administered in a sustained-release oral formulation.

In some embodiments, the one or more additional therapeutic agents can be administered to the subject prior to administering the neuroprotective molecule, C-myc oligonucleotide, or pharmaceutical composition (e.g., any of the neuroprotective molecules, C-myc oligonucleotides, or pharmaceutical compositions described herein). In some embodiments, the one or more additional therapeutic agents can be administered to the subject after administering the neuroprotective molecule, C-myc oligonucleotide, or pharmaceutical composition (e.g., any of the neuroprotective molecules, C-myc oligonucleotides, or pharmaceutical compositions described herein). In some embodiments, the one or more additional therapeutic agents and the neuroprotective molecule, C-myc oligonucleotide, or pharmaceutical composition (e.g., any of the neuroprotective molecules, C-myc oligonucleotides, or pharmaceutical compositions described herein) are administered to the subject such that there is an overlap in the bioactive period of the one or more additional therapeutic agents and the neuroprotective molecule or C-myc oligonucleotide (e.g., any of the neuroprotective molecules or C-myc oligonucleotides described herein) in the subject.

In some embodiments, the subject can be administered the neuroprotective molecule, C-myc oligonucleotide, or pharmaceutical composition (e.g., any of the neuroprotective molecules, C-myc oligonucleotides, or pharmaceutical compositions described herein) over an extended period of time (e.g., over a period of at least 1 week, 2 weeks, 3 weeks, 1 month, 2 months, 3 months, 4 months, 5 months, 6 months, 7 months, 8 months, 9 months, 10 months, 11 months, 12 months, 1 year, 2 years, 3 years, 4 years, 5 years, or 10 years). A skilled medical professional may determine the length of the treatment period using any of the methods described herein for diagnosing or following the effectiveness of treatment (e.g., using the methods above and those known in the art). As described herein, a skilled medical professional can also change the identity and number (e.g., increase or decrease) of neuroprotective molecules or C-myc oligonucleotides (and/or one or more additional therapeutic agents) administered to the subject and can also adjust (e.g., increase or decrease) the dosage or frequency of administration of the neuroprotective molecule or C-myc oligonucleotide (and/or one or more additional therapeutic agents) to the subject based on an assessment of the effectiveness of the treatment (e.g., using any of the methods described herein and known in the art). A skilled medical professional can further determine when to discontinue treatment (e.g., for example, when the subject's symptoms are significantly decreased).

Methods of Identifying a Candidate Translation Inhibitory Nucleic Acid

Also provided herein are methods of identifying a candidate translation inhibitory nucleic acid. These methods include (a) attaching to the 5' end of a nucleic acid sequence of between 20-50 nucleotides (e.g., 20-30 nucleotides, 30-40 nucleotides, or 40-50 nucleotides) at least four (e.g., at least five, six, or seven) guanosine-containing nucleotides, and (b) determining the level of protein translation in the presence of the molecule produced in (a). A decrease (e.g., a significant or detectable decrease) in the level of protein translation in the presence of the molecule produced in (a) relative to the level of protein synthesis in the absence of the molecule produced in (a) identifies the molecule produced in (a) as a candidate translation inhibitory nucleic acid.

In some embodiments, the nucleic acid sequence of between 20-50 nucleotides contains at least 50% (e.g., at least 55%, 60%, 65%, or 70%) guanosine-containing/cytosine-containing nucleotides. In some embodiments, the sequence of between 20-50 nucleotides is at least 80% identical to a contiguous sequence between nucleotide 1 and nucleotide 50 of a mature human tRNA sequence (e.g., any of the tRNA sequences described or referenced herein, or any mature human tRNA sequence known in the art). The nucleic acid sequence of between 20-50 nucleotides can contain at least one modified nucleotide (e.g., can contain any of the base modifications or sugar modifications described herein). The nucleic acid sequence of between 20-50 nucleotides can also contain at least one modification in the phosphate (phosphodiester) backbone (e.g., any of the linking moieties between two adjoining nucleotides described herein). The molecule produced in (a) can also contain a 5' and/or 3' protective group (e.g., a protective group that decreases nuclease degradation of the molecule produced in (a)) (e.g., any of the 5' or 3' protective groups described herein or known in the art).

In some embodiments of these methods, the level of protein translation is determined in a cell (e.g., a fibroblast, a neuron (e.g., a motor neuron), an endothelial cell, an epithelial cell, or a muscle cell) (e.g., a cell in vitro). In some embodiments, the level of protein translation is determined in a cell lysate (e.g., a reticulocyte lysate). In some embodiments of all of the above methods, the cell is a human cell.

The level of protein synthesis in these methods can be the total amount of protein translation that occurs over a specific period of time (e.g., at least 2 hours, 6 hours, 12 hours, 16 hours, 20 hours, or 24 hours) or the rate of protein synthesis. Methods for measuring or detecting protein translation are described herein. Additional methods for measuring or detecting protein synthesis are known in the art.

Candidate translation inhibitory nucleic acids identified in these methods can be further modified by the incorporation of modified nucleotides (e.g., modified bases and/or sugars), by introducing a modification in the phosphate (phosphodiester) backbone (e.g., introduction of one of the linking moieties described herein), and/or by adding a 5' and/or 3' blocking group to the molecule produced in (a), and further tested to determine the molecule's ability to decrease protein translation.

EXAMPLE

The invention is further described in the following examples, which do not limit the scope of the invention described in the claims.

Example 1

Endogenous 5'-tiRNAs Inhibit Translation

Experiments were performed in order to determine whether natural 5'- and 3'-tRNA fragments (tiRNAs) purified from angiogenin-treated U2OS cells would inhibit translation of uncapped luciferase transcripts in rabbit reticulocyte lysate (RRL). The following methods were used to perform these experiments.

Tissue Culture and Cell Treatment

U2OS cells were maintained at 37° C. in a $CO_2$ incubator in Minimal Essential Medium (DMEM) supplemented with 10% fetal bovine serum (FBS) (Sigma) and 1% of penicillin/streptomycin (Sigma). The cells were treated with angiogenin (0.5 µg/mL) as described in Kedersha et al., *Methods Enzymol.* 448:521-552, 2008.

Isolation of tiRNAs

Extraction of tiRNAs from angiogenin-treated U2OS cells was done as previously described (Yamasaki et al., *J. Cell Biol.* 185:35-42, 2009).

In Vitro Translation of mRNA Reporters in Rabbit Reticulocyte Lysates (RRLs)

The Flexi Rabbit Reticulocyte Lysate (RRL) System (Promega) was used for the in vitro analysis of mRNA translation according to the manufacture's recommendations with some modifications. In all cases, translation reactions (10 µl final volume) contained 70% of reticulocyte lysates or mixtures of RRL supplemented with 20% of microccocal nuclease-treated U2OS extract (RRL+20% U2OS lysate) and 8 units of RNasin Ribonuclease Inhibitor (Promega). Fifty ng of uncapped Firefly RNA (Promega) were used per translation reaction. One hundred picomoles of control RNAs or tiRNAs were added to translation reactions, mixed, and incubated for 30 minutes at 30° C. The reactions were stopped at 4° C. and the activity of Firefly luciferase was measured using ⅕ of the translation reactions with the Luciferase Assay System (Promega) according to the manufacture's recommendations (2 second measurement delay followed by 10 second measurement read).

Northern Blot Analysis

RNA was separated on either a 10% or 15% TBE-UREA Gel (Invitrogen) and transferred to Supercharge nylon transfer membranes (Nytran SPC; 0.45 µm pore size; Whatman). The RNA on the membranes was UV cross-linked using a FB-UVXL-1000 cross-linker (Fisher Scientific). The membranes were then pre-hybridized in hybridization solution (5×SSC, 20 mM $Na_2HPO_4$ pH 7.4, 7% SDS, 1×Denhardt's) at 47° C. for 30 minutes and then hybridized with the $^{32}P$ 5'-end labeled oligonucleotide probe (ME8: 5'CTTTAT-GTTTTTGGCGTCTTCCATCTCGAGGC3'; SEQ ID NO: 175) overnight at 47° C. The membranes were washed twice for 15 minutes at 47° C. with 3×SSC/5% SDS and once with 1×SSC/1% SDS for 15 minutes at room temperature. After washing, RNA signals were detected by autoradiography on X-Omat film (Kodak) after overnight exposure at −80° C.

Results

Figure 1:
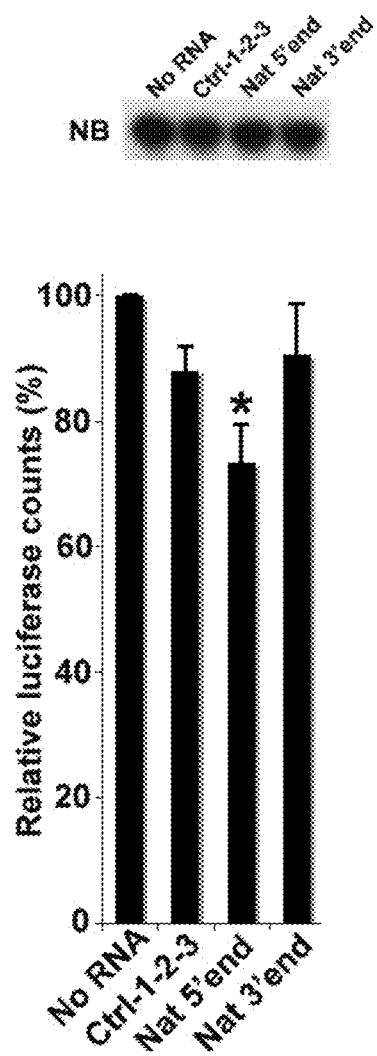
FIG. 1 is a graph showing the relative amount of luciferase expression in rabbit reticulocyte lysate (RRL) containing uncapped luciferase mRNA following treatment with a control RNA mix (Ctrl 1-2-3), natural 5'-tiRNAs (Nat 5' end), or natural 3'-tiRNAs (Nat 3' end) compared to luciferase expression in untreated lysates (bottom), and a Northern blot showing the levels of luciferase mRNA in these experiments (top). The means and standard deviations shown are from three independent experiments (*p=0.01-0.02, Student's t-test, n=3).

Uncapped Firefly luciferase mRNA (Promega) was translated in RRL in the presence of a control RNA mix (Ctrl 1-2-3; derived from Piwi-interacting RNAs (piRNAs) or randon sequences), natural 5'-tiRNAs (Nat 5' end), or natural 3'-tiRNAs (Nat 3'end) using the methods described above. Luciferase expression was compared to the level of expression in the absence of RNA (No RNA=100%). The data from these experiments show that natural 5'-tiRNAs (but not 3'-tiRNAs) gel-purified from angiogenin-treated U2OS cells significantly inhibit translation of uncapped luciferase transcripts in RRLs (FIG. 1, bottom). Northern blotting analysis confirmed that the luciferase transcripts were not degraded during the experiment (FIG. 1, top).

Example 2

Selected Synthetic 5'-tiRNAs are Potent Inhibitors of Translation

Since natural tiRNA preparations are contaminated with ribosomal and mRNA fragments, experiments were performed to compare the activity of synthetic 5'-end phosphorylated 5'-tiRNAs (5'-tiRNAs) and unphosphorylated 3'-tiRNAs (3'-tiRNAs) (Emara et al., *J. Biol. Chem.* 285:10959-10968, 2010) in the above-described in vitro RRL translation assay. The synthetic tiRNAs used in this study were synthesized by Integrated DNA Technology and were at least 95% homogenous. The synthetic sequences used in these experiments were:

Ctrl1:
(SEQ ID NO: 1)
5'-UGA AGG GUU UUU UGU GUC UCU AUU UCC UUC-3'
(piR006650);

Ctrl2:
(SEQ ID NO: 2)
5'-phospho-UGU GAG UCA CGU GAG GGC AGA AUC UGC

UC-3' (piR58620)

Ctrl3:
(SEQ ID NO: 3)
5'-phospho-GCA UUC ACU UGG AUA GUA AAU CCA AGC

UGA A-3' (random)

5'Ala:
(SEQ ID NO: 4)
5'-Phospho-GGG GGU GUA GCU CAG UGG UAG AGC GCG

UGC-3';

5'-Val:
(SEQ ID NO: 5)
5'-phospho-GUU UCC GUA GUG UAG UGG UUA UCA CGU

UCG CC-3';

5'-Gly-GCC:
(SEQ ID NO: 6)
5'-Phospho-GCA UGG GUG GUU CAG UGG UAG AAU UCU

CGC-3';

5'-GlyCCC:
(SEQ ID NO: 7)
5'-phospho-GCG CCG CUG GUG UAG UGG UAU CAU GCA

AGA U-3';

5'-Pro:
(SEQ ID NO: 8)
5'-Phospho-GGC UCG UUG GUC UAG GGG UAU GAU UCU

CGG-3';

5'-Gln:
(SEQ ID NO: 9)
5'-Phospho-GGU UCC AUG GUG UAA UGG UUA GCA CUC

UG-3';

5'-Cys:
(SEQ ID NO: 10)
5'-Phospho-GGG GGU AUA GCU CAG UGG UAG AGC AUU

UGA-3';

5'-Met:
(SEQ ID NO: 11)
5'-Phospho-GCC UCG UUA GCG CAG UAG GUA GCG CGU

CAG U-3';

5'-Met-I:
(SEQ ID NO: 12)
5'-Phospho-AGC AGA GUG GCG CAG CGG AAG CGU GCU

GG-3';

3'-Ala:
(SEQ ID NO: 13)
5'-CUU AGC AUG CAC GAG GCC CCG GGU UCA AUC CCC

GGC ACC UCCA-3';

3'-Arg:
(SEQ ID NO: 14)
5'-GGA UCA GAA GAU UGA GGG UUC GGG UCC CUU CGU

GGU CG-3';

3'-Gly:
(SEQ ID NO: 15)
5'-CCA CGC GGG AGG CCC GGG UUC GAU UCC CGG CCA

AUG CA-3';

3'-Gln:
(SEQ ID NO: 16)
5'-GAC UCU GAA UCC AGC GAU CCG AGU UCA AAU CUC GGU

GGA ACC U-3';
and

3'-Pro:
(SEQ ID NO: 17)
5'-UUA GGA UGC GAG AGG UCC CGG GUU CAA AUC CCG GAC

GAG CCC-3'.

The levels of luciferase mRNA were also determined in these experiments using Northern blot using the methods described above.

Figure 2:
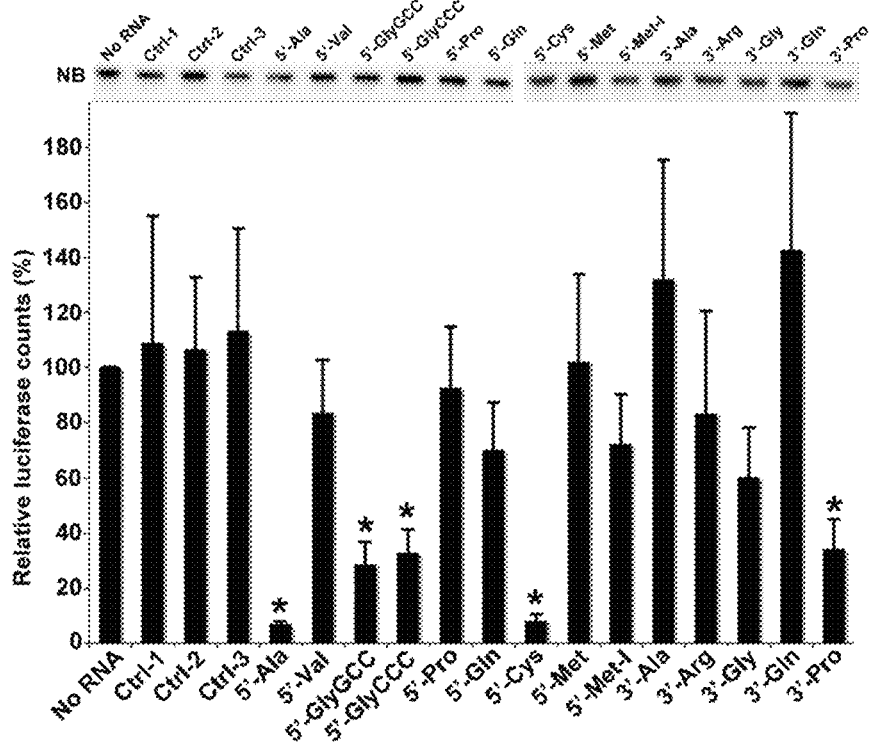
FIG. 2 is a graph showing the relative amount of luciferase expression in RRL containing uncapped luciferase mRNA (50 ng/10 μL) following treatment with synthetic 5'-tiRNAs or 3'-tiRNAs (100 picomoles/10 μL) compared to luciferase expression in untreated lysates (*p<0.05, Student's t-test, n=4) (bottom), and a Northern blot showing the levels of luciferase mRNA in these experiments (top).
Figure 3:
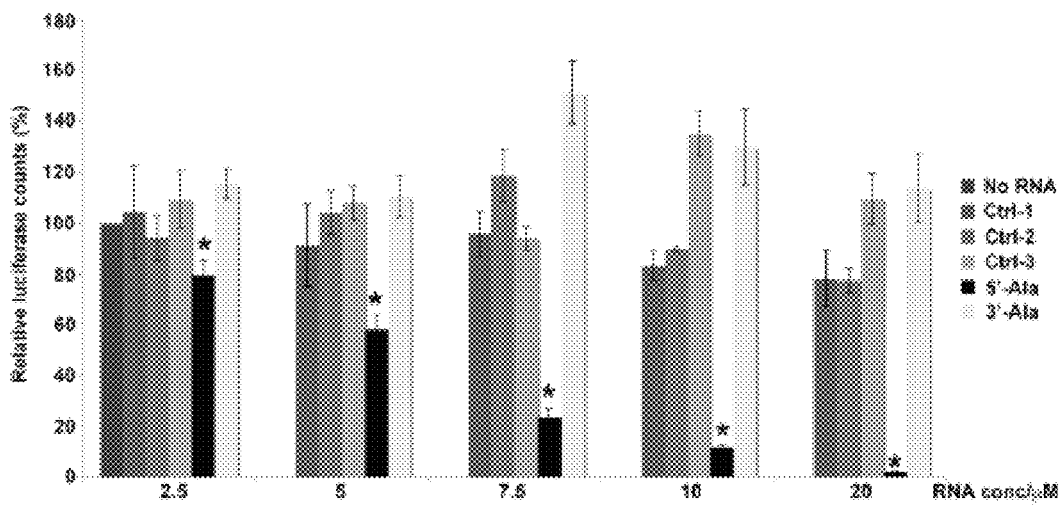
FIG. 3 is a graph showing the dose-dependent inhibition of uncapped luciferase mRNA translation in RRL following treatment with control RNAs (ctrl-1, ctrl-2, and ctrl-3), synthetic 5'-tiRNA$^{Ala}$ (5'-Ala), or synthetic 3'-tiRNA$^{Ala}$ (3'-Ala). Translation of the reporter in the absence of any RNA (No RNA) was assigned a relative value of 100%. The error bars reflect the standard deviations of the mean (*p<0.05, relative to no RNA and all three control RNAs (ctrl-1, ctrl-2, and ctrl-3), Student's t-test, n=3).

The data from these experiments show that although several tiRNAs significantly inhibit translation, 5'-tiRNA$^{Ala}$ and 5'-tiRNA$^{Cys}$ are particularly potent translational inhibitors (FIG. 2, bottom). Northern blotting analysis confirmed that luciferase transcripts were not degraded under these conditions (FIG. 2, top). Data from a dose response experiment comparing 5'- and 3'-tiRNA$^{Ala}$ shows that 5'-tiRNA$^{Ala}$ represses translation at low micromolar concentrations (FIG. 3). Since the abundance of tiRNAs in angiogenin- or ansenite-treated cells is ~10-fold less than that of tRNA (intracellular tRNA concentration is estimated to be ~10-200 μM depending on cell type), similar inhibitory concentrations of tiRNAs are likely found in stressed cells. These calculations indicate that the ratio of tiRNAs to mRNAs in stressed cells is ~8, which is consistent with their ability to repress translation in vivo.

Additional experiments were performed to determine whether 5'-tiRNA$^{Ala}$ and 3'-tiRNA$^{Ala}$ inhibit the translation of capped luciferase transcripts. These experiments were performed using the RRL translation assay described above with 10 nm of capped Firefly mRNA. To prepare capped Firefly luciferase mRNA, 2 μg of commercial uncapped Firefly luciferase mRNA (Promega) was capped by Vaccinia Virus Capping enzyme using ScriptCap m$^7$G Capping System (EPICENTRE Biotechnologies) according to the manufacture's recommendations. Capped mRNA was purified by standard ethanol precipitation and quantified by spectrophotometry (Beckman DU 640 instrument).

Figure 4:
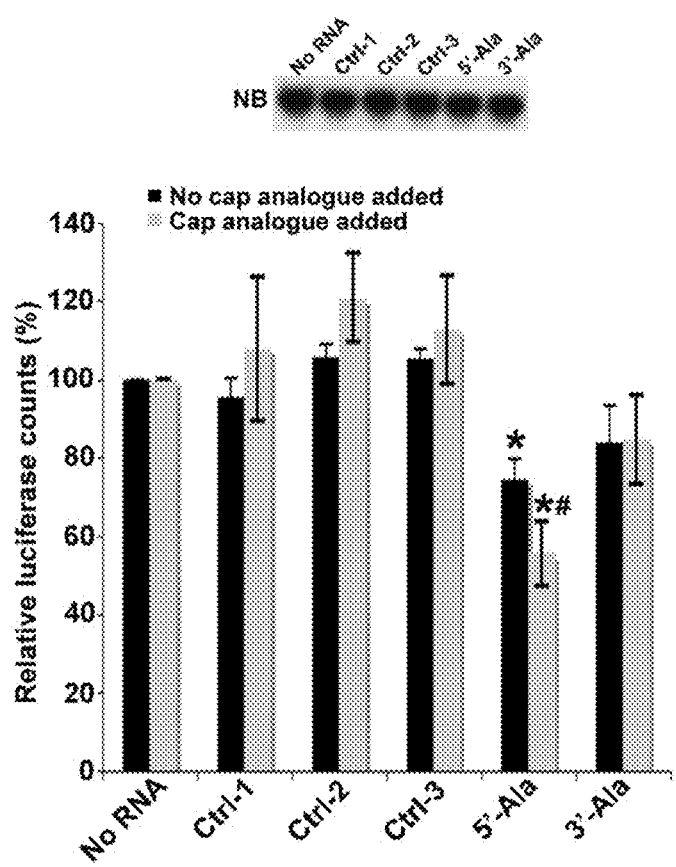
FIG. 4 is a graph showing the relative amount of luciferase expression in RRL containing capped luciferase mRNA (10 ng/10 μL) in the presence or absence of the indicated synthetic RNAs (100 picomoles/10 μL) in the absence (dark bars) or presence (light bars) of cap analogue (m$^7$GpppG, 0.1 mM) (*p<0.05, comparing 5'-tiRNA$^{Ala}$ in the presence or absence of the cap analogue, Student's t-test, n=3) (bottom), and a Northern blot showing the levels of luciferase mRNA in these experiments (top).

The data from these experiments show that 5'-tiRNA$^{Ala}$ (but not 3'-tiRNA$^{Ala}$) also significantly inhibits the translation of capped luciferase transcripts (FIG. 4, bottom), and that the addition of a cap analogue that inhibits cap-dependent translation significantly increases the relative translational repression. The cap analogue reduces the basal level of capped mRNA translation by ~2.5-fold. Northern blotting analysis (performed as described above) confirmed that luciferase transcripts are not degraded under these conditions (FIG. 4, top). Since translation of uncapped mRNAs or capped mRNAs in the presence of cap analogue depends on eIF4G binding to the 5'-terminus of mRNA (De Gregorio et al., RNA 4:828-836, 1998), these data suggest that 5'-tiR-NA$^A$ interferes with some functions of eIF4G (e.g., binding to mRNA and/or to eIF4E).

Example 3

Encephalomyocarditis Virus Internal Ribosomal Entry Site (EMCV IRES)-Mediated Translation Additional experiments were performed in order to determine the role of eIF4G in tiRNA-mediated translational repression. In these experiments, the translation of capped or uncapped bicistronic reporter transcripts encoding an upstream Firefly luciferase and a downstream EMCV IRES-driven Renilla luciferase in the absence or presence of tiRNAs was quantitated. These experiments were performed using the methods generally described above with the modifications described below.

RNA transcripts for use in the RRL assay were prepared by first linearizing the bicistronic reporter plasmid (pF/R) (Bochkov et al., BioTechniques 41:283-284, 286, 288, 2006) by digestion with HpaI (New England Biolabs), separating the cut plasmids on 1% agarose gel, and then purifying the plasmids from the gel with QIAquick Gel Extraction Kit (Qiagen). Riboprobe T7 in vitro transcription System (Promega) was used to synthesize pF/R RNA using T7 RNA Polymerase according to the manufacturer's recommendations. Subsequently, in vitro transcribed RNA was purified using Trizol (Invitrogen) extraction followed by isopropanol precipitation. Purified RNA was analyzed for purity on a formaldehyde gel and quantified by spectrophotometry (Beckman DU 640). One hundred nanograms of pF/R bicistronic mRNA were used per translation reaction and the activities of Firefly and Renilla luciferase were measured using ⅕ of translation reactions with the Dual-Luciferase Reporter Assay System (Promega).

Figure 5:
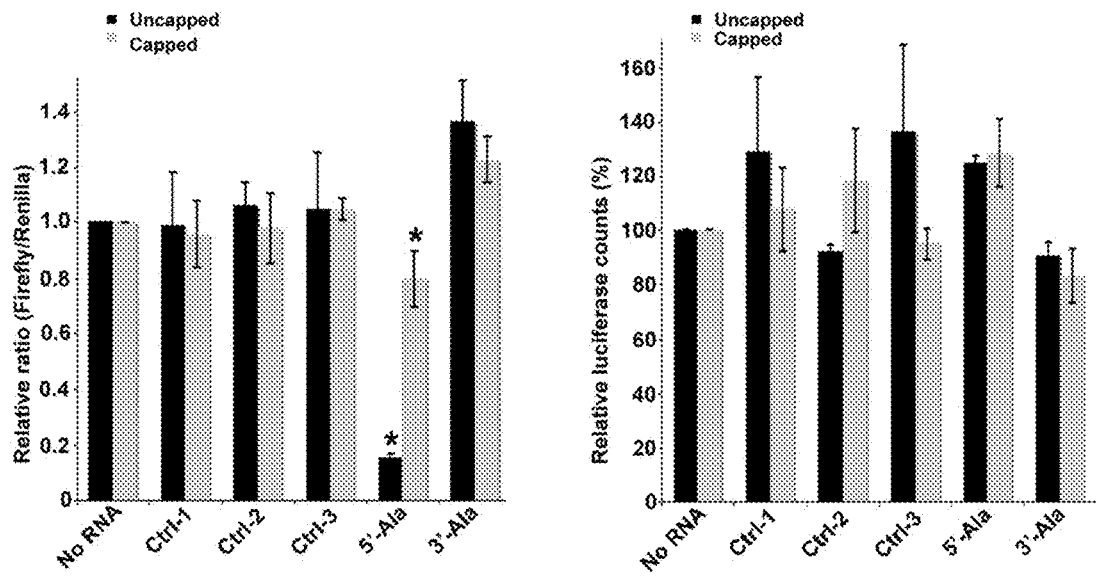
FIG. 5 is a graph showing the relative ratio of Firefly to *Renilla* luciferase counts produced in a RRL assay using uncapped (dark bars) or capped (light bars) pF/R bicistronic transcripts in the presence of 5'-tiRNA$^{Ala}$ (*p<0.05, compared to no RNA and three control RNAs (ctrl-1, -2, and -3), Student's t-test, n=3-4) (right panel), and a graph showing the luciferase counts from EMCV IRES-driven translation of the *Renilla* ORF relative to the no RNA control (100%)

The data from these experiments show that 5'- (but not 3'-tiRNA$^{Ala}$) significantly reduces the Firefly/Renilla luciferase ratio (FIG. 5, left panel) without affecting the translation of Renilla luciferase (FIG. 5, right panel). This result indicates that 5'-tiRNA$^{Ala}$ does not prevent the recruitment of eIF4G to the EMCV IRES. As this result was not consistent with the ability of tiRNAs to preferentially inhibit the eIF4G-dependent translation of uncapped RNA, additional experiments were performed using an EMCV IRES variant that has reduced affinity for eIF4G and less efficient translation initiation (Bockhov et al., supra; Kaminski et al., EMBO J. 13:1673-1681, 1998).

The recruitment of eIF4G to the EMCV IRES is critically dependent upon binding to the J-K domain which includes a $UA_6$ bifurcation loop located upstream from the AUG translation start site. A variant bifurcation loop ($UA_7$) reduces the binding of eIF4G to reduce translation efficiency and infectivity of encephalomyocarditis virus. Additional experiments were performed to compare the ability of control RNAs and tiRNAs to inhibit the translation of luciferase from monocistronic luciferase constructs expressing the wild type ($UA_6$) or mutant ($UA_7$) EMCV IRES. The experiments were performed using the methods generally described above with the modifications described below.

The pCDNA3-EMCV-R-luc (EMCV-UA6) plasmid used in these experiments was prepared by amplifying a fragment of the pF/R plasmid encoding EMCV IRES by PCR and subcloning the fragment into pCDNA3 vector using BamHI and XhoI sites. The ORF of Renilla luciferase was amplified by PCR and inserted into pCDNA3-EMCV construct using XhoI and XbaI sites.

RNA transcripts for use in the RRL assay were prepared by first linearizing the plasmids pCDNA3-EMCV-R-luc (EMCV-UA$_6$), pRL-5boxB, and pEMCV-RL-5boxB by digestion with XbaI (New England Biolabs), and separating and purifying the linearized plasmids as described above. Riboprobe T7 in vitro transcription System (Promega) was used to synthesize corresponding RNA and the RNA was purified as described above. Luciferase expression was also measured as described above.

The resulting data show that 5'-tiRNA$^{Ala}$ does not inhibit translation from the wild type ($UA_6$) IRES (FIG. 6, upper panel), but potently inhibits translation from the mutant ($UA_7$) IRES (FIG. 6, lower panel). These data suggest that 5'-tiRNA$^{Ala}$-mediated translational repression is a function of the strength of the eIF4G-RNA interaction. Recombinant eIF4E inhibits the translation of uncapped mRNAs by ~50%. This is presumably due to the fact that eIF4E:eIF4G complexes do not efficiently bind to the 5'-end of uncapped mRNA. The ability of tiRNAs to inhibit EMCV-IRES ($UA_7$) makes it unlikely that eIF4E is the primary target for translational repression. To further support this conclusion, additional experiments were performed to determine whether recombinant eIF4E competitively inhibits tiRNA$^{Ala}$-induced translational repression in RRL. These experiments were performed as described above.

The resulting data show that eIF4E does not competitively inhibit tiRNA$^{Ala}$-induced translational repression (FIG. 7). In fact, the combination of tiRNA$^{Ala}$ and recombinant eIF4E results in 2.5-fold more inhibition than tiRNA$^{Ala}$ alone: a result suggesting that these two factors act independently to inhibit translation.

Example 4

5'-tiRNAs Displace eIF4G

Additional experiments were performed to determine whether 5'-tiRNAs displace eIF4G from RNA. In these experiments, biotin-tagged capped or uncapped luciferase transcripts were added to heterologous (80% RRL+20% U2OS) lysates containing control RNA or tiRNAs in the above described in vitro translation assays. After streptavidin pull down, the reporter RNA-bound proteins were quantitated by immunoblotting. These experiments were performed as described above with the additions or modifications described below.

Poly-A biotinylated mRNAs used for streptavidin pull-down assays were prepared by polyadenylating capped or uncapped pRL-5boxB RNAs using Poly(A) Polymerase Tailing Kit (EPICENTRE Biotechnologies) according to the manufacturer's recommendation, but in the presence of 10 nM biotin-ATP (PerkinElmer).

Streptavidin agarose beads (Invitrogen) (40 µL per sample) were washed twice with RNAse-free Biotin Binding Buffer (10 mM Tris-HCl, pH 7.2, 100 mM NaCl, 1 mM EDTA, 0.1% NP-40). Five hundred pmoles of biotinylated RNAs were added to streptavidin beads and incubated for 1 hour at room temperature with rotation in 0.75 mL of Biotin Binding Buffer. After incubation, immobilized biotinylated RNA-streptavidin complexes were washed twice with RNAse-free Wash Buffer II (15 mM Tris HCl, pH 7.2, 750 mM NaCl, 1 mM EDTA, 0.1% NP-40) and once with ice-cold RNAse-free Wash Buffer I (15 mM Tris HCl, pH 7.2, 150 mM NaCl, 1 mM EDTA, 0.1% NP-40) at room temperature to remove unbound RNA. Pre-cleared U2OS lysates (200 µl of lysate per reaction, corresponding to 20% of lysate (in Lysis Buffer: 50 mM Tris-HCl, pH 7.2, 100 mM NaCl, 1 mM EDTA, 0.5% NP-40, with protease inhibitor cocktail "Complete," Roche) prepared from one 15-cm dish of 80% confluent U2OS cells) were added to the biotinylated RNA-streptavidin bead complexes, incubated for 2 hours at 4° C. with rotation, and washed 3 times with Wash Buffers (15 mM Tris HCl, pH 7.2, 1 mM EDTA, 0.1% NP-40) containing different NaCl concentrations (0.1 M, 0.3 M or 0.5 M). Proteins were eluted using 60 µl of 1×SDS PAGE Loading Buffer.

For pull-down of biotinylated polyA mRNAs, 200 ng of capped or uncapped pRL-5boxB mRNAs were used for in vitro translation in rabbit reticulocyte lysate supplemented with 20% U2OS extract under the conditions described above. This heterologous in vitro translation system (RRL with cell extract) is capable of translating mRNAs with similar to Flexi Rabbit Reticulocyte Lysate System efficiency, but allows for the detection of eIF4G (human) by Western Blotting (the antibodies used do not detect eIF4G of rabbit origin). One hundred picomoles of control RNAs or tiRNAs were added to translation reactions. After completion of translation, streptavidin agarose beads (Invitrogen) (40 µL per sample) were added to reactions and incubated at 4° C. for 30 minutes. Streptavidin beads were precipitated by centrifugation (1000 rpm, 5 minutes), the supernatants were removed, and the beads were washed once with ice-cold Wash buffer (15 mM Tris HCl, pH 7.2, 150 mM NaCl, 1 mM EDTA, 0.1% NP-40). The resulting mRNA-protein complexes were eluted from the beads using 60 µl of 1×SDS PAGE Loading Buffer.

For Western blotting, proteins were separated on a 4-20% gradient SDS-PAGE (Invitrogen) and transferred to nitrocellulose filter membranes (0.45 µm pore size; Invitrogen). The membranes were blocked with 5% normal horse serum (NHS) in 1×TBS at room temperature for 1 hour and incubated with protein-specific antibodies in TBS containing 5% NHS overnight at 4° C. The membranes were washed three times with 1×TBS containing 0.1% Tween-20 and incubated with secondary antibodies conjugated with horseradish peroxidase (GE Healthcare). After washing, the specific proteins were detected using the Super Signal chemiluminescent detection system (Pierce) and autoradiography on X-Omat film (Kodak).

The data from these experiments show that uncapped RNA is bound to eIF4G, but not eIF4E (FIG. 8, lower panel): these results are consistent with the ability of eIF4G to bind to the 5'-end of uncapped transcripts. 5'-tiRNA$^{Ala}$, but not control RNAs or the cap analogue, quantitatively displaces eIF4G from these uncapped transcripts (FIG. 8, lower panel). In contrast, biotin-tagged capped mRNA is bound to eIF4G and eIF4E (FIG. 9, lower panel). 5'-tiRNA$^{Ala}$ only partially displaces eIF4G (~75% displacement) suggesting that stabilization of eIF4G conferred by cap-bound eIF4E may inhibit tiRNA-induced displacement (FIG. 9). 5'-tiRNAs also modestly displace eIF4E suggesting that its effect on eIF4G may reduce the affinity of eIF4E:cap interactions.

Example 5

5'-tiRNAs Displace eIF4F from the m$^7$G Cap

Additional experiments were performed in order to determine whether 5'-tiRNAs affect eIF4F:cap interactions. For these experiments, eIF4E complexes were assembled (e.g., eIF4F (eIF4E:eIF4G) and eIF4E:4E-BP1) on m$^7$GTP-Sepharose from U2OS cell lysates. The Sepharose-bound complexes were incubated with 3'-end biotinylated control or tiRNAs before analyzing retained components of the eIF4E-containing complexes using Western blotting. The methods used to perform these experiments are described in detail below.

7-Methyl GTP Sepharose Chromatography

A 7-methyl-GTP-Sepharose 4B (m$^7$GTP-Sepharose, GE Healthcare) suspension was washed twice with ice-cold RNAse-free Buffer A (15 mM Tris HCl, pH 7.0, 100 mM NaCl, 1 mM EDTA) to remove sodium azide. U2OS cells were grown until 70-80% confluence in 15-cm dishes under standard conditions, and then collected by scraping with Lysis Buffer (50 mM Tris-HCl, pH 7.2, 100 mM NaCl, 1 mM EDTA, 0.5% NP-40) supplemented with protease inhibitors (Protease Inhibitor Cocktail "Complete," Roche) into Eppendorf tubes followed by tumbling at 4° C. for 15 minutes. Cell debris and nuclei were removed by centrifugation (20 minutes, 13200 rpm, 4° C.), the cytoplasmic fraction (supernatant) was applied to pre-washed m$^7$GTP-Sepharose, and incubated for 1 hour at 4° C. Typically, 10-20 µl of m$^7$GTP-Sepharose suspension was used per sample of synthetic RNA (50 or 100 pmoles). After incubation, the m$^7$GTP-Sepharose was washed three times with Lysis Buffer and m$^7$GTP-bound protein complexes were divided into equal parts. Synthetic RNAs (50 or 100 pmoles, final concentrations 20-40 nM) were added to the complexes and incubated for 1 hour at 4° C. Unbound proteins were removed by washing once with Lysis Buffer and the proteins bound to m$^7$GTP-Sepharose were eluted with 60 µl of 1×SDS PAGE Loading Buffer. Eluted proteins were analyzed by Western Blotting using protein-specific antibodies.

Goat polyclonal anti-eIF3b, goat polyclonal anti-eIF4A, rabbit polyclonal anti-eIF4G, mouse monoclonal anti-eIF4E were purchased from Santa Cruz Biotechnology. Rabbit polyclonal anti-eIF4EBP1 was purchased from Cell Signaling. Anti-mouse, anti-goat, and anti-rabbit secondary antibodies conjugated with horseradish peroxidase (HRP) were purchased from GE Healthcare.

The resulting data show that although control RNAs did not displace initiation factors from m$^7$GTP-Sepharose, 5'-tiRNA$^{Ala}$ (but not 3'-tiRNA$^{Ala}$) completely displaces eIF4G and eIF4A, and partially displaces (~50%) eIF4E from the beads (FIG. 10, left panel). In contrast, 4E-BP1 is not displaced from the beads, suggesting that the retained eIF4E is complexed with 4E-BP1. Cap analogue displaces both eIF4F and eIF4E:4E-BP1 from m$^7$GTP-Sepharose (FIG. 10, left panel; cap). The supernatants containing displaced initiation factors were collected and streptavidin beads were used to capture biotin-RNA oligonucleotides and their associated proteins. Western blot analysis reveals that biotin-5'-tiRNA$^{Ala}$ is in a stable complex with eIF4G and eIF4E (FIG. 10, right panel). These data suggest that 5'-tiRNA* binds, directly or indirectly, to an eIF4E:eIF4G complex and causes its disassociation from m$^7$GTP-Sepharose in U2OS lysate much more efficiently than it displaces eIF4G from capped mRNA in RRL (FIG. 9). Similar results were obtained using heterologous lysate (80% RRL+20% U2OS extract, FIG. 11), suggesting that this difference is not conferred by the nature of the lysate.

Example 6

Structure/Function Analyses of tiRNAs tRNA$^{Ala}$ and tRNA$^{Cys}$ are the only human tRNAs with terminal oligo-guanine (TOG) motifs (4-5 guanine residues) at their 5' ends (up-to-date alignments for *H. sapiens* tRNAs can be found at the Lowe Lab website at the address: lowelab.ucsc.edu/GtRNAdb/Hsapi19/Hsapi19-align.html) (see, secondary structure of tRNA$^{Ala}$, FIG. 12). This structural feature in tRNA$^{Ala}$ and tRNA$^{Cys}$ is extremely well-conserved among all vertebrates, insects, and worms (>95% of all tRNA$^{Ala}$ and tRNA$^{Cys}$ genes), well conserved in plants (>95% of all tRNA^Ala genes), and less conserved in fungi and protozoa (<50% of all tRNA^Ala genes). In contrast, 5'-TOG motifs are extremely rare in all other tRNAs.

Additional experiments were performed to determine whether these 5'-TOG motifs are required for translation repression. In these experiments, the ability of truncation and substitution mutants to inhibit translation was determined using the RRL translation assays described herein using Firefly luciferase mRNAs. The specific tiRNAs and control oligonucleotides used in these experiments were synthesized and purified by Integrated DNA Technology (at least 95% homogenous), and are listed below.

```
Ctrl1:
                                     (SEQ ID NO: 1)
5'-UGA AGG GUU UUU UGU GUC UCU AUU UCC UUC-3'
(piR006650)

Ctrl2:
                                     (SEQ ID NO: 2)
5'-phospho-UGU GAG UCA CGU GAG GGC AGA AUC UGC UC-3' (piR58620)

Ctrl3:
                                     (SEQ ID NO: 3)
5'-phospho-GCA UUC ACU UGG AUA GUA AAU CCA AGC UGA A-3' (random)

5'Ala:
                                     (SEQ ID NO: 4)
'-phospho-GGG GGU GUA GCU CAG UGG UAG AGC GCG

UGC-3'

U4G:
                                     (SEQ ID NO: 18)
5'-phospho-UGG GGU GUA GCU CAG UGG UAG AGC GCG

UGC-3'

4G:
                                     (SEQ ID NO: 19)
5'-phospho-GG GGU GUA GCU CAG UGG UAG AGC GCG

UGC-3'

UU3G:
                                     (SEQ ID NO: 20)
5'-phospho-UUG GGU GUA GCU CAG UGG UAG AGC GCG

UGC-3'

3G:
                                     (SEQ ID NO: 21)
5'-phospho-G GGU GUA GCU CAG UGG UAG AGC GCG

UGC-3'

GG-UU:
                                     (SEQ ID NO: 22)
5'-phospho-GGG GGU GUA GCU CAG UUU UAG AGC GCG

UGC-3'

27mer:
                                     (SEQ ID NO: 23)
5'-phospho-GGG GGU GUA GCU CAG UGG UAG AGC GCG-3'

24mer:
                                     (SEQ ID NO: 24)
5'-phospho-GGG GGU GUA GCU CAG UGG UAG AGC-3'

21mer:
                                     (SEQ ID NO: 25)
5'-phospho-GGG GGU GUA GCU CAG UGG UAG-3'
```

To determine whether the 5'-TOG structural feature is required for translational repression the ability of truncation and substitution mutants of tiRNAs (FIG. 13) to inhibit the translation of reporter mRNA in RRL was determined. These data show that while 5'-tiRNA^Ala mutants with a singly truncated (4G) or G to U substituted (U4G) guanine residue retain their activity, mutants with doubly truncated (3G) or GG to UU substituted (UU3G) guanine residues are completely inactive (FIG. 14). Thus, at least four guanines at or near to the 5'-end of tiRNAs are absolutely required for translational repression. In contrast, substitution of two invariant guanine residues within the D-loop region (GG to UU) does not prevent translational repression. RNAfold predicts that 5'-tiRNAs are composed of a single stranded 5'-TOG motif followed by a stem-loop structure resembling the D-loop of tRNA, followed by a single stranded 3' region (FIGS. 12 and 13). Truncations from the 3' end of 5'-tiR-NA^Ala retain their activity until the region of the tRNA D-loop is encroached upon (i.e., 21-mer; see, FIG. 14) suggesting that the structure formed by the D-loop region may contribute to translational repression.

Additional experiments were performed to determine whether the ability of the 5'-tiRNA^Ala mutants to inhibit mRNA translation closely correlates with their ability to displace eIF4F from m$^7$GTP-Sepharose, or their ability to induce stress granule assembly (when transfected into U2OS cells). The m$^7$GTP-Sepharose experiments were performed as described above using the 5'-tiRNA^Ala mutants described herein. The transfection of U2OS cells and the methods for determining stress granule assembly are described below.

Cell Transfections

Cells were transfected with the RNA oligonucleotides using Lipofectamine 2000 (Invitrogen). Before transfection, RNA-complexes were pre-incubated in serum-free medium (Opti-MEM medium, Invitrogen) for 20 minutes at room temperature. U2OS cells (1×10$^5$/well) were plated in 24-well plates for 24 hours, and then transfected with 750 nM synthetic tiRNAs using 2.5 µl Lipofectamine 2000.

Immunofluorescence Microscopy and Quantification of Stress Granules Cells (1×10$^5$) were seeded onto coverslips (Fisher Scientific) and were transfected with synthetic tiR-NAs using Lipofectamine 2000 24-hours later (Invitrogen). After 7 hours, the cells were fixed in 4% para-formaldehyde for 15 minutes and permeabilized using 100% chilled methanol for 10 minutes. The cells were rinsed several times with PBS and incubated overnight with blocking buffer (5% normal horse serum in PBS containing 0.02% sodium azide) at 4° C. An appropriate primary antibody diluted in blocking buffer (1:200 for anti-eIF3b, anti-eIF4G, and anti-G3BP antibody) was then added to the cells and incubated for 1 hour at room temperature or overnight at 4° C. (Kedersha et al., *Methods Enzymol.* 448:521-522, 2007). The cells were washed three times with PBS and incubated with the appropriate secondary antibodies (Jackson Immunoresearch, ML grade) diluted 1:200 in blocking buffer containing 0.5 µg/ml Hoechst 33258 dye (Molecular probes) for 1 hour at room temperature. After washing with PBS, the cover slips were mounted in polyvinyl mounting medium, and the cells were viewed and photographed with an Eclipse E800 (Nikon) microscope equipped with a digital camera (CCD-SPOT RT; Diagnostic Instrument) using 60× oil immersion objective lens. The images were merged and analyzed using Adobe Photoshop (v. 10).

Quantification of Stress Granules

U2OS cells (1×10$^5$) were seeded onto coverslips (Fisher Scientific) and were transfected 24 hours later with the indicated RNA oligonucleotides (final concentration of 750 nM) using Lipofectamine 2000. After 7 hours, the cells were subjected to immunofluorescence microscopy as described above. The coverslips were coded and all quantifications were done blindly and repeated at least twice. The percentage of cells with stress granules was quantified by counting 200-350 cells/experiment.

The resulting data show that the ability of 5'-tiRNA$^{Ala}$ and its mutants to inhibit mRNA translation closely correlates with their ability to displace eIF4F from m$^7$GTP-Sepharose (FIG. 15). In addition, the ability of 5'-tiRNA$^{Ala}$ and its mutants to inhibit mRNA translation closely correlates with their ability to induce the assembly of stress granules when transfected into U2OS cells (FIG. 16).

Additional immunoblotting experiments were performed to determine whether transfection with these oligonucleotides induced the phosphorylation of eIF2α, a classical trigger of stress granule assembly. These data show that transfection of wild type or mutant 5'-tiRNA$^{Ala}$ does not induce phosphorylation of eIF2α (FIG. 17). The data show that 5'-tiRNA$^{Ala}$ inhibits translation in live cells (in which most of the target transcripts are presumably capped). The close correlation between translational repression in RRL, displacement of eIF4F from m$^7$GTP-Sepharose, and stress granule assembly suggests that eIF4F is a target for tiRNA-induced translational repression.

Example 7

Addition of 5'-TOG Activates 5'-tiRNA$^{Met}$

Additional experiments were performed to confirm the importance of the 5'-TOG motif for tiRNA activity. In these experiments, the first 5 nucleotides of non-TOG-containing 5'-tiRNA$^{Met}$ was substituted with 5 guanine residues (FIG. 13) (5'-phospho-GGG UUA GCG CAG UAG GUA GCG CGU CAG U-3'; SEQ ID NO: 26). This substituted 5'-tiRNA$^{Met}$ was used in RRL translation assays, the eIF4F displacement assays using m$^7$GTP-Sepharose assays, and stress granule formation assays (cellular assays) performed as described above. The resulting data show that although endogenous 5'-tiRNA$^{Met}$ does not inhibit translation in RRL (FIG. 18), displace eIF4F from m$^7$GTP-Sepharose (FIG. 19), or induce the assembly of stress granules (FIG. 20), the addition of a 5'-TOG motif to 5'-tiRNA$^{Met}$ is sufficient to confer these activities on this tRNA fragment (FIGS. 18-20).

Example 8

Identification of tiRNA-Interacting

Pull-down of RNA-protein complexes using biotinylated control RNA or 5'-tiRNA$^{Ala}$ immobilized on streptavidin beads was used to purify proteins that interact with these RNAs. RNA-bound proteins were identified by mass spectrometry. Independent pull-down experiments were performed to confirm the ability of several of these proteins to interact with tiRNA$^{Ala}$. These experiments were performed using biotinylated control or 5'-tiRNA$^{Ala}$ using streptavidin beads as described above. The individual 3'-biotinylated oligonucleotides used in these assays were synthesized by and purchased from Integrated DNA Technology (listed below). Silver staining and mass spectrometry identification of tiRNA-binding proteins was performed as described below.

Biotinylated Oligonucleotides

```
Ctrl1-bio:
                                              (SEQ ID NO: 27)
5'-UGA AGG GUU UUU UGU GUC UCU AUU UCC UUC-3'-biotin Ctrl2-bio:
                                              (SEQ ID NO: 28)
5'-phospho-UGU GAG UCA CGU GAG GGC AGA AUC UGC UC-3'-biotin Ctrl3-bio:
                                              (SEQ ID NO: 29)
5'-Phospho-GCA UUC ACU UGG AUA GUA AAU CCA AGC UGA A-3'-biotin 5'-Ala-bio:
                                              (SEQ ID NO: 30)
5'-phospho-GGG GGU GUA GCU CAG UGG UAG AGC GCG UGC-3'-biotin 3'-Ala-bio:
                                              (SEQ ID NO: 31)
5'-CUU AGC AUG CAC GAG GCC CCG GGU UCA AUC CCC GGC ACC UCCA-3'-biotin
```

Silver Staining of SDS PAGE Gels

To detect proteins recovered from affinity purification with biotinylated RNAs, eluted protein samples were run on gradient 4-20% SDS PAGE gels (Invitrogen) and fixed with Protein Fixation Buffer (30% ethanol:10% acetic acid) for 30 minutes. SilverSNAP Stain Kit II (Pierce) was used according to the manufacture's recommendation to detect proteins.

Mass Spectrometry Identification of tiRNA-Binding Proteins

For mass spectrometry, protein solutions from affinity purification using 3'-end biotinylated RNAs were precipitated with trichloroacetic acid (TCA). Briefly, eluted protein samples were adjusted to 20% final volume of TCA using 100% TCA (in water) solution. The resulting mixture was placed on ice for 20 minutes followed by centrifugation (20 minutes, 13200 rpm, 4° C.). Protein pellet was washed once with 1 ml of cold (−20° C.) acetone (HPLC grade, Sigma), followed by centrifugation (20 minutes, 13200 rpm, 4° C.). The supernatant was carefully removed and the pellet was air-dried for 10 minutes at room temperature. The identification of tiRNA-binding proteins was done by Taplin Mass Spectrometry Facility according to standard protocols (Harvard Medical School).

The resulting data confirmed that several proteins involved in the regulation of RNA metabolism, including TDP-43 (TARDBP), Vigilin (HDLBP), YB-1 (YBX1), eIF4E, FXR1, eIF4G, CAPRIN1 (CAPRIN), Argonaute-2 (EIF2C2), and PABP1 (PABPC1) bind to 5'-tiRNA$^{Ala}$ more strongly than control RNA (FIG. 21). Some of these interactions (e.g., YB-1, FXR-1, and PABP1) are maintained under high salt wash conditions.

Example 9 tiRNA-Binding Proteins are Required for 5'-tiRNA$^{Ala}$-Induced Stress Granule Assembly Additional experiments were performed to determine whether the identified 5'-tiRNA$^{Ala}$ binding proteins are required for translational repression. In these experiments, AGO2, PABP1, YB-1, Vigilin, and FXR1 were knocked down using siRNA prior to quantifying tiRNA-induced stress granule assembly in U2OS cells (assays performed as described above). These data show that, of the tested binding proteins, YB-1 was the only 5'-tiRNA$^{Ala}$ binding protein required for the assembly of stress granules (FIG. 22). YB-1 is a protein that inhibits translation of both uncapped and capped mRNAs by displacing eIF4G from the eIF4F complex and by displacing eIF4E from the m$^7$G cap.

Example 10

Synthetic DNA Equivalents of 5'-tiRNA$^{Ala}$ and Anti-Proliferative DNAs Inhibit Translation and Induce Stress Granule Formation Experiments were performed to test the ability of synthetic DNA equivalents of 5'-tiRNA$^{Ala}$ and anti-proliferative G-rich oligodeoxynucleotides (shown in FIG. 23) to inhibit translation of luciferase transcripts in RRL assays, induce stress granule formation in cells, and displace eIF4G, eIF4A, and eIF4E from m$^7$GTP-Sepharose in vitro (performed generally as described above).

The resulting data show that 5'-tiDNA$^{Ala}$, AS1411, and c-myc oligodeoxynucleotides are potent inhibitors of translation in the RRL assay (none of these compounds alters the amount of luciferase RNA as assessed by Northern blotting analysis performed as described above) (FIG. 24). In contrast, neither TEL4, nor GT-oligo inhibit translation in this assay. Thus, some G-rich oligodeoxynucleotides inhibit translation, whereas others do not.

The data also show that the ability of the 5'-tiRNAs to inhibit translation correlates with their ability to trigger stress granule assembly in cells (following cellular transfection with these molecules) (FIG. 25). In U2OS cells, 5'-tiDNA$^{Ala}$, AS1411, and c-myc oligodeoxynucleotides induce stress granule assembly, whereas TEL4 and GT-oligo did not (FIG. 25). Similar results were observed in NSC34 cells, indicating that selected G-rich oligodeoxynucleotides can promote stress granule assembly in motor neurons. The molecular mechanism(s) by which these oligodeoxynucleotides mediate translation inhibition was further investigated by determining their ability to displace eIF4F from m$^7$-GTP Sepharose. The data from these experiments show that, in lysates from both U2OS (FIG. 26A) and NSC34 cells (FIG. 26B), 5'-tiRNA$^{Ala}$, 5'-tiDNA$^{Ala}$, and AS1411 displace eIF4G, eIF4A, and eIF4E from m$^7$G in vitro. These data suggest that these oligodeoxynucleotides mimic angiogenin-induced tiRNAs in their ability to trigger a stress response program.

Example 11

Cellular Uptake of Synthetic 5' G-Rich Oligodeoxynucleotides

Additional experiments were performed in order to determine whether the 5' G-rich oligodeoxynucleotides would be taken up by motor neurons in the absence of transfection agents. In these experiments NSC34 cells were treated with biotin-labeled C-myc, biotin-labeled AS1411, or biotin-labeled C-rich control oligodeoxynucleotides and cellular uptake was detected using Cy3-streptavidin. The resulting data show that AS1411 and c-myc, but not control oligodeoxynucleotides were found in cytoplasmic puncta within NSC34 cells: a result that is consistent with endosomal uptake (FIG. 27). In addition, some cells showed diffuse fluorescence consistent with cytoplasmic localization. Similar results were obtained with 5'-tiDNA$^{Ala}$. These results indicate the ability of these G-rich oligodeoxynucleotides to spontaneously enter motor neurons and gain access to the cytoplasm.

Example 12

Functional Effect of G-Rich Oligodeoxynucleotides

Additional experiments were performed to test the effect of the G-rich oligodeoxynucleotides on motor neurons. A first set of dose response experiments were performed in order to determine whether the tested G-rich oligodeoxynucleotides were toxic to motor neurons in vitro. These data show that the AS1411 and oligo-GT oligodeoxynucleotides markedly increased NSC34 cell death at the end of a 72-hour incubation (FIG. 28). In contrast, the control piDNA (ctrl 25, AAAAAACTCG AGATGGCGCACGCTG; SEQ ID NO: 38), C-rich control (CRO26, CCTCCTCCTCCTTCTC-CTCCTCCTCC; SEQ ID NO: 39), 5'-tiDNA$^{Ala}$, and c-myc oligodeoxynucleotides do not reduce the numbers of viable NSC34 cells.

A second set of experiments was performed to determine whether the tested G-rich oligodeoxynucleotides are neuroprotective. In these experiments NSC34 cells were cultured in the presence of the individual oligodeoxynucleotides, then subjected to nutrient (serum starvation) or mitochondrial (rotenone) stress for 24 hours. NSC34 cells treated with either 5'-tiDNA$^{Ala}$ or c-myc oligodeoxynucleotides, but not AS1411 or oligo-GT oligodeoxynucleotides were significantly protected from the adverse effects of stress (cell death; FIG. 29). These data suggest that there are three different functional classes of G-rich oligodeoxynucleotides: Class I oligodeoxynucleotides (e.g., oligo-GT) that reduce NSC34 cell survival; Class II oligodeoxynucleotides (e.g., 5'-tiDNA$^{Ala}$ and c-myc) that promote NSC34 cell survival by activating a stress response program; and Class III oligodeoxynucleotides (e.g., AS1411) that reduce NSC34 survival, but also activate a stress response program. The modest therapeutic effects of AS1411 may be a consequence of this cytoprotective stress response program. These data identify 5'-tiDNA$^{Ala}$ and c-myc oligodeoxynucleotides as promising compounds for the development of therapeutic agent for treating a neurological disorder (e.g., a neurological disorder that involves motor neuron death, such as amyotrophic lateral sclerosis).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE APPENDIX

Additional tRNA sequences that can be used to generate any of the neuroprotective molecules described herein are listed below.

```
Homo_sapiens_chr6.trna95-AlaAGC (58249908-58249836) Ala (AGC) 73 bp Sc: 42.26
                                                                                    (SEQ ID NO: 176)
GGGGAATTAGCTCAAGCGGTAGAGCGCTCCCTTAGCATGCGAGAGGTAGCGGGATCGACGCCCCCATTCTCTA Homo_sapiens_chr6.trna25-AlaAGC (26859897-26859969) Ala (AGC) 73 bp Sc: 46.89
                                                                                    (SEQ ID NO: 177)
GGGGGATTAGCTCAAGCGGTAGGGTGCCTGCTTAGCATGCAAGAGGTAGCAGGATCGACGCCTGCATTCTCCA Homo_sapiens_chr1.trna87-AlaAGC (148284076-148284006) Ala (AGC) 71 bp Sc: 48.21
                                                                                    (SEQ ID NO: 178)
GGGGGTGTAGATCAGTGGTAGGGCGCACGCTTAGCATGCATGAGGCCCTGGGTCAATCCCCAGCACCTCCA Homo_sapiens_chr6.trna94-AlaAGC (58250620-58250548) Ala (AGC) 73 bp Sc: 54.62
                                                                                    (SEQ ID NO: 179)
GGGGATTAGCTCAAGCGGTAGAGCGCCTGCTTAGCATGCAAGAGGTAGCAGGATCGATGCCTGCATTCTCCA Homo_sapiens_chr6.trna160-AlaAGC (26881822-26881750) Ala (AGC) 73 bp Sc: 54.69
                                                                                    (SEQ ID NO: 180)
GGGGAATTGCTCAAGCGGTAGAGCGCTTGCTTAGCATGCAAGAGGTAGCAGGATCGACGCCTGCACTCTCCA Homo_sapiens_chr6.trna23-AlaAGC (26836235-26836307) Ala (AGC) 73 bp Sc: 54.69
                                                                                    (SEQ ID NO: 181)
GGGGAATTGCTCAAGCGGTAGAGCGCTTGCTTAGCATGCAAGAGGTAGCAGGATCGACGCCTGCACTCTCCA Homo_sapiens_chr6.trna90-AlaAGC (58295475-58295403) Ala (AGC) 73 bp Sc: 54.84
                                                                                    (SEQ ID NO: 182)
GGGGAATTAGCGCAAGTGGTAGAGTGCTTGCTTAGCATGCAAGAGGTAGTGGGATCGATGCCCACATTCTCCA Homo_sapiens_chr6.trna89-AlaAGC (58304654-58304582) Ala (AGC) 73 bp Sc: 57.89
                                                                                    (SEQ ID NO: 183)
GGGGAATTAGCCCAAGTGGTAGAGCGCTTGCTTAGCATGCAAGAGGTAGTGGGATCGATGCCCACATTCTCCA Homo_sapiens_chr14.trna9-AlaAGC (88515195-88515267) Ala (AGC) 73 bp Sc: 59.85
                                                                                    (SEQ ID NO: 184)
GGGGAATTAGCTCAAGTGGTAGAGCGCTCGCTTAGCATGCGAGAGGTAGTGGGATCGATGCCCGCATTCTCCA Homo_sapiens_chr6.trna18-AlaAGC (26781569-26781641) Ala (AGC) 73 bp Sc: 60.72
                                                                                    (SEQ ID NO: 185)
GGGGAATTAGCTCAAGTGGTAGAGCGCTTGCTTAGCATGCAAGAGGTAGTGGGATCAATGCCCACATTCTCCA Homo_sapiens_chr6.trna22-AlaAGC (26813585-26813657) Ala (AGC) 73 bp Sc: 61.81
                                                                                    (SEQ ID NO: 186)
GGGGAATTAGCTCAAGCGGTAGAGCGCTTGCTTAGCATGCAAGAGGTAGTGGGATCGATGCCCACATTCTCCA Homo_sapiens_chr6.trna93-AlaAGC (58272659-58272587) Ala (AGC) 73 bp Sc: 61.81
                                                                                    (SEQ ID NO: 187)
GGGGAATTAGCTCAAGCGGTAGAGCGCTTGCTTAGCATGCAAGAGGTAGTGGGATCGATGCCCACATTCTCCA Homo_sapiens_chr6.trna159-AlaAGC (26904057-26903985) Ala (AGC) 73 bp Sc: 62.45
                                                                                    (SEQ ID NO: 188)
GGGGAATTAGCTCAAGTGGTAGAGCGCTTGCTTAGCATGCAAGAGGTAGTGGGATCGATG CCCACATTCTCCA Homo_sapiens_chr6.trna19-AlaAGC (26790694-26790766) Ala (AGC) 73 bp Sc: 62.45
                                                                                    (SEQ ID NO: 189)
GGGGAATTAGCTCAAGTGGTAGAGCGCTTGCTTAGCATGCAAGAGGTAGTGGGATCGATGCCCACATTCTCCA Homo_sapiens_chr6.trna91-AlaAGC (58290710-58290638) Ala (AGC) 73 bp Sc: 62.45
                                                                                    (SEQ ID NO: 190)
GGGGAATTAGCTCAAGTGGTAGAGCGCTTGCTTAGCATGCAAGAGGTAGTGGGATCGATGCCCACATTCTCCA Homo_sapiens_chr6.trna166-AlaAGC (26680143-26680071) Ala (AGC) 73 bp Sc: 63.06
                                                                                    (SEQ ID NO: 191)
GGGGAATTAGCTCAAATGGTAGAGCGCTCGCTTAGCATGCGAGAGGTAGCGGGATCGATGCCCGCATTCTCCA Homo_sapiens_chr6.trna20-AlaAGC (26795464-26795536) Ala (AGC) 73 bp Sc: 63.16
                                                                                    (SEQ ID NO: 192)
GGGGAATTAGCTCAAGTGGTAGAGCGCTTGCTTAGCACGCAAGAGGTAGTGGGATCGATGCCCACATTCTCCA Homo_sapiens_chr6.trna161-AlaAGC (26879341-26879269) Ala (AGC) 73 bp Sc: 63.36
                                                                                    (SEQ ID NO: 193)
GGGGAATTAGCTCAGGCGGTAGAGCGCTCGCTTAGCATGCGAGAGGTAGCGGGATCGACGCCCGCATTCTCCA Homo_sapiens_chr6.trna24-AlaAGC (26838716-26838788) Ala (AGC) 73 bp Sc: 63.36
                                                                                    (SEQ ID NO: 194)
GGGGAATTAGCTCAGGCGGTAGAGCGCTCGCTTAGCATGCGAGAGGTAGCGGGATCGACGCCCGCATTCTCCA Homo_sapiens_chr2.trna3-AlaAGC (27127586-27127658) Ala (AGC) 73 bp Sc: 63.68
                                                                                    (SEQ ID NO: 195)
GGGGGATTAGCTCAAATGGTAGAGCGCTCGCTTAGCATGCGAGAGGTAGCGGGATCGATGCCCGCATCCTCCA
```

-continued

Homo_sapiens_chr8.trna6-AlaAGC (67188978-67189050) Ala (AGC) 73 bp Sc: 63.68

(SEQ ID NO: 196)

GGGGGATTAGCTCAAATGGTAGAGCGCTCGCTTAGCATGCGAGAGGTAGCGGGATCGATGCCCGCATCCTCCA

Homo_sapiens_chr6.trna68-AlaAGC (28795460-28795531) Ala (AGC) 72 bp Sc: 70.19

(SEQ ID NO: 197)

GGGGGTGTAGCTCAGTGGTAGAGCGCGTGCTTAGCATGCACGAGGCCCCGGGTTCAATCCCTGGCACCTCCA

Homo_sapiens_chr6.trna105-AlaAGC (28887899-28887828) Ala (AGC) 72 bp Sc: 71.23

(SEQ ID NO: 198)

GGGGGTATAGCTCAGCGGTAGAGCGCGTGCTTAGCATGCACGAGGTCCTGGGTTCAATCCCCAATACCTCCA

Homo_sapiens_chr6.trna67-AlaAGC (28786345-28786416) Ala (AGC) 72 bp Sc: 75.68

(SEQ ID NO: 199)

GGGGGTGTAGCTCAGTGGTAGAGCGCGTGCTTAGCATGCACGAGGCCCTGGGTTCAATCCCCAGCACCTCCA

Homo_sapiens_chr6.trna120-AlaAGC (28734064-28733993) Ala (AGC) 72 bp Sc: 75.78

(SEQ ID NO: 200)

GGGGATGTAGCTCAGTGGTAGAGCGCATGCTTAGCATGCATGAGGTCCCGGGTTCGATCCCCAGCATCTCCA

Homo_sapiens_chr6.trna65-AlaAGC (28682912-28682983) Ala (AGC) 72 bp Sc: 76.69

(SEQ ID NO: 201)

GGGGGTGTAGCTCAGTGGTAGAGCGCGTGCTTAGCATGTACGAGGTCCCGGGTTCAATCCCCGGCACCTCCA

Homo_sapiens_chr6.trna101-AlaAGC (28939512-28939441) Ala (AGC) 72 bp Sc: 77.18

(SEQ ID NO: 202)

GGGGGTGTAGCTCAGTGGTAGAGCGCGTGCTTAGCATGCACGAGGCCCCGGGTTCAATCCCCGGCACCTCCA

Homo_sapiens_chr6.trna102-AlaAGC (28914271-28914200) Ala (AGC) 72 bp Sc: 77.18

(SEQ ID NO: 203)

GGGGGTGTAGCTCAGTGGTAGAGCGCGTGCTTAGCATGCACGAGGCCCCGGGTTCAATCCCCGGCACCTCCA

Homo_sapiens_chr6.trna108-AlaAGC (28871791-28871720) Ala (AGC) 72 bp Sc: 81.12

(SEQ ID NO: 204)

GGGGGTATAGCTCAGTGGTAGAGCGCGTGCTTAGCATGCACGAGGTCCTGGGTTCGATCCCCAGTACCTCCA

Homo_sapiens_chr6.trna117-AlaCGC (28771759-28771688) Ala (CGC) 72 bp Sc: 56.63

(SEQ ID NO: 205)

GGGGGTGTAGATCAGTGGTAGAGCGCATGCTTCGCATGTACGAGGTCCCTGGTTCAATCCCTGGTACCTCCA

Homo_sapiens_chr6.trna70-AlaCGC (28805071-28805142) Ala (CGC) 72 bp Sc: 70.09

(SEQ ID NO: 206)

GGGGGTGTAGCTCAGTGGTAGAGCGCGTGCTTCGCATGTACGAGGCCCCGGGTTCGACCCCCGGCTCCTCCA

Homo_sapiens_chr2.trna13-AlaCGC (156965527-156965598) Ala (CGC) 72 bp Sc: 73.12

(SEQ ID NO: 207)

GGGGATGTAGCTCAGTGGTAGAGCGCGCGCTTCGCATGTGTGAGGTCCCGGGTTCAATCCCCGGCATCTCCA

Homo_sapiens_chr6.trna119-AlaCGC (28749663-28749592) Ala (CGC) 72 bp Sc: 74.81

(SEQ ID NO: 208)

GGGGATGTAGCTCAGTGGTAGAGCGCATGCTTCGCATGTATGAGGCCCCGGGTTCGATCCCCGGCATCTCCA

Homo_sapiens_chr6.trna10-AlaCGC (26661710-26661781) Ala (CGC) 72 bp Sc: 78.91

(SEQ ID NO: 209)

GGGGATGTAGCTCAGTGGTAGAGCGCATGCTTCGCATGTATGAGGTCCCGGGTTCGATCCCCGGCATCTCCA

Homo_sapiens_chr11.trna18-AlaTGC (50190526-50190455) Ala (TGC) 72 bp Sc: 51.06

(SEQ ID NO: 210)

GGGGGTGTAGCTCAGTGGTAGAGCGGATGCTTTGCATGTATGAGACTTTGGGTTGGATCCCCAGCACCTCCA

Homo_sapiens_chr6.trna107-AlaTGC (28878626-28878556) Ala (TGC) 71 bp Sc: 59.75

(SEQ ID NO: 211)

GGGGGTGTAGCTCAGTGGTAGAGCGCATGCTTTGCATGTATGAGGCCTCGGTTCGATCCCCGACACCTCCA

Homo_sapiens_chr6.trna113-AlaTGC (28834191-28834120) Ala (TGC) 72 bp Sc: 67.60

(SEQ ID NO: 212)

GGGGGTGTAGCTCAGTGGTAGAGCACATGCTTTGCATGTGTGAGGCCCCGGGTTCGATCCCCGGCACCTCCA

Homo_sapiens_chr6.trna104-AlaTGC (28893062-28892991) Ala (TGC) 72 bp Sc: 70.95

(SEQ ID NO: 213)

GGGGGTGTAGCTCAGTGGTAGAGCGCATGCTTTGCATGTATGAGGCCTCGGGTTCGATCCCCGACACCTCCA

Homo_sapiens_chr12.trna8-AlaTGC (123990465-123990536) Ala (TGC) 72 bp Sc: 73.41

(SEQ ID NO: 214)

GGGGATGTAGCTCAGTGGTAGAGCGCATGCTTTGCACGTATGAGGCCCCGGGTTCAATCCCCGGCATCTCCA

Homo_sapiens_chr12.trna13-AlaTGC (123972325-123972254) Ala (TGC) 72 bp Sc: 74.45

(SEQ ID NO: 215)

GGGGATGTAGCTCAGTGGTAGAGCGCATGCTTTGCATGTATGAGGCCCCGGGTTCGATCCCCGGCATCTCCA

-continued

Homo_sapiens_chr5.trna8-AlaTGC (180566474-180566545) Ala (TGC) 72 bp Sc: 74.45

(SEQ ID NO: 216)

GGGGATGTAGCTCAGTGGTAGAGCGCATGCTTTGCATGTATGAGGCCCCGGGTTCGATCCCCGGCATCTCCA

Homo_sapiens_chr6.trna66-AlaTGC (28719201-28719272) Ala (TGC) 72 bp Sc: 78.55

(SEQ ID NO: 217)

GGGGATGTAGCTCAGTGGTAGAGCGCATGCTTTGCATGTATGAGGTCCCGGGTTCGATCCCCGGCATCTCCA

Homo_sapiens_chr6.trna110-AlaTGC (28865597-28865526) Ala (TGC) 72 bp Sc: 79.16

(SEQ ID NO: 218)

GGGGGTGTAGCTCAGTGGTAGAGCGCATGCTTTGCATGTATGAGGTCCCGGGTTCGATCCCCGGCACCTCCA

Homo_sapiens_chr3.trna11-ArgACG (45705567-45705495) Arg (ACG) 73 bp Sc: 68.07

(SEQ ID NO: 219)

GGGCCAGTGGCGCAATGGATAACGCGTCTGACTACGGATCAGAAGATTCTAGGTTCGACTCCTGGCTGGCTCG

Homo_sapiens_chr6.trna138-ArgACG (27746395-27746323) Arg (ACG) 73 bp Sc: 68.07

(SEQ ID NO: 220)

GGGCCAGTGGCGCAATGGATAACGCGTCTGACTACGGATCAGAAGATTCTAGGTTCGACTCCTGGCTGGCTCG

Homo_sapiens_chr6.trna156-ArgACG (27289674-27289602) Arg (ACG) 73 bp Sc: 68.07

(SEQ ID NO: 221)

GGGCCAGTGGCGCAATGGATAACGCGTCTGACTACGGATCAGAAGATTCTAGGTTCGACTCCTGGCTGGCTCG

Homo_sapiens_chr6.trna36-ArgACG (27290931-27291003) Arg (ACG) 73 bp Sc: 68.07

(SEQ ID NO: 222)

GGGCCAGTGGCGCAATGGATAACGCGTCTGACTACGGATCAGAAGATTCTAGGTTCGACTCCTGGCTGGCTCG

Homo_sapiens_chr14.trna7-ArgACG (22468750-22468822) Arg (ACG) 73 bp Sc: 72.37

(SEQ ID NO: 223)

GGGCCAGTGGCGCAATGGATAACGCGTCTGACTACGGATCAGAAGATTCCAGGTTCGACTCCTGGCTGGCTCG

Homo_sapiens_chr6.trna6-ArgACG (26436347-26436419) Arg (ACG) 73 bp Sc: 72.37

(SEQ ID NO: 224)

GGGCCAGTGGCGCAATGGATAACGCGTCTGACTACGGATCAGAAGATTCCAGGTTCGACTCCTGGCTGGCTCG

Homo_sapiens_chr6.trna8-ArgACG (26645705-26645777) Arg (ACG) 73 bp Sc: 72.37

(SEQ ID NO: 225)

GGGCCAGTGGCGCAATGGATAACGCGTCTGACTACGGATCAGAAGATTCCAGGTTCGACTCCTGGCTGGCTCG

Homo_sapiens_chr17.trna23-ArgCCG (63446547-63446475) Arg (CCG) 73 bp Sc: 65.49

(SEQ ID NO: 226)

GACCCAGTGGCCTAATGGATAAGGCATCAGCCTCCGGAGCTGGGGATTGTGGGTTCGAGTCCCATCTGGGTCG

Homo_sapiens_chr17_random.trna1-ArgCCG (1739927-1739999) Arg (CCG) 73 bp Sc: 65.49

(SEQ ID NO: 227)

GACCCAGTGGCCTAATGGATAAGGCATCAGCCTCCGGAGCTGGGGATTGTGGGTTCGAGTCCCATCTGGGTCG

Homo_sapiens_chr16.trna1-ArgCCG (3140676-3140748) Arg (CCG) 73 bp Sc: 69.88

(SEQ ID NO: 228)

GGCCGCGTGGCCTAATGGATAAGGCGTCTGATTCCGGATCAGAAGATTGAGGGTTCGAGTCCCTTCGTGGTCG

Homo_sapiens_chr6.trna114-ArgCCG (28818780-28818708) Arg (CCG) 73 bp Sc: 69.88

(SEQ ID NO: 229)

GGCCGCGTGGCCTAATGGATAAGGCGTCTGATTCCGGATCAGAAGATTGAGGGTTCGAGTCCCTTCGTGGTCG

Homo_sapiens_chr6.trna73-ArgCCG (28957144-28957216) Arg (CCG) 73 bp Sc: 69.88

(SEQ ID NO: 230)

GGCCGCGTGGCCTAATGGATAAGGCGTCTGATTCCGGATCAGAAGATTGAGGGTTCGAGTCCCTTCGTGGTCG

Homo_sapiens_chr16.trna12-ArgCCT (3183919-3183991) Arg (CCT) 73 bp Sc: 59.77

(SEQ ID NO: 231)

GCCCCAGTGGCCTGATGGATAAGGTACTGGCCTCCTAAGCCAGGGATTGTGGGTTCGAGTTCCACCTGGGGTA

Homo_sapiens_chr7.trna3-ArgCCT (138675986-138676058) Arg (CCT) 73 bp Sc: 67.28

(SEQ ID NO: 232)

GCCCCAGTGGCCTAATGGATAAGGCATTGGCCTCCTAAGCCAGGGATTGTGGGTTCGAGTCCCATCTGGGGTG

Homo_sapiens_chr16.trna2-ArgCCT (3142902-3142974) Arg (CCT) 73 bp Sc: 71.53

(SEQ ID NO: 233)

GCCCCGGTGGCCTAATGGATAAGGCATTGGCCTCCTAAGCCAGGGATTGTGGGTTCGAGTCCCACCCGGGGTA

Homo_sapiens_chr17.trna21-ArgCCT (70542193-70542121) Arg (CCT) 73 bp Sc: 73.41

(SEQ ID NO: 234)

GCCCCAGTGGCCTAATGGATAAGGCACTGGCCTCCTAAGCCAGGGATTGTGGGTTCGAGTCCCACCTGGGGTG

Homo_sapiens_chr17.trna18-ArgCCT (70541596-70541668) Arg (CCT) 73 bp Sc: 73.88

(SEQ ID NO: 235)

GCCCCAGTGGCCTAATGGATAAGGCACTGGCCTCCTAAGCCAGGGATTGTGGGTTCGAGTCCCACCTGGGGTA

Homo_sapiens_chr9.trna2-ArgTCG (112000624-112000696) Arg (TCG) 73 bp Sc: 56.18

(SEQ ID NO: 236)

GGCCGTGTGGCCTAATGGATAAGGCGTCTGACTTCGGATCAAAAGATTGCAGGTTTGAGTTCTGCCACGGTCG

Homo_sapiens_chr6.trna124-ArgTCG (28618942-28618870) Arg (TCG) 73 bp Sc: 69.08

(SEQ ID NO: 237)

GACCACGTGGCCTAATGGATAAGGCGTCTGACTTCGGATCAGAAGATTGAGGGTTCGAATCCCTTCGTGGTTG

Homo_sapiens_chr6.trna3-ArgTCG (26407884-26407956) Arg (TCG) 73 bp Sc: 69.55

(SEQ ID NO: 238)

GACCACGTGGCCTAATGGATAAGGCGTCTGACTTCGGATCAGAAGATTGAGGGTTCGAATCCCTTCGTGGTTA

Homo_sapiens_chr17.trna19-ArgTCG (70542803-70542875) Arg (TCG) 73 bp Sc: 70.52

(SEQ ID NO: 239)

GACCGCGTGGCCTAATGGATAAGGCGTCTGACTTCGGATCAGAAGATTGAGGGTTCGAGTCCCTTCGTGGTCG

Homo_sapiens_chr6.trna4-ArgTCG (26431025-26431097) Arg (TCG) 73 bp Sc: 72.33

(SEQ ID NO: 240)

GACCACGTGGCCTAATGGATAAGGCGTCTGACTTCGGATCAGAAGATTGAGGGTTCGAATCCCTCCGTGGTTA

Homo_sapiens_chr15.trna4-ArgTCG (87679308-87679380) Arg (TCG) 73 bp Sc: 76.93

(SEQ ID NO: 241)

GGCCGCGTGGCCTAATGGATAAGGCGTCTGACTTCGGATCAGAAGATTGCAGGTTCGAGTCCTGCCGCGGTCG

Homo_sapiens_chr1.trna86-ArgTCT (157378098-157378025) Arg (TCT) 74 bp Sc: 76.29

(SEQ ID NO: 242)

GTCTCTGTGGCGCAATGGACGAGCGCGCTGGACTTCTAATCCAGAGGTTCCGGGTTCGAGTCCCGGCAGAGATG

Homo_sapiens_chr9.trna4-ArgTCT (130142266-130142176) Arg (TCT) 91 bp Sc: 67.17

(SEQ ID NO: 243)

GGCTCTGTGGCGCAATGGATAGCGCATTGGACTTCTAGCTGAGCCTAGTGTGGTCATTCAAAGGTTGTGGGTTCGAGTCCCACCAGAGTCG

Homo_sapiens_chr6.trna52-ArgTCT (27637942-27638028) Arg (TCT) 87 bp Sc: 65.24

(SEQ ID NO: 244)

GGCTCTGTGGCGCAATGGATAGCGCATTGGACTTCTAGCCTAAATCAAGAGATTCAAAGGTTGCGGGTTCGAGTCCCTCCAGAGTCG

Homo_sapiens_chr11.trna3-ArgTCT (59075343-59075428) Arg (TCT) 86 bp Sc: 71.13

(SEQ ID NO: 245)

GGCTCTGTGGCGCAATGGATAGCGCATTGGACTTCTAGATAGTTAGAGAAATTCAAAGGTTGTGGGTTCGAGTCCCACCAGAGTCG

Homo_sapiens_chr17.trna4-ArgTCT (7964968-7965055) Arg (TCT) 88 bp Sc: 71.27

(SEQ ID NO: 246)

GGCTCTGTGGCGCAATGGATAGCGCATTGGACTTCTAGTGACGAATAGAGCAATTCAAAGGTTGTGGGTTCGAATCCCACCAGAGTCG

Homo_sapiens_chr1.trna9-ArgTCT (94085717-94085801) Arg (TCT) 85 bp Sc: 71.18

(SEQ ID NO: 247)

GGCTCCGTGGCGCAATGGATAGCGCATTGGACTTCTAGAGGCTGAAGGCATTCAAAGGTTCCGGGTTCGAGTCCCGGCGGAGTCG

Homo_sapiens_chr1.trna20-AsnATT (146185653-146185726) Asn (ATT) 74 bp Sc: 52.07

(SEQ ID NO: 248)

GTCTCTGTGGCGCAATCGGTCAGAGCGTTCGGCTATTAACCGAACGGTGAGTAGTTCAAGACCACCCAGGGACG

Homo_sapiens_chr1.trna13-AsnGTT (144097086-144097161) Asn (GTT) 76 bp Sc: 44.21

(SEQ ID NO: 249)

GTCTCTGTGGCGCCATCGGTTAGTGCCTTCGGCTGTTTGAACCGAAAGGCTGGTGGTTCAAGCCCACCCAGAGATG

Homo_sapiens_chr1.trna93-AsnGTT (147936754-147936681) Asn (GTT) 74 bp Sc: 46.92

(SEQ ID NO: 250)

ATCTCCGTGGAGCAATTGGTTAGCGCGTTCGGCCGTTAACCGGAAAGTTGGTGGTTCGAGCCTACCCAGGGACG

Homo_sapiens_chr1.trna134-AsnGTT (16731553-16731480) Asn (GTT) 74 bp Sc: 48.81

(SEQ ID NO: 251)

GTCTCTGTGGTGCAATCGGTTAGCGCGTTCGGCTGTTAACCATAAGGTTGGTGGTTACAGACCACCCAGGGACG

Homo_sapiens_chr1.trna50-AsnGTT (159858089-159858162) Asn (GTT) 74 bp Sc: 49.69

(SEQ ID NO: 252)

GTTTCTGTAGCGCGATCGGTTAGCGCCTTCGGCTGTTAAACGAAAGGTTGGTGGTTCGTTCCCACCCCGGGACA

Homo_sapiens_chr1.trna10-AsnGTT (142481551-142481624) Asn (GTT) 74 bp Sc: 49.96

(SEQ ID NO: 253)

GTCTCTGTGGCGCAATCGGTTAGCGCGTTTGACTGTTAACTGAAAGGTTGGTGGTGCAAGCCCATCCAGGGATG

Homo_sapiens_chr1.trna122-AsnGTT (143200273-143200200) Asn (GTT) 74 bp Sc: 49.96

(SEQ ID NO: 254)

GTCTCTGTGGCGCAATCGGTTAGCGCGTTTGACTGTTAACTGAAAGGTTGGTGGTGCAAGCCCATCCAGGGATG

Homo_sapiens_chr1.trna123-AsnGTT (143020044-143019971) Asn (GTT) 74 bp Sc: 49.96

(SEQ ID NO: 255)

GTCTCTGTGGCGCAATCGGTTAGCGCGTTTGACTGTTAACTGAAAGGTTGGTGGTGCAAGCCCATCCAGGGATG

Homo_sapiens_chr1.trna24-AsnGTT (146344161-146344234) Asn (GTT) 74 bp Sc: 49.96

(SEQ ID NO: 256)

GTCTCTGTGGCGCAATCGGTTAGCGCGTTTGACTGTTAACTGAAAGGTTGGTGGTGCAAGCCCATCCAGGGATG

Homo_sapiens_chr1.trna30-AsnGTT (147875233-147875306) Asn (GTT) 74 bp Sc: 49.96

(SEQ ID NO: 257)

GTCTCTGTGGCGCAATCGGTTAGCGCGTTTGACTGTTAACTGAAAGGTTGGTGGTGCAAGCCCATCCAGGGATG

Homo_sapiens_chr1.trna101-AsnGTT (147551200-147551127) Asn (GTT) 74 bp Sc: 51.19

(SEQ ID NO: 258)

ATCTCCGTGGAGCAATTGGTTAGCGCGTTCGGCTGTTAACCGGAAAGTTGGTGGTTCGAGCCTACCCAGGGACG

Homo_sapiens_chr1.trna12-AsnGTT (143193197-143193270) Asn (GTT) 74 bp Sc: 53.66

(SEQ ID NO: 259)

GTCTCTGTGGTGCAATCGGTTAGCGCGTTCCGCTGTTAACCGAAAGCTTGGTGGTTTGAGCCCACCCAGGGATG

Homo_sapiens_chr1.trna6-AsnGTT (17074545-17074618) Asn (GTT) 74 bp Sc: 56.35

(SEQ ID NO: 260)

GTCTCTGTGGTGCAATCGGTTAGCGCGTTCGGCTGTTAACCATAAGGTTGGTGGTTAGAGACCACCCAGGGACG

Homo_sapiens_chr1.trna97-AsnGTT (147592969-147592896) Asn (GTT) 74 bp Sc: 59.90

(SEQ ID NO: 261)

GTCTCTGTGGCGCAATCGGCTAGCGCGTTTGGCTGTTAACTAAAAGTTGGTGGTTCGAACACACCCAGAGGCG

Homo_sapiens_chr1.trna11-AsnGTT (143012968-143013041) Asn (GTT) 74 bp Sc: 60.57

(SEQ ID NO: 262)

GTCTCTGTGGTGCAATCGGTTAGCGCGTTCCGCTGTTAACCGAAAGCTTGGTGGTTCGAGCCCACCCAGGGATG

Homo_sapiens_chr1.trna95-AsnGTT (147882314-147882241) Asn (GTT) 74 bp Sc: 60.57

(SEQ ID NO: 263)

GTCTCTGTGGTGCAATCGGTTAGCGCGTTCCGCTGTTAACCGAAAGCTTGGTGGTTCGAGCCCACCCAGGGATG

Homo_sapiens_chr1_random.trna2-AsnGTT (906435-906508) Asn (GTT) 74 bp Sc: 66.79

(SEQ ID NO: 264)

GTCTCTGTGGCGCAATCGGCTAGCGCGTTTGGCTGTTAACTAAAAGGTTGGCGGTTCGAACCCACCCAGAGGCG

Homo_sapiens_chr1.trna113-AsnGTT (145987464-145987391) Asn (GTT) 74 bp Sc: 70.44

(SEQ ID NO: 265)

GTCTCTGTGGCGCAATCGGTTAGCGCGTTCGGCTGTTAACTGAAAGGTTAGTGGTTCGAGCCCACCCGGGGACG

Homo_sapiens_chr1.trna115-AsnGTT (144690464-144690391) Asn (GTT) 74 bp Sc: 70.44

(SEQ ID NO: 266)

GTCTCTGTGGCGCAATCGGTTAGCGCGTTCGGCTGTTAACTGAAAGGTTAGTGGTTCGAGCCCACCCGGGGACG

Homo_sapiens_chr1.trna89-AsnGTT (147978495-147978422) Asn (GTT) 74 bp Sc: 71.43

(SEQ ID NO: 267)

GTCTCTGTGGCGCAATCGGCTAGCGCGTTTGGCTGTTAACTAAAAGGTTGGTGGTTCGAACCCACCCAGAGGCG

Homo_sapiens_chr1.trna25-AsnGTT (146467429-146467502) Asn (GTT) 74 bp Sc: 72.61

(SEQ ID NO: 268)

GTCTCTGTGGCGTAGTCGGTTAGCGCGTTCGGCTGTTAACCGAAAAGTTGGTGGTTCGAGCCCACCCAGGAACG

Homo_sapiens_chr1.trna103-AsnGTT (147497267-147497194) Asn (GTT) 74 bp Sc: 77.16

(SEQ ID NO: 269)

GTCTCTGTGGCGCAATGGGTTAGCGCGTTCGGCTGTTAACCGAAAGGTTGGTGGTTCGAGCCCATCCAGGGACG

Homo_sapiens_chr1.trna135-AsnGTT (16719740-16719667) Asn (GTT) 74 bp Sc: 77.65

(SEQ ID NO: 270)

GTCTCTGTGGCGCAATCGGTTAGCGCGTTCGGCTGTTAACTGAAAGGTTGGTGGTTCGAGCCCACCCAGGGACG

Homo_sapiens_chr1.trna7-AsnGTT (17088759-17088832) Asn (GTT) 74 bp Sc: 80.35

(SEQ ID NO: 271)

GTCTCTGTGGCGCAATCGGTTAGCGCGTTCGGCTGTTAACCGAAAGATTGGTGGTTCGAGCCCACCCAGGGACG

Homo_sapiens_chr1.trna107-AsnGTT (147027053-147026980) Asn (GTT) 74 bp Sc: 80.52

(SEQ ID NO: 272)

GTCTCTGTGGCGCAATCGGTTAGCGCATTCGGCTGTTAACCGAAAGGTTGGTGGTTCGAGCCCACCCAGGGACG

Homo_sapiens_chr1.trna108-AsnGTT (146865011-146864938) Asn (GTT) 74 bp Sc: 80.52

(SEQ ID NO: 273)

GTCTCTGTGGCGCAATCGGTTAGCGCATTCGGCTGTTAACCGAAAGGTTGGTGGTTCGAGCCCACCCAGGGACG

Homo_sapiens_chr1.trna26-AsnGTT (146614739-146614812) Asn (GTT) 74 bp Sc: 82.24

(SEQ ID NO: 274)

GTCTCTGTGGCGCAATCGGTTAGCGCGTTCGGCTGTTAACCGAAAGGTTGGTGGTTCGAGCCCACCCAGGGACG

Homo_sapiens_chr1.trna83-AsnGTT (159664564-159664491) Asn (GTT) 74 bp Sc: 82.24

(SEQ ID NO: 275)

GTCTCTGTGGCGCAATCGGTTAGCGCGTTCGGCTGTTAACCGAAAGGTTGGTGGTTCGAGCCCACCCAGGGACG

-continued

Homo_sapiens_chr10.trna4-AsnGTT (22558517-22558444) Asn (GTT) 74 bp Sc: 82.24

(SEQ ID NO: 276)

GTCTCTGTGGCGCAATCGGTTAGCGCGTTCGGCTGTTAACCGAAAGGTTGGTGGTTCGAGCCCACCCAGGGACG

Homo_sapiens_chr13.trna7-AsnGTT (30146174-30146101) Asn (GTT) 74 bp Sc: 82.24

(SEQ ID NO: 277)

GTCTCTGTGGCGCAATCGGTTAGCGCGTTCGGCTGTTAACCGAAAGGTTGGTGGTTCGAGCCCACCCAGGGACG

Homo_sapiens_chr17.trna31-AsnGTT (34161633-34161560) Asn (GTT) 74 bp Sc: 82.24

(SEQ ID NO: 278)

GTCTCTGTGGCGCAATCGGTTAGCGCGTTCGGCTGTTAACCGAAAGGTTGGTGGTTCGAGCCCACCCAGGGACG

Homo_sapiens_chr19.trna1-AsnGTT (1334562-1334635) Asn (GTT) 74 bp Sc: 82.24

(SEQ ID NO: 279)

GTCTCTGTGGCGCAATCGGTTAGCGCGTTCGGCTGTTAACCGAAAGGTTGGTGGTTCGAGCCCACCCAGGGACG

Homo_sapiens_chr1.trna47-AsnGTT (159776655-159776728) Asn (GTT) 74 bp Sc: 83.66

(SEQ ID NO: 280)

GTCTCTGTGGCGCAATCGGTTAGCGCGTTCGGCTGTTAACCGAAAGGTTGGTGGTTCGATCCCACCCAGGGACG

Homo_sapiens_chr1.trna48-AspGTC (159841212-159841283) Asp (GTC) 72 bp Sc: 30.22

(SEQ ID NO: 281)

TCCTTGTTACTATAGTGGTAAGTATCTCTGCCTGTCATGCATGAGAGAGGGGTCGATTCCCTGACGGGGAG

Homo_sapiens_chr12.trna7-AspGTC (121426877-121426947) Asp (GTC) 71 bp Sc: 32.33

(SEQ ID NO: 282)

TCCTTGTTAGTATAGTGGTGAGTGTTTCTGCCTGTCATGTGGAGACTGGAGTTTGAGTCCCCAACAGGGAG

Homo_sapiens_chr1.trna46-AspGTC (159768539-159768610) Asp (GTC) 72 bp Sc: 34.08

(SEQ ID NO: 283)

TACTCGTTAGTATAGTGGTGCGTATCCCCGTCTGTCACGCGGGAGAGCGGGGTTCGCTCTCCCGACGGGGAG

Homo_sapiens_chr3.trna3-AspGTC (185848859-185848789) Asp (GTC) 71 bp Sc: 43.84

(SEQ ID NO: 284)

TTCTTGTTAATATAGTGGTGAGTATTCCCACCTGTCATGCGGGAGACGGGGTTCAATTCCCTGATGGGGAG

Homo_sapiens_chr5.trna22-AspGTC (141754243-141754172) Asp (GTC) 72 bp Sc: 54.87

(SEQ ID NO: 285)

TCCTCATCAGTATAGTGGTGAGTATCCCCGCCTGTCACGCGGGAGACTGGGGTTCGATTCCCTGAGGAGGAG

Homo_sapiens_chr9.trna6-AspGTC (76707881-76707810) Asp (GTC) 72 bp Sc: 54.95

(SEQ ID NO: 286)

TCCTCGTTAGTATGGTGGTGAGTATCCCTGCCTGTCACGCGGGAGACCGGGGTTCGATTCCCCAACGGGGAG

Homo_sapiens_chr6.trna144-AspGTC (27659286-27659215) Asp (GTC) 72 bp Sc: 64.62

(SEQ ID NO: 287)

TCCTCGTTAGTATAGTGGTGAGTGTCCCCGTCTGTCACGCGGGAGACCGGGGTTCGATTCCCCGACGGGGAG

Homo_sapiens_chr1.trna69-AspGTC (159706900-159706829) Asp (GTC) 72 bp Sc: 72.92

(SEQ ID NO: 288)

TCCTCGTTAGTATAGTGGTGAGTATCCCCGCCTGTCACGCGGGAGACCGGGGTTCGATTCCCCGACGGGGAG

Homo_sapiens_chr1.trna72-AspGTC (159699519-159699448) Asp (GTC) 72 bp Sc: 72.92

(SEQ ID NO: 289)

TCCTCGTTAGTATAGTGGTGAGTATCCCCGCCTGTCACGCGGGAGACCGGGGTTCGATTCCCCGACGGGGAG

Homo_sapiens_chr1.trna75-AspGTC (159692109-159692038) Asp (GTC) 72 bp Sc: 72.92

(SEQ ID NO: 290)

TCCTCGTTAGTATAGTGGTGAGTATCCCCGCCTGTCACGCGGGAGACCGGGGTTCGATTCCCCGACGGGGAG

Homo_sapiens_chr1.trna78-AspGTC (159684728-159684657) Asp (GTC) 72 bp Sc: 72.92

(SEQ ID NO: 291)

TCCTCGTTAGTATAGTGGTGAGTATCCCCGCCTGTCACGCGGGAGACCGGGGTTCGATTCCCCGACGGGGAG

Homo_sapiens_chr1.trna81-AspGTC (159677310-159677239) Asp (GTC) 72 bp Sc: 72.92

(SEQ ID NO: 292)

TCCTCGTTAGTATAGTGGTGAGTATCCCCGCCTGTCACGCGGGAGACCGGGGTTCGATTCCCCGACGGGGAG

Homo_sapiens_chr12.trna10-AspGTC (123990217-123990146) Asp (GTC) 72 bp Sc: 72.92

(SEQ ID NO: 293)

TCCTCGTTAGTATAGTGGTGAGTATCCCCGCCTGTCACGCGGGAGACCGGGGTTCGATTCCCCGACGGGGAG

Homo_sapiens_chr12.trna12-AspGTC (123977915-123977844) Asp (GTC) 72 bp Sc: 72.92

(SEQ ID NO: 294)

TCCTCGTTAGTATAGTGGTGAGTATCCCCGCCTGTCACGCGGGAGACCGGGGTTCGATTCCCCGACGGGGAG

Homo_sapiens_chr12.trna4-AspGTC (94953930-94954001) Asp (GTC) 72 bp Sc: 72.92

(SEQ ID NO: 295)

TCCTCGTTAGTATAGTGGTGAGTATCCCCGCCTGTCACGCGGGAGACCGGGGTTCGATTCCCCGACGGGGAG

-continued

Homo_sapiens_chr17.trna38-AspGTC (8066352-8066281) Asp (GTC) 72 bp Sc: 72.92

(SEQ ID NO: 296)

TCCTCGTTAGTATAGTGGTGAGTATCCCCGCCTGTCACGCGGGAGACCGGGGTTCGATTCCCCGACGGGGAG

Homo_sapiens_chr6.trna45-AspGTC (27555432-27555503) Asp (GTC) 72 bp Sc: 72.92

(SEQ ID NO: 297)

TCCTCGTTAGTATAGTGGTGAGTATCCCCGCCTGTCACGCGGGAGACCGGGGTTCGATTCCCCGACGGGGAG

Homo_sapiens_chr6.trna48-AspGTC (27579502-27579573) Asp (GTC) 72 bp Sc: 72.92

(SEQ ID NO: 298)

TCCTCGTTAGTATAGTGGTGAGTATCCCCGCCTGTCACGCGGGAGACCGGGGTTCGATTCCCCGACGGGGAG

Homo_sapiens_chr12.trna5-AspGTC (97421412-97421483) Asp (GTC) 72 bp Sc: 74.76

(SEQ ID NO: 299)

TCCTCGTTAGTATAGTGGTTAGTATCCCCGCCTGTCACGCGGGAGACCGGGGTTCAATTCCCCGACGGGGAG

Homo_sapiens_chr17.trna30-CysGCA (34243572-34243501) Cys (GCA) 72 bp Sc: 51.58

(SEQ ID NO: 300)

GGGGGTAGGGCTCAGGGATAGAGCATTTGACTGCAGATCAAGAGGTCCCCGGTTCGAATCTAGGTGCCCCCT

Homo_sapiens_chr7.trna19-CysGCA (148923309-148923238) Cys (GCA) 72 bp Sc: 57.52

(SEQ ID NO: 301)

GGGGGTATAGCTCACAGGTAGAGCATTTGACTGCAGATCAAGAGGTCCCCGGTTCAAATCCGGTTACTCCCT

Homo_sapiens_chr7.trna8-CysGCA (148884735-148884806) Cys (GCA) 72 bp Sc: 59.93

(SEQ ID NO: 302)

GGGCGTATAGCTCAGGGGTAGAGCATTTGACTGCAGATCAAGAGGTCCCCAGTTCAAATCTGGGTGCCCACT

Homo_sapiens_chr7.trna14-CysGCA (148992848-148992919) Cys (GCA) 72 bp Sc: 60.15

(SEQ ID NO: 303)

GGGGGTATAGCTCACAGGTAGAGCATTTGACTGCAGATCAAGAGGTCCCCGGTTCAAATCTGGGTGCCCCCT

Homo_sapiens_chr7.trna11-CysGCA (148925979-148926050) Cys (GCA) 72 bp Sc: 65.84

(SEQ ID NO: 304)

GGGCGTATAGCTCAGGGGTAGAGCATTTGACTGCAGATCAAGAGGTCCCCAGTTCAAATCTGGGTGCCCCCT

Homo_sapiens_chr7.trna18-CysGCA (148941160-148941089) Cys (GCA) 72 bp Sc: 67.69

(SEQ ID NO: 305)

GGGGGTATAGCTCAGGGGTAGAGCATTTGACTGCAAATCAAGAGGTCCCTGATTCAAATCCAGGTGCCCCCT

Homo_sapiens_chr7.trna23-CysGCA (148703854-148703783) Cys (GCA) 72 bp Sc: 68.91

(SEQ ID NO: 306)

GGGGGTATAGTTCAGGGGTAGAGCATTTGACTGCAGATCAAGAGGTCCCTGGTTCAAATCCAGGTGCCCCCT

Homo_sapiens_chr7.trna16-CysGCA (149019276-149019205) Cys (GCA) 72 bp Sc: 69.30

(SEQ ID NO: 307)

GGGGATATAGCTCAGGGGTAGAGCATTTGACTGCAGATCAAGAGGTCCCCGGTTCAAATCCGGGTGCCCCCC

Homo_sapiens_chr7.trna7-CysGCA (148874564-148874635) Cys (GCA) 72 bp Sc: 69.62

(SEQ ID NO: 308)

GGGGGTATAGCTCAGGGGTAGAGCACTTGACTGCAGATCAAGAAGTCCTTGGTTCAAATCCAGGTGCCCCCT

Homo_sapiens_chr7.trna10-CysGCA (148912749-148912820) Cys (GCA) 72 bp Sc: 69.82

(SEQ ID NO: 309)

GGGGGTATAGCTCAGGGGTAGAGCATTTGACTGCAGATCAAGAGGTCTCTGGTTCAAATCCAGGTGCCCCCT

Homo_sapiens_chr17.trna29-CysGCA (34271534-34271463) Cys (GCA) 72 bp Sc: 70.63

(SEQ ID NO: 310)

GGGGGTATAGCTCAGGGGTAGAGCATTTGACTGCAGATCAAGAAGTCCCCGGTTCAAATCCGGGTGCCCCCT

Homo_sapiens_chr7.trna25-CysGCA (148683770-148683699) Cys (GCA) 72 bp Sc: 71.19

(SEQ ID NO: 311)

GGGGGTATAGCTCAGGGGTAGAGCATTTGACTGCAGATCAAGAGGTCCCCAGTTCAAATCTGGGTGCCCCCT

Homo_sapiens_chr7.trna17-CysGCA (148975050-148974979) Cys (GCA) 72 bp Sc: 71.81

(SEQ ID NO: 312)

GGGGGTATAGCTTAGGGGTAGAGCATTTGACTGCAGATCAAAAGGTCCCTGGTTCAAATCCAGGTGCCCCTT

Homo_sapiens_chr7.trna21-CysGCA (148743233-148743162) Cys (GCA) 72 bp Sc: 73.76

(SEQ ID NO: 313)

GGGGGTATAGCTTAGCGGTAGAGCATTTGACTGCAGATCAAGAGGTCCCCGGTTCAAATCCGGGTGCCCCCT

Homo_sapiens_chr7.trna22-CysGCA (148705605-148705534) Cys (GCA) 72 bp Sc: 73.86

(SEQ ID NO: 314)

GGGGGTATAGCTCAGGGGTAGAGCATTTGACTGCAGATCAAGAGGTCCCTGGTTCAAATCCAGGTGCCCCCC

Homo_sapiens_chr3.trna6-CysGCA (133433403-133433332) Cys (GCA) 72 bp Sc: 74.20

(SEQ ID NO: 315)

GGGGGTATAGCTCAGGGGTAGAGCATTTGACTGCAGATCAAGAGGTCCCTGGTTCAAATCCAGGTGCCCCCT

-continued

Homo_sapiens_chr7.trna13-CysGCA (148963711-148963782) Cys (GCA) 72 bp Sc: 74.20

(SEQ ID NO: 316)

GGGGGTATAGCTCAGGGGTAGAGCATTTGACTGCAGATCAAGAGGTCCCTGGTTCAAATCCAGGTGCCCCCT

Homo_sapiens_chr7.trna15-CysGCA (149035693-149035764) Cys (GCA) 72 bp Sc: 74.20

(SEQ ID NO: 317)

GGGGGTATAGCTCAGGGGTAGAGCATTTGACTGCAGATCAAGAGGTCCCTGGTTCAAATCCAGGTGCCCCCT

Homo_sapiens_chr7.trna6-CysGCA (148659153-148659224) Cys (GCA) 72 bp Sc: 74.20

(SEQ ID NO: 318)

GGGGGTATAGCTCAGGGGTAGAGCATTTGACTGCAGATCAAGAGGTCCCTGGTTCAAATCCAGGTGCCCCCT

Homo_sapiens_chr14.trna8-CysGCA (72499432-72499503) Cys (GCA) 72 bp Sc: 74.26

(SEQ ID NO: 319)

GGGGGTATAGCTCAGGGGTAGAGCATTTGACTGCAGATCAAGAGGTCCCCGGTTCAAATCCGGGTGCCCCCT

Homo_sapiens_chr1.trna126-CysGCA (93754494-93754422) Cys (GCA) 73 bp Sc: 74.38

(SEQ ID NO: 320)

GGGGGTATAGCTCAGGTGGTAGAGCATTTGACTGCAGATCAAGAGGTCCCCGGTTCAAATCCGGGTGCCCCCT

Homo_sapiens_chr3.trna7-CysGCA (133430705-133430634) Cys (GCA) 72 bp Sc: 74.42

(SEQ ID NO: 321)

GGGGGTGTAGCTCAGTGGTAGAGCATTTGACTGCAGATCAAGAGGTCCCTGGTTCAAATCCAGGTGCCCCCT

Homo_sapiens_chr15.trna3-CysGCA (77824052-77824124) Cys (GCA) 73 bp Sc: 74.95

(SEQ ID NO: 322)

GGGGGTATAGCTCAGTGGGTAGAGCATTTGACTGCAGATCAAGAGGTCCCCGGTTCAAATCCGGGTGCCCCCT

Homo_sapiens_chr17.trna28-CysGCA (34279142-34279071) Cys (GCA) 72 bp Sc: 77.18

(SEQ ID NO: 323)

GGGGGTATAGCTCAGTGGTAGAGCATTTGACTGCAGATCAAGAGGTCCCTGGTTCAAATCCGGGTGCCCCCT

Homo_sapiens_chr7.trna20-CysGCA (148917168-148917097) Cys (GCA) 72 bp Sc: 77.55

(SEQ ID NO: 324)

GGGGGTATAGCTCAGGGGTAGAGCACTTGACTGCAGATCAAGAGGTCCCTGGTTCAAATCCAGGTGCCCCCT

Homo_sapiens_chr17.trna15-CysGCA (34277424-34277495) Cys (GCA) 72 bp Sc: 77.71

(SEQ ID NO: 325)

GGGGGTATAGCTCAGTGGTAGAGCATTTGACTGCAGATCAAGAGGTCCCCGGTTCAAATCCGGGTGCCCCCT

Homo_sapiens_chr17.trna26-CysGCA (34564341-34564270) Cys (GCA) 72 bp Sc: 77.71

(SEQ ID NO: 326)

GGGGGTATAGCTCAGTGGTAGAGCATTTGACTGCAGATCAAGAGGTCCCCGGTTCAAATCCGGGTGCCCCCT

Homo_sapiens_chr17.trna27-CysGCA (34563584-34563513) Cys (GCA) 72 bp Sc: 77.71

(SEQ ID NO: 327)

GGGGGTATAGCTCAGTGGTAGAGCATTTGACTGCAGATCAAGAGGTCCCCGGTTCAAATCCGGGTGCCCCCT

Homo_sapiens_chr4.trna3-CysGCA (124649526-124649455) Cys (GCA) 72 bp Sc: 77.71

(SEQ ID NO: 328)

GGGGGTATAGCTCAGTGGTAGAGCATTTGACTGCAGATCAAGAGGTCCCCGGTTCAAATCCGGGTGCCCCCT

Homo_sapiens_chr7.trna5-CysGCA (148638214-148638285) Cys (GCA) 72 bp Sc: 79.54

(SEQ ID NO: 329)

GGGGGCATAGCTCAGTGGTAGAGCATTTGACTGCAGATCAAGAGGTCCCTGGTTCAAATCCAGGTGCCCCCT

Homo_sapiens_chr16.trna21-GlnCTG (70282391-70282464) Gln (CTG) 74 bp Sc: 20.83

(SEQ ID NO: 330)

GGCAGTATGGTAGAGTGGTTAAGATCATGAACTCTGAAGTCAGAGATACTTGAATTTGAATGCTGGTTCTGTCA

Homo_sapiens_chr20.trna1-GlnCTG (17803142-17803219) Gln (CTG) 78 bp Sc: 21.25

(SEQ ID NO: 331)

GGCAGTGTAGCCCAGAGGTTCAAGGGCATTCGCTCTGGTATCAGAAGGGTCTGGGTTCAAATCCCTTGTGCACTGCTT

Homo_sapiens_chr9.trna5-GlnCTG (125695415-125695343) Gln (CTG) 73 bp Sc: 22.97

(SEQ ID NO: 332)

GAGCTGTAGCATAGTGATTAGGGACATGGACTCTGGAGCCAAATCTGCCTGGGTTCTAGTCCCAGCTGTCTCA

Homo_sapiens_chr12.trna3-GlnCTG (73137449-73137521) Gln (CTG) 73 bp Sc: 34.73

(SEQ ID NO: 333)

GGTTCCATGGTGTAATGGTAAGCACCCTGGACTCTGAATCCAGCAACCAGAGTTCCAGTCTCAGCGTGGACCT

Homo_sapiens_chr1.trna114-GlnCTG (144943455-144943384) Gln (CTG) 72 bp Sc: 40.01

(SEQ ID NO: 334)

GGTTCCATGGTGTAATGGTGACCACTTTGGACTCTGAATACAGTGATCAGAGTTCAAGTCTCACTGGAACCT

Homo_sapiens_chr1.trna120-GlnCTG (144090748-144090677) Gln (CTG) 72 bp Sc: 44.40

(SEQ ID NO: 335)

GGTTCCATGGTGTAATGGTGAGCACTTTGGACTCTGAATACAGTGATCAGAGTTCAAGTCTCACTGGGACCT

-continued

Homo_sapiens_chr1.trna121-GlnCTG (143550864-143550793) Gln (CTG) 72 bp Sc: 44.40

GGTTCCATGGTGTAATGGTGAGCACTTTGGACTCTGAATACAGTGATCAGAGTTCAAGTCTCACTGGGACCT (SEQ ID NO: 336)

Homo_sapiens_chr1_random.trna1-GlnCTG (553277-553348) Gln (CTG) 72 bp Sc: 44.40

GGTTCCATGGTGTAATGGTGAGCACTTTGGACTCTGAATACAGTGATCAGAGTTCAAGTCTCACTGGGACCT (SEQ ID NO: 337)

Homo_sapiens_chr1.trna22-GlnCTG (146267561-146267632) Gln (CTG) 72 bp Sc: 56.30

GGTTCCATGGTGTAATGGTAAGCACTCTGGACTCTGAATCCAGCCATCTGAGTTCGAGTCTCTGTGGAACCT (SEQ ID NO: 338)

Homo_sapiens_chr6.trna131-GlnCTG (27867185-27867114) Gln (CTG) 72 bp Sc: 66.25

GGCCCCATGGTGTAATGGTCAGCACTCTGGACTCTGAATCCAGCGATCCGAGTTCAAATCTCGGTGGGACCC (SEQ ID NO: 339)

Homo_sapiens_chr6.trna42-GlnCTG (27371191-27371262) Gln (CTG) 72 bp Sc: 68.41

GGTTCCATGGTGTAATGGTTAGCACTCTGGACTCTGAATCCGGTAATCCGAGTTCAAATCTCGGTGGAACCT (SEQ ID NO: 340)

Homo_sapiens_chr1.trna112-GlnCTG (146204077-146204006) Gln (CTG) 72 bp Sc: 68.84

GGTTCCATGGTGTAATGGTAAGCACTCTGGACTCTGAATCCAGCGATCCGAGTTCGAGTCTCGGTGGAACCT (SEQ ID NO: 341)

Homo_sapiens_chr1.trna28-GlnCTG (147452749-147452820) Gln (CTG) 72 bp Sc: 68.84

GGTTCCATGGTGTAATGGTAAGCACTCTGGACTCTGAATCCAGCGATCCGAGTTCGAGTCTCGGTGGAACCT (SEQ ID NO: 342)

Homo_sapiens_chr1.trna15-GlnCTG (144674661-144674732) Gln (CTG) 72 bp Sc: 70.16

GGTTCCATGGTGTAATGGTGAGCACTCTGGACTCTGAATCCAGCGATCCGAGTTCGAGTCTCGGTGGAACCT (SEQ ID NO: 343)

Homo_sapiens_chr1.trna19-GlnCTG (145971662-145971733) Gln (CTG) 72 bp Sc: 70.16

GGTTCCATGGTGTAATGGTGAGCACTCTGGACTCTGAATCCAGCGATCCGAGTTCGAGTCTCGGTGGAACCT (SEQ ID NO: 344)

Homo_sapiens_chr6.trna146-GlnCTG (27623581-27623510) Gln (CTG) 72 bp Sc: 72.00

GGTTCCATGGTGTAATGGTTAGCACTCTGGACTCTGAATCCAGCGATCCGAGTTCAAGTCTCGGTGGAACCT (SEQ ID NO: 345)

Homo_sapiens_chr15.trna7-GlnCTG (63948525-63948454) Gln (CTG) 72 bp Sc: 73.65

GGTTCCATGGTGTAATGGTTAGCACTCTGGACTCTGAATCCAGCGATCCGAGTTCAAATCTCGGTGGAACCT (SEQ ID NO: 346)

Homo_sapiens_chr17.trna3-GlnCTG (7963795-7963866) Gln (CTG) 72 bp Sc: 73.65

GGTTCCATGGTGTAATGGTTAGCACTCTGGACTCTGAATCCAGCGATCCGAGTTCAAATCTCGGTGGAACCT (SEQ ID NO: 347)

Homo_sapiens_chr6.trna1-GlnCTG (18944381-18944452) Gln (CTG) 72 bp Sc: 73.65

GGTTCCATGGTGTAATGGTTAGCACTCTGGACTCTGAATCCAGCGATCCGAGTTCAAATCTCGGTGGAACCT (SEQ ID NO: 348)

Homo_sapiens_chr6.trna49-GlnCTG (27595287-27595358) Gln (CTG) 72 bp Sc: 73.65

GGTTCCATGGTGTAATGGTTAGCACTCTGGACTCTGAATCCAGCGATCCGAGTTCAAATCTCGGTGGAACCT (SEQ ID NO: 349)

Homo_sapiens_chr6.trna99-GlnCTG (29017428-29017357) Gln (CTG) 72 bp Sc: 73.65

GGTTCCATGGTGTAATGGTTAGCACTCTGGACTCTGAATCCAGCGATCCGAGTTCAAATCTCGGTGGAACCT (SEQ ID NO: 350)

Homo_sapiens_chr6.trna79-GlnTTG (37395973-37396045) Gln (TTG) 73 bp Sc: 21.80

GTGCAGAGTAGTACAGTGGTTAAACCATGGTCTTTGGAGCCAGACTGCCTGGGGTCGGATCCCAGCTCTCACA (SEQ ID NO: 351)

Homo_sapiens_chr16.trna14-GlnTTG (3359814-3359885) Gln (TTG) 72 bp Sc: 30.33

TAGGACTTGGTGTAATGGGTAGCACAGAGAATTTTGGATTCTCAGGGGTGGGTTCAATTCCTTTCGTCCTAG (SEQ ID NO: 352)

Homo_sapiens_chr4.trna4-GlnTTG (40603572-40603500) Gln (TTG) 73 bp Sc: 31.57

GACCATGTGGCCTAAGGGAAAAGACATCTCACTTTGGGTCAGAAGATTGAGGGTTCAAGTCCTTTCATGGTCA (SEQ ID NO: 353)

Homo_sapiens_chr2.trna23-GlnTTG (117499050-117498979) Gln (TTG) 72 bp Sc: 33.55

TAGGACATGGTGTAATAGGTAGAATGGAGAATTTTGAATTCTCAGGGGTAGGTTCAATTCCTATAGTTCTAG (SEQ ID NO: 354)

Homo_sapiens_chr6.trna84-GlnTTG (145545552-145545623) Gln (TTG) 72 bp Sc: 59.31

GGTCCCATGGTGTAATGGTTAGCACTCTGGGCTTTGAATCCAGCAATCCGAGTTCGAATCTTGGTGGGACCT (SEQ ID NO: 355)

-continued

Homo_sapiens_chr6.trna130-GlnTTG (27871690-27871619) Gln (TTG) 72 bp Sc: 68.31

(SEQ ID NO: 356)

GGCCCCATGGTGTAATGGTTAGCACTCTGGACTTTGAATCCAGCGATCCGAGTTCAAATCTCGGTGGGACCT

Homo_sapiens_chr6.trna173-GlnTTG (26420025-26419954) Gln (TTG) 72 bp Sc: 68.31

(SEQ ID NO: 357)

GGCCCCATGGTGTAATGGTTAGCACTCTGGACTTTGAATCCAGCGATCCGAGTTCAAATCTCGGTGGGACCT

Homo_sapiens_chr6.trna174-GlnTTG (26419474-26419403) Gln (TTG) 72 bp Sc: 68.31

(SEQ ID NO: 358)

GGCCCCATGGTGTAATGGTTAGCACTCTGGACTTTGAATCCAGCGATCCGAGTTCAAATCTCGGTGGGACCT

Homo_sapiens_chr17.trna16-GlnTTG (44624889-44624960) Gln (TTG) 72 bp Sc: 73.77

(SEQ ID NO: 359)

GGTCCCATGGTGTAATGGTTAGCACTCTGGACTTTGAATCCAGCGATCCGAGTTCAAATCTCGGTGGGACCT

Homo_sapiens_chr1.trna29-GluCTC (147600896-147600964) Glu (CTC) 69 bp Sc: 21.64

(SEQ ID NO: 360)

TCCCTGGTAGTCTAGTGGCTAAAGTTTGGCGCTCTCACCGCCGGGACTGGTTGATTCCAGATCAGGGGA

Homo_sapiens_chr3.trna8-GluCTC (126895938-126895867) Glu (CTC) 72 bp Sc: 29.87

(SEQ ID NO: 361)

CCCCTGGTGGTCTATCGGTTAGGATTCAGACCTCTCACCACTGCTACCCATGCTCGATTCCTGGTCAGGGAA

Homo_sapiens_chr18.trna1-GluCTC (41553749-41553820) Glu (CTC) 72 bp Sc: 32.13

(SEQ ID NO: 362)

CCCCGGGTGGTGTAGTGGATGGGATTTGGCGCTCTCACCACCATGGCCCGGATTTGATTCCCGGTCAGGGAA

Homo_sapiens_chr8.trna3-GluCTC (59667352-59667422) Glu (CTC) 71 bp Sc: 33.87

(SEQ ID NO: 363)

TCCTTGATGTCTAGTGGTTAGGATTTGGTGCTCTCACTGCAGCAGCCTGGGTTCATTTCTCAGTCAGGGAA

Homo_sapiens_chr13.trna4-GluCTC (40928132-40928061) Glu (CTC) 72 bp Sc: 41.44

(SEQ ID NO: 364)

CCCCTGGTGGTCTAGTGCTTAGGATTCGGTGCTCTCACCGCTGCTGCCTGCGTTCGATTCCCGGTCAGGGAA

Homo_sapiens_chr1.trna59-GluCTC (247135070-247135141) Glu (CTC) 72 bp Sc: 71.50

(SEQ ID NO: 365)

TCCCTGGTGGTCTAGTGGTTAGGATTCGGCGCTCTCACCGCCGCGGCCCGGGTTCGATTCCCGGTCAGGAAA

Homo_sapiens_chr1.trna116-GluCTC (144110661-144110590) Glu (CTC) 72 bp Sc: 76.61

(SEQ ID NO: 366)

TCCCTGGTGGTCTAGTGGTTAGGATTCGGCGCTCTCACCGCCGCGGCCCGGGTTCGATTCCCGGTCAGGGAA

Homo_sapiens_chr1.trna71-GluCTC (159705884-159705813) Glu (CTC) 72 bp Sc: 76.61

(SEQ ID NO: 367)

TCCCTGGTGGTCTAGTGGTTAGGATTCGGCGCTCTCACCGCCGCGGCCCGGGTTCGATTCCCGGTCAGGGAA

Homo_sapiens_chr1.trna74-GluCTC (159698504-159698433) Glu (CTC) 72 bp Sc: 76.61

(SEQ ID NO: 368)

TCCCTGGTGGTCTAGTGGTTAGGATTCGGCGCTCTCACCGCCGCGGCCCGGGTTCGATTCCCGGTCAGGGAA

Homo_sapiens_chr1.trna77-GluCTC (159691093-159691022) Glu (CTC) 72 bp Sc: 76.61

(SEQ ID NO: 369)

TCCCTGGTGGTCTAGTGGTTAGGATTCGGCGCTCTCACCGCCGCGGCCCGGGTTCGATTCCCGGTCAGGGAA

Homo_sapiens_chr1.trna80-GluCTC (159683713-159683642) Glu (CTC) 72 bp Sc: 76.61

(SEQ ID NO: 370)

TCCCTGGTGGTCTAGTGGTTAGGATTCGGCGCTCTCACCGCCGCGGCCCGGGTTCGATTCCCGGTCAGGGAA

Homo_sapiens_chr6.trna77-GluCTC (29057955-29058026) Glu (CTC) 72 bp Sc: 76.61

(SEQ ID NO: 371)

TCCCTGGTGGTCTAGTGGTTAGGATTCGGCGCTCTCACCGCCGCGGCCCGGGTTCGATTCCCGGTCAGGGAA

Homo_sapiens_chr6.trna87-GluCTC (126143157-126143086) Glu (CTC) 72 bp Sc: 76.61

(SEQ ID NO: 372)

TCCCTGGTGGTCTAGTGGTTAGGATTCGGCGCTCTCACCGCCGCGGCCCGGGTTCGATTCCCGGTCAGGGAA

Homo_sapiens_chr1.trna31-GluTTC (147986426-147986494) Glu (TTC) 69 bp Sc: 21.27

(SEQ ID NO: 373)

TCCCTGGTAGTCTAGTGGCTAAAGTTTGGCGCTTTCACCGCCGGGACTGGTTGATTCCAGATCAGGGGA

Homo_sapiens_chr2.trna6-GluTTC (74977554-74977622) Glu (TTC) 69 bp Sc: 23.54

(SEQ ID NO: 374)

GCCTGTGGTCTAGTGGTTAGAATTCAGTGTTTTCAGTGCTCTAGTCCAGGTTCAATTCCTGGTCAGGGA

Homo_sapiens_chr1.trna64-GluTTC (170424230-170424162) Glu (TTC) 69 bp Sc: 26.19

(SEQ ID NO: 375)

CCCTGTGGTCTAGTGGTTAGGAGTTGGTGCTTTCGTCATGACAGCCCAGGTTCAATTCCTGGTTAGAGA

```
Homo_sapiens_chr14.trna14-GluTTC (31306637-31306567) Glu (TTC) 71 bp Sc: 28.80
                                                                                    (SEQ ID NO: 376)
ACCCTGTGGTCTAGTGGCTAAGACTTTGTGCTTTCATTGCTGCATCCTAGGTTCAATTCCCAGTCAGGGAA Homo_sapiens_chr1.trna94-GluTTC (147931051-147930979) Glu (TTC) 73 bp Sc: 40.45
                                                                                    (SEQ ID NO: 377)
TCCCTGGTGGTCTAGTGGCTAGGATTCGGCGCTTTCACCGCCTGCAGCTCGAGTTCGATTCCTGGTCAGGGAA Homo_sapiens_chr1.trna49-GluTTC (159849132-159849203) Glu (TTC) 72 bp Sc: 54.07
                                                                                    (SEQ ID NO: 378)
GCGTTGGTGGTGTAGTGGTGAGCACAGCTGCCTTTCAAGCAGTTAACGCGGGTTCGATTCCCGGGTAACGAA Homo_sapiens_chr1.trna133-GluTTC (16734432-16734361) Glu (TTC) 72 bp Sc: 72.33
                                                                                    (SEQ ID NO: 379)
TCCCTGGTGGTCTAGTGGCTAGGATTCGGCGCTTTCACCGCCGCGGGCCCGGGTTCGATTCCCGGTCAGGAA Homo_sapiens_chr1.trna84-GluTTC (159658578-159658507) Glu (TTC) 72 bp Sc: 72.33
                                                                                    (SEQ ID NO: 380)
TCCCTGGTGGTCTAGTGGCTAGGATTCGGCGCTTTCACCGCCGCGGGCCCGGGTTCGATTCCCGGTCAGGAA Homo_sapiens_chr1.trna5-GluTTC (17071665-17071736) Glu (TTC) 72 bp Sc: 75.96
                                                                                    (SEQ ID NO: 381)
TCCCTGGTGGTCTAGTGGCTAGGATTCGGCGCTTTCACCGCCGCGGGCCCGGGTTCGATTCCCGGCCAGGAA Homo_sapiens_chr13.trna3-GluTTC (44390133-44390062) Glu (TTC) 72 bp Sc: 76.26
                                                                                    (SEQ ID NO: 382)
TCCCACATGGTCTAGCGGTTAGGATTCCTGGTTTTCACCCAGGCGGCCCGGGTTCGACTCCCGGTGTGGGAA Homo_sapiens_chr15.trna11-GluTTC (23878545-23878474) Glu (TTC) 72 bp Sc: 76.26
                                                                                    (SEQ ID NO: 383)
TCCCACATGGTCTAGCGGTTAGGATTCCTGGTTTTCACCCAGGCGGCCCGGGTTCGACTCCCGGTGTGGGAA Homo_sapiens_chr13.trna5-GluTTC (40532945-40532874) Glu (TTC) 72 bp Sc: 76.46
                                                                                    (SEQ ID NO: 384)
TCCCATATGGTCTAGCGGTTAGGATTCCTGGTTTTCACCCAGGTGGCCCGGGTTCGACTCCCGGTATGGGAA Homo_sapiens_chr2.trna20-GluTTC (130811242-130811171) Glu (TTC) 72 bp Sc: 76.46
                                                                                    (SEQ ID NO: 385)
TCCCATATGGTCTAGCGGTTAGGATTCCTGGTTTTCACCCAGGTGGCCCGGGTTCGACTCCCGGTATGGGAA Homo_sapiens_chr1.trna2-GlyCCC (16926367-16926437) Gly (CCC) 71 bp Sc: 63.06
                                                                                    (SEQ ID NO: 386)
GCCTTGGTGGTGCAGTGGTAGAATTCTCGCCTCCCACGTGGGAGACCCGGGTTCAATTCCCGGCCAATGCA Homo_sapiens_chr1.trna130-GlyCCC (16877423-16877353) Gly (CCC) 71 bp Sc: 69.75
                                                                                    (SEQ ID NO: 387)
GCGTTGGTGGTTTAGTGGTAGAATTCTCGCCTCCCATGCGGGAGACCCGGGTTCAATTCCCGGCCACTGCA Homo_sapiens_chr17.trna13-GlyCCC (19704767-19704837) Gly (CCC) 71 bp Sc: 70.13
                                                                                    (SEQ ID NO: 388)
GCATTGGTGGTTCAATGGTAGAATTCTCGCCTCCCACGCAGGAGACCCAGGTTCGATTCCTGGCCAATGCA Homo_sapiens_chr16.trna34-GlyCCC (626807-626737) Gly (CCC) 71 bp Sc: 76.98
                                                                                    (SEQ ID NO: 389)
GCGCCGCTGGTGTAGTGGTATCATGCAAGATTCCCATTCTTGCGACCCGGGTTCGATTCCCGGGCGGCGCA Homo_sapiens_chr2.trna27-GlyCCC (70329697-70329627) Gly (CCC) 71 bp Sc: 76.98
                                                                                    (SEQ ID NO: 390)
GCGCCGCTGGTGTAGTGGTATCATGCAAGATTCCCATTCTTGCGACCCGGGTTCGATTCCCGGGCGGCGCA Homo_sapiens_chr1.trna132-GlyCCC (16745091-16745021) Gly (CCC) 71 bp Sc: 78.31
                                                                                    (SEQ ID NO: 391)
GCATTGGTGGTTCAGTGGTAGAATTCTCGCCTCCCACGCGGGAGACCCGGGTTCAATTCCCGGCCAATGCA Homo_sapiens_chr1.trna4-GlyCCC (17061003-17061073) Gly (CCC) 71 bp Sc: 78.31
                                                                                    (SEQ ID NO: 392)
GCATTGGTGGTTCAGTGGTAGAATTCTCGCCTCCCACGCGGGAGACCCGGGTTCAATTCCCGGCCAATGCA Homo_sapiens_chr6.trna82-GlyGCC (142620469-142620539) Gly (GCC) 71 bp Sc: 46.73
                                                                                    (SEQ ID NO: 393)
GCATGGGTGATTCAGTGGTAGAATTTTCACCTGCCATGCAGGAGGTCCAGGTTCATTTCCTGGCCTATGCA Homo_sapiens_chr16.trna18-GlyGCC (69380098-69380168) Gly (GCC) 71 bp Sc: 56.35
                                                                                    (SEQ ID NO: 394)
GCATTGGTGGTTCAGTGGTAGAATTCTCGCCTGCCATGCGGGCGGCCGGGCTTCGATTCCTGGCCAATGCA Homo_sapiens_chr1.trna43-GlyGCC (159716980-159717050) Gly (GCC) 71 bp Sc: 69.02
                                                                                    (SEQ ID NO: 395)
GCATAGGTGGTTCAGTGGTAGAATTCTTGCCTGCCACGCAGGAGGCCCAGGTTTGATTCCTGGCCCATGCA
```

-continued

Homo_sapiens_chr16.trna25-GlyGCC (69369685-69369615) Gly (GCC) 71 bp Sc: 73.97

(SEQ ID NO: 396)

GCATTGGTGGTTCAGTGGTAGAATTCTCGCCTGCCACGCGGGAGGCCCGGGTTTGATTCCCGGCCAGTGCA

Homo_sapiens_chr1.trna68-GlyGCC (159760331-159760261) Gly (GCC) 71 bp Sc: 81.62

(SEQ ID NO: 397)

GCATTGGTGGTTCAGTGGTAGAATTCTCGCCTGCCACGCGGGAGGCCCGGGTTCGATTCCCGGCCAATGCA

Homo_sapiens_chr16.trna19-GlyGCC (69380911-69380981) Gly (GCC) 71 bp Sc: 81.62

(SEQ ID NO: 398)

GCATTGGTGGTTCAGTGGTAGAATTCTCGCCTGCCACGCGGGAGGCCCGGGTTCGATTCCCGGCCAATGCA

Homo_sapiens_chr16.trna24-GlyGCC (69370513-69370443) Gly (GCC) 71 bp Sc: 81.62

(SEQ ID NO: 399)

GCATTGGTGGTTCAGTGGTAGAATTCTCGCCTGCCACGCGGGAGGCCCGGGTTCGATTCCCGGCCAATGCA

Homo_sapiens_chr17.trna5-GlyGCC (7969789-7969859) Gly (GCC) 71 bp Sc: 81.62

(SEQ ID NO: 400)

GCATTGGTGGTTCAGTGGTAGAATTCTCGCCTGCCACGCGGGAGGCCCGGGTTCGATTCCCGGCCAATGCA

Homo_sapiens_chr2.trna19-GlyGCC (156965975-156965905) Gly (GCC) 71 bp Sc: 81.62

(SEQ ID NO: 401)

GCATTGGTGGTTCAGTGGTAGAATTCTCGCCTGCCACGCGGGAGGCCCGGGTTCGATTCCCGGCCAATGCA

Homo_sapiens_chr6.trna128-GlyGCC (27978735-27978665) Gly (GCC) 71 bp Sc: 81.62

(SEQ ID NO: 402)

GCATTGGTGGTTCAGTGGTAGAATTCTCGCCTGCCACGCGGGAGGCCCGGGTTCGATTCCCGGCCAATGCA

Homo_sapiens_chr1.trna35-GlyGCC (159679718-159679788) Gly (GCC) 71 bp Sc: 82.15

(SEQ ID NO: 403)

GCATGGGTGGTTCAGTGGTAGAATTCTCGCCTGCCACGCGGGAGGCCCGGGTTCGATTCCCGGCCCATGCA

Homo_sapiens_chr1.trna37-GlyGCC (159687091-159687161) Gly (GCC) 71 bp Sc: 82.15

(SEQ ID NO: 404)

GCATGGGTGGTTCAGTGGTAGAATTCTCGCCTGCCACGCGGGAGGCCCGGGTTCGATTCCCGGCCCATGCA

Homo_sapiens_chr1.trna39-GlyGCC (159694522-159694592) Gly (GCC) 71 bp Sc: 82.15

(SEQ ID NO: 405)

GCATGGGTGGTTCAGTGGTAGAATTCTCGCCTGCCACGCGGGAGGCCCGGGTTCGATTCCCGGCCCATGCA

Homo_sapiens_chr1.trna41-GlyGCC (159701882-159701952) Gly (GCC) 71 bp Sc: 82.15

(SEQ ID NO: 406)

GCATGGGTGGTTCAGTGGTAGAATTCTCGCCTGCCACGCGGGAGGCCCGGGTTCGATTCCCGGCCCATGCA

Homo_sapiens_chr21.trna2-GlyGCC (17749048-17748978) Gly (GCC) 71 bp Sc: 82.15

(SEQ ID NO: 407)

GCATGGGTGGTTCAGTGGTAGAATTCTCGCCTGCCACGCGGGAGGCCCGGGTTCGATTCCCGGCCCATGCA

Homo_sapiens_chr1.trna82-GlyTCC (159676656-159676585) Gly (TCC) 72 bp Sc: 55.96

(SEQ ID NO: 408)

GCGTTGGTGGTATAGTGGTGAGCATAGTTGCCTTCCAAGCAGTTGACCCGGGCTCGATTCCCGCCCAACGCA

Homo_sapiens_chr17.trna10-GlyTCC (8065591-8065662) Gly (TCC) 72 bp Sc: 71.94

(SEQ ID NO: 409)

GCGTTGGTGGTATAGTGGTAAGCATAGCTGCCTTCCAAGCAGTTGACCCGGGTTCGATTCCCGGCCAACGCA

Homo_sapiens_chr1.trna117-GlyTCC (144109292-144109221) Gly (TCC) 72 bp Sc: 73.26

(SEQ ID NO: 410)

GCGTTGGTGGTATAGTGGTGAGCATAGCTGCCTTCCAAGCAGTTGACCCGGGTTCGATTCCCGGCCAACGCA

Homo_sapiens_chr1.trna45-GlyTCC (159767527-159767598) Gly (TCC) 72 bp Sc: 73.26

(SEQ ID NO: 411)

GCGTTGGTGGTATAGTGGTGAGCATAGCTGCCTTCCAAGCAGTTGACCCGGGTTCGATTCCCGGCCAACGCA

Homo_sapiens_chr1.trna70-GlyTCC (159706242-159706171) Gly (TCC) 72 bp Sc: 73.26

(SEQ ID NO: 412)

GCGTTGGTGGTATAGTGGTGAGCATAGCTGCCTTCCAAGCAGTTGACCCGGGTTCGATTCCCGGCCAACGCA

Homo_sapiens_chr1.trna73-GlyTCC (159698861-159698790) Gly (TCC) 72 bp Sc: 73.26

(SEQ ID NO: 413)

GCGTTGGTGGTATAGTGGTGAGCATAGCTGCCTTCCAAGCAGTTGACCCGGGTTCGATTCCCGGCCAACGCA

Homo_sapiens_chr1.trna76-GlyTCC (159691451-159691380) Gly (TCC) 72 bp Sc: 73.26

(SEQ ID NO: 414)

GCGTTGGTGGTATAGTGGTGAGCATAGCTGCCTTCCAAGCAGTTGACCCGGGTTCGATTCCCGGCCAACGCA

Homo_sapiens_chr1.trna79-GlyTCC (159684070-159683999) Gly (TCC) 72 bp Sc: 73.26

(SEQ ID NO: 415)

GCGTTGGTGGTATAGTGGTGAGCATAGCTGCCTTCCAAGCAGTTGACCCGGGTTCGATTCCCGGCCAACGCA

-continued

Homo_sapiens_chr19.trna2-GlyTCC (4675082-4675153) Gly (TCC) 72 bp Sc: 76.83

(SEQ ID NO: 416)

GCGTTGGTGGTATAGTGGTTAGCATAGCTGCCTTCCAAGCAGTTGACCCGGGTTCGATTCCCGGCCAACGCA

Homo_sapiens_chr3.trna4-HisGTG (149799324-149799253) His (GTG) 72 bp Sc: 22.51

(SEQ ID NO: 417)

GCAGTGACTCGTATAGTGGTTAGCACTCTGTGTTGTGGCCACAGCAACCATGGTTCAAATCTGAGTCATGACA

Homo_sapiens_chr1.trna106-HisGTG (147422523-147422452) His (GTG) 72 bp Sc: 61.09

(SEQ ID NO: 418)

GCCATGATCGTATAGTGGTTAGTACTCTGCGCTGTGGCCGCAGCAACCTCGGTTCGAATCCGAGTCACGGCA

Homo_sapiens_chr1.trna111-HisGTG (146241540-146241469) His (GTG) 72 bp Sc: 64.63

(SEQ ID NO: 419)

GCCGTGATCGTATAGTGGTTAGTACTCTGCGTTGTGGCCGCAGCAACCTCGGTTCGAATCCGAGTCACGGCA

Homo_sapiens_chr1.trna118-HisGTG (144108309-144108238) His (GTG) 72 bp Sc: 64.63

(SEQ ID NO: 420)

GCCGTGATCGTATAGTGGTTAGTACTCTGCGTTGTGGCCGCAGCAACCTCGGTTCGAATCCGAGTCACGGCA

Homo_sapiens_chr1.trna16-HisGTG (145011397-145011468) His (GTG) 72 bp Sc: 64.63

(SEQ ID NO: 421)

GCCGTGATCGTATAGTGGTTAGTACTCTGCGTTGTGGCCGCAGCAACCTCGGTTCGAATCCGAGTCACGGCA

Homo_sapiens_chr1.trna21-HisGTG (146220095-146220166) His (GTG) 72 bp Sc: 64.63

(SEQ ID NO: 422)

GCCGTGATCGTATAGTGGTTAGTACTCTGCGTTGTGGCCGCAGCAACCTCGGTTCGAATCCGAGTCACGGCA

Homo_sapiens_chr15.trna1-HisGTG (43280641-43280712) His (GTG) 72 bp Sc: 64.63

(SEQ ID NO: 423)

GCCGTGATCGTATAGTGGTTAGTACTCTGCGTTGTGGCCGCAGCAACCTCGGTTCGAATCCGAGTCACGGCA

Homo_sapiens_chr15.trna8-HisGTG (43279974-43279903) His (GTG) 72 bp Sc: 64.63

(SEQ ID NO: 424)

GCCGTGATCGTATAGTGGTTAGTACTCTGCGTTGTGGCCGCAGCAACCTCGGTTCGAATCCGAGTCACGGCA

Homo_sapiens_chr15.trna9-HisGTG (43278167-43278096) His (GTG) 72 bp Sc: 64.63

(SEQ ID NO: 425)

GCCGTGATCGTATAGTGGTTAGTACTCTGCGTTGTGGCCGCAGCAACCTCGGTTCGAATCCGAGTCACGGCA

Homo_sapiens_chr6.trna33-HisGTG (27233885-27233956) His (GTG) 72 bp Sc: 64.63

(SEQ ID NO: 426)

GCCGTGATCGTATAGTGGTTAGTACTCTGCGTTGTGGCCGCAGCAACCTCGGTTCGAATCCGAGTCACGGCA

Homo_sapiens_chr9.trna7-HisGTG (14424009-14423938) His (GTG) 72 bp Sc: 64.63

(SEQ ID NO: 427)

GCCGTGATCGTATAGTGGTTAGTACTCTGCGTTGTGGCCGCAGCAACCTCGGTTCGAATCCGAGTCACGGCA

Homo_sapiens_chr6.trna38-IleAAT (27349718-27349791) Ile (AAT) 74 bp Sc: 75.35

(SEQ ID NO: 428)

GGCTGGTTAGTTCAGTTGGTTAGAGCGTGGTGCTAATAACGCCAAGGTCGTGGGTTCGATCCCCATATCGGCCA

Homo_sapiens_chr6.trna57-IleAAT (27744341-27744414) Ile (AAT) 74 bp Sc: 76.09

(SEQ ID NO: 429)

GGCCGGTTAGCTCAGTCGGCTAGAGCGTGGTGCTAATAACGCCAAGGTCGCGGGTTCGATCCCCGTACGGGCCA

Homo_sapiens_chr6.trna165-IleAAT (26829273-26829200) Ile (AAT) 74 bp Sc: 78.57

(SEQ ID NO: 430)

GGCCGGTTAGCTCAGTTGGTCAGAGCGTGGTGCTAATAACGCCAAGGTCGCGGGTTCGATCCCCGTACGGGCCA

Homo_sapiens_chr6.trna28-IleAAT (26888811-26888884) Ile (AAT) 74 bp Sc: 78.57

(SEQ ID NO: 431)

GGCCGGTTAGCTCAGTTGGTCAGAGCGTGGTGCTAATAACGCCAAGGTCGCGGGTTCGATCCCCGTACGGGCCA

Homo_sapiens_chr6.trna163-IleAAT (26853307-26853234) Ile (AAT) 74 bp Sc: 79.57

(SEQ ID NO: 432)

GGCCGGTTAGCTCAGTTGGTTAGAGCGTGGTGCTAATAACGCTAAGGTCGCGGGTTCGATCCCCGTACTGGCCA

Homo_sapiens_chr14.trna10-IleAAT (101853182-101853255) Ile (AAT) 74 bp Sc: 80.66

(SEQ ID NO: 433)

GGCCGGTTAGCTCAGTTGGTTAGAGCGTGGTGCTAATAACGCCAAGGTCGCGGGTTCGATCCCCGTACGGGCCA

Homo_sapiens_chr17.trna9-IleAAT (8031636-8031709) Ile (AAT) 74 bp Sc: 80.66

(SEQ ID NO: 434)

GGCCGGTTAGCTCAGTTGGTTAGAGCGTGGTGCTAATAACGCCAAGGTCGCGGGTTCGATCCCCGTACGGGCCA

Homo_sapiens_chr6.trna11-IleAAT (26662329-26662402) Ile (AAT) 74 bp Sc: 80.66

(SEQ ID NO: 435)

GGCCGGTTAGCTCAGTTGGTTAGAGCGTGGTGCTAATAACGCCAAGGTCGCGGGTTCGATCCCCGTACGGGCCA

-continued

Homo_sapiens_chr6.trna154-IleAAT (27313402-27313329) Ile (AAT) 74 bp Sc: 80.66

(SEQ ID NO: 436)

GGCCGGTTAGCTCAGTTGGTTAGAGCGTGGTGCTAATAACGCCAAGGTCGCGGGTTCGATCCCCGTACGGGCCA

Homo_sapiens_chr6.trna158-IleAAT (27253046-27252973) Ile (AAT) 74 bp Sc: 80.66

(SEQ ID NO: 437)

GGCCGGTTAGCTCAGTTGGTTAGAGCGTGGTGCTAATAACGCCAAGGTCGCGGGTTCGATCCCCGTACGGGCCA

Homo_sapiens_chr17.trna34-IleAAT (8071107-8071034) Ile (AAT) 74 bp Sc: 80.89

(SEQ ID NO: 438)

GGCCGGTTAGCTCAGTTGGTTAGAGCGTGGTGCTAATAACGCCAAGGTCGCGGGTTCGAACCCCGTACGGGCCA

Homo_sapiens_chr6.trna153-IleAAT (27351042-27350969) Ile (AAT) 74 bp Sc: 82.10

(SEQ ID NO: 439)

GGCTGGTTAGCTCAGTTGGTTAGAGCGTGGTGCTAATAACGCCAAGGTCGCGGGTTCGATCCCCGTACTGGCCA

Homo_sapiens_chr6.trna59-IleAAT (27763946-27764019) Ile (AAT) 74 bp Sc: 83.32

(SEQ ID NO: 440)

GGCCGGTTAGCTCAGTTGGTTAGAGCGTGGTGCTAATAACGCCAAGGTCGCGGGTTCGATCCCCGTACTGGCCA

Homo_sapiens_chr6.trna80-IleAAT (58257213-58257286) Ile (AAT) 74 bp Sc: 83.55

(SEQ ID NO: 441)

GGCCGGTTAGCTCAGTTGGTTAGAGCGTGGCGCTAATAACGCCAAGGTCGCGGGTTCGATCCCCGTACGGGCCA

Homo_sapiens_chrX.trna5-IleGAT (3843344-3843271) Ile (GAT) 74 bp Sc: 72.42

(SEQ ID NO: 442)

GGCCGGTTAGCTCAGTTGGTAAGAGCGTGGTGCTGATAACACCAAGGTCGCGGGCTCGACTCCCGCACCGGCCA

Homo_sapiens_chrX.trna6-IleGAT (3804915-3804842) Ile (GAT) 74 bp Sc: 72.42

(SEQ ID NO: 443)

GGCCGGTTAGCTCAGTTGGTAAGAGCGTGGTGCTGATAACACCAAGGTCGCGGGCTCGACTCCCGCACCGGCCA

Homo_sapiens_chrX.trna7-IleGAT (3766491-3766418) Ile (GAT) 74 bp Sc: 72.42

(SEQ ID NO: 444)

GGCCGGTTAGCTCAGTTGGTAAGAGCGTGGTGCTGATAACACCAAGGTCGCGGGCTCGACTCCCGCACCGGCCA

Homo_sapiens_chrX_random.trna1-IleGAT (118398-118471) Ile (GAT) 74 bp Sc: 72.42

(SEQ ID NO: 445)

GGCCGGTTAGCTCAGTTGGTAAGAGCGTGGTGCTGATAACACCAAGGTCGCGGGCTCGACTCCCGCACCGGCCA

Homo_sapiens_chrX_random.trna2-IleGAT (406943-407016) Ile (GAT) 74 bp Sc: 72.42

(SEQ ID NO: 446)

GGCCGGTTAGCTCAGTTGGTAAGAGCGTGGTGCTGATAACACCAAGGTCGCGGGCTCGACTCCCGCACCGGCCA

Homo_sapiens_chrX_random.trna3-IleGAT (465544-465617) Ile (GAT) 74 bp Sc: 72.42

(SEQ ID NO: 447)

GGCCGGTTAGCTCAGTTGGTAAGAGCGTGGTGCTGATAACACCAAGGTCGCGGGCTCGACTCCCGCACCGGCCA

Homo_sapiens_chrX_random.trna4-IleGAT (399021-398948) Ile (GAT) 74 bp Sc: 72.42

(SEQ ID NO: 448)

GGCCGGTTAGCTCAGTTGGTAAGAGCGTGGTGCTGATAACACCAAGGTCGCGGGCTCGACTCCCGCACCGGCCA

Homo_sapiens_chrX_random.trna5-IleGAT (86496-86423) Ile (GAT) 74 bp Sc: 72.42

(SEQ ID NO: 449)

GGCCGGTTAGCTCAGTTGGTAAGAGCGTGGTGCTGATAACACCAAGGTCGCGGGCTCGACTCCCGCACCGGCCA

Homo_sapiens_chr6.trna29-IleTAT (27096104-27096197) Ile (TAT) 94 bp Sc: 67.58

(SEQ ID NO: 450)

GCTCCAGTGGCGCAATCGGTTAGCGCGCGGTACTTATATGGCAGTATGTGTGCGAGTGATGCCGAGGTTGTGAGTTCGAGCCTCACCTGGAGCA

Homo_sapiens_chr6.trna55-IleTAT (27707179-27707272) Ile (TAT) 94 bp Sc: 68.23

(SEQ ID NO: 451)

GCTCCAGTGGCGCAATCGGTTAGCGCGCGGTACTTATACAACAGTATATGTGCGGGTGATGCCGAGGTTGTGAGTTCGAGCCTCACCTGGAGCA

Homo_sapiens_chr6.trna63-IleTAT (28613346-28613439) Ile (TAT) 94 bp Sc: 65.86

(SEQ ID NO: 452)

GCTCCAGTGGCGCAATCGGTTAGCGCGCGGTACTTATAAGACAGTGCACCTGTGAGCAATGCCGAGGTTGTGAGTTCAAGCCTCACCTGGAGCA

Homo_sapiens_chr2.trna5-IleTAT (42891180-42891272) Ile (TAT) 93 bp Sc: 68.11

(SEQ ID NO: 453)

GCTCCAGTGGCGCAATCGGTTAGCGCGCGGTACTTATACAGCAGTACATGCAGAGCAATGCCGAGGTTGTGAGTTCGAGCCTCACCTGGAGCA

Homo_sapiens_chr19.trna10-IleTAT (44594740-44594648) Ile (TAT) 93 bp Sc: 68.39

(SEQ ID NO: 454)

GCTCCAGTGGCGCAATCGGTTAGCGCGCGGTACTTATATGACAGTGCGAGCGGAGCAATGCCGAGGTTGTGAGTTCGATCCTCACCTGGAGCA

Homo_sapiens_chr3.trna5-LeuAAG (149703999-149703918) Leu (AAG) 82 bp Sc: 20.79

(SEQ ID NO: 455)

GGTAGCATGGCTGAGTGGTCTAAGATTCTGAATTAAGTCTCCAGTCTCTTTGGGGGCGTGGTTTTCAATCCCACCGCTGCTA

-continued

Homo_sapiens_chr20.trna6-LeuAAG (48385830-48385749) Leu (AAG) 82 bp Sc: 40.72

(SEQ ID NO: 456)

GGTAGGGTGGCCGAGCGGTCTAAGGCACTGTATTAAGACTCCAGTCTCTTCAGAGGCATGGGTTTGAATCCCACTGCTGCCA

Homo_sapiens_chr2.trna4-LeuAAG (30131072-30131144) Leu (AAG) 73 bp Sc: 46.12

(SEQ ID NO: 457)

GGGCCAGTGGCTCAATGGATAATGCGTCTGACTAAGAATCAGAAGATTCCAGCCTTGACTCCTGGCTGGCTCA

Homo_sapiens_chr6.trna126-LeuAAG (28554460-28554379) Leu (AAG) 82 bp Sc: 59.09

(SEQ ID NO: 458)

GGTAGCGTGGCCGAGTGGTCTAAGACGCTGGATTAAGGCTCCAGTCTCTTCGGGGCGTGGGTTTGAATCCCACCGCTGCCA

Homo_sapiens_chr6.trna78-LeuAAG (29064758-29064839) Leu (AAG) 82 bp Sc: 68.10

(SEQ ID NO: 459)

GGTAGCGTGGCCGAGCGGTCTAAGGCGCTGGATTAAGGCTCCAGTCTCTTCGGGGCGTGGGTTCAAATCCCACCGCTGCCA

Homo_sapiens_chr14.trna1-LeuAAG (20148131-20148212) Leu (AAG) 82 bp Sc: 69.84

(SEQ ID NO: 460)

GGTAGCGTGGCCGAGCGGTCTAAGGCGCTGGATTAAGGCTCCAGTCTCTTCGGGGCGTGGGTTCGAATCCCACCGCTGCCA

Homo_sapiens_chr16.trna16-LeuAAG (22215962-22216043) Leu (AAG) 82 bp Sc: 69.84

(SEQ ID NO: 461)

GGTAGCGTGGCCGAGCGGTCTAAGGCGCTGGATTAAGGCTCCAGTCTCTTCGGGGCGTGGGTTCGAATCCCACCGCTGCCA

Homo_sapiens_chr5.trna7-LeuAAG (180547307-180547388) Leu (AAG) 82 bp Sc: 69.84

(SEQ ID NO: 462)

GGTAGCGTGGCCGAGCGGTCTAAGGCGCTGGATTAAGGCTCCAGTCTCTTCGGGGCGTGGGTTCGAATCCCACCGCTGCCA

Homo_sapiens_chr6.trna98-LeuAAG (29019459-29019378) Leu (AAG) 82 bp Sc: 69.84

(SEQ ID NO: 463)

GGTAGCGTGGCCGAGCGGTCTAAGGCGCTGGATTAAGGCTCCAGTCTCTTCGGGGCGTGGGTTCGAATCCCACCGCTGCCA

Homo_sapiens_chr5.trna16-LeuAAG (180533731-180533650) Leu (AAG) 82 bp Sc: 71.96

(SEQ ID NO: 464)

GGTAGCGTGGCCGAGCGGTCTAAGGCGCTGGATTAAGGCTCCAGTCTCTTCGGAGGCGTGGGTTCGAATCCCACCGCTGCCA

Homo_sapiens_chr5.trna19-LeuAAG (180457161-180457080) Leu (AAG) 82 bp Sc: 71.96

(SEQ ID NO: 465)

GGTAGCGTGGCCGAGCGGTCTAAGGCGCTGGATTAAGGCTCCAGTCTCTTCGGAGGCGTGGGTTCGAATCCCACCGCTGCCA

Homo_sapiens_chr5.trna3-LeuAAG (180461446-180461527) Leu (AAG) 82 bp Sc: 71.96

(SEQ ID NO: 466)

GGTAGCGTGGCCGAGCGGTCTAAGGCGCTGGATTAAGGCTCCAGTCTCTTCGGAGGCGTGGGTTCGAATCCCACCGCTGCCA

Homo_sapiens_chr1.trna66-LeuCAA (159848443-159848360) Leu (CAA) 84 bp Sc: 59.01

(SEQ ID NO: 467)

GTCAGGATGGCCGAGCAGTCTTAAGGCGCTGCGTTCAAATCGCACCCTCCGCTGGAGGCGTGGGTTCGAATCCCACTTTTGACA

Homo_sapiens_chr11.trna1-LeuCAA (9253366-9253439) Leu (CAA) 74 bp Sc: 60.99

(SEQ ID NO: 468)

GCCTCCTTAGTGCAGTAGGTAGCGCATCAGTCTCAAAATCTGAATGGTCCTGAGTTCAAGCCTCAGAGGGGCA

Homo_sapiens_chr1.trna58-LeuCAA (247134677-247134782) Leu (CAA) 106 bp Sc: 65.69

(SEQ ID NO: 469)

GTCAGGATGGCCGAGTGGTCTAAGGCGCCAGACTCAAGGTAAGCACCTTGCCTGCGGGCTTTCTGGTCTCCGGATGGAGGCGTGGGTTCGAATCCCACTTCTG

ACA

Homo_sapiens_chr6.trna141-LeuCAA (27678433-27678327) Leu (CAA) 107 bp Sc: 68.19

(SEQ ID NO: 470)

GTCAGGATGGCCGAGTGGTCTAAGGCGCCAGACTCAAGTTGCTACTTCCCAGGTTTGGGCTTCTGGTCTCCGCATGGAGGCGTGGGTTCGAATCCCACTTCT

GACA

Homo_sapiens_chr6.trna140-LeuCAA (27681503-27681396) Leu (CAA) 108 bp Sc: 68.53

(SEQ ID NO: 471)

GTCAGGATGGCCGAGTGGTCTAAGGCGCCAGACTCAAGCTTACTGCTTCCTGTGTTCGGGTCTTCTGGTCTCCGTATGGAGGCGTGGGTTCGAATCCCACTTC

TGACA

Homo_sapiens_chr6.trna100-LeuCAA (28972084-28971979) Leu (CAA) 106 bp Sc: 68.23

(SEQ ID NO: 472)

GTCAGGATGGCCGAGTGGTCTAAGGCGCCAGACTCAAGCTAAGCTTCCTCCGCGGTGGGGATTCTGGTCTCCAATGGAGGCGTGGGTTCGAATCCCACTTCTG

ACA

-continued

Homo_sapiens_chr6.trna74-LeuCAA (29016809-29016913) Leu (CAA) 105 bp Sc: 69.73
(SEQ ID NO: 473)
GTCAGGATGGCCGAGTGGTCTAAGGCGCCAGACTCAAGCTTGGCTTCCTCGTGTTGAGGATTCTGGTCTCCAATGGAGGCGGGGTTCGAATCCCACTTCTGAC
AT Homo_sapiens_chr5.trna20-LeuCAG (159324696-159324619) Leu (CAG) 78 bp Sc: 20.45
(SEQ ID NO: 474)
GGCAGTGGAGTTTAGTGGTTAAGGACCTGCTCAGACATCACAGGTAGGTAGATCTGGGTTCAAACCCTAGCCCTGGCA Homo_sapiens_chr16.trna17-LeuCAG (55891364-55891446) Leu (CAG) 83 bp Sc: 75.90
(SEQ ID NO: 475)
GTCAGGATGGCCGAGCGGTCTAAGGCGCTGCGTTCAGGTCGCAGTCTCCCCTGGAGGCGTGGGTTCGAATCCCACTTCTGACA Homo_sapiens_chr16.trna26-LeuCAG (55891975-55891893) Leu (CAG) 83 bp Sc: 75.90
(SEQ ID NO: 476)
GTCAGGATGGCCGAGCGGTCTAAGGCGCTGCGTTCAGGTCGCAGTCTCCCCTGGAGGCGTGGGTTCGAATCCCACTTCTGACA Homo_sapiens_chr1.trna34-LeuCAG (159677947-159678029) Leu (CAG) 83 bp Sc: 77.22
(SEQ ID NO: 477)
GTCAGGATGGCCGAGCGGTCTAAGGCGCTGCGTTCAGGTCGCAGTCTCCCCTGGAGGCGTGGGTTCGAATCCCACTCCTGACA Homo_sapiens_chr1.trna36-LeuCAG (159685365-159685447) Leu (CAG) 83 bp Sc: 77.22
(SEQ ID NO: 478)
GTCAGGATGGCCGAGCGGTCTAAGGCGCTGCGTTCAGGTCGCAGTCTCCCCTGGAGGCGTGGGTTCGAATCCCACTCCTGACA Homo_sapiens_chr1.trna38-LeuCAG (159692746-159692828) Leu (CAG) 83 bp Sc: 77.22
(SEQ ID NO: 479)
GTCAGGATGGCCGAGCGGTCTAAGGCGCTGCGTTCAGGTCGCAGTCTCCCCTGGAGGCGTGGGTTCGAATCCCACTCCTGACA Homo_sapiens_chr1.trna40-LeuCAG (159700156-159700238) Leu (CAG) 83 bp Sc: 77.22
(SEQ ID NO: 480)
GTCAGGATGGCCGAGCGGTCTAAGGCGCTGCGTTCAGGTCGCAGTCTCCCCTGGAGGCGTGGGTTCGAATCCCACTCCTGACA Homo_sapiens_chr1.trna42-LeuCAG (159707537-159707619) Leu (CAG) 83 bp Sc: 77.22
(SEQ ID NO: 481)
GTCAGGATGGCCGAGCGGTCTAAGGCGCTGCGTTCAGGTCGCAGTCTCCCCTGGAGGCGTGGGTTCGAATCCCACTCCTGACA Homo_sapiens_chr1.trna67-LeuCAG (159766838-159766756) Leu (CAG) 83 bp Sc: 77.22
(SEQ ID NO: 482)
GTCAGGATGGCCGAGCGGTCTAAGGCGCTGCGTTCAGGTCGCAGTCTCCCCTGGAGGCGTGGGTTCGAATCCCACTCCTGACA Homo_sapiens_chr6.trna7-LeuCAG (26629415-26629497) Leu (CAG) 83 bp Sc: 77.22
(SEQ ID NO: 483)
GTCAGGATGGCCGAGCGGTCTAAGGCGCTGCGTTCAGGTCGCAGTCTCCCCTGGAGGCGTGGGTTCGAATCCCACTCCTGACA Homo_sapiens_chrX.trna2-LeuTAA (55224554-55224480) Leu (TAA) 75 bp Sc: 28.07
(SEQ ID NO: 484)
GTTAAGATGGCAGAGCCCGGCAATTGCATAAGACTTAAAACTTTATAATCAGAGGTTCAACTCCTCTCATTAACA Homo_sapiens_chr6.trna81-LeuTAA (69971099-69971181) Leu (TAA) 83 bp Sc: 34.00
(SEQ ID NO: 485)
ACTCATTTGGCTGAGTGGTTAAGGCATTGGACTTAAGATCCAATGGAGTAGTGGCTGTGTGGGTTTAAACCCCACTACTGGTA Homo_sapiens_chr4.trna2-LeuTAA (156604502-156604428) Leu (TAA) 75 bp Sc: 48.70
(SEQ ID NO: 486)
GTTAAGATGGCAGAGCCTGGTAATTGCATAAAACTTAAAATTTTATAATCAGAGGTTCAACTCCTCTTCTTAACA Homo_sapiens_chr6.trna155-LeuTAA (27306395-27306313) Leu (TAA) 83 bp Sc: 74.34
(SEQ ID NO: 487)
ACCGGGATGGCTGAGTGGTTAAGGCGTTGGACTTAAGATCCAATGGACAGGTGTCCGCGTGGGTTCGAGCCCCACTCCCGGTA Homo_sapiens_chr11.trna4-LeuTAA (59075804-59075886) Leu (TAA) 83 bp Sc: 79.52
(SEQ ID NO: 488)
ACCAGAATGGCCGAGTGGTTAAGGCGTTGGACTTAAGATCCAATGGATTCATATCCGCGTGGGTTCGAACCCCACTTCTGGTA Homo_sapiens_chr6.trna134-LeuTAA (27796959-27796877) Leu (TAA) 83 bp Sc: 80.48
(SEQ ID NO: 489)
ACCGGGATGGCCGAGTGGTTAAGGCGTTGGACTTAAGATCCAATGGGCTGGTGCCCGCGTGGGTTCGAACCCCACTCTCGGTA Homo_sapiens_chr6.trna83-LeuTAA (144579377-144579459) Leu (TAA) 83 bp Sc: 80.77
(SEQ ID NO: 490)
ACCAGGATGGCCGAGTGGTTAAGGCGTTGGACTTAAGATCCAATGGACATATGTCCGCGTGGGTTCGAACCCCACTCCTGGTA Homo_sapiens_chr16.trna27-LeuTAG (22114614-22114533) Leu (TAG) 82 bp Sc: 68.14
(SEQ ID NO: 491)
GGTAGCGTGGCCGAGTGGTCTAAGGCGCTGGATTTAGGCTCCAGTCATTTCGATGGCGTGGGTTCGAATCCCACCGCTGCCA Homo_sapiens_chr14.trna2-LeuTAG (20163369-20163450) Leu (TAG) 82 bp Sc: 68.82

(SEQ ID NO: 492)

GGTAGTGTGGCCGAGCGGTCTAAGGCGCTGGATTTAGGCTCCAGTCTCTTCGGGGGCGTGGGTTCGAATCCCACCACTGCCA

Homo_sapiens_chr17.trna42-LeuTAG (7964438-7964357) Leu (TAG) 82 bp Sc: 72.19

(SEQ ID NO: 493)

GGTAGCGTGGCCGAGCGGTCTAAGGCGCTGGATTTAGGCTCCAGTCTCTTCGGAGGCGTGGGTTCGAATCCCACCGCTGCCA

Homo_sapiens_chr11.trna2-LysCTT (51216476-51216548) Lys (CTT) 73 bp Sc: 40.00

(SEQ ID NO: 494)

AACCGAATAGCTTAGTTGATGAAGCGTGAGAGCTCTTAATCTCAGGGTAGTGGGTTCAAGCCCCACATTGGACA

Homo_sapiens_chr19.trna6-LysCTT (57117280-57117208) Lys (CTT) 73 bp Sc: 51.97

(SEQ ID NO: 495)

CTGCAGCTAGCTCAGTCGGTAGAGCATGAGACTCTTAATCTCAGGGTCATGGGTTCGTGCCCCATGTTGGGTG

Homo_sapiens_chr19.trna5-LysCTT (40758590-40758662) Lys (CTT) 73 bp Sc: 52.67

(SEQ ID NO: 496)

GCCCAGCTAGCTCAGTCGGTAGAGCATAAGACTCTTAATCTCAGGGTTGTGGATTCGTGCCCCATGCTGGGTG

Homo_sapiens_chr5.trna24-LysCTT (26234368-26234296) Lys (CTT) 73 bp Sc: 53.34

(SEQ ID NO: 497)

GCCCGACTACCTCAGTCGGTGGAGCATGGGACTCTTCATCCCAGGGTTGTGGGTTCGAGCCCCACATTGGGCA

Homo_sapiens_chr16.trna5-LysCTT (3154940-3155012) Lys (CTT) 73 bp Sc: 54.80

(SEQ ID NO: 498)

GCCTGGCTAGCTCAGTCGGCAAAGCATGAGACTCTTAATCTCAGGGTCGTGGGCTCGAGCTCCATGTTGGGCG

Homo_sapiens_chr1.trna127-LysCTT (55196202-55196130) Lys (CTT) 73 bp Sc: 58.75

(SEQ ID NO: 499)

GCCCAGCTAGCTCAGTCGGTAGAGCATGAGACTCTTAATCTCAGGGTCATGGGTTTGAGCCCCACGTTTGGTG

Homo_sapiens_chr18.trna4-LysCTT (41923341-41923269) Lys (CTT) 73 bp Sc: 60.42

(SEQ ID NO: 500)

GACGAGCTAGCTCAGTCGGTAGAGCATGGGACTCTTAATCCCAGGGTCGTGGGTTTGAGCCCCATGTTGGGCA

Homo_sapiens_chr16.trna30-LysCTT (3170628-3170556) Lys (CTT) 73 bp Sc: 64.91

(SEQ ID NO: 501)

GCCCGGCTAGCTCAGTCGGATAGAGCATGAGACTCTTAATCTCAGGGTCGTGGGTTCGAGCCGCACGTTGGGCG

Homo_sapiens_chr16.trna10-LysCTT (3181502-3181574) Lys (CTT) 73 bp Sc: 74.61

(SEQ ID NO: 502)

GCCCGGCTAGCTCAGTCGGTAGAGCATGGGACTCTTAATCTCAGGGTCGTGGGTTCGAGCCCCACGTTGGGCG

Homo_sapiens_chr16.trna32-LysCTT (3147479-3147407) Lys (CTT) 73 bp Sc: 76.19

(SEQ ID NO: 503)

GCCCGGCTAGCTCAGTCGGTAGAGCATGAGACCCTTAATCTCAGGGTCGTGGGTTCGAGCCCCACGTTGGGCG

Homo_sapiens_chr1.trna119-LysCTT (144106951-144106879) Lys (CTT) 73 bp Sc: 80.47

(SEQ ID NO: 504)

GCCCGGCTAGCTCAGTCGGTAGAGCATGAGACTCTTAATCTCAGGGTCGTGGGTTCGAGCCCCACGTTGGGCG

Homo_sapiens_chr16.trna7-LysCTT (3165693-3165765) Lys (CTT) 73 bp Sc: 80.47

(SEQ ID NO: 505)

GCCCGGCTAGCTCAGTCGGTAGAGCATGAGACTCTTAATCTCAGGGTCGTGGGTTCGAGCCCCACGTTGGGCG

Homo_sapiens_chr5.trna11-LysCTT (180581657-180581585) Lys (CTT) 73 bp Sc: 80.47

(SEQ ID NO: 506)

GCCCGGCTAGCTCAGTCGGTAGAGCATGAGACTCTTAATCTCAGGGTCGTGGGTTCGAGCCCCACGTTGGGCG

Homo_sapiens_chr5.trna9-LysCTT (180567361-180567433) Lys (CTT) 73 bp Sc: 80.47

(SEQ ID NO: 507)

GCCCGGCTAGCTCAGTCGGTAGAGCATGAGACTCTAATCTCAGGGTCGTGGGTTCGAGCCCCACGTTGGGCG

Homo_sapiens_chr6.trna13-LysCTT (26664753-26664825) Lys (CTT) 73 bp Sc: 80.47

(SEQ ID NO: 508)

GCCCGGCTAGCTCAGTCGGTAGAGCATGAGACTCTTAATCTCAGGGTCGTGGGTTCGAGCCCCACGTTGGGCG

Homo_sapiens_chr14.trna13-LysCTT (57776438-57776366) Lys (CTT) 73 bp Sc: 80.72

(SEQ ID NO: 509)

GCCCGGCTAGCTCAGTCGGTAGAGCATGGGACTCTTAATCCCAGGGTCGTGGGTTCGAGCCCCACGTTGGGCG

Homo_sapiens_chr15.trna2-LysCTT (76939959-76940031) Lys (CTT) 73 bp Sc: 80.72

(SEQ ID NO: 510)

GCCCGGCTAGCTCAGTCGGTAGAGCATGGGACTCTTAATCCCAGGGTCGTGGGTTCGAGCCCCACGTTGGGCG

Homo_sapiens_chr19.trna3-LysTTT (19713207-19713277) Lys (TTT) 71 bp Sc: 28.27

(SEQ ID NO: 511)

ACCCTGTGGTACAGGGGCTAATATGCTGGGCCTTTACCACTTCAGCCCAGGTTCGATTCCTGGTCAGGGAA

-continued

Homo_sapiens_chr19.trna7-LysTTT (54729817-54729745) Lys (TTT) 73 bp Sc: 48.15

(SEQ ID NO: 512)

ACCTGGGTAGCTTAGTTGGTAGAGCATTGGACTTTTAATTTGAGGGCCCAGGTTTCAAGTCCCTGTTTGGGTG

Homo_sapiens_chr12.trna1-LysTTT (27734573-27734645) Lys (TTT) 73 bp Sc: 49.92

(SEQ ID NO: 513)

ACCCAGATAGCTCAGTCAGTAGAGCATCAGACTTTTAATCTGAGGGTCCAAGGTTCATGTCCCTTTTTGGGTG

Homo_sapiens_chr6.trna53-LysTTT (27651825-27651897) Lys (TTT) 73 bp Sc: 59.40

(SEQ ID NO: 514)

ACCTGGGTAGCTCAGTAGGTAGAACATCAGACTTTTAATCTGAGGGTCTAGGGTTCAAGTCCCTGTCCAGGCG

Homo_sapiens_chr1.trna55-LysTTT (203709894-203709966) Lys (TTT) 73 bp Sc: 62.89

(SEQ ID NO: 515)

GCCCGGAGAGCTCAGTGGGTAGAGCATCAGACTTTTAATCTGAGGGTCCAGGGTTCAAGTCCTCGTTCGGGCA

Homo_sapiens_chr7_random.trna1-LysTTT (397621-397697) Lys (TTT) 77 bp Sc: 68.40

(SEQ ID NO: 516)

GCCCACGTAGCTCAATGGTCAGAGCGTGCGGCTTTTAACCGCAAGGAAGGCTGCGAGTTCGACCCTCGCCGTGGGCT

Homo_sapiens_chr6.trna71-LysTTT (28823500-28823572) Lys (TTT) 73 bp Sc: 72.00

(SEQ ID NO: 517)

GCCTGGATAGCTCAGTTGGTAGAACATCAGACTTTTAATCTGACGGTGCAGGGTTCAAGTCCCTGTTCAGGCG

Homo_sapiens_chr6.trna149-LysTTT (27410820-27410748) Lys (TTT) 73 bp Sc: 81.41

(SEQ ID NO: 518)

GCCTGGGTAGCTCAGTCGGTAGAGCATCAGACTTTTAATCTGAGGGTCCAGGGTTCAAGTCCCTGTCCAGGCG

Homo_sapiens_chr11.trna5-LysTTT (59080478-59080550) Lys (TTT) 73 bp Sc: 82.14

(SEQ ID NO: 519)

GCCCGGATAGCTCAGTCGGTAGAGCATCAGACTTTTAATCTGAGGGTCCGGGGTTCAAGTCCCTGTTCGGGCG

Homo_sapiens_chr6.trna143-LysTTT (27667644-27667572) Lys (TTT) 73 bp Sc: 83.31

(SEQ ID NO: 520)

GCCTGGATAGCTCAGTCGGTAGAGCATCAGACTTTTAATCTGAGGGTCCAGGGTTCAAGTCCCTGTTCAGGCG

Homo_sapiens_chr1.trna54-LysTTT (202742278-202742350) Lys (TTT) 73 bp Sc: 83.80

(SEQ ID NO: 521)

GCCCGGATAGCTCAGTCGGTAGAGCATCAGACTTTTAATCTGAGGGTCCAGGGTTCAAGTCCCTGTTCGGGCG

Homo_sapiens_chr1.trna62-LysTTT (202742853-202742781) Lys (TTT) 73 bp Sc: 83.80

(SEQ ID NO: 522)

GCCCGGATAGCTCAGTCGGTAGAGCATCAGACTTTTAATCTGAGGGTCCAGGGTTCAAGTCCCTGTTCGGGCG

Homo_sapiens_chr11.trna14-LysTTT (59084456-59084384) Lys (TTT) 73 bp Sc: 83.80

(SEQ ID NO: 523)

GCCCGGATAGCTCAGTCGGTAGAGCATCAGACTTTTAATCTGAGGGTCCAGGGTTCAAGTCCCTGTTCGGGCG

Homo_sapiens_chr17.trna2-LysTTT (7963198-7963270) Lys (TTT) 73 bp Sc: 83.80

(SEQ ID NO: 524)

GCCCGGATAGCTCAGTCGGTAGAGCATCAGACTTTTAATCTGAGGGTCCAGGGTTCAAGTCCCTGTTCGGGCG

Homo_sapiens_chr6.trna76-LysTTT (29026785-29026857) Lys (TTT) 73 bp Sc: 83.80

(SEQ ID NO: 525)

GCCCGGATAGCTCAGTCGGTAGAGCATCAGACTTTTAATCTGAGGGTCCAGGGTTCAAGTCCCTGTTCGGGCG

Homo_sapiens_chr11.trna11-LysTTT (121935865-121935937) Lys (TTT) 73 bp Sc: 83.96

(SEQ ID NO: 526)

GCCTGGATAGCTCAGTTGGTAGAGCATCAGACTTTTAATCTGAGGGTCCAGGGTTCAAGTCCCTGTTCAGGCG

Homo_sapiens_chr16.trna23-LysTTT (72069789-72069717) Lys (TTT) 73 bp Sc: 84.43

(SEQ ID NO: 527)

GCCTGGATAGCTCAGTTGGTAGAGCATCAGACTTTTAATCTGAGGGTCCAGGGTTCAAGTCCCTGTTCAGGCA

Homo_sapiens_chr9.trna1-MetCAT (19393996-19394070) Met (CAT) 75 bp Sc: 43.49

(SEQ ID NO: 528)

AGCAGAGTGGTGCAGTGGAAGCATACCTATGGGCCCATAACCCAGAGGTTGATGGATGGAAACCATCCTCTGCTA

Homo_sapiens_chr6.trna61-MetCAT (27853643-27853714) Met (CAT) 72 bp Sc: 62.43

(SEQ ID NO: 529)

AGCAGAGTGGCGCAGCGGAAGCGTGCTGGGCCCATAACCCAGAGGTCGATGGATCTAAACCATCCTCTGCTA

Homo_sapiens_chr6.trna92-MetCAT (58276523-58276451) Met (CAT) 73 bp Sc: 64.33

(SEQ ID NO: 530)

GCCCTCTTAGTGCAGCTGGCAGCGCGTCAGTTTCATAATCTGAAAGTCCTGAGTTCAAGCCTCAGAGAGGGCA

Homo_sapiens_chr1.trna32-MetCAT (151910350-151910421) Met (CAT) 72 bp Sc: 68.98

(SEQ ID NO: 531)

AGCAGAGTGGCGCAGCGGAAGCGTGCTGGGCCCATAACCCAGAGGTCGATGGATCGAAACCATCCTCTGCTA

```
Homo_sapiens_chr17.trna20-MetCAT (78045957-78045886) Met (CAT) 72 bp Sc: 68.98
                                                                                        (SEQ ID NO: 532)
AGCAGAGTGGCGCAGCGGAAGCGTGCTGGGCCCATAACCCAGAGGTCGATGGATCGAAACCATCCTCTGCTA Homo_sapiens_chr6.trna129-MetCAT (27978321-27978250) Met (CAT) 72 bp Sc: 68.98
                                                                                        (SEQ ID NO: 533)
AGCAGAGTGGCGCAGCGGAAGCGTGCTGGGCCCATAACCCAGAGGTCGATGGATCGAAACCATCCTCTGCTA Homo_sapiens_chr6.trna142-MetCAT (27668650-27668579) Met (CAT) 72 bp Sc: 68.98
                                                                                        (SEQ ID NO: 534)
AGCAGAGTGGCGCAGCGGAAGCGTGCTGGGCCCATAACCCAGAGGTCGATGGATCGAAACCATCCTCTGCTA Homo_sapiens_chr6.trna150-MetCAT (27408814-27408743) Met (CAT) 72 bp Sc: 68.98
                                                                                        (SEQ ID NO: 535)
AGCAGAGTGGCGCAGCGGAAGCGTGCTGGGCCCATAACCCAGAGGTCGATGGATCGAAACCATCCTCTGCTA Homo_sapiens_chr6.trna169-MetCAT (26438579-26438508) Met (CAT) 72 bp Sc: 68.98
                                                                                        (SEQ ID NO: 536)
AGCAGAGTGGCGCAGCGGAAGCGTGCTGGGCCCATAACCCAGAGGTCGATGGATCGAAACCATCCTCTGCTA Homo_sapiens_chr6.trna171-MetCAT (26421402-26421331) Met (CAT) 72 bp Sc: 68.98
                                                                                        (SEQ ID NO: 537)
AGCAGAGTGGCGCAGCGGAAGCGTGCTGGGCCCATAACCCAGAGGTCGATGGATCGAAACCATCCTCTGCTA Homo_sapiens_chr6.trna2-MetCAT (26394733-26394804) Met (CAT) 72 bp Sc: 68.98
                                                                                        (SEQ ID NO: 538)
AGCAGAGTGGCGCAGCGGAAGCGTGCTGGGCCCATAACCCAGAGGTCGATGGATCGAAACCATCCTCTGCTA Homo_sapiens_chr16.trna22-MetCAT (85975201-85975129) Met (CAT) 73 bp Sc: 74.51
                                                                                        (SEQ ID NO: 539)
GCCTCGTTAGCGCAGTAGGCAGCGCGTCAGTCTCATAATCTGAAGGTCGTGAGTTCGAGCCTCACACGGGCA Homo_sapiens_chr6.trna21-MetCAT (26809691-26809763) Met (CAT) 73 bp Sc: 75.06
                                                                                        (SEQ ID NO: 540)
GCCCTCTTAGCGCAGCTGGCAGCGCGTCAGTCTCATAATCTGAAGGTCCTGAGTTCAAGCCTCAGAGAGGGCA Homo_sapiens_chr6.trna162-MetCAT (26866601-26866529) Met (CAT) 73 bp Sc: 75.76
                                                                                        (SEQ ID NO: 541)
GCCCTCTTAGCGCAGCGGGCAGCGCGTCAGTCTCATAATCTGAAGGTCCTGAGTTCGAGCCTCAGAGAGGGCA Homo_sapiens_chr6.trna164-MetCAT (26843625-26843553) Met (CAT) 73 bp Sc: 75.76
                                                                                        (SEQ ID NO: 542)
GCCCTCTTAGCGCAGCGGGCAGCGCGTCAGTCTCATAATCTGAAGGTCCTGAGTTCGAGCCTCAGAGAGGGCA Homo_sapiens_chr6.trna27-MetCAT (26874423-26874495) Met (CAT) 73 bp Sc: 75.76
                                                                                        (SEQ ID NO: 543)
GCCCTCTTAGCGCAGCGGGCAGCGCGTCAGTCTCATAATCTGAAGGTCCTGAGTTCGAGCCTCAGAGAGGGCA Homo_sapiens_chr6.trna75-MetCAT (29020331-29020403) Met (CAT) 73 bp Sc: 76.58
                                                                                        (SEQ ID NO: 544)
GCCTCCTTAGCGCAGTAGGCAGCGCGTCAGTCTCATAATCTGAAGGTCCTGAGTTCGAACCTCAGAGGGGCA Homo_sapiens_chr6.trna97-MetCAT (29029093-29029021) Met (CAT) 73 bp Sc: 76.58
                                                                                        (SEQ ID NO: 545)
GCCTCCTTAGCGCAGTAGGCAGCGCGTCAGTCTCATAATCTGAAGGTCCTGAGTTCGAACCTCAGAGGGGCA Homo_sapiens_chr16.trna20-MetCAT (70017897-70017969) Met (CAT) 73 bp Sc: 78.21
                                                                                        (SEQ ID NO: 546)
GCCCTCTTAGCGCAGTGGGCAGCGCGTCAGTCTCATAATCTGAAGGTCCTGAGTTCGAGCCTCAGAGAGGGCA Homo_sapiens_chr8.trna10-MetCAT (124238723-124238651) Met (CAT) 73 bp Sc: 79.85
                                                                                        (SEQ ID NO: 547)
GCCTCGTTAGCGCAGTAGGTAGCGCGTCAGTCTCATAATCTGAAGGTCGTGAGTTCGATCCTCACACGGGCA Homo_sapiens_chr6.trna56-PheGAA (27740524-27740599) Phe (GAA) 76 bp Sc: 53.54
                                                                                        (SEQ ID NO: 548)
GCCGAAATAGCTCAATTGGGAGAGTGTTAGACTGAAGATCTTCTGCAGGTCTCTGGTTCAATTCCGGGTTTCGACA Homo_sapiens_chr6.trna112-PheGAA (28839426-28839353) Phe (GAA) 74 bp Sc: 56.32
                                                                                        (SEQ ID NO: 549)
GCTGAAATAGCTCAGTTGGGAGAGCGTTAGACTGAAGATCTTAAAGTTCCCTGGTTCAACCCTGGGTTTCAGCC Homo_sapiens_chr6.trna72-PheGAA (28840143-28840215) Phe (GAA) 73 bp Sc: 59.98
                                                                                        (SEQ ID NO: 550)
GCCAAAATTGCTCAGTTGGGAGAGCGTTAGACTGAAGATCTAAAGGTCCCTGGTTCGATCCCGGGTTTCACCA Homo_sapiens_chr6.trna103-PheGAA (28899145-28899072) Phe (GAA) 74 bp Sc: 67.94
                                                                                        (SEQ ID NO: 551)
GCCGAAATAGCTCAGTTGGGAGAGCGTTAGACCGAAGATCTTAAAGGTCCCTGGTTCAATCCCGGGTTTCGGCA
```

-continued

Homo_sapiens_chr6.trna106-PheGAA (28883661-28883589) Phe (GAA) 73 bp Sc: 82.13

(SEQ ID NO: 552)

GCCGAGATAGCTCAGTTGGGAGAGCGTTAGACTGAAGATCTAAAGGTCCCTGGTTCAATCCCGGGTTTCGGCA

Homo_sapiens_chr11.trna13-PheGAA (59090501-59090429) Phe (GAA) 73 bp Sc: 82.45

(SEQ ID NO: 553)

GCCGAAATAGCTCAGTTGGGAGAGCGTTAGACTGAAGATCTAAAGGTCCCTGGTTCAATCCCGGGTTTCGGCA

Homo_sapiens_chr11.trna15-PheGAA (59081618-59081546) Phe (GAA) 73 bp Sc: 84.19

(SEQ ID NO: 554)

GCCGAAATAGCTCAGTTGGGAGAGCGTTAGACTGAAGATCTAAAGGTCCCTGGTTCGATCCCGGGTTTCGGCA

Homo_sapiens_chr12.trna11-PheGAA (123978414-123978342) Phe (GAA) 73 bp Sc: 84.19

(SEQ ID NO: 555)

GCCGAAATAGCTCAGTTGGGAGAGCGTTAGACTGAAGATCTAAAGGTCCCTGGTTCGATCCCGGGTTTCGGCA

Homo_sapiens_chr13.trna1-PheGAA (93999977-93999905) Phe (GAA) 73 bp Sc: 84.19

(SEQ ID NO: 556)

GCCGAAATAGCTCAGTTGGGAGAGCGTTAGACTGAAGATCTAAAGGTCCCTGGTTCGATCCCGGGTTTCGGCA

Homo_sapiens_chr19.trna14-PheGAA (1334433-1334361) Phe (GAA) 73 bp Sc: 84.19

(SEQ ID NO: 557)

GCCGAAATAGCTCAGTTGGGAGAGCGTTAGACTGAAGATCTAAAGGTCCCTGGTTCGATCCCGGGTTTCGGCA

Homo_sapiens_chr6.trna109-PheGAA (28866550-28866478) Phe (GAA) 73 bp Sc: 84.19

(SEQ ID NO: 558)

GCCGAAATAGCTCAGTTGGGAGAGCGTTAGACTGAAGATCTAAAGGTCCCTGGTTCGATCCCGGGTTTCGGCA

Homo_sapiens_chr6.trna96-PheGAA (29057500-29057428) Phe (GAA) 73 bp Sc: 84.19

(SEQ ID NO: 559)

GCCGAAATAGCTCAGTTGGGAGAGCGTTAGACTGAAGATCTAAAGGTCCCTGGTTCGATCCCGGGTTTCGGCA

Homo_sapiens_chr1.trna65-ProAGG (165951420-165951349) Pro (AGG) 72 bp Sc: 75.92

(SEQ ID NO: 560)

GGCTCGTTGGTCTAGGGGTATGATTCTCGCTTAGGGTGCGAGAGGTCCCGGGTTCAAATCCCGGACGAGCCC

Homo_sapiens_chr11.trna9-ProAGG (75624205-75624276) Pro (AGG) 72 bp Sc: 75.92

(SEQ ID NO: 561)

GGCTCGTTGGTCTAGGGGTATGATTCTCGCTTAGGGTGCGAGAGGTCCCGGGTTCAAATCCCGGACGAGCCC

Homo_sapiens_chr14.trna22-ProAGG (20151471-20151400) Pro (AGG) 72 bp Sc: 75.92

(SEQ ID NO: 562)

GGCTCGTTGGTCTAGGGGTATGATTCTCGCTTAGGGTGCGAGAGGTCCCGGGTTCAAATCCCGGACGAGCCC

Homo_sapiens_chr14.trna23-ProAGG (20147406-20147335) Pro (AGG) 72 bp Sc: 75.92

(SEQ ID NO: 563)

GGCTCGTTGGTCTAGGGGTATGATTCTCGCTTAGGGTGCGAGAGGTCCCGGGTTCAAATCCCGGACGAGCCC

Homo_sapiens_chr16.trna29-ProAGG (3172707-3172636) Pro (AGG) 72 bp Sc: 75.92

(SEQ ID NO: 564)

GGCTCGTTGGTCTAGGGGTATGATTCTCGCTTAGGGTGCGAGAGGTCCCGGGTTCAAATCCCGGACGAGCCC

Homo_sapiens_chr16.trna9-ProAGG (3179635-3179706) Pro (AGG) 72 bp Sc: 75.92

(SEQ ID NO: 565)

GGCTCGTTGGTCTAGGGGTATGATTCTCGCTTAGGGTGCGAGAGGTCCCGGGTTCAAATCCCGGACGAGCCC

Homo_sapiens_chr6.trna12-ProAGG (26663477-26663548) Pro (AGG) 72 bp Sc: 75.92

(SEQ ID NO: 566)

GGCTCGTTGGTCTAGGGGTATGATTCTCGCTTAGGGTGCGAGAGGTCCCGGGTTCAAATCCCGGACGAGCCC

Homo_sapiens_chr7.trna2-ProAGG (128210740-128210811) Pro (AGG) 72 bp Sc: 75.92

(SEQ ID NO: 567)

GGCTCGTTGGTCTAGGGGTATGATTCTCGCTTAGGGTGCGAGAGGTCCCGGGTTCAAATCCCGGACGAGCCC

Homo_sapiens_chr16.trna11-ProAGG (3181990-3182061) Pro (AGG) 72 bp Sc: 77.31

(SEQ ID NO: 568)

GGCTCGTTGGTCTAGGGGTATGATTCTCGCTTAGGATGCGAGAGGTCCCGGGTTCAAATCCCGGACGAGCCC

Homo_sapiens_chr16.trna4-ProAGG (3150387-3150481) Pro (AGG) 95 bp Sc: 43.10

(SEQ ID NO: 569)

GGCTCGTTGGTCTAGGGGTGTGGTTCTCGCTTAGGGACCACAGGGACAAGCCCGGGAGACCCAAGAGGTCCCGGGTTCAAATCCCGGACGAGCCC

Homo_sapiens_chr6.trna30-ProCGG (27167500-27167571) Pro (CGG) 72 bp Sc: 71.93

(SEQ ID NO: 570)

GGCTCGTTGGTCTAGGGGTATGATTCTCGCTTCGGGTGTGAGAGGTCCCGGGTTCAAATCCCGGACGAGCCC

Homo_sapiens_chr1.trna52-ProCGG (165950586-165950657) Pro (CGG) 72 bp Sc: 76.52

(SEQ ID NO: 571)

GGCTCGTTGGTCTAGGGGTATGATTCTCGCTTCGGGTGCGAGAGGTCCCGGGTTCAAATCCCGGACGAGCCC

-continued

Homo_sapiens_chr16.trna6-ProCGG (3162050-3162121) Pro (CGG) 72 bp Sc: 76.52

(SEQ ID NO: 572)

GGCTCGTTGGTCTAGGGGTATGATTCTCGCTTCGGGTGCGAGAGGTCCCGGGTTCAAATCCCGGACGAGCCC

Homo_sapiens_chr17.trna37-ProCGG (8066947-8066876) Pro (CGG) 72 bp Sc: 76.52

(SEQ ID NO: 573)

GGCTCGTTGGTCTAGGGGTATGATTCTCGCTTCGGGTGCGAGAGGTCCCGGGTTCAAATCCCGGACGAGCCC

Homo_sapiens_chr14.trna6-ProTGG (20222015-20222086) Pro (TGG) 72 bp Sc: 76.15

(SEQ ID NO: 574)

GGCTCGTTGGTCTAGGGGTATGATTCTCGCTTTGGGTGCGAGAGGTCCCGGGTTCAAATCCCGGACGAGCCC

Homo_sapiens_chr16.trna28-ProTGG (3174205-3174134) Pro (TGG) 72 bp Sc: 76.15

(SEQ ID NO: 575)

GGCTCGTTGGTCTAGGGGTATGATTCTCGCTTTGGGTGCGAGAGGTCCCGGGTTCAAATCCCGGACGAGCCC

Homo_sapiens_chr16.trna3-ProTGG (3148924-3148995) Pro (TGG) 72 bp Sc: 76.15

(SEQ ID NO: 576)

GGCTCGTTGGTCTAGGGGTATGATTCTCGCTTTGGGTGCGAGAGGTCCCGGGTTCAAATCCCGGACGAGCCC

Homo_sapiens_chr16.trna8-ProTGG (3178095-3178166) Pro (TGG) 72 bp Sc: 76.15

(SEQ ID NO: 577)

GGCTCGTTGGTCTAGGGGTATGATTCTCGCTTTGGGTGCGAGAGGTCCCGGGTTCAAATCCCGGACGAGCCC

Homo_sapiens_chr5.trna14-ProTGG (180548531-180548460) Pro (TGG) 72 bp Sc: 76.15

(SEQ ID NO: 578)

GGCTCGTTGGTCTAGGGGTATGATTCTCGCTTTGGGTGCGAGAGGTCCCGGGTTCAAATCCCGGACGAGCCC

Homo_sapiens_chr11.trna12-ProTGG (75624588-75624517) Pro (TGG) 72 bp Sc: 76.24

(SEQ ID NO: 579)

GGCTCGTTGGTCTAGGGGTATGATTCTCGGTTTGGGTCCGAGAGGTCCCGGGTTCAAATCCCGGACGAGCCC

Homo_sapiens_chr14.trna3-ProTGG (20171005-20171076) Pro (TGG) 72 bp Sc: 79.61

(SEQ ID NO: 580)

GGCTCGTTGGTCTAGTGGTATGATTCTCGCTTTGGGTGCGAGAGGTCCCGGGTTCAAATCCCGGACGAGCCC

Homo_sapiens_chr5.trna17-LeuAAG (180524251-180524170) Leu (AAG) 82 bp Sc: 25.68

(SEQ ID NO: 581)

GATAGCAAGGCCGAGCGGTCTAAGGCTCCGGATTAAGGCGCCGGTGTCTTCGGAGGCATGGGTTCGAATTCCACCTCTGCCA

Homo_sapiens_chr20.trna5-IleAAT (50651822-50651745) Ile (AAT) 78 bp Sc: 23.04

(SEQ ID NO: 582)

GACCAATTAGCAAGCACAGTTGGCTAGAACATGGTGCTAATAAGGCCACGGTCAGGGGTTCAATTCCCTTATGGGCTG

Homo_sapiens_chr12.trna9-IleAAT (128282151-128282225) Ile (AAT) 75 bp Sc: 27.18

(SEQ ID NO: 583)

TGGCTGATGAGCTCAGCTGGTGGGAGCATGGTGTTAATGAGGCTGAGGTCGTGGGTTCAATCCCCACCGGGCTAT

Homo_sapiens_chr6.trna39-IleAAT (27359843-27359916) Ile (AAT) 74 bp Sc: 44.67

(SEQ ID NO: 584)

GGCCGGTTAACTTAATTGGTTAGAGCGTGGTGCTAATAATGTCAAGGTTGCGGGTTGGATCCCCGAACGGGCCA

Homo_sapiens_chr5.trna1-CysACA (151968789-151968964) Cys (ACA) 176 bp Sc: 29.48

(SEQ ID NO: 585)

GGCTGTATAGCTCAGTGGTAGAGCATTTGACTACAGAATCCTATACTCAGGGGAAGGAGAACTGGGGGTTTCTCAGTGGGTCAAAGGACTTGTAGTGGTAAAT

CAAAAGCAACTCTATAAGCTATGTAACAAACTTTAAAGTCATATGTAGCTGGGTTCAAATCCTGTTTCTGCCA

Homo_sapiens_chr6.trna41-SerACT (27369650-27369723) Ser (ACT) 74 bp Sc: 49.68

(SEQ ID NO: 586)

GGCCGGTTAGCTCAGTTGGTTAGAGCGTGCTGCTACTAATGCCAGGGTCGAGGTTTCGATCCCCGTACGGGCCT

Homo_sapiens_chr20.trna2-SerAGA (29552364-29552435) Ser (AGA) 72 bp Sc: 20.36

(SEQ ID NO: 587)

GGTAATGTAGCCTCGTGGTTAGGGGCTGCATTCTAGAGCTATGCTGCCCAGGTTCAAATTCTGGTGCCACTC

Homo_sapiens_chr6.trna111-AlaAGC (28854594-28854523) Ala (AGC) 72 bp Sc: 32.22

(SEQ ID NO: 588)

GGGGGTATAGCTCAGGGACAGAGCACGTGGTTAGCATGCGTGAGGTCCTGCGTTCAACTTCCAGTATTTCCA

Homo_sapiens_chr16.trna33-ProAGG (3142681-3142610) Pro (AGG) 72 bp Sc: 23.16

(SEQ ID NO: 589)

CGCTCTTTGGTCTAGGGGTATGATCTTCGCTTAGGGTGCGAGAGGTGCCTGGATCAACTCCTTCACAAGCCG

Homo_sapiens_chr2.trna7-ProAGG (77749101-77749171) Pro (AGG) 71 bp Sc: 30.29

(SEQ ID NO: 590)

GGCTGGTTGGTCTAGGGCTATGATTCTCACTTAGGGTGCAAGAGGTCCTGGTTCAAATCCCAGAGGAGCCC

```
Homo_sapiens_chr2.trna8-ProAGG (87193084-87193155) Pro (AGG) 72 bp Sc: 37.07
                                                                                          (SEQ ID NO: 591)
GGCTGGTTGGTCTAGGGCTATGATTCTCACTTAGGGTGCAAAAGGTCCTGGGTTCAAATCCCAGAGGAGCCC Homo_sapiens_chr10.trna3-LeuCAA (34631489-34631422) Leu (CAA) 68 bp Sc: 20.90
                                                                                          (SEQ ID NO: 592)
CATAGGGTAGTGGCTAAGAACCTAAACTCTAAATTTAGATGTCCTGAGTTCAAATCCCAGCTGTATGC Homo_sapiens_chr20.trna3-ValCAC (43384415-43384487) Val (CAC) 73 bp Sc: 29.18
                                                                                          (SEQ ID NO: 593)
GCTTCTGTAATGTAGTGGTTATCACATTCGCCTCACACATGAAAGGTCACCAGTTTGAGACCGGGCCAAAACA Homo_sapiens_chr1.trna1-ValCAC (16924648-16924720) Val (CAC) 73 bp Sc: 30.83
                                                                                          (SEQ ID NO: 594)
GTTTCTGTAGTATAGTGGTTATCATGTTTGCCTCACATGTGAAAGACCCTTGGCTCGAGACTGGAGGGAAACA Homo_sapiens_chr1.trna131-ValCAC (16746819-16746747) Val (CAC) 73 bp Sc: 41.96
                                                                                          (SEQ ID NO: 595)
GTTTCTGTGGTGTAGTGGTTATTATGTTCGCTTCACATATGAAAGGTCTCTGGTTCGAGACTGCGTGGGAACA Homo_sapiens_chr1.trna3-ValCAC (17059280-17059352) Val (CAC) 73 bp Sc: 41.96
                                                                                          (SEQ ID NO: 596)
GTTTCTGTGGTGTAGTGGTTATTATGTTCGCTTCACATATGAAAGGTCTCTGGTTCGAGACTGCGTGGGAACA Homo_sapiens_chr2.trna1-GlyCCC (11609278-11609349) Gly (CCC) 72 bp Sc: 43.42
                                                                                          (SEQ ID NO: 597)
TACTCAGTGGTCTAGTGGTTAGGATTCAGCGCTCCCACCGCCGCAGCCCGGGTTCGATTCCCGGTCATGGAA Homo_sapiens_chr1.trna91-GlyCCC (147946904-147946834) Gly (CCC) 71 bp Sc: 49.64
                                                                                          (SEQ ID NO: 598)
GCACTGGTGGTTCAGTGGTAGAATTCTCGCCTCCCACGCGGGAGACCCGGGTTTAATTCCCGGTCAAGATA Homo_sapiens_chr11.trna7-ArgCCT (63418343-63418411) Arg (CCT) 69 bp Sc: 21.47
                                                                                          (SEQ ID NO: 599)
GCATTCGTAGTTCAGCGGCAGAAATTTCGTCTCCTACGCGGGAGACTCGGGTTCGACTTCGGCCATGCA Homo_sapiens_chr1.trna88-ArgCCT (147994965-147994895) Arg (CCT) 71 bp Sc: 21.62
                                                                                          (SEQ ID NO: 600)
GGATTTGTGGTCCAGTGGTAGAATTCTCACCGCCTGCATAGGAGACCCTGGGTTTAATTCCTGGCCAATGCA Homo_sapiens_chr1.trna96-ArgCCT (147609775-147609705) Arg (CCT) 71 bp Sc: 27.53
                                                                                          (SEQ ID NO: 601)
GGATTGGTGGTCCAGTGGTAGAATTCTCACCGCCTGCATAGGAGACCCTGGGTTTAATTCCTGGCCAATGCA Homo_sapiens_chr1.trna14-ArgCCT (144652936-144653006) Arg (CCT) 71 bp Sc: 34.62
                                                                                          (SEQ ID NO: 602)
GCATTGGTAGTTCAGCGGTGGCATTCTCCCCACCTACGCGGGAGACCTGGGTTCAACTCCCGGCCAAAGCA Homo_sapiens_chr1.trna18-ArgCCT (145949915-145949985) Arg (CCT) 71 bp Sc: 34.62
                                                                                          (SEQ ID NO: 603)
GCATTGGTAGTTCAGCGGTGGCATTCTCCCCACCTACGCGGGAGACCTGGGTTCAACTCCCGGCCAAAGCA Homo_sapiens_chr14.trna11-SupCTA (77770663-77770591) Sup (CTA) 73 bp Sc: 26.26
                                                                                          (SEQ ID NO: 604)
GGCGGGATAATGTAGTGGTTAAAGGCATGGGCTCTAGAGCCAGACTTCCTGGGTTCAAATCTCAGACCTGCTA Homo_sapiens_chr3.trna1-SupCTA (13808887-13808954) Sup (CTA) 68 bp Sc: 26.42
                                                                                          (SEQ ID NO: 605)
GGCAGGGTAGGGTAGAGGTTAAAACCATGGATTCTAGAGCCAGATGGGTTCAAATCCCGGCTCTGCCG Homo_sapiens_chrX.trna3-GluCTC (51322923-51322852) Glu (CTC) 72 bp Sc: 20.35
                                                                                          (SEQ ID NO: 606)
TCCCTGGTGTTCCGGTGGTTAGGATTTGGCATTCTCACTGTTGTGGTGCGGATTCAATCCTGGCTTAGGGTA Homo_sapiens_chr12.trna14-GluCTC (112871000-112870928) Glu (CTC) 73 bp Sc: 22.05
                                                                                          (SEQ ID NO: 607)
CCGTGGATAGCCCAGCGGCTATGGGAGCCGGGCTCTCACTCTGACGTCCTGGGTTCAAGTCCCAGTGTGCACA Homo_sapiens_chr2.trna25-GluCTC (71127068-71126996) Glu (CTC) 73 bp Sc: 22.62
                                                                                          (SEQ ID NO: 608)
CCCCTGGCGGTCTAGTGGTTAGGATTCGGCGCTCTCATCCACCGCGGCCTGGGTTCGACTCGTGGTCAGAGTG Homo_sapiens_chr8.trna7-GluCTC (70234894-70234968) Glu (CTC) 75 bp Sc: 22.64
                                                                                          (SEQ ID NO: 609)
CTCTGGTGGTTTAGTGGCTAGGATTCACCTCTCTCACTGCTGCAGCCCAGGGTTCCATTCCCTGGGAGTCAGATG Homo_sapiens_chr2.trna24-GluCTC (95580992-95580921) Glu (CTC) 72 bp Sc: 23.39
                                                                                          (SEQ ID NO: 610)
CCCCTTGTAGTCTAGTGGTTAGAATTCTGCGGTCTCACAGCCGCGGCCCGGGTTCGATTCCCATTCCGGAA
```

-continued

Homo_sapiens_chr3.trna10-GluCTC (105362285-105362214) Glu (CTC) 72 bp Sc: 25.40

(SEQ ID NO: 611)

TTATTATTATACCTGTGGTTAGGATTCGGCGCTCTCACCGCCACGACCCGGGTTCAATTCCCGGTCAGGGAA

Homo_sapiens_chr8.trna1-GluCTC (11830789-11830860) Glu (CTC) 72 bp Sc: 26.22

(SEQ ID NO: 612)

CCCCTGGTAGTCTAGTGGTTAGGCTTTGCCGCTCTCAGTGCCGCTGCCTGGGTTGGATTCCCAGTCATGTGA

Homo_sapiens_chr20.trna7-GluCTC (13918541-13918470) Glu (CTC) 72 bp Sc: 27.08

(SEQ ID NO: 613)

TCCCTGCTTGTCTAGTGGTTAGAATTCAGCACTCTCACTGCCACAGCCCAGGTTCAATTCCCTGTCAGAGAA

Homo_sapiens_chr2.trna12-GluCTC (150927523-150927595) Glu (CTC) 73 bp Sc: 29.78

(SEQ ID NO: 614)

TTCCCCTTGGTCTAGTGGTTAGGATTCAACACTCTCACCGCCGCAGCCCGGGTTTGATTCCCAGGCAGGGAAG

Homo_sapiens_chr2.trna18-GluCTC (159446488-159446417) Glu (CTC) 72 bp Sc: 31.33

(SEQ ID NO: 615)

CCCCTGGTGGTCTAGTGCTTAGGATTTGGCACTCTCGCCACCGCAGCCTGCGTTCAATTCCCGGTCAGGGAA

Homo_sapiens_chr13.trna2-GluCTC (57356622-57356551) Glu (CTC) 72 bp Sc: 34.44

(SEQ ID NO: 616)

TCCCTGGTGGTCTAATGGTTAGGAGTCGGCACTCTCACCGCCGCGGCTGGGGTTTGATTCCCAGTCATGTAA

Homo_sapiens_chr2.trna15-GlnCTG (219199376-219199451) Gln (CTG) 76 bp Sc: 22.40

(SEQ ID NO: 617)

GTGAGACTGCACAGCCCAGTGGTGCAGGGCATGGCTCTGACACCTGGCGGCCTGGGTTCAAATCCCAGCTTCTACA

Homo_sapiens_chr1.trna128-GlnCTG (17053558-17053487) Gln (CTG) 72 bp Sc: 25.51

(SEQ ID NO: 618)

GGTTCCATGATGTAATGGTGAGCGCTTTGGACTCTGAGTACGGTGATCAGCGTTCAAGTCTCAGTGGGACCT

Homo_sapiens_chr5.trna21-GlnCTG (151228338-151228267) Gln (CTG) 72 bp Sc: 25.76

(SEQ ID NO: 619)

GGTAGTGTAGTCTACTGGTTAAACGCTTGGGCTCTGACATTAACGTCCTGGGTTCAAATCCCAGCTTTGTCA

Homo_sapiens_chr10.trna5-GlnCTG (20076688-20076614) Gln (CTG) 75 bp Sc: 26.31

(SEQ ID NO: 620)

CTAGGACGTGGTGTAATAGGTAGCACAGAGAATTCTGGATTCTCAGGGGTAGGTTCAATTCCTATAGAACCTAGG

Homo_sapiens_chr1.trna27-GlnCTG (147345988-147346059) Gln (CTG) 72 bp Sc: 39.31

(SEQ ID NO: 621)

GGTTCCATGGTGTAATGGTGAGGGCTTTGGACTCTGACTACAGTGATCAGAGTTCAAGTCTCAGTGGGACCT

Homo_sapiens_chr1.trna23-GlnCTG (146292313-146292384) Gln (CTG) 72 bp Sc: 43.68

(SEQ ID NO: 622)

GGTTCCATGGGTTAATGGTGAGCACCCTGGACTCTGAATCAAGCGATCCGAGTTCAAATCTCGGTGGTACCT

Homo_sapiens_chr15.trna6-LysCTT (74461893-74461820) Lys (CTT) 74 bp Sc: 37.12

(SEQ ID NO: 623)

GCCTGGCTACCTCAGTTGGTAGAGCATGGGACTCTTAATCCCAGAGTCAGTGGGTTCAAGCCTCACATTGAGTG

Homo_sapiens_chr16.trna13-LysCTT (3186154-3186226) Lys (CTT) 73 bp Sc: 41.66

(SEQ ID NO: 624)

GCCCAGCTAGCTCAGCGGTAGAGCACAAGACTCTTAATCTCAGGGTCGTGGGTTTGAGCCCTGTGTTGAGCA

Homo_sapiens_chr1.trna51-LysCTT (163832774-163832846) Lys (CTT) 73 bp Sc: 42.42

(SEQ ID NO: 625)

GTCTAGCTAGATCAGTTGGTAGAGCATAAGACTCTTAATCTCAGGGTCATGGGTTTGAGCCCTACGTTGGGCG

Homo_sapiens_chr1.trna8-LysCTT (39742782-39742854) Lys (CTT) 73 bp Sc: 46.90

(SEQ ID NO: 626)

ACCAGCATGTCTCAGTCGGTATAGTGTGAGACTCTTAATCTCAGGGTCGTGGGTTCAAGCCCCACATTGGGCG

Homo_sapiens_chr8.trna9-PheGAA (124339978-124339906) Phe (GAA) 73 bp Sc: 20.84

(SEQ ID NO: 627)

GCCAAAATAGCTCAGCTGGGAGAGTATTAGGTTGAAGATACAAAGTTCCTTGGCTCAATCCCAGAGTTTGGGGG

Homo_sapiens_chr6.trna116-PheGAA (28802906-28802834) Phe (GAA) 73 bp Sc: 27.39

(SEQ ID NO: 628)

GCTGAGATAGCTCGGTTGGGAGGGCATCAGCCTGAAGATCTAAAGGAGACTGGTTCAATTCTGGGTTTTGGCA

Homo_sapiens_chr1.trna92-PheGAA (147939600-147939529) Phe (GAA) 72 bp Sc: 32.31

(SEQ ID NO: 629)

TGCATGGTTGTCTAGTGGCTAGGATTCGGTGCTGAAAGCGTCACGGCCCGGGTTCGATTCCCGGTCAGGGAA

Homo_sapiens_chr1.trna100-PheGAA (147554054-147553983) Phe (GAA) 72 bp Sc: 32.35

(SEQ ID NO: 630)

TGCATGGTTGTCTAGTGGCTAGGATTCGGTGCTGAAAGAGCCACGGCCCGGGTTCGATTCCCGGTCAGGGAA

```
Homo_sapiens_chr6.trna88-PheGAA (79724801-79724729) Phe (GAA) 73 bp Sc: 43.56
                                                                                (SEQ ID NO: 631)
GCCAAAATAGCTCAGCTGGGAGAGCATTAGACTGAAGATCTAAAGGTCTCTGGTTTGATCCTGGGTTTCAGAA Homo_sapiens_chr3.trna12-CysGCA (17716468-17716396) Cys (GCA) 73 bp Sc: 36.14
                                                                                (SEQ ID NO: 632)
GGGGGTATATCTCAGGGGGCAGAGCATTTGACTGCAGATCAAGAGGTCCCCGGTTGAAATCCGGGTGCTGGAT Homo_sapiens_chr10.trna1-ProGGG (22892585-22892657) Pro (GGG) 73 bp Sc: 34.81
                                                                                (SEQ ID NO: 633)
GGCAGTGTGGCCATAGTGGTTAGAAATGTGCGCTCTGGGGCTGCTGATCCCAGGCTCAAACCCTGGCGCTGTCA Homo_sapiens_chr15.trna5-TyrGTA (90055378-90055306) Tyr (GTA) 73 bp Sc: 24.21
                                                                                (SEQ ID NO: 634)
GTCAGTGTTGCACAACGGTTAAGTGAAGAGGCTGTAAACCCAGACTGGATGGGTTCAATTCCCATCTCTGCCG Homo_sapiens_chr7.trna24-TyrGTA (148684753-148684678) Tyr (GTA) 76 bp Sc: 33.50
                                                                                (SEQ ID NO: 635)
TCAATTATAGCTCAGTGGTAGAGCATTTAACTGTAGATCAAGAGGTCCCTGGATCAACTCTGGGTGCCCCCTTTAA Homo_sapiens_chr1.trna44-AspGTC (159759559-159759630) Asp (GTC) 72 bp Sc: 27.96
                                                                                (SEQ ID NO: 636)
TCCTTGTTACTATAGTGGTGAGTATCTCTGCCTGTCATGCGTGAGAGAGGGGTCGATTCCCCGACGGGGAG Homo_sapiens_chr1.trna109-AsnGTT (146317757-146317684) Asn (GTT) 74 bp Sc: 34.29
                                                                                (SEQ ID NO: 637)
GTCTCTGTGGCACAATCGGTTAGCTTGTTCGGCTGTTAATCTAGAGGTTGGTGGTTAGAGCCCACTGAGGGATG Homo_sapiens_chr1.trna104-AsnGTT (147478645-147478572) Asn (GTT) 74 bp Sc: 41.72
                                                                                (SEQ ID NO: 638)
GTCTCTGTGGCACAATCGGTTAGAGCGTTCGGCTGTTAATCTAAAGGTTGGTGGCTAGAACCCACTGAGGGACG Homo_sapiens_chr1.trna124-AsnGTT (142455154-142455081) Asn (GTT) 74 bp Sc: 43.05
                                                                                (SEQ ID NO: 639)
GTCTCTGTGGCACAATCGGTTAGCGCGTTCGGCTGTTAATCTAGAGGTTGGTGGTTAGAGCCCACTGAGGGATG Homo_sapiens_chr8.trna13-LeuTAA (47859277-47859203) Leu (TAA) 75 bp Sc: 20.57
                                                                                (SEQ ID NO: 640)
GTTAAGATGGCATAGCCCAGCAATTGCATAAAACTTAAGACTTTATAATTAGAAGTTCAACACCTCTTCTTAACA Homo_sapiens_chr20.trna4-LeuTAA (55366909-55366835) Leu (TAA) 75 bp Sc: 25.92
                                                                                (SEQ ID NO: 641)
GTTAAGATGGCAGAGCCCAGCGATTGCATAAAACTTAACACTTTATAATCAGAGGTTCAACTCCTCTTCTTAACA Homo_sapiens_chr1.trna60-LeuTAA (236173653-236173579) Leu (TAA) 75 bp Sc: 29.87
                                                                                (SEQ ID NO: 642)
GTTAAGATGGCAGAGCCCAGCAATTGCATAAAACTTAAAACTTTACAATCAGAGGTTCAACTCCTCTTCTTAACA Homo_sapiens_chr2.trna9-LeuTAA (117497887-117497961) Leu (TAA) 75 bp Sc: 34.06
                                                                                (SEQ ID NO: 643)
GTTAAGATGGCAGAGCCCAGCAATTGCATAAATCTTAAAACTTTATAATCAGAGGTTCGACTCCTCTTCTTAACA Homo_sapiens_chr6.trna86-ValTAC (156910812-156910738) Val (TAC) 75 bp Sc: 31.66
                                                                                (SEQ ID NO: 644)
GTTAAGACGGCAGAGCCCGGCAATTGCGTAAAATTTACAACTTTATGGGCAGAGGTTCAATTCCTCTTCTTAACA Homo_sapiens_chr14.trna15-LeuTAG (20215099-20215018) Leu (TAG) 82 bp Sc: 32.18
                                                                                (SEQ ID NO: 645)
GGTAGTGTGGTTGAATGGTCTAAGGCACTGAATTTAGGCTCCAGTCTCTTTGGGGACGTGGGTTTAAATCCCACTGCTGCAA Homo_sapiens_chr18.trna3-GlyTCC (53497175-53497246) Gly (TCC) 72 bp Sc: 32.27
                                                                                (SEQ ID NO: 646)
GTGTTGATGGTATAGTGGTGAGCATAGCTGCCTTCCAAGCAATTGACCCGACTTCAATTCCCAGCCAACGCA Homo_sapiens_chr18.trna2-GlyTCC (53496852-53496923) Gly (TCC) 72 bp Sc: 33.06
                                                                                (SEQ ID NO: 647)
GTGTTGATGGTATAGTGGTGAGCATAGCTGCCTTCCAAGCAATTGACCCGACTTCGATTCCCAGCCAATGCA Homo_sapiens_chr17.trna32-SerTGA (21952374-21952306) Ser (TGA) 69 bp Sc: 23.94
                                                                                (SEQ ID NO: 648)
GAAAAAGTCATAGGGGTTATGAGGCTGGCTTGAAACCAGCCTTAGGAGGTTCAATTCCTTCCTTTTTTG Homo_sapiens_chr2.trna10-SerTGA (131856612-131856681) Ser (TGA) 70 bp Sc: 27.03
                                                                                (SEQ ID NO: 649)
GAGAAGGTCATAGAGGTTATGGGATTGGCTTGAAACCAGTCTCTGGGGGGTTCGATTCCCTCCTTTTTCA Homo_sapiens_chr11.trna6-AlaTGC (60520084-60520153) Ala (TGC) 70 bp Sc: 20.74
                                                                                (SEQ ID NO: 650)
GGGGGAGTGGTGTGGTTACGAATGTGGCCTCTGCAAGCAGACAGCCTGGGTTCAATTCCCAGCTTGGCCA
```

-continued

Homo_sapiens_chr6.trna122-AlaTGC (28709909-28709838) Ala (TGC) 72 bp Sc: 42.75

(SEQ ID NO: 651)

GTGGATGTAGTTTAGTGGTAGAACGCGCGCTTTGCATGTATGAGGTCCCGGTTTCGATCCCTGGCGTTTCCA

Homo_sapiens_chr1.trna61-ProTGG (205244853-205244777) Pro (TGG) 77 bp Sc: 23.61

(SEQ ID NO: 652)

GCCAGGAGAGCTCAGTGGTGATGGGATGAGATCTGGACTCACACCTCTAGGCCTGGGTTCAAATCCCAGGTCTAGCG

Homo_sapiens_chr1.trna57-ProTGG (236172485-236172556) Pro (TGG) 72 bp Sc: 33.27

(SEQ ID NO: 653)

TAGGACTTGGTGTAATAGGTAGCACGAAGAGATTTGGATTCTCAGGGGTAGGTTCAATTCCTATAGTTCTGG

Homo_sapiens_chr16.trna31-ProTGG (3161032-3160962) Pro (TGG) 71 bp Sc: 37.53

(SEQ ID NO: 654)

GGCCTGTTGGTCTAGAGGTATGATTCTCGCTTTGGGTGCGAGAGGCCCCGGTGCGAGTCCCAGAGGAGCCC

Homo_sapiens_chr4.trna5-SupTTA (7376810-7376739) Sup (TTA) 72 bp Sc: 21.73

(SEQ ID NO: 655)

GGCAGCCTGGCTTAGTGGAAAGGGAATAGGCTTTAGAGCCAGACTGCCTGGGTTTGAATCCCAGCCCCGCCA

Homo_sapiens_chr6.trna85-GluTTC (163130072-163130004) Glu (TTC) 69 bp Sc: 22.25

(SEQ ID NO: 656)

TCCCTGGTCTAGTGGTTAGGATTTATTATTTTCATGGCTGTGGCCTGAGTTCAATTTCCAATCAGGGAA

Homo_sapiens_chr1.trna17-GluTTC (145016802-145016873) Glu (TTC) 72 bp Sc: 23.38

(SEQ ID NO: 657)

TCCCTGGTGGTCTGGTGGCTAGAATTTAGCGCTTTCACCGCCGCAGCTCGGGTTGGATTACCAGTCAGGGAA

Homo_sapiens_chr1.trna102-GluTTC (147545481-147545409) Glu (TTC) 73 bp Sc: 35.32

(SEQ ID NO: 658)

TCCGTGGTGGTCTAGTGGCTAGGATTCGGCGCTTTCACCGCCTGCAGCTCGAGTTCGATTCCTGGTCAGGGAA

Homo_sapiens_chr2.trna17-GluTTC (203937446-203937376) Glu (TTC) 71 bp Sc: 39.76

(SEQ ID NO: 659)

GCAATGGTGGTTCAGTGGTAGAATTCTCGCCTTTCACACAGGAGACCCGGGTTCAATTCCTGACCCATGTA

Homo_sapiens_chr1.trna105-GluTTC (147428323-147428252) Glu (TTC) 72 bp Sc: 41.70

(SEQ ID NO: 660)

TGTCTGGTGGTCAAGTGGCTAGGATTTGGCGCTTTCACTGCCGCGGCCCGCGTTCGATTCCCGGTCAGGGAA

Homo_sapiens_chr1.trna110-GluTTC (146247725-146247654) Glu (TTC) 72 bp Sc: 43.43

(SEQ ID NO: 661)

TCCTTGGTGGTCTAGTGGCTAGGATTCGGTGCTTTCACCTGTGCGGCCCGGGTTCAATTCCCGATGAAGGAA

Homo_sapiens_chr4.trna1-GlnTTG (156603338-156603409) Gln (TTG) 72 bp Sc: 20.26

(SEQ ID NO: 662)

TAGGACGTGGTGTGATAGGTAGCACAGAGAATTTTGGATTCTCAGGGGTAGGTTAAATTCCTATAGTACTAG

Homo_sapiens_chr7.trna26-GlnTTG (57257993-57257922) Gln (TTG) 72 bp Sc: 22.05

(SEQ ID NO: 663)

TAGGACGTGGTGTGATAGGTAGCATGGGGAATTTTGGATTCTCAGGGGTGGGTTCAATTCCTATAGTTCTAG

Homo_sapiens_chr12.trna15-GlnTTG (96014895-96014822) Gln (TTG) 74 bp Sc: 22.16

(SEQ ID NO: 664)

GGCAATGTAGCATTGTGGCTAAGTGCACAGGCTTTGGAAACTGGCAGGCCTGGGTTCAAATCCCAGCTTATTCA

Homo_sapiens_chr17.trna33-GlnTTG (19447250-19447179) Gln (TTG) 72 bp Sc: 22.33

(SEQ ID NO: 665)

TAGGATGTGGTGTAATAGGTGGCATGGAGAATTTTGGATTATCAGGGGTAGGTTCAATTCCTATAGTTCTAG

Homo_sapiens_chr8.trna14-GlnTTG (32992259-32992188) Gln (TTG) 72 bp Sc: 22.66

(SEQ ID NO: 666)

TAGTACATAGTGTAATAGGTAGCACAGATAATTTTGGATTCTCAGGGGTAGGTTCAATTCTTATAGTTCTAG

Homo_sapiens_chr19.trna12-GlnTTG (9011428-9011356) Gln (TTG) 73 bp Sc: 23.15

(SEQ ID NO: 667)

AGCAGTGTAGCCTAGTGGCTAGGTCCTCTGACTTTGAAACCACGTGGTCTGGGTTTAAGTCTCAGCTGTGCTA

Homo_sapiens_chr13.trna6-GlnTTG (35537818-35537747) Gln (TTG) 72 bp Sc: 23.74

(SEQ ID NO: 668)

TAGGATGTGGTGTGACAGGTAGCATGGAGAATTTTGGATTCTCAGGGTTAGGTTCAATTCCTATAGTTCTAG

Homo_sapiens_chr5.trna23-GlnTTG (77354604-77354532) Gln (TTG) 73 bp Sc: 24.04

(SEQ ID NO: 669)

AGCTGTATATTATAGTGGAATAAATGTGGACTTTGAAGTTAGATACACCTGGGTTCAAATCCCAGTGCTGTCA

Homo_sapiens_chr2.trna11-GlnTTG (131859603-131859674) Gln (TTG) 72 bp Sc: 25.61

(SEQ ID NO: 670)

TAGGACGTGGTGTGATAGGTAGCACGGAGAATTTTGGATTCTCAGGGATGGGTTCAATTCCTGTAGTTCTAG

```
Homo_sapiens_chrY.trna1-GlnTTG (8300214-8300140) Gln (TTG) 75 bp Sc: 27.14
                                                                                (SEQ ID NO: 671)
TTTAGGACGTGGTGTAATAGGTAGCACAGAGAATTTTGGATTCTCAGGTGCAGGTTCAATTCCTATATTCTAGAG Homo_sapiens_chr2.trna22-GlnTTG (130746452-130746381) Gln (TTG) 72 bp Sc: 28.85
                                                                                (SEQ ID NO: 672)
TAGGACGTGGTGTGATAGGTAGCATGGAGAATTTTGGATTCTCAGGGATGGGTTCAATTCCTATAGTCCTAG Homo_sapiens_chr12.trna16-GlnTTG (48497531-48497457) Gln (TTG) 75 bp Sc: 29.85
                                                                                (SEQ ID NO: 673)
TCTAGGATGTGGTGTGATAGGTAGCATGGAGAATTTTGGATTCTCAGGGGTAGGTTCAATTCCTATATTCTAGAA Homo_sapiens_chr3.trna9-GlnTTG (108103639-108103568) Gln (TTG) 72 bp Sc: 32.34
                                                                                (SEQ ID NO: 674)
TAGGATGTGGTGTATTAGGTAGCACAGAGAATTTTGGATTCTCAGGGGTAGGTTCGATTCCTATAATTCTAC Homo_sapiens_chr7.trna4-GlnTTG (141149826-141149897) Gln (TTG) 72 bp Sc: 34.30
                                                                                (SEQ ID NO: 675)
TAGGACGTGGTGTAGTAGGTAGCATGGAGAATGTTGAATTCTCAGGGGTAGGTTCAATTCCTATAGTTCTAG Homo_sapiens_chrX.trna1-GlnTTG (55223391-55223462) Gln (TTG) 72 bp Sc: 34.66
                                                                                (SEQ ID NO: 676)
TAGGACATGGTGTGATAGGTAGCATGGAGAATTTTGGATTCTCAGGGGTAGGTTCAATTCCTACAGTTCTAG Homo_sapiens_chr2.trna28-GlnTTG (45791017-45790945) Gln (TTG) 73 bp Sc: 35.83
                                                                                (SEQ ID NO: 677)
GGCTGTGTACCTCAGTGGGCAAGGGTATGGACTTTGAAGCCAGACTATTTGGGTTCAAATCCCAGCTTGGCCT Homo_sapiens_chr8.trna2-LysTTT (18164483-18164552) Lys (TTT) 70 bp Sc: 20.79
                                                                                (SEQ ID NO: 678)
TCCTATAGCCCAGTGATTAGGATTCTTTGCTTTTACTACCATGACCTGGGTTCAATACCCAGTCAGGGAA Homo_sapiens_chr2.trna16-LysTTT (223894631-223894559) Lys (TTT) 73 bp Sc: 34.01
                                                                                (SEQ ID NO: 679)
GTTGGGGTAACTCAGTTGGTAGAGTAGCAGACTTTTCATCTGAGGGTCCAGGGTTTAAGTCCATGTCCAGGCA Homo_sapiens_chr14.trna12-LysTTT (73125354-73125282) Lys (TTT) 73 bp Sc: 38.73
                                                                                (SEQ ID NO: 680)
ACCCAGATAGCTCAGTTGATAGAGCATCAGACTTTTAATCTGAGGGTCCAGGGTTCATGTCCCTGTTCCTTAA Homo_sapiens_chr6.trna118-LysTTT (28769039-28768966) Lys (TTT) 74 bp Sc: 44.65
                                                                                (SEQ ID NO: 681)
GCCTGGGTAGCTCAGTCGGTAGAGCTATCAGACTTTTAGCCTGAGGATTCAGGGTTCAATCCCTTGCTGGGCG Homo_sapiens_chr19.trna9-LysTTT (46440054-46439982) Lys (TTT) 73 bp Sc: 53.63
                                                                                (SEQ ID NO: 682)
GCCAGGATAGTTCAGGTGGTAGAGCATCAGACTTTTAACCTGAGGGTTCAGGGTTCAAGTCTCTGTTTGGGCG Homo_sapiens_chr17.trna25-SeCTCA (35527152-35527079) SeC (TCA) 74 bp Sc: 47.88
                                                                                (SEQ ID NO: 683)
GACCGTGTGGCCTTAATGGATAAGGTGTCTGACTTCAGATCAGAAGATTGAGGGTTTGAGTCCCTTTGTGGTCA Homo_sapiens_chr22.trna1-SeC(e)TCA (42877870-42877955) SeC(e) (TCA) 86 bp Sc: 62.60
                                                                                (SEQ ID NO: 684)
GCTCGGATGATCCTCAGTGGTCTGGGGTGCAGGCTTCAAACCTGTAGCTGTCTAGTGACAGAGTGGTTCAATTCCACCTTTGTAGG Homo_sapiens_chr19.trna8-SeC(e)TCA (50673785-50673700) SeC(e) (TCA) 86 bp Sc: 75.99
                                                                                (SEQ ID NO: 685)
GCCCGGATGATCCTCAGTGGTCTGGGGTGCAGGCTTCAAACCTGTAGCTGTCTAGCGACAGAGTGGTTCAATTCCACCTTTCGGGC Homo_sapiens_chr11.trna10-SerAGA (108541249-108541330) Ser (AGA) 82 bp Sc: 29.13
                                                                                (SEQ ID NO: 686)
TGAGTTGTAGCTGAGTGGTTAAGGCAACGAGCTAGAAATTCGTTGGTTTCTCTCTGTGCAGGTTTGAATCCTGCTAATTATG Homo_sapiens_chr7.trna12-SerAGA (148936400-148936471) Ser (AGA) 72 bp Sc: 62.08
                                                                                (SEQ ID NO: 687)
GGGTGTATGGCTCAGGGGTAGAGAATTTGACTAGAGATCAAGAGGTCCCTGGTTCAAATCCAGGTGCCCCCT Homo_sapiens_chr6.trna145-SerAGA (27629252-27629171) Ser (AGA) 82 bp Sc: 79.96
                                                                                (SEQ ID NO: 688)
GTAGTCGTGGCCGAGTGGTTAAGGTGATGGACTAGAAACCCATTGGGGTCTCCCCGCGCAGGTTCGAATCCTGCCGACTACG Homo_sapiens_chr6.trna50-SerAGA (27607966-27608047) Ser (AGA) 82 bp Sc: 86.61
                                                                                (SEQ ID NO: 689)
GTAGTCGTGGCCGAGTGGTTAAGGCGATGGACTAGAAATCCATTGGGGTTTCCCCACGCAGGTTCGAATCCTGCCGACTACG Homo_sapiens_chr17.trna35-SerAGA (8070734-8070653) Ser (AGA) 82 bp Sc: 88.01
                                                                                (SEQ ID NO: 690)
GTAGTCGTGGCCGAGTGGTTAAGGCGATGGACTAGAAATCCATTGGGGTCTCCCCGCGCAGGTTCGAATCCTGCCGACTACG
```

Homo_sapiens_chr6.trna44-SerAGA (27554570-27554651) Ser (AGA) 82 bp Sc: 88.01

(SEQ ID NO: 691)

GTAGTCGTGGCCGAGTGGTTAAGGCGATGGACTAGAAATCCATTGGGGTCTCCCCGCGCAGGTTCGAATCCTGCCGACTACG

Homo_sapiens_chr6.trna46-SerAGA (27571572-27571653) Ser (AGA) 82 bp Sc: 88.01

(SEQ ID NO: 692)

GTAGTCGTGGCCGAGTGGTTAAGGCGATGGACTAGAAATCCATTGGGGTCTCCCCGCGCAGGTTCGAATCCTGCCGACTACG

Homo_sapiens_chr6.trna47-SerAGA (27578797-27578878) Ser (AGA) 82 bp Sc: 88.01

(SEQ ID NO: 693)

GTAGTCGTGGCCGAGTGGTTAAGGCGATGGACTAGAAATCCATTGGGGTCTCCCCGCGCAGGTTCGAATCCTGCCGACTACG

Homo_sapiens_chr6.trna5-SerAGA (26435796-26435877) Ser (AGA) 82 bp Sc: 88.01

(SEQ ID NO: 694)

GTAGTCGTGGCCGAGTGGTTAAGGCGATGGACTAGAAATCCATTGGGGTCTCCCCGCGCAGGTTCGAATCCTGCCGACTACG

Homo_sapiens_chr8.trna11-SerAGA (96351142-96351061) Ser (AGA) 82 bp Sc: 88.01

(SEQ ID NO: 695)

GTAGTCGTGGCCGAGTGGTTAAGGCGATGGACTAGAAATCCATTGGGGTCTCCCCGCGCAGGTTCGAATCCTGCCGACTACG

Homo_sapiens_chr6.trna147-SerAGA (27617614-27617533) Ser (AGA) 82 bp Sc: 88.50

(SEQ ID NO: 696)

GTAGTCGTGGCCGAGTGGTTAAGGCGATGGACTAGAAATCCATTGGGGTTTCCCCGCGCAGGTTCGAATCCTGCCGACTACG

Homo_sapiens_chr12.trna2-SerCGA (54870415-54870496) Ser (CGA) 82 bp Sc: 89.14

(SEQ ID NO: 697)

GTCACGGTGGCCGAGTGGTTAAGGCGTTGGACTCGAAATCCAATGGGGTTTCCCCGCACAGGTTCGAATCCTGTTCGTGACG

Homo_sapiens_chr6.trna137-SerCGA (27748289-27748208) Ser (CGA) 82 bp Sc: 89.16

(SEQ ID NO: 698)

GCTGTGATGGCCGAGTGGTTAAGGTGTTGGACTCGAAATCCAATGGGGTTCCCCGCGCAGGTTCAAATCCTGCTCACAGCG

Homo_sapiens_chr6.trna35-SerCGA (27285607-27285688) Ser (CGA) 82 bp Sc: 90.35

(SEQ ID NO: 699)

GCTGTGATGGCCGAGTGGTTAAGGCGTTGGACTCGAAATCCAATGGGGTCTCCCCGCGCAGGTTCAAATCCTGCTCACAGCG

Homo_sapiens_chr17.trna41-SerCGA (7983005-7982924) Ser (CGA) 82 bp Sc: 92.09

(SEQ ID NO: 700)

GCTGTGATGGCCGAGTGGTTAAGGCGTTGGACTCGAAATCCAATGGGGTCTCCCCGCGCAGGTTCGAATCCTGCTCACAGCG

Homo_sapiens_chr6.trna175-SerGCT (26413780-26413697) Ser (GCT) 84 bp Sc: 67.16

(SEQ ID NO: 701)

GGAGAGGCCTGGCCGAGTGGTTAAGGCGATGGACTGCTAATCCATTGTGCTCTGCACGCGTGGGTTCGAATCCCATCCTCGTCG

Homo_sapiens_chr6.trna62-SerGCT (28288794-28288875) Ser (GCT) 82 bp Sc: 83.46

(SEQ ID NO: 702)

GACGAGGTGGCCGAGTGGTTAAGGCGATGGACTGCTAATCCATTGTGCTCTGCACACGTGGGTTCGAATCCCATCCTCGTCG

Homo_sapiens_chr15.trna10-SerGCT (38673396-38673315) Ser (GCT) 82 bp Sc: 85.34

(SEQ ID NO: 703)

GACGAGGTGGCCGAGTGGTTAAGGCGATGGACTGCTAATCCATTGTGCTCTGCACGCGTGGGTTCGAATCCCATCCTCGTCG

Homo_sapiens_chr17.trna7-SerGCT (8030909-8030990) Ser (GCT) 82 bp Sc: 85.34

(SEQ ID NO: 704)

GACGAGGTGGCCGAGTGGTTAAGGCGATGGACTGCTAATCCATTGTGCTCTGCACGCGTGGGTTCGAATCCCATCCTCGTCG

Homo_sapiens_chr6.trna123-SerGCT (28673177-28673096) Ser (GCT) 82 bp Sc: 85.34

(SEQ ID NO: 705)

GACGAGGTGGCCGAGTGGTTAAGGCGATGGACTGCTAATCCATTGTGCTCTGCACGCGTGGGTTCGAATCCCATCCTCGTCG

Homo_sapiens_chr11.trna8-SerGCT (65872167-65872248) Ser (GCT) 82 bp Sc: 85.83

(SEQ ID NO: 706)

GACGAGGTGGCCGAGTGGTTAAGGCGATGGACTGCTAATCCATTGTGCTTTGCACGCGTGGGTTCGAATCCCATCCTCGTCG

Homo_sapiens_chr6.trna43-SerGCT (27373754-27373835) Ser (GCT) 82 bp Sc: 86.80

(SEQ ID NO: 707)

GACGAGGTGGCCGAGTGGTTAAGGCGATGGACTGCTAATCCATTGTGCTCTGCACGCGTGGGTTCGAATCCCACCTTCGTCG

Homo_sapiens_chr6.trna31-SerGCT (27173064-27173145) Ser (GCT) 82 bp Sc: 88.12

(SEQ ID NO: 708)

GACGAGGTGGCCGAGTGGTTAAGGCGATGGACTGCTAATCCATTGTGCTCTGCACGCGTGGGTTCGAATCCCACCCTCGTCG

Homo_sapiens_chr2.trna21-SerTGA (130749563-130749494) Ser (TGA) 70 bp Sc: 31.73

(SEQ ID NO: 709)

GAGAAGGTCACAGAGGTTATGGGATTGGCTTGAAACCAGTCTGTGGGGGGTTCGATTCCCTCCTTTTTCA

Homo_sapiens_chr6.trna148-SerTGA (27581667-27581586) Ser (TGA) 82 bp Sc: 84.78

(SEQ ID NO: 710)

GTAGTCGTGGCCGAGTGGTTAAGGCGATGGACTTGAAATCCATTGGGGTTTCCCCGCGCAGGTTCGAATCCTGTCGGCTACG

Homo_sapiens_chr6.trna172-SerTGA (26420884-26420803) Ser (TGA) 82 bp Sc: 88.25

(SEQ ID NO: 711)

GTAGTCGTGGCCGAGTGGTTAAGGCGATGGACTTGAAATCCATTGGGGTCTCCCCGCGCAGGTTCGAATCCTGCCGACTACG

Homo_sapiens_chr6.trna51-SerTGA (27621447-27621528) Ser (TGA) 82 bp Sc: 88.73

(SEQ ID NO: 712)

GTAGTCGTGGCCGAGTGGTTAAGGCGATGGACTTGAAATCCATTGGGGTTTCCCCGCGCAGGTTCGAATCCTGCCGACTACG

Homo_sapiens_chr10.trna2-SerTGA (69194267-69194348) Ser (TGA) 82 bp Sc: 90.86

(SEQ ID NO: 713)

GCAGCGATGGCCGAGTGGTTAAGGCGTTGGACTTGAAATCCAATGGGGTCTCCCCGCGCAGGTTCGAACCCTGCTCGCTGCG

Homo_sapiens_chr17.trna11-SupCTA (15349410-15349483) Sup (CTA) 74 bp Sc: 28.00

(SEQ ID NO: 714)

GGCAGTGACGCCTACTGGTTTAGAGCACAGATTCTAGATCGAGACATTCCTGGGTTCAAATCCCAGCACTGTTG

Homo_sapiens_chr21.trna1-SupTTA (14848387-14848457) Sup (TTA) 71 bp Sc: 22.35

(SEQ ID NO: 715)

GGCAGTGACATGTAATGGTTATGAGGGTGGACTTTAACCACACTGCCTAGGTTCAAATCCTGACTCTGTCA

Homo_sapiens_chr17.trna17-SupTTA (56218375-56218445) Sup (TTA) 71 bp Sc: 57.62

(SEQ ID NO: 716)

GCCCGGATAGTTCAGTTGGTAGAGCATCAGACTTAATCAGAGGGTCCAGGGTTCAAGTCCCTGTTTGGGTG

Homo_sapiens_chr17.trna24-ThrAGT (59957453-59957380) Thr (AGT) 74 bp Sc: 43.90

(SEQ ID NO: 717)

AGCACCATGGCTTAGCTGGTTAAAGCACCTGTCTAGTAAACAGGAGATCCTGAGTTTCAATTCCAATGGTGCCT

Homo_sapiens_chr6.trna34-ThrAGT (27238029-27238102) Thr (AGT) 74 bp Sc: 80.30

(SEQ ID NO: 718)

GGCCCTGTGGCTTAGCTGGTCAAAGCGCCTGTCTAGTAAACAGGAGATCCTGGGTTCGAATCCCAGCGGGGCCT

Homo_sapiens_chr6.trna60-ThrAGT (27802452-27802525) Thr (AGT) 74 bp Sc: 81.60

(SEQ ID NO: 719

GGCTTCGTGGCTTAGCTGGTTAAAGCGCCTGTCTAGTAAACAGGAGATCCTGGGTTCGAATCCCAGCGAGGCCT

Homo_sapiens_chr17.trna40-ThrAGT (7983568-7983495) Thr (AGT) 74 bp Sc: 81.60

(SEQ ID NO: 720)

GGCGCCGTGGCTTAGCTGGTTAAAGCGCCTGTCTAGTAAACAGGAGATCCTGGGTTCGAATCCCAGCGGTGCCT

Homo_sapiens_chr6.trna69-ThrAGT (28801774-28801847) Thr (AGT) 74 bp Sc: 82.17

(SEQ ID NO: 721)

GGCTCCGTAGCTTAGTTGGTTAAAGCGCCTGTCTAGTAAACAGGAGATCCTGGGTTCGACTCCCAGCGGGGCCT

Homo_sapiens_chr6.trna135-ThrAGT (27760526-27760453) Thr (AGT) 74 bp Sc: 83.05

(SEQ ID NO: 722)

GGCTCCGTGGCTTAGCTGGTTAAAGCGCCTGTCTAGTAAACAGGAGATCCTGGGTTCGAATCCCAGCGGGGCCT

Homo_sapiens_chr6.trna167-ThrAGT (26641197-26641124) Thr (AGT) 74 bp Sc: 83.05

(SEQ ID NO: 723)

GGCTCCGTGGCTTAGCTGGTTAAAGCGCCTGTCTAGTAAACAGGAGATCCTGGGTTCGAATCCCAGCGGGGCCT

Homo_sapiens_chr17.trna36-ThrAGT (8070351-8070278) Thr (AGT) 74 bp Sc: 84.06

(SEQ ID NO: 724)

GGCGCCGTGGCTTAGTTGGTTAAAGCGCCTGTCTAGTAAACAGGAGATCCTGGGTTCGAATCCCAGCGGTGCCT

Homo_sapiens_chr17.trna8-ThrAGT (8031203-8031276) Thr (AGT) 74 bp Sc: 84.06

(SEQ ID NO: 725)

GGCGCCGTGGCTTAGTTGGTTAAAGCGCCTGTCTAGTAAACAGGAGATCCTGGGTTCGAATCCCAGCGGTGCCT

Homo_sapiens_chr19.trna4-ThrAGT (38359803-38359876) Thr (AGT) 74 bp Sc: 84.06

(SEQ ID NO: 726)

GGCGCCGTGGCTTAGTTGGTTAAAGCGCCTGTCTAGTAAACAGGAGATCCTGGGTTCGAATCCCAGCGGTGCCT

Homo_sapiens_chr6.trna151-ThrCGT (27379618-27379547) Thr (CGT) 72 bp Sc: 46.44

(SEQ ID NO: 727)

GGCAGAGTGGTGCAGCGGAAGCGTGCTGGGCCCGTAACCCAGAGGTCAATGGATCGAAGCCATCCTTGGCTA

Homo_sapiens_chr6.trna54-ThrCGT (27694114-27694187) Thr (CGT) 74 bp Sc: 63.29

(SEQ ID NO: 728)

GGCCCTGTAGCTCAGCGGTTGGAGCGCTGGTCTCGTAAACCTAGGGGTCGTGAGTTCAAATCTCACCAGGGCCT

Homo_sapiens_chr17.trna14-ThrCGT (26901213-26901284) Thr (CGT) 72 bp Sc: 79.77

(SEQ ID NO: 729)

GGCGCGGTGGCCAAGTGGTAAGGCGTCGGTCTCGTAAACCGAAGATCGCGGGTTCGAACCCCGTCCGTGCCT

Homo_sapiens_chr6.trna121-ThrCGT (28724036-28723963) Thr (CGT) 74 bp Sc: 80.30

(SEQ ID NO: 730)

GGCTCTGTGGCTTAGTTGGCTAAAGCGCCTGTCTCGTAAACAGGAGATCCTGGGTTCGAATCCCAGCGGGGCCT

-continued

Homo_sapiens_chr16.trna15-ThrCGT (14287251-14287322) Thr (CGT) 72 bp Sc: 80.42

(SEQ ID NO: 731)

GGCGCGGTGGCCAAGTGGTAAGGCGTCGGTCTCGTAAACCGAAGATCACGGGTTCGAACCCCGTCCGTGCCT

Homo_sapiens_chr6.trna125-ThrCGT (28564822-28564749) Thr (CGT) 74 bp Sc: 80.88

(SEQ ID NO: 732)

GGCTCTATGGCTTAGTTGGTTAAAGCGCCTGTCTCGTAAACAGGAGATCCTGGGTTCGACTCCCAGTGGGGCCT

Homo_sapiens_chr5.trna13-ThrTGT (180551364-180551293) Thr (TGT) 72 bp Sc: 75.64

(SEQ ID NO: 733)

GGCTCCATAGCTCAGGGGTTAGAGCACTGGTCTTGTAAACCAGGGTCGCGAGTTCAAATCTCGCTGGGGCCT

Homo_sapiens_chr14.trna4-ThrTGT (20219689-20219761) Thr (TGT) 73 bp Sc: 78.79

(SEQ ID NO: 734)

GGCCCTATAGCTCAGGGGTTAGAGCACTGGTCTTGTAAACCAGGGGTCGCGAGTTCAAATCTCGCTGGGGCCT

Homo_sapiens_chr14.trna20-ThrTGT (20169231-20169159) Thr (TGT) 73 bp Sc: 79.46

(SEQ ID NO: 735)

GGCTCCATAGCTCAGGGGTTAGAGCACTGGTCTTGTAAACCAGGGGTCGCGAGTTCAAATCTCGCTGGGGCCT

Homo_sapiens_chr14.trna21-ThrTGT (20151861-20151789) Thr (TGT) 73 bp Sc: 80.94

(SEQ ID NO: 736)

GGCTCCATAGCTCAGGGGTTAGAGCGCTGGTCTTGTAAACCAGGGGTCGCGAGTTCAATTCTCGCTGGGGCCT

Homo_sapiens_chr1.trna56-ThrTGT (220704970-220705042) Thr (TGT) 73 bp Sc: 83.03

(SEQ ID NO: 737)

GGCTCCATAGCTCAGTGGTTAGAGCACTGGTCTTGTAAACCAGGGGTCGCGAGTTCGATCCTCGCTGGGGCCT

Homo_sapiens_chr6.trna127-ThrTGT (28550381-28550308) Thr (TGT) 74 bp Sc: 84.82

(SEQ ID NO: 738)

GGCTCTATGGCTTAGTTGGTTAAAGCGCCTGTCTTGTAAACAGGAGATCCTGGGTTCGAATCCCAGTAGAGCCT

Homo_sapiens_chr11.trna19-TrpCCA (45246849-45246776) Trp (CCA) 74 bp Sc: 21.17

(SEQ ID NO: 739)

GGAAGGATGGGGCCAAGCTGGAAAGCCTGTGGGCTCCACAGTCATGTGCCTGGGTTCAATTCCCAGTTCTGCAT

Homo_sapiens_chr7.trna1-TrpCCA (98905243-98905314) Trp (CCA) 72 bp Sc: 70.08

(SEQ ID NO: 740)

GACCTCGTGGCGCAACGGCAGCGCGTCTGACTCCAGATCAGAAGGTTGCGTGTTCAAATCACGTCGGGGTCA

Homo_sapiens_chr12.trna6-TrpCCA (97422161-97422232) Trp (CCA) 72 bp Sc: 71.65

(SEQ ID NO: 741)

GACCTCGTGGCGCAACGGTAGCGCGTCTGACTCCAGATCAGAAGGCTGCGTGTTCGAATCACGTCGGGGTCA

Homo_sapiens_chr17.trna6-TrpCCA (8030401-8030472) Trp (CCA) 72 bp Sc: 74.00

(SEQ ID NO: 742)

GACCTCGTGGCGCAACGGTAGCGCGTCTGACTCCAGATCAGAAGGTTGCGTGTTCAAATCACGTCGGGGTCA

Homo_sapiens_chr6.trna168-TrpCCA (26439722-26439651) Trp (CCA) 72 bp Sc: 74.00

(SEQ ID NO: 743)

GACCTCGTGGCGCAACGGTAGCGCGTCTGACTCCAGATCAGAAGGTTGCGTGTTCAAATCACGTCGGGGTCA

Homo_sapiens_chr6.trna170-TrpCCA (26427380-26427309) Trp (CCA) 72 bp Sc: 74.00

(SEQ ID NO: 744)

GACCTCGTGGCGCAACGGTAGCGCGTCTGACTCCAGATCAGAAGGTTGCGTGTTCAAATCACGTCGGGGTCA

Homo_sapiens_chr17.trna12-TrpCCA (19352086-19352157) Trp (CCA) 72 bp Sc: 74.80

(SEQ ID NO: 745)

GACCTCGTGGCGCAATGGTAGCGCGTCTGACTCCAGATCAGAAGGTTGCGTGTTCAAGTCACGTCGGGGTCA

Homo_sapiens_chr17.trna39-TrpCCA (8064983-8064912) Trp (CCA) 72 bp Sc: 74.81

(SEQ ID NO: 746)

GGCCTCGTGGCGCAACGGTAGCGCGTCTGACTCCAGATCAGAAGGTTGCGTGTTCAAATCACGTCGGGGTCA

Homo_sapiens_chr9.trna3-TrpCCA (114656810-114656908) Trp (CCA) 99 bp Sc: 23.38

(SEQ ID NO: 747)

GGCAGAGGAGGGTGCAGTTGGCAGCCTGTCCAAGTCCAGCACGGTTGGAGCACAGGATTTAGAATGGGATGGTCCTGGGTTCAAACCCCAGCTGCGCCC

Homo_sapiens_chr2.trna14-TyrATA (218818794-218818886) Tyr (ATA) 93 bp Sc: 55.93

(SEQ ID NO: 748)

CCTTCAATAGTTCAGCTGGTAGAGCAGAGGACTATAGCTACTTCCTCAGTAGGAGACGTCCTTAGGTTGCTGGTTCGATTCCAGCTTGAAGGA

Homo_sapiens_chr7.trna9-TyrGTA (148886066-148886138) Tyr (GTA) 73 bp Sc: 49.38

(SEQ ID NO: 749)

GGGGGTATAGCTCAGGGCTAGAGCTTTTTGACTGTAGAGCAAGAGGTCCCTGGTTCAAATCCAGGTTCTCCCT

Homo_sapiens_chr14.trna19-TyrGTA (20191191-20191098) Tyr (GTA) 94 bp Sc: 74.71

(SEQ ID NO: 750)

CCTTCGATAGCTCAGCTGGTAGAGCGGAGGACTGTAGCCTGTAGAAACATTTGTGGACATCCTTAGGTCGCTGGTTCGATTCCGGCTCGAAGGA

Homo_sapiens_chr14.trna18-TyrGTA (20195556-20195463) Tyr (GTA) 94 bp Sc: 75.82

(SEQ ID NO: 751)

CCTTCGATAGCTCAGCTGGTAGAGCGGAGGACTGTAGATTGTATAGACATTTGCGGACATCCTTAGGTCGCTGGTTCGATTCCAGCTCGAAGGA

Homo_sapiens_chr14.trna17-TyrGTA (20198050-20197957) Tyr (GTA) 94 bp Sc: 71.83

(SEQ ID NO: 752)

CCTTCGATAGCTCAGCTGGTAGAGCGGAGGACTGTAGACTGCGGAAACGTTTGTGGACATCCTTAGGTCGCTGGTTCAATTCCGGCTCGAAGGA

Homo_sapiens_chr14.trna16-TyrGTA (20201284-20201191) Tyr (GTA) 94 bp Sc: 74.71

(SEQ ID NO: 753)

CCTTCGATAGCTCAGCTGGTAGAGCGGAGGACTGTAGATTGTACAGACATTTGCGGACATCCTTAGGTCGCTGGTTCGATTCCGGCTCGAAGGA

Homo_sapiens_chr14.trna5-TyrGTA (20221272-20221360) Tyr (GTA) 89 bp Sc: 75.42

(SEQ ID NO: 754)

CCTTCGATAGCTCAGCTGGTAGAGCGGAGGACTGTAGTACTTAATGTGTGGTCATCCTTAGGTCGCTGGTTCGATTCCGGCTCGAAGGA

Homo_sapiens_chr6.trna14-TyrGTA (26677065-26677155) Tyr (GTA) 91 bp Sc: 76.45

(SEQ ID NO: 755)

CCTTCGATAGCTCAGTTGGTAGAGCGGAGGACTGTAGTTGGCTGTGTCCTTAGACATCCTTAGGTCGCTGGTTCGAATCCGGCTCGAAGGA

Homo_sapiens_chr6.trna15-TyrGTA (26683777-26683866) Tyr (GTA) 90 bp Sc: 72.82

(SEQ ID NO: 756)

CTTTCGATAGCTCAGTTGGTAGAGCGGAGGACTGTAGGTTCATTAAACTAAGGCATCCTTAGGTCGCTGGTTCGAATCCGGCTCGAAGGA

Homo_sapiens_chr6.trna16-TyrGTA (26685311-26685399) Tyr (GTA) 89 bp Sc: 77.01

(SEQ ID NO: 757)

CCTTCGATAGCTCAGTTGGTAGAGCGGAGGACTGTAGGCTCATTAAGCAAGGTATCCTTAGGTCGCTGGTTCGAATCCGGCTCGAAGGA

Homo_sapiens_chr6.trna17-TyrGTA (26703081-26703169) Tyr (GTA) 89 bp Sc: 73.91

(SEQ ID NO: 758)

CCTTCGATAGCTCAGCTGGTAGAGCGGAGGACTGTAGGGGTTTGAATGTGGTCATCCTTAGGTCGCTGGTTCGAATCCGGCTCGGAGGA

Homo_sapiens_chr2.trna2-TyrGTA (27127154-27127242) Tyr (GTA) 89 bp Sc: 75.87

(SEQ ID NO: 759)

CCTTCGATAGCTCAGTTGGTAGAGCGGAGGACTGTAGTGGATAGGGCGTGGCAATCCTTAGGTCGCTGGTTCGATTCCGGCTCGAAGGA

Homo_sapiens_chr8.trna12-TyrGTA (66772173-66772086) Tyr (GTA) 88 bp Sc: 46.11

(SEQ ID NO: 760)

TCTTCAATAGCTCAGCTGGTAGAGCGGAGGACTGTAGGTGCACGCCCGTGGCCATTCTTAGGTGCTGGTTTGATTCCGACTTGGAGAG

Homo_sapiens_chr8.trna4-TyrGTA (67188156-67188248) Tyr (GTA) 93 bp Sc: 73.04

(SEQ ID NO: 761)

CCTTCGATAGCTCAGCTGGTAGAGCGGAGGACTGTAGCTACTTCCTCAGCAGGAGACATCCTTAGGTCGCTGGTTCGATTCCGGCTCGAAGGA

Homo_sapiens_chr8.trna5-TyrGTA (67188777-67188865) Tyr (GTA) 89 bp Sc: 69.69

(SEQ ID NO: 762)

CCTTCGATAGCTCAGCTGGTAGAGCGGAGGACTGTAGGCGCGCGCCCGTGGCCATCCTTAGGTCGCTGGTTCGATTCCGGCTCGAAGGA

Homo_sapiens_chr1.trna63-ValAAC (178450971-178450899) Val (AAC) 73 bp Sc: 48.28

(SEQ ID NO: 763)

GTTTCCATAGTGTACTGGTTATCACATTCACCTAACACGCGAAAGGTCCTTGGTTTGAAACCAGGCAGAAACA

Homo_sapiens_chr6.trna115-ValAAC (28811256-28811185) Val (AAC) 72 bp Sc: 64.08

(SEQ ID NO: 764)

GGGGGTGTAGCTCAGTGGTAGAGCGTATGCTTAACATTCATGAGGCTCTGGGTTCGATCCCCAGCACTTCCA

Homo_sapiens_chr6.trna37-ValAAC (27311267-27311339) Val (AAC) 73 bp Sc: 74.63

(SEQ ID NO: 765)

GTTTCCGTAGTGTAGTGGTTATCACGTTTGCCTAACACGCGAAAGGTCCCCGGTTCGAAACCGGGCAGAAACA

Homo_sapiens_chr6.trna136-ValAAC (27756936-27756864) Val (AAC) 73 bp Sc: 79.68

(SEQ ID NO: 766)

GTTTCCGTAGTGTAGTGGTTATCACGTTCGCCTAACACGCGAAAGGTCCGCGGTTCGAAACCGGGCGGAAACA

Homo_sapiens_chr6.trna139-ValAAC (27726758-27726686) Val (AAC) 73 bp Sc: 81.58

(SEQ ID NO: 767)

GTTTCCGTAGTGTAGTGGTTATCACGTTCGCCTAACACGCGAAAGGTCCCTGGATCAAAACCAGGCGGAAACA

Homo_sapiens_chr5.trna15-ValAAC (180548094-180548022) Val (AAC) 73 bp Sc: 84.70

(SEQ ID NO: 768)

GTTTCCGTAGTGTAGTGGTCATCACGTTCGCCTAACACGCGAAAGGTCCCCGGTTCGAAACCGGGCGGAAACA

Homo_sapiens_chr3.trna2-ValAAC (170972712-170972784) Val (AAC) 73 bp Sc: 86.79

(SEQ ID NO: 769)

GTTTCCGTAGTGTAGTGGTTATCACGTTCGCCTAACACGCGAAAGGTCCCCGGTTCGAAACCGGGCGGAAACA

Homo_sapiens_chr5.trna12-ValAAC (180577948-180577876) Val (AAC) 73 bp Sc: 86.79

(SEQ ID NO: 770)

GTTTCCGTAGTGTAGTGGTTATCACGTTCGCCTAACACGCGAAAGGTCCCCGGTTCGAAACCGGGCGGAAACA

-continued

Homo_sapiens_chr5.trna4-ValAAC (180523760-180523832) Val (AAC) 73 bp Sc: 86.79

(SEQ ID NO: 771)

GTTTCCGTAGTGTAGTGGTTATCACGTTCGCCTAACACGCGAAAGGTCCCCGGTTCGAAACCGGGCGGAAACA

Homo_sapiens_chr5.trna5-ValAAC (180529216-180529288) Val (AAC) 73 bp Sc: 86.79

(SEQ ID NO: 772)

GTTTCCGTAGTGTAGTGGTTATCACGTTCGCCTAACACGCGAAAGGTCCCCGGTTCGAAACCGGGCGGAAACA

Homo_sapiens_chr6.trna132-ValAAC (27829230-27829158) Val (AAC) 73 bp Sc: 86.79

(SEQ ID NO: 773)

GTTTCCGTAGTGTAGTGGTTATCACGTTCGCCTAACACGCGAAAGGTCCCCGGTTCGAAACCGGGCGGAAACA

Homo_sapiens_chr6.trna58-ValCAC (27758467-27758540) Val (CAC) 74 bp Sc: 33.44

(SEQ ID NO: 774)

TTTTCTGTAGTGTAGTTGTTAACACGTTCGCCTCACACGCTTAAAGTTCTCTGGTTGGATACCAGATGGAAATG

Homo_sapiens_chr1.trna129-ValCAC (16879160-16879088) Val (CAC) 73 bp Sc: 52.98

(SEQ ID NO: 775)

GTTTCTGTGGTGTAGTGGTTATCATGTTCGCCTCACACGAGAAAAGTCCCTGATTCGAGACTGGGTGGGAACG

Homo_sapiens_chr6.trna32-ValCAC (27226001-27226073) Val (CAC) 73 bp Sc: 56.94

(SEQ ID NO: 776)

GTTTCTGTAGTATGGTGGTTATCACGTTAGTCTCACACGTGAAAGGTCCCTGGTTCGAAACCAGGTGGAAACA

Homo_sapiens_chr1.trna99-ValCAC (147561360-147561290) Val (CAC) 71 bp Sc: 60.62

(SEQ ID NO: 777)

GCACTGGTGGTTCAGTGGTAGAATTCTCGCCTCACACGCGGGACACCCGGGTTCAATTCCCGGTCAAGGCA

Homo_sapiens_chr6.trna133-ValCAC (27804378-27804306) Val (CAC) 73 bp Sc: 64.50

(SEQ ID NO: 778)

GTTTCCGTAGTGTAGTGGTTATTATGTTCGCCTCACACGCGAAAGTCCCCGGTTCGAAATCAGGCGGGAACA

Homo_sapiens_chr6.trna157-ValCAC (27281918-27281846) Val (CAC) 73 bp Sc: 73.23

(SEQ ID NO: 779)

GTTTCCGTAGTGGAGTGGTTATCACGTTCGCCTCACACGCGAAAGGTCCCCGGTTTGAAACCAGGCGGAAACA

Homo_sapiens_chr1.trna90-ValCAC (147950785-147950712) Val (CAC) 74 bp Sc: 77.15

(SEQ ID NO: 780)

GTTTCCGTAGTGTAGTGGTTATCACGTTCGCCTCACACGCGTAAAGGTCCCCGGTTCGAAACCGGGCGAAACA

Homo_sapiens_chr1.trna98-ValCAC (147565251-147565179) Val (CAC) 73 bp Sc: 82.06

(SEQ ID NO: 781)

GTTTCCGTAGTGTAGTGGTTATCACGTTCGCCTCACACGCGAAAGGTCCCCGGTTCGAAACTGGGCGGAAACA

Homo_sapiens_chr19.trna13-ValCAC (4675719-4675647) Val (CAC) 73 bp Sc: 84.20

(SEQ ID NO: 782)

GTTTCCGTAGTGTAGCGGTTATCACATTCGCCTCACACGCGAAAGGTCCCCGGTTCGATCCCGGGCGGAAACA

Homo_sapiens_chr6.trna152-ValCAC (27356100-27356028) Val (CAC) 73 bp Sc: 87.34

(SEQ ID NO: 783)

GCTTCTGTAGTGTAGTGGTTATCACGTTCGCCTCACACGCGAAAGGTCCCCGGTTCGAAACCGGGCAGAAGCA

Homo_sapiens_chr1.trna85-ValCAC (159636186-159636114) Val (CAC) 73 bp Sc: 87.39

(SEQ ID NO: 784)

GTTTCCGTAGTGTAGTGGTTATCACGTTCGCCTCACACGCGAAAGGTCCCCGGTTCGAAACCGGGCGGAAACA

Homo_sapiens_chr5.trna10-ValCAC (180582073-180582001) Val (CAC) 73 bp Sc: 87.39

(SEQ ID NO: 785)

GTTTCCGTAGTGTAGTGGTTATCACGTTCGCCTCACACGCGAAAGGTCCCCGGTTCGAAACCGGGCGGAAACA

Homo_sapiens_chr5.trna18-ValCAC (180461931-180461859) Val (CAC) 73 bp Sc: 87.39

(SEQ ID NO: 786)

GTTTCCGTAGTGTAGTGGTTATCACGTTCGCCTCACACGCGAAAGGTCCCCGGTTCGAAACCGGGCGGAAACA

Homo_sapiens_chr5.trna2-ValCAC (180456676-180456748) Val (CAC) 73 bp Sc: 87.39

(SEQ ID NO: 787)

GTTTCCGTAGTGTAGTGGTTATCACGTTCGCCTCACACGCGAAAGGTCCCCGGTTCGAAACCGGGCGGAAACA

Homo_sapiens_chr5.trna6-ValCAC (180533256-180533328) Val (CAC) 73 bp Sc: 87.39

(SEQ ID NO: 788)

GTTTCCGTAGTGTAGTGGTTATCACGTTCGCCTCACACGCGAAAGGTCCCCGGTTCGAAACCGGGCGGAAACA

Homo_sapiens_chr6.trna9-ValCAC (26646261-26646333) Val (CAC) 73 bp Sc: 87.39

(SEQ ID NO: 789)

GTTTCCGTAGTGTAGTGGTTATCACGTTCGCCTCACACGCGAAAGGTCCCCGGTTCGAAACCGGGCGGAAACA

Homo_sapiens_chr6.trna40-ValTAC (27366384-27366456) Val (TAC) 73 bp Sc: 76.42

(SEQ ID NO: 790)

GTTTCCGTGGTGTAGTGGTTATCACATTCGCCTTACACGCGAAAGGTCCTCGGGTCGAAACCGAGCGGAAACA

-continued

Homo_sapiens_chr10.trna6-ValTAC (5935752-5935680) Val (TAC) 73 bp Sc: 81.67

(SEQ ID NO: 791)

GGTTCCATAGTGTAGTGGTTATCACATCTGCTTTACACGCAGAAGGTCCTGGGTTCAAGCCCCAGTGGAACCA

Homo_sapiens_chr11.trna16-ValTAC (59075108-59075036) Val (TAC) 73 bp Sc: 82.67

(SEQ ID NO: 792)

GGTTCCATAGTGTAGCGGTTATCACGTCTGCTTTACACGCAGAAGGTCCTGGGTTCGAGCCCCAGTGGAACCA

Homo_sapiens_chr11.trna17-ValTAC (59074750-59074678) Val (TAC) 73 bp Sc: 85.12

(SEQ ID NO: 793)

GGTTCCATAGTGTAGTGGTTATCACGTCTGCTTTACACGCAGAAGGTCCTGGGTTCGAGCCCCAGTGGAACCA

Homo_sapiens_chrX.trna4-ValTAC (18603022-18602950) Val (TAC) 73 bp Sc: 85.12

(SEQ ID NO: 794)

GGTTCCATAGTGTAGTGGTTATCACGTCTGCTTTACACGCAGAAGGTCCTGGGTTCGAGCCCCAGTGGAACCA

Homo_sapiens_chr9.trna8-GlnTTG (5085156-5085085) Gln (TTG) 72 bp Sc: 21.75

(SEQ ID NO: 795)

TAGGATATGGTTTAATAGGTAGCATGGAGAATTTTGGAGTCTCAGGGATAGGTTCAATTCCTATAGTTCCAG

Homo_sapiens_chr6.trna64-GlnTTG (28665135-28665206) Gln (TTG) 72 bp Sc: 71.88

(SEQ ID NO: 796)

GGTCCCATGGTGTAATGGTTAGCACTCTGGACTTTGAATCCAGCAATCCGAGTTCGAATCTCGGTGGGACCT

---

What is claimed is:

1. A neuroprotective molecule consisting of:

(i) a sequence of 25-35 contiguous nucleotides that is identical to a contiguous sequence between nucleotide 1 and nucleotide 50 of a mature human transfer ribonucleic acid (tRNA) having a sequence selected from the group consisting of SEQ ID NOs: 10 and 58-62, wherein a first nucleotide of the 25-35 contiguous nucleotides corresponds to nucleotide position 1 of the mature human tRNA sequence; at least part of the sequence of 25-35 contiguous nucleotides forms a D-loop stem structure;

(ii) optionally a 5' monophosphate, one or more modified nucleotides, and/or one or more modifications in a phosphate backbone in the nucleotide(s) in (i) of the neuroprotective molecule; and (iii) optionally a 5'-protective group and/or a 3'-protective group;

wherein at least four contiguous nucleotides in (i) of the neuroprotective molecule at the 5'-end are guanosine deoxyribonucleotides; and the neuroprotective molecule is capable of decreasing protein translation in a rabbit reticulocyte assay.

2. The neuroprotective molecule of claim 1, wherein the neuroprotective molecule binds YB-1.

3. The neuroprotective molecule of claim 1, wherein at least part of the sequence of 25-35 contiguous nucleotides binds to YB-1.

4. The neuroprotective molecule of claim 1, wherein the neuroprotective molecule comprises a 5'-monophosphate, one or more modified nucleotides, and/or one or more modifications in a phosphate backbone of the nucleotide(s) in (i) and (ii) of the neuroprotective molecule.

5. The neuroprotective molecule of claim 4, wherein the at least one modified nucleotide contains a modified base or a modified sugar.

6. The neuroprotective molecule of claim 1, wherein the neuroprotective molecule comprises a 5'-and/or a 3'-protective group.

7. The neuroprotective molecule of claim 1, wherein the neuroprotective molecule has a total length of between 39 to 60 nucleotides.

8. A pharmaceutical composition comprising at least one neuroprotective molecule of claim 1.

9. A neuroprotective molecule consisting of:
(i) a sequence of 25-35 contiguous nucleotides that is identical to a contiguous sequence between nucleotide 1 and nucleotide 50 of mature human tRNA$^{Cys}$, wherein a first nucleotide of the 25-35 contiguous nucleotides corresponds to nucleotide position 1 of the mature human tRNA sequence; at least part of the sequence of 25-35 contiguous nucleotides forms a D-loop stem structure; and at least part of the sequence of 25-35 contiguous nucleotides binds to YB-1;
(ii) optionally a 5'-monophosphate, one or more modified nucleotides, and/or one or more modifications in a phosphate backbone of the nucleotide(s) in (i) of the neuroprotective molecule; and
(iii) optionally a 5'-protective group and/or a 3'-protective group;
wherein at least four contiguous nucleotides in (i) of the neuroprotective molecule at the 5'-end are guanosine deoxyribonucleotides; the neuroprotective molecule binds YB-1; and the neuroprotective molecule is capable of decreasing protein translation in a rabbit reticulocyte assay.

10. The neuroprotective molecule of claim 9, wherein the neuroprotective molecule comprises a 5'-monophosphate, one or more modified nucleotides, and/or one or more modifications in a phosphate backbone of the nucleotide(s) in (i) and (ii) of the neuroprotective molecule.

11. The neuroprotective molecule of claim 10, wherein the at least one modified nucleotide contains a modified base or a modified sugar.

12. The neuroprotective molecule of claim 9, wherein the neuroprotective molecule comprises a 5'-and/or a 3'-protective group.

13. The neuroprotective molecule of claim 9, wherein the neuroprotective molecule has a total length of between 39 to 60 nucleotides.

14. A pharmaceutical composition comprising at least one neuroprotective molecule of claim 9.

15. A neuroprotective molecule consisting of:
(i) a sequence of 25-35 contiguous nucleotides that is identical to a contiguous sequence between nucleotide 1 and nucleotide 50 of a mature human transfer ribonucleic acid (tRNA) having the sequence SEQ ID NO:10, wherein a first nucleotide of the 25-35 contiguous nucleotides corresponds to nucleotide position 1 of the mature human tRNA sequence; at least part of the sequence of 25-35 contiguous nucleotides forms a D-loop stem structure;
(ii) at least four contiguous guanosine-containing nucleotides at the 5'-end of (i);
(iii) optionally a 5' monophosphate, one or more modified nucleotides, and/or one or more modifications in a phosphate backbone in the nucleotide(s) in (i) of the neuroprotective molecule; and
(iv) optionally a 5'-protective group and/or a 3'-protective group;
wherein the at least four contiguous nucleotides in (ii) are guanosine deoxyribonucleotides; and the neuroprotective molecule is capable of decreasing protein translation in a rabbit reticulocyte assay.

16. The neuroprotective molecule of claim 15, wherein the neuroprotective molecule binds YB-1.

17. The neuroprotective molecule of claim 15, wherein at least part of the sequence of 25-35 contiguous nucleotides binds to YB-1.

18. The neuroprotective molecule of claim 15, wherein the neuroprotective molecule comprises a 5'-monophosphate, one or more modified nucleotides, and/or one or more modifications in a phosphate backbone of the nucleotide(s) in (i) and (iii) of the neuroprotective molecule.

19. The neuroprotective molecule of claim 18, wherein the at least one modified nucleotide contains a modified base or a modified sugar.

20. The neuroprotective molecule of claim 15, wherein the neuroprotective molecule comprises a 5'- and/or a 3'-protective group.

21. The neuroprotective molecule of claim 15, wherein the neuroprotective molecule has a total length of between 39 to 60 nucleotides.

22. A pharmaceutical composition comprising at least one neuroprotective molecule of claim 15.

* * * * *

UNITED STATES PATENT AND TRADEMARK OFFICE
CERTIFICATE OF CORRECTION

PATENT NO. : 10,457,939 B2
APPLICATION NO. : 15/590344
DATED : October 29, 2019
INVENTOR(S) : Paul Anderson, Pavel Ivanov and Mohammed Emara It is certified that error appears in the above-identified patent and that said Letters Patent is hereby corrected as shown below:

In the Specification

Column 1, Line 18, replace "STATEMENT AS TO FEDERALLY-SPONSORED RESEARCH
This invention was made with government support under federal research grant AI0658568 awarded by the National Institutes of Health. The government has certain rights in the invention."

With -- STATEMENT OF FEDERALLY SPONSORED RESEARCH
This invention was made with government support under Grant Nos. AI658568, CA168872, and AI033600 awarded by the National Institutes of Health. The government has certain rights in the invention. --

Signed and Sealed this
Sixteenth Day of May, 2023

*Katherine Kelly Vidal*

Katherine Kelly Vidal
*Director of the United States Patent and Trademark Office*